United States Patent
Sattler et al.

(10) Patent No.: US 9,840,504 B2
(45) Date of Patent: Dec. 12, 2017

(54) PYRAZOLOPYRIDINE DERIVATIVES AND THEIR USE IN THERAPY

(71) Applicant: HELMHOLTZ ZENTRUM MUENCHEN—DEUTSCHES FORSCHUNGSZENTRUM FUER GESUNDHEIT UND UMWELT(GMBH), Neuherberg (DE)

(72) Inventors: Michael Sattler, Munich (DE); Grzegorz Popowicz, Hallbergmoos (DE); Maciej Dawidowski, Munich (DE); Leonidas Emmanouilidis, Munich (DE); Ralf Erdmann, Bochum (DE); Wolfgang Schliebs, Herten (DE); Vishal Kalel, Maharashtra (IN)

(73) Assignee: HELMHOLTZ ZENTRUM MUENCHEN—DEUTSCHES FORSCHUNGZENTRUM FUER GESUNDHEIT UN, Neuherberg (DE)

( * ) Notice: Subject to any disclaimer, the term of this patent is extended or adjusted under 35 U.S.C. 154(b) by 0 days.

(21) Appl. No.: 15/507,824

(22) PCT Filed: Sep. 8, 2015

(86) PCT No.: PCT/EP2015/070513
§ 371 (c)(1),
(2) Date: Mar. 1, 2017

(87) PCT Pub. No.: WO2016/038045
PCT Pub. Date: Mar. 17, 2016

(65) Prior Publication Data
US 2017/0247375 A1 Aug. 31, 2017

(30) Foreign Application Priority Data
Sep. 8, 2014 (EP) ..................... 14183991

(51) Int. Cl.
*C07D 401/14* (2006.01)
*A61K 31/437* (2006.01)
*C07D 471/04* (2006.01)
*C07D 519/00* (2006.01)
*C07D 471/14* (2006.01)

(52) U.S. Cl.
CPC ......... *C07D 471/04* (2013.01); *C07D 471/14* (2013.01); *C07D 519/00* (2013.01)

(58) Field of Classification Search
CPC .................. C07D 401/14; A61K 31/437
USPC ........................... 546/119; 514/303
See application file for complete search history.

(56) References Cited

U.S. PATENT DOCUMENTS

| | | | |
|---|---|---|---|
| 4,439,196 A | 3/1984 | Higuchi | |
| 4,447,224 A | 5/1984 | Decant, Jr. et al. | |
| 4,447,233 A | 5/1984 | Mayfield | |
| 4,475,916 A | 10/1984 | Himmelstein | |
| 4,486,194 A | 12/1984 | Ferrara | |
| 4,487,603 A | 12/1984 | Harris | |
| 4,522,811 A | 6/1985 | Eppstein et al. | |
| 4,596,556 A | 6/1986 | Morrow et al. | |
| 4,790,824 A | 12/1988 | Morrow et al. | |
| 4,941,880 A | 7/1990 | Burns | |
| 5,064,413 A | 11/1991 | McKinnon et al. | |
| 5,312,335 A | 5/1994 | McKinnon et al. | |
| 5,374,548 A | 12/1994 | Caras | |
| 5,383,851 A | 1/1995 | McKinnon et al. | |
| 5,399,163 A | 3/1995 | Peterson et al. | |
| 5,399,331 A | 3/1995 | Loughrey et al. | |
| 5,416,016 A | 5/1995 | Low et al. | |
| 2006/0089378 A1 | 4/2006 | Xia et al. | |
| 2007/0093515 A1* | 4/2007 | Arrington | C07D 401/04 514/266.21 |

OTHER PUBLICATIONS

International Search Report mailed in PCT/EP2015/070513 dated Dec. 22, 2015.
Furuya, T., PNAS, vol. 99, Oct. 29, 2002, pp. 14177-14182.
World Health Organization, Fact Sheet No. 259, Oct. 2010, pp. 1-6.
Food and Agriculture Organization of the United Nations webpage, www.fao.org/about.
Ward, E. S., et al., Binding activities of a repertoire of single immunoglobulin . . . , Nature, vol. 341, Oct. 12, 1989, pp. 544-546.
Bird, R. E. et al, Single-Chain Antigen-Binding Proteins, Science, Oct. 21, 1988, vol. 242, pp. 423-423.
Huston, J. S. et al., Protein engineering of antibody binding sites: Recovery . . . , PNAS, Aug. 1988, vol. 85, pp. 5879-5883.
Berge, S. et al., Pharmaceutical Salts, Journal of Pharmaceutical Sciences, Jan. 1977, vol. 66, pp. 1-19.
Strejan, G. H. et al., Suppression of Chronic-Relapsing Experimental Allergic . . . , 1984/85, Journal of Neuroimmunology, vol. 7, pp. 27-41.
Ranade, V. V., Drug Delivery Systems. 1. Site-Specific Drug Delivery Using Liposomes as Carriers, J. Clin. Pharmacol, 1989, vol. 29, pp. 685-694.
Umezawa, F. et al., Liposome Targeting to Mouse Brain: Mannose as a Recognition Marker, Biochemical and Biophysical Research Communications, Jun. 30, 1988, vol. 153, 1038-1044.
Bloemen et al., Adhesion molecules: a new target for immunoliposome-mediated drug delivery, FEBS Letters, 1995, vol. 357, pp. 140-144.
Owais et al., Chloroquine Encapsulated in Malaria-Infected Erythrocyte-Specific Antibody Bearing Liposomes . . . , Antimicrobial Agents and Chemotherapy, Jan. 1995, vol. 39, pp. 180-184.

(Continued)

*Primary Examiner* — Niloofar Rahmani
(74) *Attorney, Agent, or Firm* — Dilworth IP LLC

(57) ABSTRACT

The present invention relates to pyrazolopyridine derivatives, which are useful as medicaments, pharmaceutical compositions comprising one or more of the pyrazolopyridine derivatives, and the use of one or more of the pyrazolopyridine derivatives in methods for treating and/or preventing a disease caused or mediated by a parasite of the family Trypanosomatidae.

16 Claims, 5 Drawing Sheets

(56) References Cited

OTHER PUBLICATIONS

Neufeld et al., Structural basis for competitive interactions of Pex14 with the import receptors Pex5 and Pex19, The EMBO Journal, 2009, vol. 28, pp. 745-754.

Spinks et al., Design, Synthesis and Biological Evaluation of Trypanosoma brucei Trypanothione Synthetase Inhibitors, ChemMedChem, 2012, vol. 7, pp. 95-106.

* cited by examiner

A)

B)

A)

B)

A)

```
T. brucei    E--KRVSNAVEFLLDSRVRRTPTSSKVHFLKSKGLSAEEICEAFTKVGQPKTL
T. cruzi     R--KRVSSAVQFLHDSRVKITPAANKIQFLKSKGLTTEEVCEAFEKAGQT---
T. congo     KA-QRIANAVEFLLDPRVKNASTANKVRFLKSKNLSAEEICEAFVKC------
L. donovani  DADPTVQSAIRFLQDSRVRRSPVESQIRFLKGKGVPDEQIKYALAKVGRA---
H. sapiens   E--PLIATAVKFLQNSRVRQSPLATRRAFLKKKGLTDEEIDMAFQQSGTA---
Consensus        : .*:.** :.**: :.   .:   *** *.:. *::   *: :
```

B)

SEQUENCE LISTING

```
<160> NUMBER OF SEQ ID NOS: 5

<210> SEQ ID NO 1
<211> LENGTH: 51
<212> TYPE: PRT
<213> ORGANISM: Trypanosoma brucei

<400> SEQUENCE: 1

Glu Lys Arg Val Ser Asn Ala Val Glu Phe Leu Leu Asp Ser Arg Val
1               5                   10                  15

Arg Arg Thr Pro Thr Ser Ser Lys Val His Phe Leu Lys Ser Lys Gly
            20                  25                  30
```

```
Leu Ser Ala Glu Glu Ile Cys Glu Ala Phe Thr Lys Val Gly Gln Pro
        35                  40                  45

Lys Thr Leu
        50

<210> SEQ ID NO 2
<211> LENGTH: 48
<212> TYPE: PRT
<213> ORGANISM: Trypanosoma cruzi

<400> SEQUENCE: 2

Arg Lys Arg Val Ser Ser Ala Val Gln Phe Leu His Asp Ser Arg Val
1               5                   10                  15

Lys Ile Thr Pro Ala Ala Asn Lys Ile Gln Phe Leu Lys Ser Lys Gly
            20                  25                  30

Leu Thr Thr Glu Glu Val Cys Glu Ala Phe Glu Lys Ala Gly Gln Thr
        35                  40                  45

<210> SEQ ID NO 3
<211> LENGTH: 46
<212> TYPE: PRT
<213> ORGANISM: Trypanosoma congolense

<400> SEQUENCE: 3

Lys Ala Gln Arg Ile Ala Asn Ala Val Glu Phe Leu Leu Asp Pro Arg
1               5                   10                  15

Val Lys Asn Ala Ser Thr Ala Asn Lys Val Arg Phe Leu Lys Ser Lys
            20                  25                  30

Asn Leu Ser Ala Glu Glu Ile Cys Glu Ala Phe Val Lys Cys
        35                  40                  45

<210> SEQ ID NO 4
<211> LENGTH: 50
<212> TYPE: PRT
<213> ORGANISM: Leishmania donovani

<400> SEQUENCE: 4

Asp Ala Asp Pro Thr Val Gln Ser Ala Ile Arg Phe Leu Gln Asp Ser
1               5                   10                  15

Arg Val Arg Arg Ser Pro Val Glu Ser Gln Ile Arg Phe Leu Lys Gly
            20                  25                  30

Lys Gly Val Pro Asp Glu Gln Ile Lys Tyr Ala Leu Ala Lys Val Gly
        35                  40                  45

Arg Ala
    50

<210> SEQ ID NO 5
<211> LENGTH: 48
<212> TYPE: PRT
<213> ORGANISM: Homo sapiens

<400> SEQUENCE: 5

Glu Pro Leu Ile Ala Thr Ala Val Lys Phe Leu Gln Asn Ser Arg Val
1               5                   10                  15

Arg Gln Ser Pro Leu Ala Thr Arg Arg Ala Phe Leu Lys Lys Lys Gly
            20                  25                  30

Leu Thr Asp Glu Glu Ile Asp Met Ala Phe Gln Gln Ser Gly Thr Ala
        35                  40                  45
```

PYRAZOLOPYRIDINE DERIVATIVES AND THEIR USE IN THERAPY

TECHNICAL FIELD OF THE INVENTION

The present invention relates to pyrazolopyridine derivatives, which are useful as medicaments, pharmaceutical compositions comprising one or more of the pyrazolopyridine derivatives, and the use of one or more of the pyrazolopyridine derivatives in methods for treating and/or preventing a disease caused or mediated by a parasite of the family Trypanosomatidae.

BACKGROUND OF THE INVENTION

Trypanosomes infect a variety of hosts and cause various diseases, including the fatal human diseases sleeping sickness, caused by *Trypanosoma brucei*, and Chagas disease, caused by *Trypanosoma cruzi*. The parasites use glycosomes—organelles similar to peroxisomes to compartmentalize glucose metabolism. Proteins PEX14 and PEX5 are essential parts of the glycosomal import machinery. They bind each other by direct protein-protein interface. It has been shown that in the absence of PEX14 glucose is toxic to the parasite (Furuya, et al., PNAS 99 (2002), 14177-14182).

Current treatment of trypanosomiasis is complex and can trigger dangerous, adverse reactions. This makes practical treatment difficult in developing countries. E.g. approximately 70 million people are living in endangered areas with regard to African sleeping sickness. Despite treatment efforts, the estimated number of cases in 2009 exceeded 30 000 (Source: WHO fact sheet N° 259). In addition, the parasite causes approximately 3 million deaths in cattle per year, amounting to an estimated loss of 4.75 billion dollars per year. The main currently used trypanolytic drugs in human medicine are pentamidine, suramin, melarsoprol and eflornithine. All these compounds are abundant in undesirable side effects and require strict and difficult application regimen (WHO fact sheet N° 259). Regarding the therapy in the veterinary field, there are three trypanolytic drugs available—isometamidium chloride, diminazene aceturate and homidium (bromide and chloride). One risk of using existing trypanolytic drugs is the development and spread of drug resistance in parasite populations. Resistance to one or more of the trypanolytic drugs used in cattle has been reported in at least 13 countries of sub-Saharan Africa (Source: webpage of the Food And Agriculture Organization of the United Nations).

Thus, there is still a need to identify alternative, improved and/or integrated means or methods that address one or more problems, including those described above such as in the treatment (including prophylactic treatment) of one or more conditions, disorders or diseases (or related conditions or symptoms) caused or mediated by a parasite of the family Trypanosomatidae and/or agents and pharmaceutical compositions useful for such treatment. Such an object underlying the present invention is solved by the subject-matter as disclosed or defined anywhere herein, for example by the subject-matter of the attached claims.

SUMMARY OF THE INVENTION

The present invention is related to compounds able to interfere only with the PEX14-PEX5 protein complex formation in parasites of the family Trypanosomatidae leading to damage of the glycosomal system biogenesis of the parasites. These compounds were developed by utilizing structural differences between human PEX14 protein and PEX14 protein of a parasite of the family Trypanosomatidae.

Failure of glycosome biogenesis causes the release of the enzymes hexokinase (HK) and phosphofructokinase (PFK) into the cytosol. Mislocalization of HK and PFK into the cytosol leads to runaway phosphorylation of hexoses (using cytosolic pool of ATP), ATP depletion, and specific parasite cell death. Thus, the compounds of the present invention lead to a specific lethal attack of parasites of the family Trypanosomatidae.

In a first aspect, the present invention provides a compound selected from the group consisting of a pyrazolopyridine derivative having the general formula (Ia) or (Ib)

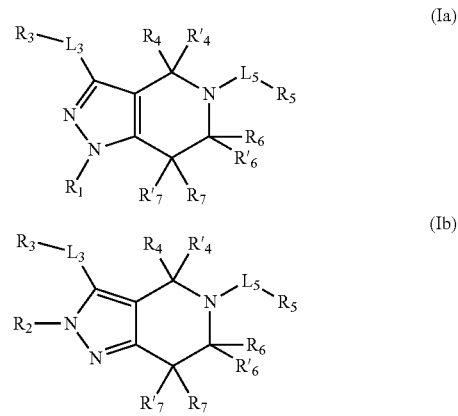

and solvates, salts, complexes, polymorphs, crystalline forms, racemic mixtures, diastereomers, enantiomers, tautomers, isotopically labeled forms, prodrugs, and combinations thereof, wherein $R_1$ to $R_7$, $R'_4$, $R'_6$, $R'_7$, $L_3$ and $L_5$ are as specified here or in any one of the attached claims.

In a second aspect, the present application provides a compound as specified in the first aspect for use in medicine.

In a third aspect, the present invention provides a pharmaceutical composition comprising a compound as specified in the first aspect and a pharmaceutically acceptable excipient.

In a fourth aspect, the present invention provides a compound as specified in the first aspect or a pharmaceutical composition as specified in the third aspect for use in a method of treating or preventing a disease caused or mediated by a parasite of the family Trypanosomatidae.

In a fifth aspect, the present invention provides a method of treating an individual with a need thereof (in particular an animal), comprising administering a pharmaceutically effective amount of (in particular a therapeutically effective dose of) a compound as specified in the first aspect.

Further aspects of the invention are disclosed herein.

The PEX5 protein helix (green) presents two large, hydrophobic side chains of Trp103 and Phe107 to the corresponding pockets of PEX14 (blue). The pockets are separated by two phenylalanines (Phe35, Phe52). Both sides of the interface show an extensive network of aromatic π-stacking and hydrophobic interactions.

Figure 2:
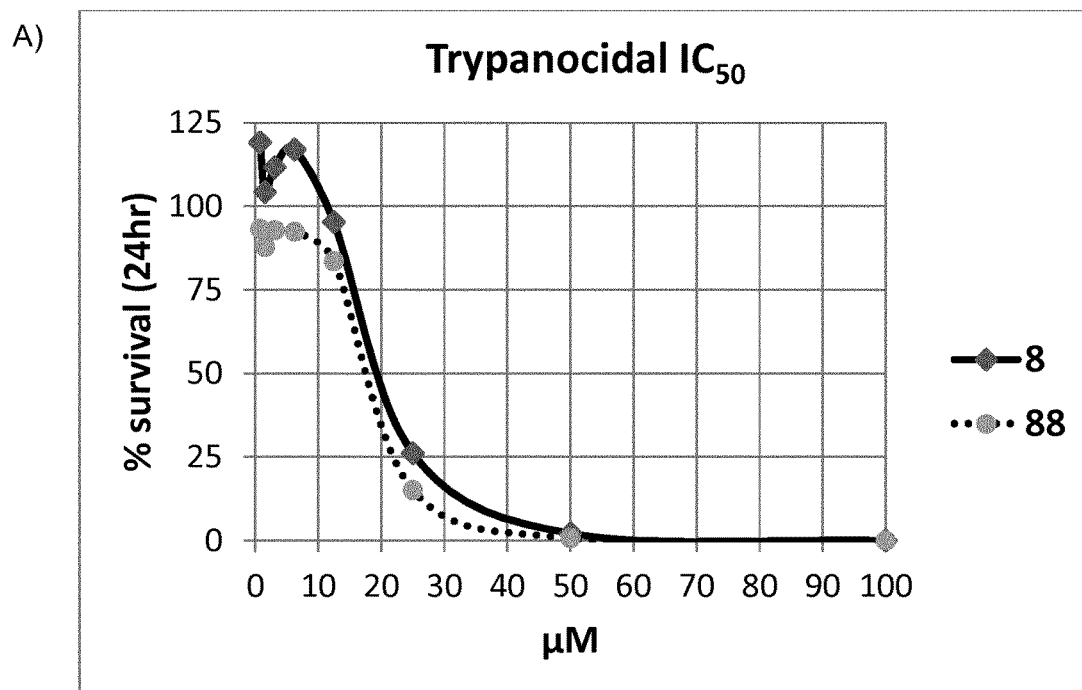
Figure 2:
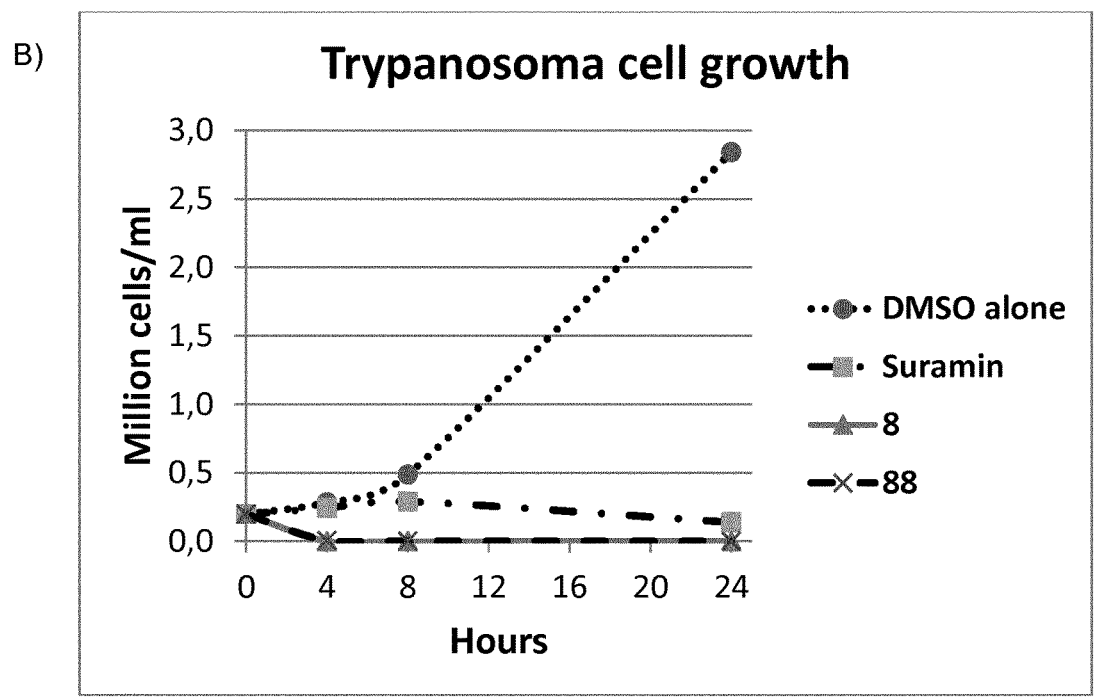

FIG. 2 Activity of compounds of the invention against *trypanosoma* cells.

(A) The *trypanosoma* cell count and growth were evaluated at different doses of compounds of the invention. The values of compounds 8 and 88 are percent relative to single concentration of DMSO (0.2%) which is equivalent to the highest concentration of drugs tested (100 µM). The calculated $IC_{50}$ values for compounds 8 and 88 were 20 µM. (B) Growth curves of bloodstream trypanosomes under various conditions are depicted (DMSO alone (negative control, 0.2%), Suramin (positive control, 1 µM), compounds 8 and 88 (compounds of the invention, 100 µM)). The compounds of the invention prevented *trypanosoma* cell growth completely.

Figure 3:
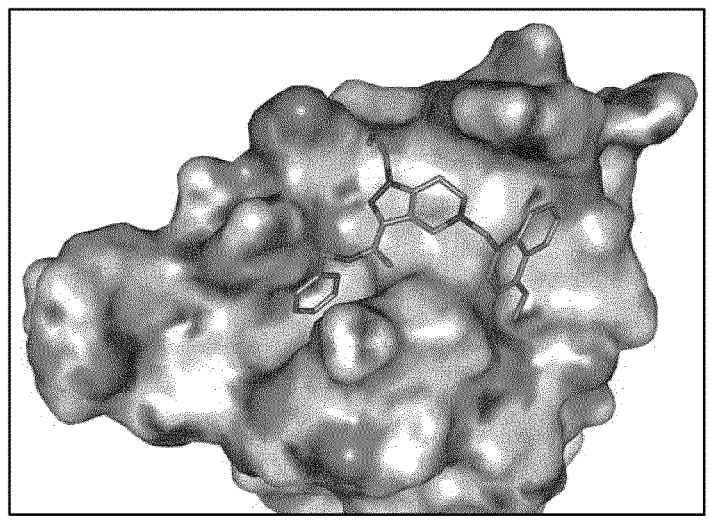
Figure 3:
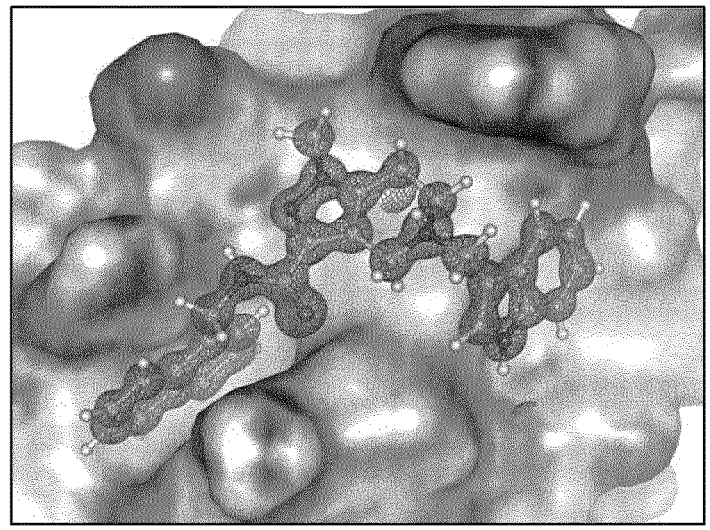

FIG. 3 Crystallographic structures of complexes of *T. brucei brucei* PEX-14 with compounds of the invention.

Compounds 21 (A) and 32 (B) fill the same binding sites as PEX5. The structure of the complex with compound 32 was solved with an exceptionally high resolution of 0.92 Å (electron density of the ligand shown).

Figure 4:
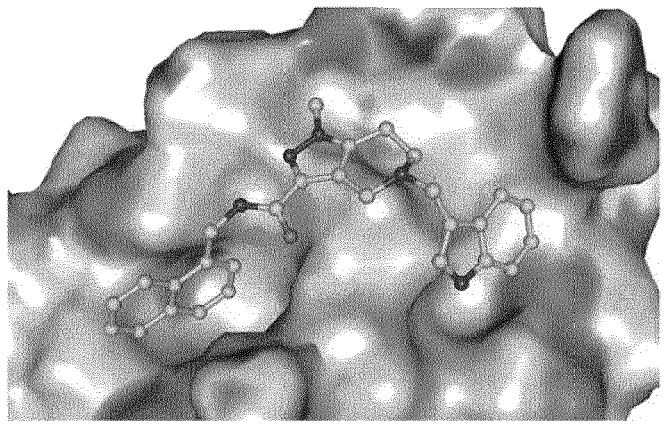

FIG. 4 Binding of compounds of the present invention to the *Leishmania* PEX14 proteins.

(A) Sequence alignment of the amino acid sequences of PEX14 from Trypanosome strains, *Leishmania donovani* and human. Residues responsible for direct formation of the PEX5 binding site (highlighted in grey) are nearly identical. The compounds of the invention were designed to minimize interaction with human PEX14. This has been achieved using structural differences between protozoan and human protein (underlined). (B) The model of *Leishmania* PEX14 was generated by PHYRE server and then compound 32 was modelled to the *Leishmania* PEX14. The structure of the complex with *Leishmania* PEX14 is nearly identical to the structure of the complex with *Trypanosoma* PEX14 (RMSD=0.83 Å) shown in FIG. 3B.

Figure 5:
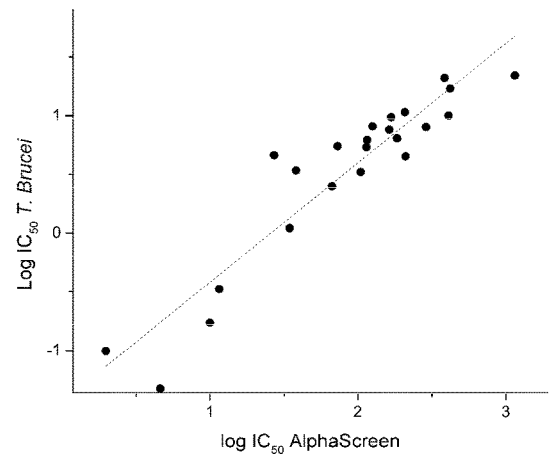

FIG. 5 Correlation between cellular activity and biophysical assay results.

The results of the cellular activity were correlated with the results of the biophysical assay for several of the compounds of the invention. Correlation coefficient equals 0.87. Values are given in log(IM).

Figure 6:
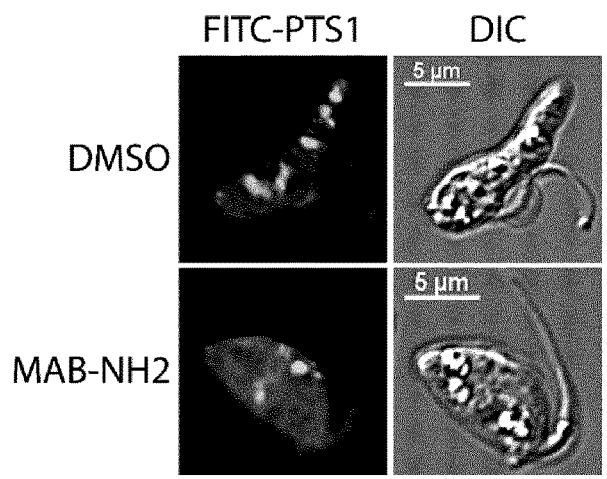

FIG. 6 Compounds of the invention cause glycosomal transport failure.

Upper part: The fluorescent labelled glycosomal cargo (FITC-PTS peptide) is compartmentalized to the glycosomes. Lower part: In the presence of a compound of the invention the compartmentalization is disrupted and fluorescent cargo spread over cell volume. The same phenotype was observed previously by RNAi knock down of Pex14.

DETAILED DESCRIPTION OF THE PRESENT INVENTION

Although the present invention is further described in more detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims and other disclosures herein. Unless defined otherwise, all technical and scientific terms used herein have the same meanings as commonly understood by one of ordinary skill in the art.

In the following, the elements of the present invention will be described in more detail. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in one embodiment $R_3$ of the compound of the invention is $C_{6-10}$ aryl (such as phenyl or naphthyl) and in another embodiment of the compound of the invention $R_5$ is indolyl or naphthyl, then in a preferred embodiment, $R_3$ of the compound of the invention is $C_{6-10}$ aryl (such as phenyl or naphthyl) and $R_5$ is indolyl or naphthyl.

Preferably, the terms used herein are defined as described in "A multilingual glossary of biotechnological terms: (IUPAC Recommendations)", H. G. W. Leuenberger, B. Nagel, and H. Kiilbl, Eds., Helvetica Chimica Acta, CH-4010 Basel, Switzerland, (1995).

The practice of the present invention will employ, unless otherwise indicated, conventional methods of chemistry, biochemistry, and molecular biology (including recombinant DNA techniques) which are explained in the literature in the field (cf., e.g., Molecular Cloning: A Laboratory Manual, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The term "consisting essentially of" means excluding other members, integers or steps of any essential significance. For example, a pharmaceutical composition consisting essentially of the members/components as defined herein (such as a pyrazolopyridine derivative and optionally one additional active compound) would exclude further active compounds (besides the pyrazolopyridine derivative and the optional one additional active compound) but would not exclude contaminants (e.g., those from the isolation and purification method) in trace amounts (e.g., the amount of the contaminant (preferably the amount of all contaminants present in the composition) is less than 5% by weight, such as less than 4% by weight, 3% by weight, 2% by weight, 1% by weight, 0.5% by weight, 0.1% by weight, with respect to the total composition) and/or pharmaceutically acceptable excipients (such as carriers, e.g., phosphate buffered saline, preservatives, and the like). The term "consisting of" means excluding all other members, integers or steps of significance. For example, a pharmaceutical composition consisting of the members/components as defined herein (such as a pyrazolopyridine derivative, one excipient, and optionally one additional active compound) would exclude any other compound (including a second or further excipient) in an amount of more than 2% by weight (such as any other compound in an amount of more 1% by weight, more than 0.5% by weight, more than 0.4% by weight, more than 0.3% by weight, more than 0.2% by weight, more than 0.1% by weight, more than 0.09% by weight, more than 0.08% by weight, more than 0.07% by weight, more than 0.06% by weight, more than 0.05% by weight, more than 0.04% by weight, more than 0.03% by weight, more than 0.02% by weight, more than 0.01% by weight) with respect to the total composition. The term "comprising" encompasses the term "consisting essentially of" which, in turn, encompasses the term "consisting of". Thus, at each occurrence in the present application, the term "comprising" may be replaced with the term "consisting essentially of" or "consisting of". Likewise, at each occurrence in the present application, the term "consisting essentially of" may be replaced with the term "consisting of".

The terms "a" and "an" and "the" and similar reference used in the context of describing the invention (especially in the context of the claims) are to be construed to cover both the singular and the plural, unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The term "alkyl" refers to a monoradical of a saturated straight or branched hydrocarbon. Preferably, the alkyl group comprises from 1 to 10 carbon atoms, i.e., 1, 2, 3, 4, 5, 6, 7, 8, 9, or 10 carbon atoms, more preferably 1 to 8 carbon atoms, such as 1 to 6 or 1 to 4 carbon atoms. Exemplary alkyl groups include methyl, ethyl, propyl, iso-propyl, butyl, iso-butyl, tert-butyl, n-pentyl, iso-pentyl, sec-pentyl, neo-pentyl, 1,2-dimethyl-propyl, iso-amyl, n-hexyl, iso-hexyl, sec-hexyl, n-heptyl, iso-heptyl, n-octyl, 2-ethyl-hexyl, n-nonyl, n-decyl, and the like.

The term "alkylene" refers to a diradical of a saturated straight or branched hydrocarbon. Preferably, the alkylene comprises from 1 to 10 carbon atoms, i.e., 1, 2, 3, 4, 5, 6, 7, 8, 9, or 10 carbon atoms, more preferably 1 to 8 carbon atoms, such as 1 to 6 or 1 to 4 carbon atoms. Exemplary alkylene groups include methylene, ethylene (i.e., 1,1-ethylene, 1,2-ethylene), propylene (i.e., 1,1-propylene, 1,2-propylene (—CH(CH$_3$)CH$_2$—), 2,2-propylene (—C(CH$_3$)$_2$—), and 1,3-propylene), the butylene isomers (e.g., 1,1-butylene, 1,2-butylene (also called 1,2-butanediyl), 2,2-butylene, 1,3-butylene, 2,3-butylene (cis or trans or a mixture thereof), 1,4-butylene, 1,1-iso-butylene, 1,2-iso-butylene, and 1,3-iso-butylene), the pentylene isomers (e.g., 1,1-pentylene, 1,2-pentylene, 1,3-pentylene, 1,4-pentylene, 1,5-pentylene, 1,1-iso-pentylene, 1,1-sec-pentyl, 1,1-neo-pentyl), the hexylenisomers (e.g., 1,1-hexylene, 1,2-hexylene, 1,3-hexylene, 1,4-hexylene, 1,5-hexylene, 1,6-hexylene, and 1,1-isohexylene), and the like.

The term "alkenyl" refers to a monoradical of an unsaturated straight or branched hydrocarbon having at least one carbon-carbon double bond. Generally, the maximal number of carbon-carbon double bonds in the alkenyl group can be equal to the integer which is calculated by dividing the number of carbon atoms in the alkenyl group by 2 and, if the number of carbon atoms in the alkenyl group is uneven, rounding the result of the division down to the next integer. For example, for an alkenyl group having 9 carbon atoms, the maximum number of carbon-carbon double bonds is 4. Preferably, the alkenyl group has 1 to 4, i.e., 1, 2, 3, or 4, carbon-carbon double bonds. Preferably, the alkenyl group comprises from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkenyl group comprises from 2 to 10 carbon atoms and 1, 2, 3, 4, or 5 carbon-carbon double bonds, more preferably it comprises 2 to 8 carbon atoms and 1, 2, 3, or 4 carbon-carbon double bonds, such as 2 to 6 carbon atoms and 1, 2, or 3 carbon-carbon double bonds or 2 to 4 carbon atoms and 1 or 2 carbon-carbon double bonds. The carbon-carbon double bond(s) may be in cis (Z) or trans (E) configuration. Exemplary alkenyl groups include vinyl, 1-propenyl, 2-propenyl (i.e., allyl), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, and the like. If an alkenyl group is attached to a nitrogen atom, the double bond cannot be alpha to the nitrogen atom.

The term "alkynyl" refers to a monoradical of an unsaturated straight or branched hydrocarbon having at least one carbon-carbon triple bond. Generally, the maximal number of carbon-carbon triple bonds in the alkynyl group can be equal to the integer which is calculated by dividing the number of carbon atoms in the alkynyl group by 2 and, if the number of carbon atoms in the alkynyl group is uneven, rounding the result of the division down to the next integer. For example, for an alkynyl group having 9 carbon atoms, the maximum number of carbon-carbon triple bonds is 4. Preferably, the alkynyl group has 1 to 4, i.e., 1, 2, 3, or 4, more preferably 1 or 2 carbon-carbon triple bonds. Preferably, the alkynyl group comprises from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkynyl group comprises from 2 to 10 carbon atoms and 1, 2, 3, 4, or 5 (preferably 1, 2, or 3) carbon-carbon triple bonds, more preferably it comprises 2 to 8 carbon atoms and 1, 2, 3, or 4 (preferably 1 or 2) carbon-carbon triple bonds, such as 2 to 6 carbon atoms and 1, 2 or 3 carbon-carbon triple bonds or 2 to 4 carbon atoms and 1 or 2 carbon-carbon triple bonds. Exemplary alkynyl groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonylyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, 9-decynyl, and the like. If an alkynyl group is attached to a nitrogen atom, the triple bond cannot be alpha to the nitrogen atom.

The term "aryl" or "aromatic ring" refers to a monoradical of an aromatic cyclic hydrocarbon. Preferably, the aryl group contains 3 to 14 (e.g., 5 to 10, such as 5, 6, 10, or 14) carbon atoms which can be arranged in one ring (e.g., phenyl) or two or more condensed rings (e.g., naphthyl, phenanthryl). For example, 3- to 14-membered aryl encompasses monocyclic aryl (e.g., 5- or 6-membered), bicyclic aryl (e.g., 9- or 10-membered), and tricyclic aryl (e.g., 13- or 14-membered). Exemplary aryl groups include cyclopropenylium, cyclopentadienyl, phenyl, indenyl, naphthyl, azulenyl, fluorenyl, anthryl, and phenanthryl. Preferably, "aryl" refers to a monocyclic ring containing 6 carbon atoms, an aromatic bicyclic ring system containing 10 carbon atoms, or an aromatic tricyclic ring system containing 14 carbon atoms. Preferred examples are phenyl, naphthyl, and phenanthryl.

The term "heteroaryl" or "heteroaromatic ring" means an aryl group as defined above in which one or more carbon atoms in the aryl group are replaced by heteroatoms of O, S, or N. Preferably, heteroaryl refers to a five- or six-membered aromatic monocyclic ring wherein 1, 2, or 3 carbon atoms are replaced by the same or different heteroatoms of O, N, or S. Alternatively, it means an aromatic bicyclic or tricyclic ring system, wherein 1, 2, 3, 4, or 5 carbon atoms are replaced with the same or different heteroatoms of O, N, or S. Preferably, in each ring of the heteroaryl group the maximum number of O atoms is 1, the maximum number of S atoms is 1, and the maximum total number of O and S atoms is 2. For example, 3- to 14-membered heteroaryl encompasses monocyclic heteroaryl (e.g., 5- or 6-membered), bicyclic heteroaryl (e.g., 9- or 10-membered), and tricyclic heteroaryl (e.g., 13- or 14-membered). Exemplary heteroaryl groups include furyl, thienyl, oxazolyl, isoxazolyl, oxadiazolyl (1,2,5- and 1,2,3-), pyrrolyl, imidazolyl, pyrazolyl, triazolyl (1,2,3- and 1,2,4-), tetrazolyl, thiazolyl, isothiazolyl, thiadiazolyl (1,2,3- and 1,2,5-), pyridyl, pyrimidinyl, pyrazinyl, triazinyl (1,2,3-, 1,2,4-, and 1,3,5-), benzofuranyl (1- and 2-), indolyl, isoindolyl, benzothienyl (1- and 2-), 1H-indazolyl, benzimidazolyl, benzoxazolyl, indoxazinyl, benzisoxazolyl, benzothiazolyl, benzisothiazolyl, benzotriazolyl, quinolinyl, isoquinolinyl, benzodiazinyl, quinoxalinyl, quinazolinyl, benzotriazinyl (1,2,3- and 1,2,4- benzotriazinyl), pyridazinyl, phenoxazinyl, thiazolopyridinyl, pyrrolothiazolyl, phenothiazinyl, isobenzofuranyl, chromenyl, xanthenyl, phenoxathiinyl, pyrrolizinyl, indolizinyl, indazolyl, purinyl, quinolizinyl, phthalazinyl, naphthyridinyl (1,5-, 1,6-, 1,7-, 1,8-, and 2,6-), cinnolinyl, pteridinyl, carbazolyl, phenanthridinyl, acridinyl, perimidinyl, phenanthrolinyl (1,7-, 1,8-, 1,10-, 3,8-, and 4,7-), phenazinyl, oxazolopyridinyl, isoxazolopyridinyl, pyrrolooxazolyl, and pyrrolopyrrolyl. Exemplary 5- or 6-membered heteroaryl groups include furyl, thienyl, oxazolyl, isoxazolyl, oxadiazolyl (1,2,5- and 1,2,3-), pyrrolyl, imidazolyl, pyrazolyl, triazolyl (1,2,3- and 1,2,4-), thiazolyl, isothiazolyl, thiadiazolyl (1,2,3- and 1,2,5-), pyridyl, pyrimidinyl, pyrazinyl, triazinyl (1,2,3-, 1,2,4-, and 1,3,5-), and pyridazinyl.

The term "cycloalkyl" or "cycloaliphatic" represents cyclic non-aromatic versions of "alkyl" and "alkenyl" with preferably 3 to 14 carbon atoms, such as 3 to 10 carbon atoms, i.e., 3, 4, 5, 6, 7, 8, 9, or 10 carbon atoms, more preferably 3 to 7 carbon atoms. Exemplary cycloalkyl groups include cyclopropyl, cyclopropenyl, cyclobutyl, cyclobutenyl, cyclopentyl, cyclopentenyl, cyclohexyl, cyclohexenyl, cycloheptyl, cycloheptenyl, cyclooctyl, cyclooctenyl, cyclononyl, cyclononenyl, cylcodecyl, cylcodecenyl, and adamantyl. The term "cycloalkyl" is also meant to include bicyclic and tricyclic versions thereof. If bicyclic rings are formed it is preferred that the respective rings are connected to each other at two adjacent carbon atoms, however, alternatively the two rings are connected via the same carbon atom, i.e., they form a spino ring system or they form "bridged" ring systems. For example, 3- to 14-membered cycloalkyl encompasses monocyclic cycloalkyl (e.g., 3-, 4-, 5-, 6-, or to 7-membered), bicyclic cycloalkyl (e.g., 8-, 9-, or 10-membered), and tricyclic cycloalkyl (e.g., 12-, 13-, or 14-membered). Preferred examples of cycloalkyl include $C_3$-$C_8$-cycloalkyl, in particular cyclopropyl, cyclobutyl, cyclopentyl, cyclohexyl, cycloheptyl, cyclooctyl, spiro[3,3]heptyl, spiro[3,4]octyl, spiro[4,3]octyl, bicyclo[4.1.0]heptyl, bicyclo[3.2.0]heptyl, bicyclo[2.2.1]heptyl, bicyclo[2.2.2]octyl, bicyclo[5.1.0]octyl, and bicyclo[4.2.0] octyl.

The term "cyclopropylene" means a cyclopropyl group as defined above in which one hydrogen atom has been removed resulting in a diradical. The cyclopropylene may link two atoms or moieties via the same carbon atom (1,1-cyclopropylene, i.e., a geminal diradical) or via two carbon atoms (1,2-cyclopropylene).

The term "heterocyclyl" or "heterocyclic ring" means a cycloalkyl group as defined above in which from 1, 2, 3, or 4 carbon atoms in the cycloalkyl group are replaced by heteroatoms of O, S, or N. Preferably, in each ring of the heterocyclyl group the maximum number of O atoms is 1, the maximum number of S atoms is 1, and the maximum total number of O and S atoms is 2. For example, 3- to 14-membered heterocyclyl encompasses monocyclic heterocyclyl (e.g., 3-, 4-, 5-, 6-, or 7-membered), bicyclic heterocyclyl (e.g., 8-, 9-, or 10-membered), and tricyclic heterocyclyl (e.g., 12-, 13-, or 14-membered). The term "heterocyclyl" is also meant to encompass partially or completely hydrogenated forms (such as dihydro, tetrahydro, hexahydro, octahydro, decahydro, dodecahydro, etc., or perhydro forms) of the above-mentioned heteroaryl groups. Exemplary heterocyclyl groups include morpholino, isochromanyl, chromanyl, pyrrolidinyl, imidazolidinyl, pyrazolidinyl, piperidinyl, piperazinyl, indolinyl, isoindolinyl, triazininanyl (1,2,3-, 1,2,4-, and 1,3,5-), di- and tetrahydrofuranyl, di- and tetrahydrothienyl, di- and tetrahydrooxazolyl, di- and tetrahydroisoxazolyl, di- and tetrahydrooxadiazolyl (1,2,5- and 1,2,3-), dihydropyrrolyl, dihydroimidazolyl, dihydropyrazolyl, di- and tetrahydrotriazolyl (1,2,3- and 1,2,4-), di- and tetrahydrothiazolyl, di- and tetrahydrothiazolyl, di- and tetrahydrothiadiazolyl (1,2, 3- and 1,2,5-), di- and tetrahydropyridyl, di-, tetra- and hexahydropyrimidinyl, di- and tetrahydropyrazinyl, di- and tetrahydrotriazinyl (1,2,3-, 1,2,4-, and 1,3,5-), di-, tetra-, hexa- and octahydrobenzofuranyl (1- and 2-), di-, tetra-, hexa- and octahydroindolyl, di-, tetra-, hexa- and octahydroisoindolyl, di-, tetra-, hexa- and octahydrobenzothienyl (1- and 2), di-, tetra-, hexa- and octahydro-1H-indazolyl, di-, tetra-, hexa- and octahydrobenzimidazolyl, di-, tetra-, hexa- and octahydrobenzoxazolyl, di-, tetra-, hexa- and octahydroindoxazinyl, di-, tetra-, hexa- and octahydrobenzisoxazolyl, di-, tetra-, hexa- and octahydrobenzothiazolyl, di-, tetra-, hexa- and octahydrobenzisothiazolyl, di-, tetra-, hexa- and octahydrobenzotriazolyl, di-, tetra-, hexa-, octa- and decahydroquinolinyl, di-, tetra-, hexa-, octa- and decahydroisoquinolinyl, di-, tetra-, hexa-, octa- and decahydrobenzodiazinyl, di-, tetra-, hexa-, octa- and decahydroquinoxalinyl, di-, tetra-, hexa-, octa- and decahydroquinazolinyl, di-, tetra-, hexa-, octa- and decahydrobenzotriazinyl (1,2,3- and 1,2,4-), di-, tetra-, and hexahydropyridazinyl, di-, tetra-, hexa-, octa-, deca- and dodecahydrophenoxazinyl, di-, tetra-, hexa-, and octahydrothiazolopyridinyl, di-, tetra-, and hexahydropyrrolothiazolyl, di-, tetra-, hexa-, octa- and decahydrophenothiazinyl, di-, tetra-, hexa-, and octahydroisobenzofuranyl, di-, tetra-, hexa-, and octahydrochromenyl, di-, tetra-, hexa-, octa-, deca-, and dodecahydroxanthenyl, di-, tetra-, hexa-, octa-, deca-, and dodecahydrophenoxathiinyl, di-, tetra-, and hexahydropyrrolizinyl, di-, tetra-, hexa-, and octahydroindolizinyl, di-, tetra-, hexa-, and octahydroindazolyl, di-, tetra-, hexa-, and octahydropurinyl, di-, tetra-, hexa-, and octahydroquinolizinyl, di-, tetra-, hexa-, octa- and decahydrophthalazinyl, di-, tetra-, hexa-, octa- and decahydronaphthyridinyl (1,5-, 1,6-, 1,7-, 1,8-, and 2,6-), di-, tetra-, hexa-, octa- and decahydrocinnolinyl, di-, tetra-, hexa-, octa-, and decahydropteridinyl, di-, tetra-, hexa-, octa-, deca- and dodecahydrocarbazolyl, di-, tetra-, hexa-, octa-, deca-, dodeca-, and tetradecahydrophenanthridinyl, di-, tetra-, hexa-, octa-, deca-, dodeca-, and tetradecahydroacridinyl, di-, tetra-, hexa-, octa-, deca- and dodecahydroperimidinyl, di-, tetra-, hexa-, octa-, deca-, dodeca-, and tetradecahydrophenanthrolinyl (1,7-, 1,8-, 1,10-, 3,8-, and 4,7-), di-, tetra-, hexa-, octa-, deca-, dodeca-, and tetradecahydrophenazinyl, di-, tetra-, hexa- and octahydrooxazolopyridinyl, di-, tetra-, hexa- and octahydroisoxazolopyridinyl, di-, tetra-, and hexahydropyrrolooxazolyl, di-, tetra-, and hexahydropyrrolopyrrolyl, di-, tetra-, hexa- and octahydrocyclopentapyrrolyl, di-, tetra-, hexa- and octahydrocyclopentpyrazolyl, di-, tetra-, hexa- and octahydrocyclopentaimidazolyl, di-, tetra-, hexa- and octahydrocyclopentathiazolyl, di-, tetra-, hexa- and octahydrocyclopentaoxazolyl, di-, tetra-, hexa- and octahydropyrrolopyrrolyl, di-, tetra-, hexa- and octahydropyrrolopyrazolyl, di-, tetra-, hexa- and octahydropyrroloimidazolyl, di-, tetra-, hexa- and octahydropyrrolothiazolyl, di-, tetra-, hexa- and octahydropyrrolooxazolyl, di-, tetra-, hexa- and octahydropyrazolopyrazolyl, di-, tetra-, hexa- and octahydropyrazoloimidazolyl, di-, tetra-, hexa- and octahydropyrazolothiazolyl, di-, tetra-, hexa- and octahydropyrazolooxazolyl, di-, tetra-, hexa- and octahydroimidazoimidazolyl, di-, tetra-, hexa- and octahydroimidazothiazolyl, di-, tetra-, hexa- and octahydroimidazooxazolyl, di-, tetra-, hexa- and octahydrothiazolothiazolyl, di-, tetra-, hexa- and octahydrothiazolooxazolyl, and di-, tetra-, hexa- and octahydrooxazolooxazolyl.

The term "polycyclic" as used herein means that the structure has two or more (such as 2, 3, 4, 5, 6, 7, 8, 9, or 10), preferably, 2, 3, 4, or 5, more preferably, 2, 3, or 4, rings. Therefore, according to the invention, the term "polycyclic" does not encompass monocyclic structures, wherein the structures only contain one ring. Examples of polycyclic groups are fused structures (such as naphthyl or anthryl), spiro compounds, rings that are linked via single or double bonds (such as biphenyl), and bridged structures (such as bornyl). Exemplary polycyclic structures are those aryl, heteroaryl, cycloalkyl, and heterocyclyl groups specified above which have at least two rings.

The term "halogen" or "halo" means fluoro, chloro, bromo, or iodo.

The term "azido" means $N_3$.

The term "any two $R^{30}$ which are bound to the same carbon atom of a cycloalkyl or heterocyclyl group may join together to form $=X^1$" as used herein means that two monoradicals (i.e., $R^{30}$) when substituting in total 2 hydrogen atoms bound to only one ring atom (preferably a ring carbon atom) of a cycloalkyl or heterocyclyl group can form the diradical=$X^1$. For example, according to the invention, $R_3$ being

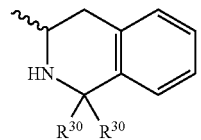

encompasses not only (1) the possibility that both $R^{30}$ groups are monoradicals independently selected from the particular moieties specified herein (e.g., methyl, —Cl, —OH, or —C(O)CH$_3$)) but also (2) the possibility that the two $R^{30}$ groups join together to form the diradical=$X^1$ resulting in a ring A having the following formula:

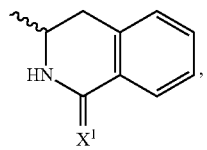

wherein $X^1$ is O, S, or $N(R^{81})$. Similar terms such as "any two $R^{30}$ which are bound to the same carbon atom of a cycloalkyl or heterocyclyl group may join together to form =$X^2$" as used herein are to be interpreted in an analogous manner.

The term "optionally substituted" indicates that one or more (such as 1 to the maximum number of hydrogen atoms bound to a group, e.g., 1, 2, 3, 4, 5, 6, 7, 8, 9, or up to 10, such as between 1 to 5, 1 to 4, or 1 to 3, or 1 or 2) hydrogen atom(s) may be replaced with a group (i.e., a $1^{st}$ level substituent) different from hydrogen such as alkyl (preferably, $C_{1-6}$ alkyl), alkenyl (preferably, $C_{2-6}$ alkenyl), alkynyl (preferably, $C_{2-6}$ alkynyl), aryl (preferably, 3- to 14-membered aryl), heteroaryl (preferably, 3- to 14-membered heteroaryl), cycloalkyl (preferably, 3- to 14-membered cycloalkyl), heterocyclyl (preferably, 3- to 14-membered heterocyclyl), halogen, —CN, azido, —NO$_2$, —OR$^{71}$, —N(R$^{72}$)(R$^{73}$), —ON(R$^{72}$)(R$^{73}$), —N$^+$(—O$^-$)(R$^{72}$)(R$^{73}$), —S(O)$_{0-2}$R$^{71}$, —S(O)$_{0-2}$OR$^{71}$, —OS(O)$_{0-2}$R$^{71}$, —OS(O)$_{0-2}$OR$^{71}$, —S(O)$_{0-2}$N(R$^{72}$)(R$^{73}$), —OS(O)$_{0-2}$N(R$^{72}$)(R$^{73}$), —N(R$^{71}$)S(O)$_{0-2}$R$^{71}$, —NR$^{71}$S(O)$_{0-2}$OR$^{71}$, —NR$^{71}$S(O)$_{0-2}$N(R$^{72}$)(R$^{73}$), —C(=X$^1$)R$^{71}$, —C(=X$^1$)X$^1$R$^{71}$, —X$^1$C(=X$^1$)R$^{71}$, and —X$^1$C(=X$^1$)X$^1$R$^{71}$, and/or any two $1^{st}$ level substituents which are bound to the same carbon atom of a cycloalkyl or heterocyclyl group may join together to form =X$^1$, wherein each of the alkyl, alkenyl, alkynyl, aryl, heteroaryl, cycloalkyl, and heterocyclyl groups of the $1^{st}$ level substituent may themselves be substituted by one, two or three substituents (i.e., a $2^{nd}$ level substituent) selected from the group consisting of $C_{1-6}$ alkyl, $C_{2-6}$ alkynyl, 3- to 14-membered aryl, 3- to 14-membered heteroaryl, 3- to 14-membered cycloalkyl, 3- to 14-membered heterocyclyl, halogen, —CF$_3$, —CN, azido, —NO$_2$, —OR$^{81}$, —N(R$^{82}$)(R$^{83}$), —ON(R$^{82}$)(R$^{83}$), —N$^+$(—O$^-$)(R$^{82}$)(R$^{83}$), —S(O)$_{0-2}$R$^{81}$, —S(O)$_{0-2}$OR$^{81}$, —OS(O)$_{0-2}$R$^{81}$, —OS(O)$_{0-2}$OR$^{81}$, —S(O)$_{0-2}$N(R$^{82}$)(R$^{83}$), —OS(O)$_{0-2}$N(R$^{82}$)(R$^{83}$), —N(R$^{81}$)S(O)$_{0-2}$R$^{81}$, —NR$^{81}$S(O)$_{0-2}$OR$^{81}$, —NR$^{81}$S(O)$_{0-2}$N(R$^{82}$)(R$^{83}$), —C(=X$^2$)R$^{81}$, —C(=X$^2$)X$^2$R$^{81}$, —X$^2$C(=X$^2$)R$^{81}$, and —X$^2$C(=X$^2$)X$^2$R$^{81}$, and/or any two $2^{nd}$ level substituents which are bound to the same carbon atom of a cycloalkyl or heterocyclyl group may join together to form =X$^2$, wherein each of the $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, 3- to 14-membered heterocyclyl groups of the $2^{nd}$ level substituent is optionally substituted with one, two or three substituents (i.e., a $3^{rd}$ level substituent) independently selected from the group consisting of $C_{1-3}$ alkyl, halogen, —$CF_3$, —CN, azido, —$NO_2$, —OH, —$O(C_{1-3}$ alkyl), —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —C(=O)OH, —C(=O)O($C_{1-3}$ alkyl), —C(=O)$NH_{2-z}$ ($C_{1-3}$ alkyl)$_z$, —NHC(=O)($C_{1-3}$ alkyl), —NHC(=NH) $NH_{z-2}$ ($C_{1-3}$ alkyl)$_z$, and —N($C_{1-3}$ alkyl)C(=NH)$NH_{2-z}$($C_{1-3}$ alkyl)$_z$, wherein z is 0, 1, or 2 and $C_{1-3}$ alkyl is methyl, ethyl, propyl or isopropyl, and/or any two $3^{rd}$ level substituents which are bound to the same carbon atom of a cycloalkyl or heterocyclyl group may join together to form =O, =S, =NH, or =N($C_{1-3}$ alkyl);

wherein $R^{71}$, $R^{72}$, and $R^{73}$ are independently selected from the group consisting of —H, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl, wherein each of the alkyl, alkenyl, alkynyl, cycloalkyl, aryl, heteroaryl, and heterocyclyl groups is optionally substituted with one, two or three substituents selected from the group consisting of $C_{1-3}$ alkyl, 3- to 7-membered cycloalkyl, 5- or 6-membered aryl, 5- or 6-membered heteroaryl, 3- to 7-membered heterocyclyl, halogen, —$CF_3$, —CN, azido, —$NO_2$, —OH, —$O(C_{1-3}$ alkyl), —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —C(=O)OH, —C(=O) O($C_{1-3}$ alkyl), —C(=O)$NH_{2-z}$($C_{1-3}$ alkyl)$_z$, —NHC(=O) ($C_{1-3}$ alkyl), —NHC(=NH)$NH_{z-2}$($C_{1-3}$ alkyl)$_z$, and —N($C_{1-3}$ alkyl)C(=NH)$NH_{2-z}$($C_{1-3}$ alkyl)$_z$, wherein z is 0, 1, or 2 and $C_{1-3}$ alkyl is methyl, ethyl, propyl or isopropyl; $R^{81}$, $R^{82}$, and $R^{83}$ are independently selected from the group consisting of —H, $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl, wherein each of the alkyl, alkenyl, alkynyl, cycloalkyl, aryl, heteroaryl, and heterocyclyl groups is optionally substituted with one, two or three substituents selected from the group consisting of $C_{1-3}$ alkyl, halogen, —$CF_3$, —CN, azido, —$NO_2$, —OH, —$O(C_{1-3}$ alkyl), —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —C(=O)OH, —C(=O) O($C_{1-3}$ alkyl), —C(=O)$NH_{2-z}$($C_{1-3}$ alkyl)$_z$, —NHC(=O) ($C_{1-3}$ alkyl), —NHC(=NH)$NH_{z-2}$($C_{1-3}$ alkyl)$_z$, and —N($C_{1-3}$ alkyl)C(=NH)$NH_{2-z}$($C_{1-3}$ alkyl)$_z$, wherein z is 0, 1, or 2 and $C_{1-3}$ alkyl is methyl, ethyl, propyl or isopropyl; $X^1$ and $X^2$ are independently selected from O, S, and $NR^{81}$.

Typical $1^{st}$ level substituents are preferably selected from the group consisting of $C_{1-6}$ alkyl, $C_{2-6}$ alkenyl, $C_{2-6}$ alkynyl, 3- to 14-membered (such as 5- or 6-membered) aryl, 3- to 14-membered (such as 5- or 6-membered) heteroaryl, 3- to 14-membered (such as 3- to 7-membered) cycloalkyl, 3- to 14-membered (such as 3- to 7-membered) heterocyclyl, halogen, —CN, azido, —$NO_2$, —$OR^{71}$, —$N(R^{72})(R^{73})$, —$S(O)_{0-2}R^{71}$, —$S(O)_{0-2}OR^{71}$, —$OS(O)_{0-2}R^{71}$, —$OS(O)_{0-2}OR^{71}$, —$S(O)_{0-2}N(R^{72})(R^{73})$, —$OS(O)_{0-2}N(R^{72})(R^{73})$, —$N(R^{71})S(O)_{0-2}R^{71}$, —$NR^{71}S(O)_{0-2}OR^{71}$, —C(=$X^1$)$R^{71}$, —C(=$X^1$)$X^1R^{71}$, —$X^1$C(=$X^1$)$R^{71}$, and —$X^1$C(=$X^1$) $X^1R^{71}$ (such as $C_{1-4}$ alkyl, $C_{2-4}$ alkenyl, $C_{2-4}$ alkynyl, 5- or 6-membered aryl, 5- or 6-membered heteroaryl, 3- to 7-membered cycloalkyl, 3- to 7-membered heterocyclyl, halogen, —$CF_3$, —CN, azido, —$NO_2$, —OH, —$O(C_{1-3}$ alkyl), —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —C(=O)OH, —C(=O)O($C_{1-3}$ alkyl), —C(=O)$NH_{2-z}$ ($C_{1-3}$ alkyl)$_z$, —NHC(=O)($C_{1-3}$ alkyl), —NHC(=NH) $NH_{z-2}$ ($C_{1-3}$ alkyl)$_z$, and —N($C_{1-3}$ alkyl)C(=NH)$NH_{2-z}$($C_{1-3}$ alkyl)$_z$, wherein z is 0, 1, or 2 and $C_{1-3}$ alkyl is methyl, ethyl, propyl or isopropyl); $X^1$ is independently selected from O, S, $NR^{81}$ (such as NH or N(CH$_3$)); and $R^{71}$, $R^{72}$, and $R^{73}$ are as defined above or, preferably, are independently selected from the group consisting of —H, $C_{1-4}$ alkyl, $C_{2-4}$ alkenyl, $C_{2-4}$ alkynyl, 5- or 6-membered cycloalkyl, 5- or 6-membered aryl, 5- or 6-membered heteroaryl, and 5- or 6-membered heterocyclyl, wherein each of the alkyl, alkenyl, alkynyl, cycloalkyl, aryl, heteroaryl, and heterocyclyl groups is optionally substituted with one, two or three substituents selected from the group consisting of $C_{1-3}$ alkyl, 5- or 6-membered cycloalkyl, 5- or 6-membered aryl, 5- or 6-membered heteroaryl, 5- or 6-membered heterocyclyl, halogen, —$CF_3$, —CN, azido, —$NO_2$, —OH, —$O(C_{1-3}$ alkyl), —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —C(=O)OH, —C(=O)O($C_{1-3}$ alkyl), —C(=O)$NH_{2-z}$ ($C_{1-3}$ alkyl)$_z$, —NHC(=O)($C_{1-3}$ alkyl), —NHC(=NH) $NH_{z-2}$ ($C_{1-3}$ alkyl)$_z$, and —N($C_{1-3}$ alkyl)C(=NH)$NH_{2-z}$($C_{1-3}$ alkyl)$_z$, wherein z is 0, 1, or 2 and $C_{1-3}$ alkyl is methyl, ethyl, propyl or isopropyl.

Typical $2^{nd}$ level substituents are preferably selected from the group consisting of $C_{1-4}$ alkyl, $C_{2-4}$ alkenyl, $C_{2-4}$ alkynyl, 5- or 6-membered aryl, 5- or 6-membered heteroaryl, 5- or 6-membered cycloalkyl, 5- or 6-membered heterocyclyl, halogen, —$CF_3$, —CN, azido, —$NO_2$, —OH, —$O(C_{1-3}$ alkyl), —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —C(=O)OH, —C(=O)O($C_{1-3}$ alkyl), —C(=O)$NH_{2-z}$ ($C_{1-3}$ alkyl)$_z$, —NHC(=O)($C_{1-3}$ alkyl), —NHC(=NH) $NH_{z-2}$ ($C_{1-3}$ alkyl)$_z$, and —N($C_{1-3}$ alkyl)C(=NH)$NH_{2-z}$($C_{1-3}$ alkyl)$_z$, wherein z is 0, 1, or 2 and $C_{1-3}$ alkyl is methyl, ethyl, propyl or isopropyl.

Typical $3^{rd}$ level substituents are preferably selected from the group consisting of phenyl, furanyl, pyrrolyl, thienyl, imidazolyl, oxazolyl, isoxazolyl, thiazolyl, pyridyl, pyrazinyl, pyrimidinyl, pyridazinyl, partially and completely hydrogenated forms of the forgoing groups, morpholino, $C_{1-3}$ alkyl, halogen, —$CF_3$, —OH, —$OCH_3$, —$SCH_3$, —$NH_{2-z}(CH_3)_z$, —C(=O)OH, and —C(=O)$OCH_3$, wherein z is 0, 1, or 2.

The term "aromatic" as used in the context of hydrocarbons means that the whole molecule has to be aromatic. For example, if a monocyclic aryl is hydrogenated (either partially or completely) the resulting hydrogenated cyclic structure is classified as cycloalkyl for the purposes of the present invention. Likewise, if a bi- or polycyclic aryl (such as naphthyl) is hydrogenated the resulting hydrogenated bi- or polycyclic structure (such as 1,2-dihydronaphthyl) is classified as cycloalkyl for the purposes of the present invention (even if one ring, such as in 1,2-dihydronaphthyl, is still aromatic). A similar distinction is made within the present application between heteroaryl and heterocyclyl. For example, indolinyl, i.e., a dihydro variant of indolyl, is classified as heterocyclyl for the purposes of the present invention, since only one ring of the bicyclic structure is aromatic and one of the ring atoms is a heteroatom.

The phrase "partially hydrogenated form" of an unsaturated compound or group as used herein means that part of the unsaturation has been removed by formally adding hydrogen to the initially unsaturated compound or group without removing all unsaturated moieties. The phrase "completely hydrogenated form" of an unsaturated compound or group is used herein interchangeably with the term "perhydro" and means that all unsaturation has been removed by formally adding hydrogen to the initially unsaturated compound or group. For example, partially hydrogenated forms of a 5-membered heteroaryl group (containing 2 double bonds in the ring, such as furan) include dihydro forms of said 5-membered heteroaryl group (such as 2,3-dihydrofuran or 2,5-dihydrofuran), whereas the tetrahydro form of said 5-membered heteroaryl group (e.g., tetrahydrofuran, i.e., THF) is a completely hydrogenated (or perhydro) form of said 5-membered heteroaryl group. Likewise, for a 6-membered heteroaryl group having 3 double bonds in the ring (such as pyridyl), partially hydrogenated forms include di- and tetrahydro forms (such as di- and tetrahydropyridyl), whereas the hexahydro form (such as piperidinyl in case of the heteroaryl pyridyl) is the completely hydrogenated (or perhydro) derivative of said 6-membered heteroaryl group. Consequently, a hexahydro form of an aryl or heteroaryl can only be considered a partially hydrogenated form according to the present invention if the aryl or heteroaryl contains at least 4 unsaturated moieties consisting of double and triple bonds between ring atoms.

The term "optional" or "optionally" as used herein means that the subsequently described event, circumstance or condition may or may not occur, and that the description includes instances where said event, circumstance, or condition occurs and instances in which it does not occur.

"Isomers" are compounds having the same molecular formula but differ in structure ("structural isomers") or in the geometrical positioning of the functional groups and/or atoms ("stereoisomers"). "Enantiomers" are a pair of stereoisomers which are non-superimposable mirror-images of each other. A "racemic mixture" or "racemate" contains a pair of enantiomers in equal amounts and is denoted by the prefix (±). "Diastereomers" are stereoisomers which are non-superimposable mirror-images of each other. "Tautomers" are structural isomers of the same chemical substance that spontaneously interconvert with each other, even when pure.

The term "molecular probe" means an atom or molecule which can be attached to a compound of interest (e.g., a pyrazolopyridine derivative of any one of formulas (Ia), (Ib), (IIa), (IIb), (IIIa), (IIIb), (IVa), (IVb), (Va), (Vb), (VIa), (VIb), (VIIa), (VIIb), (VIIIa), and (VIIIb)) in order to label said compound (i.e., resulting in a labeled compound of interest). For example, the molecular probe can be radioactive or luminescent (e.g., fluorescent), or can comprise one member of a complementary binding pair. Thus, depending on the particular molecular probe used, the labeled compound can be detected by (i) measuring the radioactivity emitted by the labeled compound, (ii) measuring the radiation (e.g., fluorescence) emitted by the labeled compound (optionally after having applied radiation of a wavelength suitable for excitation of the molecular probe), or (iii) using the second member of the complementary binding pair. Examples of radioactive molecular probes include a radioisotope (e.g., $^{3}H$, $^{14}C$, $^{32}P$, F $^{57}Co$, $^{60}Co$, $^{90}Sr$, $^{113m}Tc$, $^{111}In$, $^{113m}In$, $^{123}I$, $^{124}I$, $^{131}I$, $^{153}Gd$, $^{137}Cs$) and a group (such as a $1^{st}$, $2^{nd}$ or $3^{rd}$ level substituent as specified herein) containing one or more of said radioisotopes (preferably one or more of $^{3}H$, $^{14}C$, and $^{32}P$), such as $^{14}CH_3$ or $CH_2CH_2(^{3}H)$. Examples of fluorescent molecular probes include fluorescent dyes and fluorescent labels. Exemplary complementary binding pairs are streptavidin and biotin, or an antibody and the antigen to which the antibody binds. The molecular probe does not abolish the activity of the compound of interest (e.g., the therapeutic activity of a pyrazolopyridine derivative of any one of formulas (Ia), (Ib), (IIa), (IIb), (IIIa), (IIIb), (IVa), (IVb), (Va), (Vb), (VIa), (VIb), (VIIa), (VIIb), (VIIIa), and (VIIIb)) against a condition, disorder or disease that is mediated or caused by a parasite of the family Trypanosomatidae as defined herein. Preferably, the activity of the labeled compound of interest is at least 50%, at least 60%, at least 70%, at least 80%, at least 90%, at least 95%, at least 98%, at least 99% of the activity of the unlabeled compound of interest. In one embodiment, the activity of the labeled compound of interest is substantially identical to the activity of the unlabeled compound of interest. In one embodiment, the activity of the labeled compound of interest is identical to or higher than the activity of the unlabeled compound of interest.

The term "fluorescent dye" means a fluorescent chemical compound which is able to absorb light energy of a specific wavelength and emit light at a longer wavelength. The emission of light by fluorescence dyes at a longer wavelength usually occurs immediately in contrast to phosphorescence dyes. For a comprehensive review on fluorescence dyes, their use and labeling of compounds with said dyes see e.g., "*The Molecular Probes® Handbook—A Guide to Fluorescent Probes and Labeling Technology*", Iain Johnson and Michelle T. Z. Spence (Editors), 11th Edition (2010).

The term "fluorescent label" means a reactive derivative of a fluorescent dye. Preferably, the fluorescent label is capable of binding to a functional group contained in a compound of interest (e.g., a pyrazolopyridine derivative of any one of formulas (Ia), (Ib), (IIa), (IIb), (IIIa), (IIIb), (IVa), (IVb), (Va), (Vb), (VIa), (VIb), (VIIa), (VIIb), (VIIIa), and (VIIIb)). In one embodiment, the fluorescent label comprises an electrophilic group which is capable of reacting with a nucleophilic group contained in a compound of interest. In another embodiment, the fluorescent label comprises a nucleophilic group which is capable of reacting with an electrophilic group contained in a compound of interest. Suitable pairs of electrophilic and nucleophilic groups are known to the skilled person and include activated esters/ amines (resulting in carboxamide linkages), acyl halides/ amines (resulting in carboxamide linkages), acyl halides/ alcohols (resulting in ester linkages), aldehydes/amines (resulting in imine linkages), alkyl halides/amines (resulting in alkyl amine linkages), alkyl halides/thiols (resulting in thio ether linkages), anhydrides/alcohols (resulting in ester linkages), epoxides/thiols (resulting in thioether linkages), haloacetamides/thiols (resulting in thioether linkages), isocyanates/amines (resulting in urea linkages), isocyanates/ alcohols (resulting in urethane linkages), isothiocyanates/ amines (resulting in thiourea linkages), maleimides/thiols (resulting in thioether linkages), silyl halides/alcohols (resulting in silyl ether linkages), and sulfonyl halides/amines (resulting in sulfonamide linkages). Examples of activated esters include succinimidyl esters, sulfosuccinimidyl esters, and benzotriazolyl esters. For example, "*The Molecular Probes® Handbook—A Guide to Fluorescent Probes and Labeling Technology*", supra, gives guidance and examples for means and conditions for attaching a fluorescent label to a compound of interest.

In case a structural formula shown in the present application can be interpreted to encompass more than one isomer, said structural formula, unless explicitly stated otherwise, encompasses all possible isomers and, hence, each individual isomer. For example, a compound of formula (Ia), wherein $L_3$ is —C(O)—N($R^8$)—CH(CH$_3$)—, encompasses both isomers, i.e., the isomer having the following formula (B1) and the isomer having the following formula (B2):

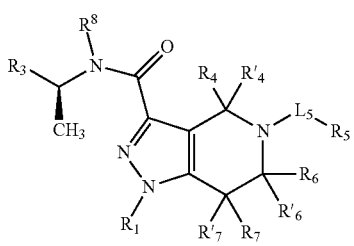

(B1)

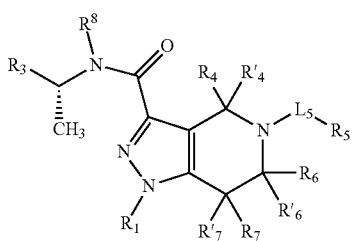

(B2)

The naming and numbering of the compounds of the present invention is exemplified with a representative compound of formula (Ia)

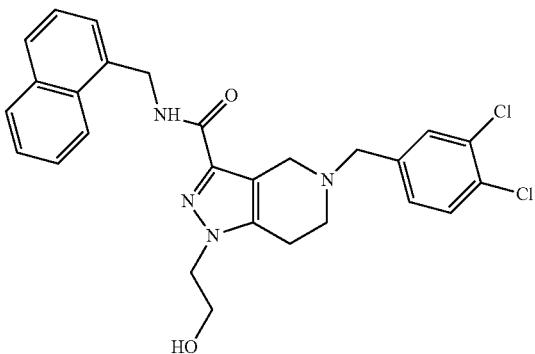 [SMILES: O=C(NCc1cccc2ccccc12)c1nn(CCO)c2c1CN(Cc1ccc(Cl)c(Cl)c1)CC2]

which is named 5-(3,4-dichlorobenzyl)-1-(2-hydroxyethyl)-N-(naphthalen-1-ylmethyl)-4,5,6,7-tetrahydro-1H-pyrazolo[4,3-c]pyridine-3-carboxamide.

"Polymorphism" as referred to herein means that a solid material (such as a compound) is able to exist in more than one form or crystalline structure, i.e., "polymorphic modifications" or "polymorphic forms". The terms "polymorphic modifications", "polymorphic forms", and "polymorphs" are used interchangeable in the present invention. According to the present invention, these "polymorphic modifications" include crystalline forms, amorphous forms, solvates, and hydrates. Mainly, the reason for the existence of different polymorphic forms lies in the use of different conditions during the crystallization process, such as the following:
  solvent effects (the packing of crystal may be different in polar and nonpolar solvents);
  certain impurities inhibiting growth pattern and favor the growth of a metastable polymorphs;
  the level of supersaturation from which material is crystallized (in which generally the higher the concentration above the solubility, the more likelihood of metastable formation);
  temperature at which crystallization is carried out;
  geometry of covalent bonds (differences leading to conformational polymorphism);
  change in stirring conditions.

Polymorphic forms may have different chemical, physical, and/or pharmacological properties, including but not limited to, melting point, X-ray crystal and diffraction pattern, chemical reactivity, solubility, dissolution rate, vapor pressure, density, hygroscopicity, flowability, stability, compactability, and bioavailability. Polymorphic forms may spontaneously convert from a metastable form (unstable form) to the stable form at a particular temperature. According to Ostwald's rule, in general it is not the most stable but the least stable polymorph that crystallizes first. Thus, quality, efficacy, safety, processability and/or manufacture of a chemical compound, such as a compound of the present invention, can be affected by polymorphism. Often, the most stable polymorph of a compound (such as a compound of the present invention) is chosen due to the minimal potential for conversion to another polymorph. However, a polymorphic form which is not the most stable polymorphic form may be chosen due to reasons other than stability, e.g. solubility, dissolution rate, and/or bioavailability.

The term "crystalline form" of a material as used herein means that the smallest components (i.e., atoms, molecule or ions) of said material form crystal structures. A "crystal structure" as referred to herein means a unique three-dimensional arrangement of atoms or molecules in a crystalline liquid or solid and is characterized by a pattern, a set of atoms arranged in a particular manner, and a lattice exhibiting long-range order and symmetry. A lattice is an array of points repeating periodically in three dimensions and patterns are located upon the points of a lattice. The subunit of the lattice is the unit cell. The lattice parameters are the lengths of the edges of a unit cell and the angles between them. The symmetry properties of the crystal are embodied in its space group. In order to describe a crystal structure the following parameters are required: chemical formula, lattice parameters, space group, the coordinates of the atoms and occupation number of the point positions.

The term "amorphous form" of a material as used herein means that the smallest components (i.e., atoms, molecule or ions) of said material are not arranged in a lattice but are arranged randomly. Thus, unlike crystals in which a short-range order (constant distances to the next neighbor atoms) and a long-range order (periodical repetition of a basic lattice) exist, only a short-range order exists in an amorphous form.

The term "complex of a compound" as used herein refers to a compound of higher order which is generated by association of the compound with other one or more other molecules. Exemplary complexes of a compound include, but are not limited to, solvates, clusters, and chelates of said compound.

The term "solvate" as used herein refers to an addition complex of a dissolved material in a solvent (such as an organic solvent (e.g., an aliphatic alcohol (such as methanol, ethanol, n-propanol, isopropanol), acetone, acetonitrile, ether, and the like), water or a mixture of two or more of these liquids), wherein the addition complex exists in the form of a crystal or mixed crystal. The amount of solvent contained in the addition complex may be stoichiometric or non-stoichiometric. A "hydrate" is a solvate wherein the solvent is water.

In isotopically labeled compounds one or more atoms are replaced by a corresponding atom having the same number of protons but differing in the number of neutrons. For example, a hydrogen atom may be replaced by a deuterium atom. Exemplary isotopes which can be used in the compounds of the present invention (in particular, the pyrazolopyridine derivatives of any one of formulas (Ia), (Ib), (IIa), (IIb), (IIIa), (IIIb), (IVa), (IVb), (Va), (Vb), (VIa), (VIb), (VIIa), (VIIb), (VIIIa), and (VIIIb)) include deuterium, $^{11}C$, $^{13}C$, $^{14}C$, $^{15}N$, $^{18}F$, $^{32}S$, $^{36}Cl$, and $^{125}I$. The term "isotopically enriched" means that the occurrence of the isotope is beyond the natural abundance.

The term "half-life" relates to the period of time which is needed to eliminate half of the activity, amount, or number of molecules. In the context of the present invention, the half-life of a compound of any one of formulas (Ia), (Ib), (IIa), (IIb), (IIIa), (IIIb), (IVa), (IVb), (Va), (Vb), (VIa), (VIb), (VIIa), (VIIb), (VIIIa), and (VIIIb) is indicative for the stability of said compound.

The term "naturally occurring", as used herein in context with an object, refers to the fact that an object can be found in nature. For example, a polypeptide or polynucleotide sequence that is present in an organism (including parasites) that can be isolated from a source in nature and which has not been intentionally modified by man in the laboratory is naturally occurring.

The term "antigen" relates to an agent such as a protein or peptide comprising an epitope against which an immune response is directed and/or is to be directed. In a preferred embodiment, an antigen is an antigen of a parasite of the family Trypanosomatidae, i.e., a constituent of said parasite or of its progeny which may be derived from the membrane, flagellum, or an intracellular protein, in particular those antigens which are produced, preferably in large quantity, intracellularly or as surface antigens on cells infected with the parasite or its progeny.

The term "epitope" refers to an antigenic determinant in a molecule, i.e., to the part in a molecule that is recognized by the immune system, for example, that is recognized by an antibody. For example, epitopes are the discrete, three-dimensional sites on an antigen, which are recognized by the immune system. Epitopes usually consist of chemically active surface groupings of molecules (such as amino acids or sugar side chains) and usually have specific three dimensional structural characteristics, as well as specific charge characteristics. Conformational and non-conformational epitopes are distinguished in that the binding to the former but not the latter is lost in the presence of denaturing solvents. An epitope of a protein preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 8, 9, 10, 11, 12, 13, 14, 15, 16, 17, 18, 19, 20, 21, 22, 23, 24, or 25 amino acids in length.

The term "antibody" refers to a glycoprotein comprising at least two heavy (H) chains and two light (L) chains inter-connected by disulfide bonds. The term "antibody" includes monoclonal antibodies, recombinant antibodies, human antibodies, humanized antibodies, chimeric antibodies, and antibody derivatives. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. Antibodies may be derived from different species, including but not limited to mouse, rat, rabbit, guinea pig and human.

The term "monoclonal antibody" as used herein refers to a preparation of antibody molecules of single molecular composition. A monoclonal antibody displays a single binding specificity and affinity. In one embodiment, the monoclonal antibodies are produced by a hybridoma which includes a B cell obtained from a non-human animal, e.g., mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "human antibody", as used herein, is intended to include antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo).

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However, the definition is not limited to this particular example.

The term "antibody derivatives" refers to any modified form of an antibody, e.g., a conjugate of the antibody and another agent or antibody, or an antibody fragment. In this respect, the term "conjugate" means that at least two substances (e.g., an antibody and another agent, e.g., a fluorescent label) are attached to each other, preferably by one or more covalent linkages. Exemplary linkages are given above within the section concerning fluorescent labels.

The term "antibody fragment" refers to one or more fragments of an antibody that retain the ability to specifically bind to an antigen. It has been shown that the antigen-binding function of an antibody can be performed by fragments of a full-length antibody. Examples of antibody fragments include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883).

The terms "patient", "individual", "subject", and "animal" relate to multicellular animals, such as vertebrates and domesticated insects (e.g., bees and bumblebees). For example, vertebrates in the context of the present invention are mammals, birds (e.g., poultry), reptiles, amphibians, bony fishes, and cartilaginous fishes, in particular domesticated animals of any of the foregoing as well as animals (in particular vertebrates) in captivity such as animals (in particular vertebrates) of zoos. Mammals in the context of the present invention include, but are not limited to, humans, non-human primates, domesticated mammals, such as dogs, cats, pigs, and ruminants (e.g., sheep, cattle, goats, horses etc.), laboratory mammals such as mice, rats, rabbits, guinea pigs, etc. as well as mammals in captivity such as mammals of zoos. The term "animal" as used herein also includes humans. Particular non-limiting examples of birds include domesticated poultry, and include birds such as chickens, turkeys, ducks, geese, guinea fowl, pigeons, pheasants etc.; while particular non-limiting examples of bony or cartilaginous fish include those suitable for cultivation by aquiculture, and include bony fish such as salmon, trout, perch, carp, cat-fish, etc. In one embodiment, the subject is selected from the group consisting of human and ruminants (such as cattle and horse).

By "treat" is meant to administer a compound or composition or a combination of compounds or compositions (e.g., pharmaceutical compositions) to a subject in order to eliminate a condition, disorder or disease; arrest or slow a condition, disorder or disease in a subject; decrease the frequency or severity of symptoms and/or recurrences in a subject who currently has or who previously has had a condition, disorder or disease (e.g., by reducing the number of parasites of the family Trypanosomatidae in a subject); and/or prolong, i.e. increase the lifespan of the subject. In particular, the term "treating a condition, disorder or disease" includes curing, shortening the duration, ameliorating, slowing down or inhibiting progression or worsening, of a condition, disorder or disease or the symptoms of said condition, disorder or disease.

According to the present invention, terms such as "protect", "prevent", "prophylactic", "preventive", or "protective" relate to the prevention of the occurrence and/or the propagation of a condition, disorder or disease in a subject and, in particular, to minimizing the chance that a subject will develop a condition, disorder or disease or to delaying the onset or development of a condition, disorder or disease (e.g., by inhibiting or slowing the development of a new condition, disorder or disease in a subject). For example, a person at risk for being infected with a parasite of the family Trypanosomatidae would be a candidate for therapy to prevent the infection with said parasite.

By "being at risk" is meant a subject that is identified as having a higher than normal chance of developing a condition, disorder or disease (in particular, a condition, disorder or disease that is mediated or caused by a parasite of the family Trypanosomatidae) compared to the general population. In addition, a subject who has had, or who currently has, a condition, disorder or disease (in particular, a condition, disorder or disease that is mediated or caused by a parasite of the family Trypanosomatidae), is a subject who has an increased risk for developing a condition, disorder or disease, as such a subject may continue to develop a condition, disorder or disease.

The terms "disease", "disorder" and "condition", when used in the context of treatment or therapy (including prophylactic therapy), are used herein interchangeably and refer to any pathological state, in particular those pathological states described herein.

The term "a condition, disorder or disease that is mediated or caused by a parasite" means any pathological state which is elicited indirectly and/or directly by the parasite. I.e., a disease caused by a parasite refers to a disease which is directly elicited by the parasite (i.e., a primary infection). In this respect, the term "primary infection" means that the disease is caused as a result of the parasite's presence or activity within the normal, healthy subject, and the parasite's intrinsic virulence is at least partially a necessary consequence of the parasite's need to reproduce and spread. An example of a primary infection is Sleeping Sickness caused by *Trypanosoma brucei*. According to the present invention, a disease mediated by a parasite refers to a disease which is indirectly elicited by the parasite (i.e., an opportunistic infection). In this respect, the term "opportunistic infection" means that the disease results from an otherwise innocuous pathogen and requires that the subject's defenses are impaired by the parasite (e.g., since the parasite weakens the immune system of the patient). An example of an opportunistic infection is AIDS-related Karposi sarcoma.

The family Trypanosomatidae can be subdivided into the genera *Blastocrithidia, Crithidia, Endotrypanum, Herpetomonas, Leishmania, Leptomonas, Phytomonas, Trypanosoma*, and *Wallaceina*.

Examples of the genus *Crithidia* include *C. bombi, C. mellificae, C. fasciculata, C. deanei, C. desouzai, C. oncopelti, C. guilhermei*, and *C. luciliae*.

Examples of the genus *Leishmania* include *L. aethiopica, L. amazonensis, L. Arabica, L. archibaldi, L. aristedesi, L.*

(Viannia) *braziliensis, L. chagasi* (syn. *L. infantum*), *L.* (Viannia) *colombiensis, L. deanei, L. donovani, L. enriettii, L. equatorensis, L. forattinii, L. garnhami, L. gerbili, L.* (Viannia) *guyanensis, L. herreri, L. hertigi, L. infantum, L. killicki, L.* (Viannia) *lainsoni, L. major, L. mexicana, L.* (Viannia) *naiffi, L.* (Viannia) *panamensis, L.* (Viannia) *peruviana, L.* (Viannia) *pifanoi, L.* (Viannia) *shawi, L. tarentolae, L. tropica, L. turanica,* and *L. venezuelensis.*

Examples of the genus *Trypanosoma* include *T. ambystomae* (amphibians), *T. avium* (birds), *T. boissoni* (elasmobranch), *T. brucei* (humans and cattle), *T. cruzi* (humans), *T. congolense* (ruminants), *T. equinum* (horses), *T. equiperdum* (horses and other Equidae), *T. evansi* (animals), *T. everetti* (birds), *T. hosei* (amphibians), *T. irwini* (koalas), *T. lewisi* (rats), *T. melophagium* (sheep), *T. paddae* (birds), *T. parroti* (amphibians), *T. percae* (species *Perca fluviatilis*), *T. rangeli, T. rotatorium* (amphibians), *T. rugosae* (amphibians), *T. sergenti* (amphibians), *T. simiae* (pigs and warthogs), *T. sinipercae* (fishes), *T. suis, T. theileri* (ruminants), *T. triglae* (marine teleosts), and *T. vivax.*

The term "parasite of the family Trypanosomatidae" refers to a parasite which can infect a subject and which causes or mediates a condition, disorder or disease in said subject. In one embodiment, the parasite of the family Trypanosomatidae is selected from the genera *Leishmania* (such as *Leishmania donovani, Leishmania chagasi* (syn. *Leishmania infantum*), *Leishmania braziliensis, Leishmania major, Leishmania tropica, Leishmania mexicana* and *Leishmania amazonensis*) and *Trypanosoma* (such as *T. brucei* (in particular *T. brucei gambiense* (T.b.g) and *T. brucei rhodesiense* (T.b.r)), *T. cruzi, T. vivax, T. equiperdum, T evansi, T. congolense, T. equinum*).

The term "parasite strain" means a genetic variant or subtype of a parasite (or parasite progeny) having a common mutation profile distinguishing the strain from the wild type parasite. The common mutation profile may alter one or more of the properties of the parasite or its progeny (such as virulence, latency, drug resistance, immunosuppression, etc.). In this respect, the term "alter" includes not only the situation that one or more of the properties of the parasite or its progeny are increased or decreased but also the situation that the mutation profile imparts a new property (such as virulence to a new subject, latency, drug resistance, immunosuppression, etc.) to the parasite strain compared to the wild-type parasite which does not have said new property.

The term "virulence" of a parasite (in particular, a parasite strain) means the degree of pathogenicity of the parasite as indicated by case fatality rates and/or the ability of the parasite to invade the tissues of the host (i.e., the parasite's infectivity). The pathogenicity of a parasite (in particular, a parasite strain) means its ability to cause or mediate a disease (i.e., disease severity). The expression "ability to cause or mediate a disease" is to be understood in the same manner as in the term "a condition, disorder or disease that is mediated or caused by a parasite" described above. I.e., the parasite's ability to cause a disease is the parasite's ability to directly elicit a disease (i.e., a primary infection), whereas the parasite's ability to mediate a disease is the parasite's ability to indirectly elicit a disease (i.e., an opportunistic infection). The parasite's pathogenicity can be determined by its virulence factors which comprise the colonization of a niche in the host (including attachment to cells), immunoevasion (i.e., the parasite's ability to evade the host's immune response), immunosuppression (i.e., the ability to inhibit the host's immune response), entry into and exit out of cells, and the ability to obtain nutrition from the host.

The term "persistent infection" means an infection in which the parasite is not cleared from the subject but remains in cells of the subject either for a long time, e.g., weeks (e.g., 1, 2, 3, 4, 5, 6, 7, or, 8 weeks), to months (e.g., 1, 2, 3, 4, 5, 6, 7, 8, 9, 10, 11, or 12 months) or years (e.g., 1, 2, 3, 4, 5, 6, 7, 8, 9, or 10 years or more) or life-long. Persistent infections can be classified into three types, i.e., latent, chronic and slow infections. Cells of a subject which are infected by a persistent infection may be cells which do not produce parasites (in particular detectable infectious parasite progeny) and/or cells which produce parasites (in particular detectable infectious parasite progeny). For example, cells of a subject which are infected by a persistent infection may produce parasite (in particular detectable infectious parasite progeny) during one or more periods of time (i.e., during productive periods), whereas during other periods of time they do not produce parasite (in particular detectable infectious parasite progeny). The productive periods may comprise recurring episodes of disease (which normally do not lead to (i) the killing of the subject or (ii) excessive (e.g., irreparable or fatal) damage of the cells of the subject) or onset of severe disease.

The term "latent infection", as used herein, means a persistent infection lacking detectable parasite (in particular detectable infectious parasite progeny) between episodes of recurrent disease. The term "parasite latency" means the ability of a parasite to lie dormant (latent) within a cell of a subject. Latency can be denoted as the phase in the life cycle of a parasite in which, after initial infection, the generation of parasites (in particular, infectious parasite progeny) ceases, although the parasite is not cleared (i.e., fully eradicated) from the subject. Consequently, the parasite can reactivate (or can be reactivated by a stimulus including changes in cell physiology, superinfection by another microorganism, physical stress or trauma, and/or immunosuppression of the subject) and begin producing parasites (in particular, infectious parasite progeny) without the subject being infected by new outside parasite and stays within the subject indefinitely.

The term "chronic infection", as used herein, means a persistent infection in which, after initial infection, the parasite (in particular detectable infectious parasite progeny) is present in the subject for a long time, e.g., weeks (e.g., 1, 2, 3, 4, 5, 6, 7, or, 8 weeks), to months (e.g., 1, 2, 3, 4, 5, 6, 7, 8, 9, 10, 11, or 12 months) or years (e.g., 1, 2, 3, 4, 5, 6, 7, 8, 9, or 10 years or more) or life-long and results in chronic or recurrent disease. A chronic infection may be eventually cleared.

The term "slow infection", as used herein, means a persistent infection having a prolonged incubation period followed by progressive disease. In contrast to latent and chronic infections, slow infection do not start with an acute period of parasite (in particular detectable infectious parasite progeny) multiplication.

The term "acute" infection, as used herein, means an infection having a short duration (i.e., in the order of several days, such as 1 to 10 days, e.g., 1, 2, 3, 4, 5, 6, 7, 8, 9, or 10 days). Usually, an acute infection is characterized by a fast onset of disease (i.e., early production of parasites (in particular, infectious parasite progeny)), a relatively short period (e.g., in the order of several days, such as 1 to 10 days, e.g., 1, 2, 3, 4, 5, 6, 7, 8, 9, or 10 days) of symptoms, and resolution within days (such as 1 to 10 days, e.g., 1, 2, 3, 4, 5, 6, 7, 8, 9, or 10 days) normally, due to the action of the immune system of the subject).

The term "parasite progeny", as used herein, means all stages of the parasite when present in the subject in which a condition, disorder or disease is mediated or caused by the parasite. For example, the progeny of *Leishmania* includes the promastigote form (with flagellum) and the amastigote form (without flagella), whereas the progeny of includes the trypomastigote form, the promastigote form, and the amastigote form.

The term "host" as used in the context of a parasite means a subject (e.g., a species thereof) or a cell of the subject which can be infected by the parasite and/or in which the parasite multiplies. Preferably, a parasite's host is a subject (e.g., a species thereof) in which a condition, disorder or disease is mediated or caused by the parasite.

The term "immunosuppression", as used herein, means the reduced activation and/or efficacy of the immune system. Immunosuppression can be deliberately induced (e.g., in order to prevent the subject's body from rejecting an organ transplant, treating graft-versus-host disease, and/or for the treatment of auto-immune diseases), for example, by drugs, surgery (e.g., splenectomy), plasmapheresis, or radiation. Immunosuppression can also be induced non-deliberately (e.g., by malnutrition, aging, many types of cancer (such as leukemia, lymphoma, multiple myeloma), and certain chronic infections such as HIV) leading to increased susceptibility to pathogens such as parasites (e.g., a parasite of the family Trypanosomatidae). An immunocompromised subject is an individual who is undergoing immunosuppression, or whose immune system is weak for other reasons (e.g., because of chemotherapy, HIV, or Lupus).

The term "parasite strain which is resistant to one or more trypanolytic drugs", as used herein, means that the one or more trypanolytic drugs exhibit a reduced effectiveness against said parasite strain (in particular a parasite strain of the family Trypanosomatidae as disclosed herein) compared to the effectiveness of the same one or more trypanolytic drugs against the wild type parasite (preferably, all experimental conditions other than the type of parasite used (i.e., resistant parasite strain vs. wild-type parasite) used to determine the effectiveness are identical or comparable). When the parasite strain is resistant against more than one trypanolytic drug (e.g., against 2, 3, or 4 trypanolytic drugs), it exhibits multidrug resistance (MDR) or is multidrug-resistant. The effectiveness may be measured with respect to (i) the amount of parasite progeny (e.g., infectious parasite progeny) released from the infected host cell; (ii) the amount of total parasite nucleic acid and/or protein in the infected host cell; (iii) the amount of specific parasite nucleic acid and/or protein in the infected host cell; (iv) the amount of trypanolytic drug required to achieve a certain result (such as the induction of a response halfway between the baseline and maximum after a specified exposure time ($EC_{50}$ value)); and/or (v) the survival time of the infected host cell. In one embodiment, the effectiveness of the one or more trypanolytic drugs against said parasite strain is reduced to at most 90% (such at most 80%, at most 70%, at most 60%, at most 50%, at most 40%, at most 30%, at most 20%, at most 10%, at most 5%, at most 1%) with respect to the effectiveness of the same one or more drugs against the wild type parasite. For example, if the effectiveness is determined on the basis of the survival time of the infected host cell, the survival time of the host cell which is infected with the resistant parasite strain and which has been treated with the one or more trypanolytic drugs may be at most 90% (such at most 80%, at most 70%, at most 60%, at most 50%, at most 40%, at most 30%, at most 20%, at most 10%, at most 5%, at most 1%) with respect to the survival time of a host cell which is infected with the wild type parasite and which has been treated with the one or more trypanolytic drugs (preferably, all experimental conditions other than the type of parasite (i.e., resistant parasite strain vs. wild-type parasite) used to determine the amount of parasite progeny are identical or comparable). If the effectiveness is determined on the basis of the amount of parasite progeny (e.g., infectious parasite progeny) released from the infected host cell, the amount of parasite progeny released from the host cell which is infected with the resistant parasite strain and which has been treated with the one or more trypanolytic drugs may be at least 110% (such as at least 125%, at least 140%, at least 165%, at least 200%, at least 250%, at least 330%, at least 500%, at least 1000%, at least 2000%, at least 10 000%) with respect to the amount of parasite progeny (e.g., infectious parasite progeny) released from a host cell which is infected with the wild type parasite and which has been treated with the one or more trypanolytic drugs (preferably, all experimental conditions other than the type of parasite (i.e., resistant parasite strain vs. wild-type parasite) used to determine the amount of trypanolytic drug required to achieve the result are identical or comparable). The same applies if the effectiveness is determined on the basis of (ii) the amount of total parasite nucleic acid and/or protein in the infected host cell; (iii) the amount of specific parasite nucleic acid and/or protein in the infected host cell; or (iv) the amount of trypanolytic drug required to achieve a certain result (such as the induction of a response halfway between the baseline and maximum after a specified exposure time ($EC_{50}$ or $IC_{50}$ value)) (i.e., the amount of total parasite nucleic acid and/or protein in the host cell which is infected with the resistant parasite strain and which has been treated with the one or more trypanolytic drugs may be at least 110% (such as at least 125%, . . . at least 10 000%) with respect to the amount of total parasite nucleic acid and/or protein in the host cell which is infected with the wild-type parasite and which has been treated with the one or more trypanolytic drugs.

The term "$EC_{50}$", as used herein, refers to the half maximal effective concentration of a compound, i.e., the molar concentration of the compound which produces a response halfway between the baseline and maximum after a specified exposure time.

The term "$IC_{50}$", as used herein, refers to the half maximal inhibitory concentration of a compound, i.e., the molar concentration of the compound which produces an inhibitory response halfway between the baseline and maximum after a specified exposure time.

Compounds

In one aspect, the present invention provides a compound selected from the group consisting of a pyrazolopyridine derivative having the general formula (Ia) or (Ib)

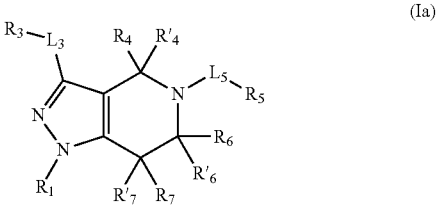

(Ia)

-continued

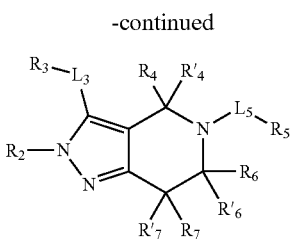

(Ib)

and solvates, salts, complexes, polymorphs, crystalline forms, racemic mixtures, diastereomers, enantiomers, tautomers, isotopically labeled forms, prodrugs, and combinations thereof,
wherein $R_1$ is selected from the group consisting of —H, alkyl, alkenyl, alkynyl, aryl, heteroaryl, cycloalkyl, heterocyclyl, —S(O)$_{1-2}$R$^{11}$, —S(O)$_{1-2}$OR$^{11}$, —S(O)$_{1-2}$N(R$^{12}$)(R$^{13}$), —C(=X)R$^{11}$, and —C(=X)XR$^{11}$, wherein each of the alkyl, alkenyl, alkynyl, aryl, heteroaryl, cycloalkyl, and heterocyclyl groups is optionally substituted with one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) independently selected R$^{30}$ or the alkyl group is substituted with one R$^{31}$;

$R_2$ is selected from the group consisting of —H, alkyl, alkenyl, alkynyl, aryl, heteroaryl, cycloalkyl, heterocyclyl, —S(O)$_{1-2}$R$^{11}$, —S(O)$_{1-2}$OR$^{11}$, —S(O)$_{1-2}$N(R$^{12}$)(R$^{13}$), —C(=X)R$^{11}$, and —C(=X)XR$^{11}$, wherein each of the alkyl, alkenyl, alkynyl, aryl, heteroaryl, cycloalkyl, and heterocyclyl groups is optionally substituted with one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) independently selected R$^{30}$ or the alkyl group is substituted with one R$^{31}$;

$R_3$ is selected from the group consisting of aryl, heteroaryl, cycloalkyl, and heterocyclyl, wherein each of the aryl, heteroaryl, cycloalkyl, and heterocyclyl groups is optionally substituted with one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) independently selected R$^{30}$;

$R_4$, $R'_4$, $R_6$, $R'_6$, $R_7$, and $R'_7$ are independently selected from the group consisting of H, alkyl, alkenyl, alkynyl, aryl, heteroaryl, cycloalkyl, heterocyclyl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —C(=X)R$^{11}$, —C(=X)XR$^{11}$, —XC(=X)R$^{11}$, and —XC(=X)XR$^{11}$, wherein each of the alkyl, alkenyl, alkynyl, aryl, heteroaryl, cycloalkyl, and heterocyclyl groups is optionally substituted with one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) independently selected R$^{30}$;

$R_5$ is selected from the group consisting of aryl, heteroaryl, cycloalkyl, and heterocyclyl, wherein each of the aryl, heteroaryl, cycloalkyl, and heterocyclyl groups is optionally substituted with one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) independently selected R$^{30}$;

$L_3$ is —C(O)—N(R$^8$)-(alkylene)-* or —N(R$^8$)—C(O)-(alkylene)-*, wherein the alkylene group is optionally substituted with one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) independently selected R$^{30}$ and * indicates the attachment point to $R_3$;

$L_5$ is selected from the group consisting of alkylene, -(alkylene)-Y$_1$-(alkylene)$_m$-*, —(C$_{1-3}$ alkylene)-[Y$_2$—C$_{1-3}$ alkylene)]$_n$-*, and —Y$_3$-(alkylene)$_o$-*, wherein * indicates the attachment point to $R_5$; m is 0 or 1; Y$_1$ is selected from the group consisting of —C(=X)—, —C(=X)X—, —XC(=X)—, —XC(=X)X—, —S(O)$_{1-2}$—, —S(O)$_{1-2}$N(R$^9$)—, —N(R$^9$)—S(O)$_{1-2}$—, and cyclopropylene; Y$_2$ is independently selected from O, S, and —N(R$^{10}$)—; n is 1, 2, or 3; Y$_3$ is selected from the group consisting of —C(=X)—, —S(O)$_{1-2}$—, and —S(O)$_{1-2}$N(R$^9$)—; o is 0 or 1; and each of the alkylene and cyclopropylene groups is optionally substituted with one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) independently selected R$^{30}$;

$R^8$ is selected from the group consisting of —H, alkyl, alkenyl, alkynyl, cycloalkyl, aryl, heteroaryl, heterocyclyl, —OR$^{11}$, and —NHR$^{20}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) independently selected R$^{30}$, or R$^8$ and R$_2$ may join together with the atoms to which they are attached to form a ring which is optionally substituted with one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) independently selected R$^{30}$ or R$^8$ and R$_3$ may join together with the atoms to which they are attached to form a polycyclic ring which is optionally substituted with one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) independently selected R$^{30}$;

$R^9$ is selected from the group consisting of —H, alkyl, alkenyl, alkynyl, cycloalkyl, aryl, heteroaryl, heterocyclyl, —OR$^{11}$, and —NHR$^{20}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) independently selected R$^{30}$;

$R^{10}$ is selected from the group consisting of —H, alkyl, alkenyl, alkynyl, cycloalkyl, aryl, heteroaryl, heterocyclyl, —OR$^{11}$, and —NHR$^{20}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) independently selected R$^{30}$;

X is independently selected from O, S, and N(R$^{14}$);

R$^{11}$ is, in each case, selected from the group consisting of —H, alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) independently selected $R^{30}$; $R^{12}$ and $R^{13}$ are, in each case, independently selected from the group consisting of —H, alkyl, alkenyl, alkynyl, cycloalkyl, aryl, heteroaryl, and heterocyclyl, or $R^{12}$ and $R^{13}$ may join together with the nitrogen atom to which they are attached to form the group —N=$CR^{15}R^{16}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) independently selected $R^{30}$;

$R^{14}$ is independently selected from the group consisting of —H, alkyl, alkenyl, alkynyl, cycloalkyl, aryl, heteroaryl, heterocyclyl, and —$OR^{11}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) independently selected $R^{30}$; $R^{15}$ and $R^{16}$ are independently selected from the group consisting of —H, alkyl, alkenyl, alkynyl, cycloalkyl, aryl, heteroaryl, heterocyclyl, and —$NH_yR^{20}_{2-y}$, or $R^{15}$ and $R^{16}$ may join together with the atom to which they are attached to form a ring which is optionally substituted with one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) independently selected $R^{30}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) independently selected $R^{30}$;

y is an integer from 0 to 2;

$R^{20}$ is selected from the group consisting of alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) independently selected $R^{30}$;

$R^{30}$ is a $1^{st}$ level substituent and is, in each case, independently selected from the group consisting of alkyl, alkenyl, alkynyl, aryl, heteroaryl, cycloalkyl, heterocyclyl, halogen, —CN, azido, —$NO_2$, —$OR^{71}$, —$N(R^{72})(R^{73})$, —$S(O)_{0-2}R^{71}$, —$S(O)_{1-2}OR^{71}$, —$OS(O)_{1-2}R^{71}$, —$OS(O)_{1-2}OR^{71}$, —$S(O)_{1-2}N(R^{72})(R^{73})$, —$OS(O)_{1-2}N(R^{72})(R^{73})$, —$N(R^{71})S(O)_{1-2}R^{71}$, —$NR^{71}S(O)_{1-2}OR^{71}$, —$NR^{71}S(O)_{1-2}N(R^{72})(R^{73})$, —$C(=X^1)R^{71}$, —$C(=X^1)X^1R^{71}$, —$X^1C(=X^1)R^{71}$, and —$X^1C(=X^1)X^1R^{71}$, and/or any two $R^{30}$ which are bound to the same carbon atom of a cycloalkyl or heterocyclyl group may join together to form =$X^1$, wherein each of the alkyl, alkenyl, alkynyl, aryl, heteroaryl, cycloalkyl, and heterocyclyl groups being a $1^{st}$ level substituent is optionally substituted by one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) $2^{nd}$ level substituents, wherein said $2^{nd}$ level substituent is, in each case, independently selected from the group consisting of $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, 3- to 14-membered heterocyclyl, halogen, —$CF_3$, —CN, azido, —$NO_2$, —$OR^{81}$, —$N(R^{82})(R^{83})$, —$S(O)_{0-2}R^{81}$, —$S(O)_{1-2}OR^{81}$, —$OS(O)_{1-2}R^{81}$, —$OS(O)_{1-2}OR^{81}$, —$S(O)_{1-2}N(R^{82})(R^{83})$, —$OS(O)_{1-2}N(R^{82})(R^{83})$, —$N(R^{81})S(O)_{1-2}R^{81}$, —$NR^{81}S(O)_{1-2}OR^{81}$, —$NR^{81}S(O)_{1-2}N(R^{82})(R^{83})$, —$C(=X^2)R^{81}$, —$C(=X^2)X^2R^{81}$, —$X^2C(=X^2)R^{81}$, and —$X^2C(=X^2)X^2R^{81}$, and/or any two $2^{nd}$ level substituents which are bound to the same carbon atom of a cycloalkyl or heterocyclyl group being a $1^{st}$ level substituent may join together to form =$X^2$, wherein each of the $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, 3- to 14-membered heterocyclyl groups being a $2^{nd}$ level substituent is optionally substituted with one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) $3^{rd}$ level substituents, wherein said $3^{rd}$ level substituent is, in each case, independently selected from the group consisting of $C_{1-3}$ alkyl, halogen, —$CF_3$, —CN, azido, —$NO_2$, —OH, —$O(C_{1-3}$ alkyl), —$OCF_3$, —$S(C_{1-3}$ alkyl), —$NH_2$, —NH$(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —$C(=O)OH$, —$C(=O)O(C_{1-3}$ alkyl), —$C(=O)NH_{2-z}(C_{1-3}$ alkyl)$_z$, —$NHC(=O)(C_{1-3}$ alkyl), —$NHC(=NH)NH_{2-z}(C_{1-3}$ alkyl)$_z$, and —$N(C_{1-3}$ alkyl)$C(=NH)NH_{2-z}(C_{1-3}$ alkyl)$_z$, wherein z is 0, 1, or 2 and $C_{1-3}$ alkyl is methyl, ethyl, propyl or isopropyl, and/or any two $3^{rd}$ level substituents which are bound to the same carbon atom of a 3- to 14-membered cycloalkyl or heterocyclyl group being a $2^{nd}$ level substituent may join together to form =O, =S, =NH, or =$N(C_{1-3}$ alkyl);

wherein $R^{71}$, $R^{72}$, and $R^{73}$ are independently selected from the group consisting of —H, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl, wherein each of the $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl groups is optionally substituted with one, two or three substituents selected from the group consisting of $C_{1-3}$ alkyl, 3- to 7-membered cycloalkyl, 5- or 6-membered aryl, 5- or 6-membered heteroaryl, 3- to 7-membered heterocyclyl, halogen, —$CF_3$, —CN, azido, —$NO_2$, —OH, —$O(C_{1-3}$ alkyl), —$OCF_3$, =O, —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —$C(=O)(C_{1-3}$ alkyl), —$C(=O)OH$, —$C(=O)O(C_{1-3}$ alkyl), —$C(=O)NH_{2-z}(C_{1-3}$ alkyl)$_z$, —$NHC(=O)(C_{1-3}$ alkyl), —$NHC(=NH)NH_{2-z}(C_{1-3}$ alkyl)$_z$, and —$N(C_{1-3}$ alkyl)$C(=NH)NH_{2-z}(C_{1-3}$ alkyl)$_z$, wherein z is 0, 1, or 2 and $C_{1-3}$ alkyl is methyl, ethyl, propyl or isopropyl;

$R^{81}$, $R^{82}$, and $R^{83}$ are independently selected from the group consisting of —H, $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl, wherein each of the $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl groups is optionally substituted with one, two or three substituents selected from the group consisting of $C_{1-3}$ alkyl, halogen, —$CF_3$, —CN, azido, —$NO_2$, —OH, —$O(C_{1-3}$ alkyl), —$OCF_3$, =O, —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —$C(=O)(C_{1-3}$ alkyl), —$C(=O)OH$, —$C(=O)O(C_{1-3}$ alkyl), —$C(=O)NH_{2-z}(C_{1-3}$ alkyl)$_z$, —$NHC(=O)(C_{1-3}$ alkyl), —$NHC(=NH)NH_{2-z}(C_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl;

X$^1$ and X$^2$ are independently selected from O, S, and N(R$^{81}$); and

R$^{31}$ is —Y$_4$—B or —B, wherein Y$_4$ is selected from the group consisting of —X—, —C(=X)-(alkylene)$_p$-, —C(=X)X-(alkylene)$_p$-, —XC(=X)-(alkylene)$_p$-, —XC(=X)X-(alkylene)$_p$-, —[O—(C$_{1-3}$ alkylene)]$_n$, —[S—(C$_{1-3}$ alkylene)]$_n$, —[N(R$^{10}$)—(C$_{1-3}$ alkylene)]$_n$, —S(O)$_{1-2}$-(alkylene)$_p$-, —OS(O)$_{1-2}$-(alkylene)$_p$-, —OS(O)$_{1-2}$O-(alkylene)$_p$-, —S(O)$_{1-2}$N(R$^9$)-(alkylene)$_p$-, —OS(O)$_{1-2}$N(R$^9$)-(alkylene)$_p$-, —N(R$^9$) S(O)$_{1-2}$-(alkylene)$_p$-, —N(R$^9$)S(O)$_{1-2}$O-(alkylene)$_p$-, and —N(R$^9$)S(O)$_{1-2}$N(R$^9$)-(alkylene)$_p$-, wherein p is 0 or 1; and B is a molecular probe.

In one embodiment, the pyrazolopyridine derivative has the general formula (IIa) or (IIb)

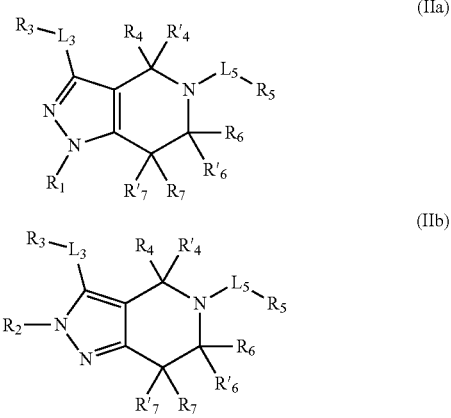

wherein R$_1$, R$_2$, R$_3$, R$_4$, R'$_4$, R$_5$, R$_6$, R'$_6$, R$_7$, R'$_7$, and L$_5$ are as defined above or below and L$_3$ is —C(O)—N(R$^8$)—(C$_{1-6}$ alkylene)-* or —N(R$^8$)—C(O)—(C$_{1-6}$ alkylene)-*, wherein * is the attachment point to R$_3$ and the alkylene group is optionally substituted with one or more (such as 1 to the maximum number of hydrogen atoms bound to the alkylene group, e.g., 1, 2, 3, 4, 5, 6, 7, 8, 9, or up to 10, such as between 1 to 5, 1 to 4, or 1 to 3, or 1 or 2) independently selected R$^{30}$. In one embodiment of the pyrazolopyridine derivative of the general formula (IIa) or (IIb), L$_3$ is —C(O)—N(R$^8$)—(C$_{1-3}$ alkylene)-* or —N(R$^8$)—C(O)—(C$_{1-3}$ alkylene)-*, wherein the alkylene group is optionally substituted with one or more (such as 1 or 2, preferably 1) independently selected R$^{30}$. In one embodiment of the pyrazolopyridine derivative of the general formula (IIa) or (IIb), L$_3$ is —C(O)—N(R$^8$)—CH$_2$—*, —N(R$^8$)—C(O)—CH$_2$—*, —C(O)—N(R$^8$)—CH(CH$_3$)—*, or —N(R$^8$)—C(O)—CH(CH$_3$)—*, preferably —C(O)—N(R$^8$)—CH$_2$—* or —C(O)—N(R$^8$)—CH(CH$_3$)—*.

In one embodiment, the pyrazolopyridine derivative has the general formula (IIIa) or (IIIb)

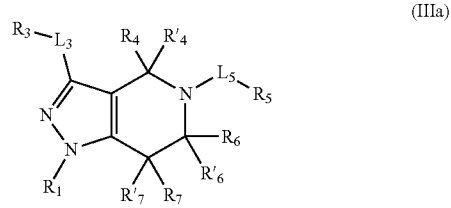

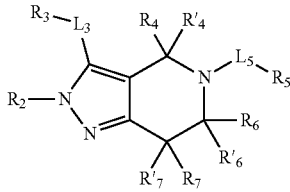

wherein R$_1$, R$_4$, R'$_4$, R$_5$, R$_6$, R'$_6$, R$_7$, R'$_7$, L$_3$, and L$_5$ are as defined above (in particular with respect to formulas (Ia), (Ib), (IIa), and (IIb)) or below and R$^8$ does not join together with R$_2$ or R$_3$ and is preferably selected from the group consisting of —H, alkyl, cycloalkyl, aryl, heteroaryl, and heterocyclyl, wherein each of the alkyl, cycloalkyl, aryl, heteroaryl, and heterocyclyl groups is optionally substituted with one or more (such as 1 to the maximum number of hydrogen atoms bound to the alkyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected R$^{30}$. In a preferred embodiment of the pyrazolopyridine derivative of the general formula (IIIa) or (IIIb), R$^8$, when it does not join together with R$_2$ or R$_3$, is selected from the group consisting of —H, C$_{1-6}$ alkyl, 3- to 7-membered cycloalkyl, C$_{6-14}$ aryl, 5- to 7-membered heteroaryl, and 5- to 7-membered heterocyclyl, wherein each of the C$_{1-6}$ alkyl, 3- to 7-membered cycloalkyl, C$_{6-14}$ aryl, 5- to 7-membered heteroaryl, and 5- to 7-heterocyclyl groups is optionally substituted with 1, 2, or 3 independently selected R$^{30}$. In one embodiment of the pyrazolopyridine derivative of the general formula (IIIa) or (IIIb), R$^8$, when it does not join together with R$_2$ or R$_3$, is selected from the group consisting of —H and C$_{1-3}$ alkyl, wherein the C$_{1-3}$ alkyl group is optionally substituted with 1, 2, or 3 independently selected R$^{30}$. In one embodiment, R$^8$ does not join together with R$_2$ or R$_3$ to form a ring and is —H, methyl, —CH$_2$COO(C$_{1-3}$ alkyl), —CH$_2$COOH, or ethyl, wherein C$_{1-3}$ alkyl is methyl, ethyl, propyl or isopropyl. In one embodiment, R$^8$ does not join together with R$_2$ or R$_3$ to form a ring and is —H, methyl, or ethyl, preferably —H.

In any of the above embodiments of the pyrazolopyridine derivative of the general formula (IIIa) or (IIIb), R$_3$, when it does not join together with R$^8$, is aryl (preferably C$_{6-14}$ aryl) or heteroaryl (preferably 5- to 10-membered heteroaryl), each of which is optionally substituted with one or more (such as 1 to the maximum number of hydrogen atoms bound to the C$_{6-14}$ aryl or 5- to 10-membered heteroaryl group, e.g., 1, 2, 3, 4, 5, 6, 7, 8, 9, or up to 10, such as between 1 to 5, 1 to 4, or 1 to 3, or 1 or 2) independently selected R$^{30}$. In one embodiment of the pyrazolopyridine derivative of the general formula (IIIa) or (IIIb), R$_3$, when it does not join together with R$^8$, is selected from the group consisting of bicyclic aryl, tricyclic aryl, bicyclic heteroaryl, and tricyclic heteroaryl (such as naphthyl, indolyl, isoindolyl, indazolyl, indolizinyl, quinolizinyl, quinolinyl, isoquinolinyl, phthalazinyl, naphthyridinyl, quinoxalinyl, quinazolinyl, cinnolinyl, and pteridinyl). In one embodiment of the pyrazolopyridine derivative of the general formula (IIIa) or (IIIb), R$_3$, when it does not join together with R$^8$, is selected from the group consisting of phenyl, pyridyl, pyrazinyl, pyrimidinyl, pyridazinyl, naphthyl, indolyl, isoindolyl, indazolyl, indolizinyl, quinolizinyl, quinolinyl, isoquinolinyl, phthalazinyl, naphthyridinyl, quinoxalinyl, quinazolinyl, cinnolinyl, and pteridinyl, each of which is optionally substituted with one, two or three independently selected $R^{30}$. In one embodiment of the pyrazolopyridine derivative of the general formula (IIIa) or (IIIb), $R_3$, when it does not join together with $R^8$, is selected from the group consisting of phenyl, naphthyl, indolyl, and quinolinyl (such as naphthyl, indolyl, and quinolinyl), each of which is optionally substituted with one, two or three independently selected $R^{30}$.

In any of the above embodiments of the pyrazolopyridine derivative of the general formula (IIIa) or (IIIb), when $R_3$ does not join together with $R^8$, $-L_3R_3$ may be —C(O)—N($R^8$)—CH$_2$—R$_3$, —N($R^8$)—C(O)—CH$_2$—R$_3$, —C(O)—N($R^8$)—CH(CH$_3$)—R$_3$, or —N($R^8$)—C(O)—CH(CH$_3$)—R$_3$ (preferably —C(O)—N($R^8$)—CH$_2$—R$_3$ or —C(O)—N($R^8$)—CH(CH$_3$)—R$_3$), wherein $R_3$ is aryl (preferably $C_{6-14}$ aryl) or heteroaryl (preferably 5- to 10-membered heteroaryl), each of which is optionally substituted with one or more (such as 1 to the maximum number of hydrogen atoms bound to the aryl or heteroaryl group, e.g., 1, 2, 3, 4, 5, 6, 7, 8, 9, or up to 10, such as between 1 to 5, 1 to 4, or 1 to 3, or 1 or 2) independently selected $R^{30}$. In this embodiment, $R_3$ is preferably selected from the group consisting of (i) bicyclic aryl, tricyclic aryl, bicyclic heteroaryl, and tricyclic heteroaryl (such as naphthyl, indolyl, isoindolyl, indazolyl, indolizinyl, quinolizinyl, quinolinyl, isoquinolinyl, phthalazinyl, naphthyridinyl, quinoxalinyl, quinazolinyl, cinnolinyl, and pteridinyl) or (ii) phenyl, pyridyl, pyrazinyl, pyrimidinyl, pyridazinyl, naphthyl, indolyl, isoindolyl, indazolyl, indolizinyl, quinolizinyl, quinolinyl, isoquinolinyl, phthalazinyl, naphthyridinyl, quinoxalinyl, quinazolinyl, cinnolinyl, and pteridinyl, each of which is optionally substituted with one, two or three independently selected $R^{30}$. More preferably, $R_3$ is selected from the group consisting of phenyl, naphthyl, indolyl, and quinolinyl (such as naphthyl, indolyl, and quinolinyl), each of which is optionally substituted with one, two or three independently selected $R^{30}$.

In any of the above embodiments of the pyrazolopyridine derivative of the general formula (IIIa) or (IIIb), $R_3$, when it does not join together with $R^8$, may be unsubstituted or, alternatively, may be substituted, wherein each of the substituents $R^{30}$ bound to $R_3$ is selected from the group consisting of the typical 1$^{st}$ level substituents, 2$^{nd}$ level substituents, and 3$^{rd}$ level substituents specified above. In a preferred embodiment of the pyrazolopyridine derivative of the general formula (IIIa) or (IIIb), wherein $R_3$ does not join together with $R^8$ and is substituted, each of the substituents $R^{30}$ bound to $R_3$ is selected from the group consisting of $C_{1-4}$ alkyl, $C_{2-4}$ alkenyl, $C_{2-4}$ alkynyl, 5- or 6-membered aryl, 5- or 6-membered heteroaryl, 3- to 7-membered cycloalkyl, 3- to 7-membered heterocyclyl, halogen, —CF$_3$, —CHF$_2$, —CH$_2$F, —CN, azido, —NO$_2$, —OH, —O(C$_{1-3}$ alkyl), —OCF$_3$, —OCHF$_2$, —OCH$_2$F, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{2-z}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and $C_{1-3}$ alkyl is methyl, ethyl, propyl or isopropyl. In one embodiment of the pyrazolopyridine derivative of the general formula (IIIa) or (IIIb), wherein $R_3$ does not join together with $R^8$ and is substituted, each of the substituents $R^{30}$ bound to $R_3$ is selected from the group consisting of $C_{1-3}$ alkyl, halogen (in particular, —F, —Cl, —Br), —CF$_3$, —CHF$_2$, —CH$_2$F, —CN, —OH, —O(C$_{1-3}$ alkyl), —OCF$_3$, —OCHF$_2$, —OCH$_2$F, —S(C$_{1-3}$ alkyl), —NH$_2$, —NH(C$_{1-3}$ alkyl), —N(C$_{1-3}$ alkyl)$_2$, —C(=O)O(C$_{1-3}$ alkyl), —C(=O)NH$_{2-z}$(C$_{1-3}$ alkyl)$_z$, and —NHC(=O)(C$_{1-3}$ alkyl), wherein z is 0, 1, or 2 and $C_{1-3}$ alkyl is methyl, ethyl, propyl or isopropyl.

In any of the above embodiments of the pyrazolopyridine derivative of the general formula (IIIb), $R_2$, when it does not join together with $R^8$, is selected from the group consisting of —H, alkyl, alkenyl, alkynyl, aryl, heteroaryl, cycloalkyl, heterocyclyl, —S(O)$_{1-2}$R$^{11}$, —S(O)$_{1-2}$OR$^{11}$, —S(O)$_{1-2}$N(R$^{12}$)(R$^{13}$), —C(=X)R$^{11}$, and —C(=X)XR$^{11}$, wherein each of the alkyl, alkenyl, alkynyl, aryl, heteroaryl, cycloalkyl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$ or the alkyl group is substituted with one $R^{31}$. In one embodiment of the pyrazolopyridine derivative of the general formula (IIIb), $R_2$, when it does not join together with $R^8$, is selected from the group consisting of —H, $C_{1-10}$ alkyl, $C_{2-10}$ alkenyl, 5- or 6-membered aryl, 5- to 7-membered heteroaryl, 3- to 10-membered cycloalkyl, 4- to 10-membered heterocyclyl, —C(=X)R$^{11}$, and —C(=X)XR$^{11}$, wherein each of the $C_{1-10}$ alkyl, $C_{2-10}$ alkenyl, 5- or 6-membered aryl, 5- to 7-membered heteroaryl, 3- to 10-membered cycloalkyl, and 4- to 10-membered heterocyclyl groups is optionally substituted with one or more (such as 1 to the maximum number of hydrogen atoms bound to the group, e.g., 1, 2, 3, 4, 5, 6, 7, 8, 9, or up to 10, such as between 1 to 5, 1 to 4, or 1 to 3, or 1 or 2) independently selected $R^{30}$ or the $C_{1-10}$ alkyl group is substituted with one $R^{31}$. In one embodiment of the pyrazolopyridine derivative of the general formula (IIIb), $R_2$, when it does not join together with $R^8$, is selected from the group consisting of —H, $C_{1-6}$ alkyl, $C_{2-6}$ alkenyl, $C_{6-14}$ aryl (such as phenyl), 5- to 10-membered heteroaryl (such as 5- or 6-membered heteroaryl), 4- to 10-membered cycloalkyl (such as 4- to 6-membered cycloalkyl), 4- to 10-membered heterocyclyl (such as 4- to 6-membered heterocyclyl), —C(=X)R$^{11}$, and —C(=X)XR$^{11}$ (such as —C(=O)O(C$_{1-3}$ alkyl) and —C(=O)NH$_{2-z}$(C$_{1-3}$ alkyl)$_z$, wherein z is 0, 1, or 2 and $C_{1-3}$ alkyl is methyl, ethyl, propyl or isopropyl), wherein each of the $C_{1-6}$ alkyl, $C_{2-6}$ alkenyl, $C_{6-14}$ aryl (such as phenyl), 5- to 10-membered heteroaryl (such as 5- or 6-membered heteroaryl), 4- to 10-membered cycloalkyl (such as 4- to 6-membered cycloalkyl), and 4- to 10-membered heterocyclyl (such as 4- to 6-membered heterocyclyl) groups is optionally substituted with one, two or three independently selected $R^{30}$ or the $C_{1-6}$ alkyl group is substituted with one $R^{31}$. In one embodiment of the pyrazolopyridine derivative of the general formula (IIIb), $R_2$, when it does not join together with $R^8$, is selected from the group consisting of —H, methyl, ethyl, propyl, isopropyl, phenyl, 5- or 6-membered heteroaryl, 4-, 5- or 6-membered cycloalkyl, 4-, 5-, or 6-membered heterocyclyl, —C(=O)O(C$_{1-3}$ alkyl), and —C(=O)NH$_{2-z}$(C$_{1-3}$ alkyl)$_z$, wherein z is 0, 1, or 2, wherein each of the methyl, ethyl, propyl, isopropyl, phenyl, 5- or 6-membered heteroaryl, 4-, 5- or 6-membered cycloalkyl, and 4-, 5-, or 6-membered heterocyclyl groups is optionally substituted with one, two, or three independently selected $R^{30}$ or the methyl, ethyl, propyl, isopropyl group is substituted with one $R^{31}$, and $C_{1-3}$ alkyl is methyl, ethyl, propyl or isopropyl.

In any of the above embodiments of the pyrazolopyridine derivative of the general formula (IIIb), $R_2$, when it does not join together with $R^8$, may be unsubstituted or, alternatively, may bear one or more (such as one, two, or three) $R^{30}$ groups, each $R^{30}$ being independently selected from the group consisting of the typical 1$^{st}$ level substituents, 2$^{nd}$ level substituents, and 3$^{rd}$ level substituents specified above, such as $C_{1-4}$ alkyl, $C_{2-4}$ alkenyl, $C_{2-4}$ alkynyl, 5- or 6-membered aryl, 5- or 6-membered heteroaryl, 3- to 7-membered cycloalkyl, 3- to 7-membered heterocyclyl, halogen, —$CF_3$, —$CHF_2$, —$CH_2F$, —CN, azido, —$NO_2$, —OH, —O($C_{1-3}$ alkyl), —$OCF_3$, —$OCHF_2$, —$OCH_2F$, —S($C_{1-3}$ alkyl), —$NH_2$, —NH($C_{1-3}$ alkyl), —N($C_{1-3}$ alkyl)$_2$, —NHS(O)$_2$ ($C_{1-3}$ alkyl), —S(O)$_2$NH$_{2-z}$($C_{1-3}$ alkyl)$_z$, —C(═O)OH, —C(═O)O($C_{1-4}$ alkyl), —C(═O)NH$_{2-z}$($C_{1-4}$ alkyl)$_z$, —NHC(═O)($C_{1-4}$ alkyl), —NHC(═NH)NH$_{2-z}$($C_{1-4}$ alkyl)$_z$, and —N($C_{1-4}$ alkyl)C(═NH)NH$_{2-z}$($C_{1-4}$ alkyl)$_z$, wherein z is 0, 1, or 2. In one embodiment, each of the substituents $R^{30}$ bound to $R_2$ is selected from the group consisting of $C_{1-3}$ alkyl, phenyl, 6-membered heteroaryl, 6-membered heterocyclyl, halogen (in particular, —F, —Cl, —Br), —$CF_3$, —$CHF_2$, —$CH_2F$, —CN, —OH, —O($C_{1-3}$ alkyl), —$OCF_3$, —$OCHF_2$, —$OCH_2F$, —S($C_{1-3}$ alkyl), —$NH_2$, —NH($C_{1-3}$ alkyl), —N($C_{1-3}$ alkyl)$_2$, —C(═O)O ($C_{1-4}$ alkyl), —C(═O)NH$_{2-z}$($C_{1-3}$ alkyl)$_z$, and —NHC(═O) ($C_{1-3}$ alkyl), wherein z is 0, 1, or 2 and $C_{1-3}$ alkyl is methyl, ethyl, propyl or isopropyl. Thus, in one embodiment of the pyrazolopyridine derivative of the general formula (IIIb), $R_2$, when it does not join together with $R^8$, is selected from the group consisting of —H; $C_{1-6}$ alkyl, optionally substituted with one substituent selected from the group consisting of OH, —C(═O)O($C_{1-4}$ alkyl), phenyl, 6-membered heteroaryl (such as pyridyl), and 6-membered heterocyclyl (such as morpholino); —C(═O)O($C_{1-3}$ alkyl); phenyl; 6-membered heteroaryl (such as pyrazinyl); and 5- or 6-membered cycloalkyl. In an alternative embodiment of the pyrazolopyridine derivative of the general formula (IIIb), when $R_2$ does not join together with $R^8$ and bears one $R^{31}$ group, $R^{31}$ may be —$Y_4$—B, wherein $Y_4$ is preferably selected from the group consisting of —C(═X)X—, —XC (═X)—, and —XC(═X)X— and B is a molecular probe, especially a fluorescent dye.

In one embodiment of the pyrazolopyridine derivative of the general formula (IIIa) or (IIIb), $R_3$ and $R^8$ join together with the atoms to which they are attached to form a polycyclic ring which is optionally substituted with one or more (such as 1 to the maximum number of hydrogen atoms bound to the polycyclic ring, e.g., 1, 2, 3, 4, 5, 6, 7, 8, 9, or up to 10, such as between 1 to 5, 1 to 4, or 1 to 3, or 1 or 2) independently selected $R^{30}$. In this embodiment, $R_2$ is as specified above, when it does not join $R^8$, and the polycyclic ring contains at least one N atom which is preferably attached to C3 of the core structure (i.e., the 4,5,6,7-tetrahydro-1H-pyrazolo[4,3-c]pyridyl moiety) via a carbonyl group (i.e., when $L_3$ is —C(O)—N($R^8$)-(alkylene)-) or directly (i.e., when $L_3$ is —N($R^8$)—C(O)-(alkylene)-)). In one embodiment of the pyrazolopyridine derivative of the general formula (IIIa) or (IIIb), the polycyclic ring formed by joining $R_3$ and $R^8$ is a bi- or tricyclic heteroaryl or heterocyclyl (such as an 8- to 14-membered bi- or tricyclic heteroaryl or 8- to 14-membered bi- or tricyclic heterocyclyl each containing a ring N atom and optionally 1, 2, 3, or 4 additional ring heteroatoms selected from O, N, and S, wherein in each ring of the heteroaryl or heterocyclyl group the maximum number of O atoms is 1, the maximum number of S atoms is 1, and the maximum total number of O and S atoms is 2), which is optionally substituted with one, two or three independently selected $R^{30}$. In one embodiment of the pyrazolopyridine derivative of the general formula (IIIa) or (IIIb), the polycyclic ring formed by joining $R_3$ and $R^8$ is selected from quinolinyl, isoquinolinyl, and partially or fully hydrated forms thereof (e.g., 1,2,3,4-tetrahydroisoquinolinyl), wherein the polycyclic ring is optionally substituted with one, two or three independently selected $R^{30}$.

In any of the above embodiments of the pyrazolopyridine derivative of the general formula (IIIa) or (IIIb), when $R_3$ and $R^8$ join together with the atoms to which they are attached to form a polycyclic ring, the polycyclic ring may be unsubstituted. Alternatively, in any of the above embodiments of the pyrazolopyridine derivative of the general formula (IIIa) or (IIIb), when $R_3$ and $R^8$ join together with the atoms to which they are attached to form a polycyclic ring, the polycyclic ring may bear one or more (such as one, two, or three) $R^{30}$ groups and each $R^{30}$ is independently selected from the group consisting of the typical 1$^{st}$ level substituents, 2$^{nd}$ level substituents, and 3$^{rd}$ level substituents specified above, such as $C_{1-4}$ alkyl, $C_{2-4}$ alkenyl, $C_{2-4}$ alkynyl, 5- or 6-membered aryl, 5- or 6-membered heteroaryl, 3- to 7-membered cycloalkyl, 3- to 7-membered heterocyclyl, halogen, —$CF_3$, —$CHF_2$, —$CH_2F$, —CN, azido, —$NO_2$, —OH, —O($C_{1-3}$ alkyl), —$OCF_3$, —$OCHF_2$, —$OCH_2F$, —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(═O)OH, —C(═O)O($C_{1-4}$ alkyl), —C(═O)NH$_{2-z}$ ($C_{1-4}$ alkyl)$_z$, —NHC(═O)($C_{1-4}$ alkyl), —NHC(═NH) NH$_{2-z}$ ($C_{1-4}$ alkyl)$_z$, and —N($C_{1-4}$ alkyl)C(═NH)NH$_{2-z}$($C_{1-4}$ alkyl)$_z$, wherein z is 0, 1, or 2; and/or any two $R^{30}$ which are bound to the same carbon atom of the ring may join together to form ═O.

In one embodiment of the pyrazolopyridine derivative of the general formula (IIIb), $R_2$ and $R^8$ join together with the atoms to which they are attached to form a ring which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$. In this embodiment, $R_3$ is as specified above, when it does not join $R^8$, and the ring contains at least two N atoms. In one embodiment of the pyrazolopyridine derivative of the general formula (IIIb), the ring formed by joining $R_2$ and $R^8$ is a monocyclic 5- to 7-membered heterocyclyl (containing two ring N atoms and optionally 1 or 2 additional ring heteroatoms selected from O, N, and S, wherein the maximum number of O atoms is 1, and the maximum number of S atoms is 1), which is optionally substituted with one, two or three independently selected $R^{30}$. In one embodiment of the pyrazolopyridine derivative of the general formula (IIIb), the ring formed by joining $R_2$ and $R^8$ is selected from di- and tetrahydroimidazolyl, piperazinyl, and diazepanyl, wherein the ring is optionally substituted with one, two or three independently selected $R^{30}$.

In any of the above embodiments of the pyrazolopyridine derivative of the general formula (IIIb), when $R_2$ and $R^8$ join together with the atoms to which they are attached to form a ring, the ring may be unsubstituted. Alternatively, in any of the above embodiments of the pyrazolopyridine derivative of the general formula (IIIb), when $R_2$ and $R^8$ join together with the atoms to which they are attached to form a ring, the ring may bear one or more (such as one, two, or three) $R^{30}$ groups and each $R^{30}$ is independently selected from the group consisting of the typical 1$^{st}$ level substituents, 2$^{nd}$ level substituents, and 3$^{rd}$ level substituents specified above, such as $C_{1-4}$ alkyl, $C_{2-4}$ alkenyl, $C_{2-4}$ alkynyl, 5- or 6-membered aryl, 5- or 6-membered heteroaryl, 3- to 7-membered cycloalkyl, 3- to 7-membered heterocyclyl, halogen, —$CF_3$, —$CHF_2$, —$CH_2F$, —CN, azido, —$NO_2$, —OH, —O($C_{1-3}$ alkyl), —$OCF_3$, —$OCHF_2$, —$OCH_2F$, —S($C_{1-3}$ alkyl), —$NH_2$, —NH($C_{1-3}$ alkyl), —N($C_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-4}$ alkyl), —C(=O)NH$_{2-z}$(C$_{1-4}$ alkyl)$_z$, —NHC(=O)(C$_{1-4}$ alkyl), —NHC(=NH)NH$_{z-2}$(C$_{1-4}$ alkyl)$_z$, and —N(C$_{1-4}$ alkyl)C(=NH)NH$_{2-z}$(C$_{1-4}$ alkyl)$_z$, wherein z is 0, 1, or 2, and/or any two R$^{30}$ which are bound to the same carbon atom of the ring may join together to form =O.

In one embodiment, the pyrazolopyridine derivative has the general formula (IVa) or (IVb)

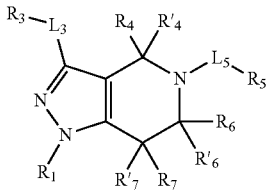

(IVa)

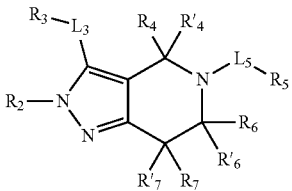

(IVb)

wherein R$_2$, R$_3$, R$_4$, R'$_4$, R$_5$, R$_6$, R'$_6$, R$_7$, R'$_7$, L$_3$ and L$_5$ are as defined above (in particular with respect to formulas (Ia), (Ib), (IIa), (IIb), (IIIa) and (IIIb)) or below and R$_1$ is selected from the group consisting of —H, C$_{1-10}$ alkyl, C$_{2-10}$ alkenyl, 5- or 6-membered aryl, 5- to 7-membered heteroaryl, 3- to 10-membered cycloalkyl, 4- to 10-membered heterocyclyl, —C(=X)R$^{11}$, and —C(=X)XR$^{11}$, wherein each of the C$_{1-10}$ alkyl, C$_{2-10}$ alkenyl, 5- or 6-membered aryl, 5- to 7-membered heteroaryl, 3- to 10-membered cycloalkyl, and 4- to 10-membered heterocyclyl groups is optionally substituted with one or more (such as 1 to the maximum number of hydrogen atoms bound to the C$_{1-10}$ alkyl, C$_{2-10}$ alkenyl, 5- or 6-membered aryl, 5- to 7-membered heteroaryl, 3- to 10-membered cycloalkyl, or 4- to 10-membered heterocyclyl group, e.g., 1, 2, 3, 4, 5, 6, 7, 8, 9, or up to 10, such as between 1 to 5, 1 to 4, or 1 to 3, or 1 or 2) independently selected R$^{30}$ or the C$_{1-10}$ alkyl group is substituted with one R$^{31}$. In one embodiment of the pyrazolopyridine derivative of the general formula (IVa) or (IVb), R$_1$ is selected from the group consisting of —H, C$_{1-6}$ alkyl, C$_{2-6}$ alkenyl, C$_{6-14}$ aryl (such as phenyl), 5- to 10-membered heteroaryl (such as 5- or 6-membered heteroaryl), 4- to 10-membered cycloalkyl (such as 4- to 6-membered cycloalkyl), 4- to 10-membered heterocyclyl (such as 4- to 6-membered heterocyclyl), —C(=X)R$^{11}$, and —C(=X)XR$^{11}$ (such as —C(=O)O(C$_{1-3}$ alkyl) and —C(=O)NH$_{2-z}$(C$_{1-3}$ alkyl)$_z$, wherein z is 0, 1, or 2 and C$_{1-3}$ alkyl is methyl, ethyl, propyl or isopropyl), wherein each of the C$_{1-6}$ alkyl, C$_{2-6}$ alkenyl, C$_{6-14}$ aryl (such as phenyl), 5- to 10-membered heteroaryl (such as 5- or 6-membered heteroaryl), 4- to 10-membered cycloalkyl (such as 4- to 6-membered cycloalkyl), and 4- to 10-membered heterocyclyl (such as 4- to 6-membered heterocyclyl) groups is optionally substituted with one, two or three independently selected R$^{30}$ or the C$_{1-6}$ alkyl group is substituted with one R$^{31}$. In one embodiment of the pyrazolopyridine derivative of the general formula (IVa) or (IVb), R$_1$ is selected from the group consisting of —H, C$_{1-6}$ alkyl (such as methyl, ethyl, propyl, isopropyl, 3,3-dimethylbutyl, preferably methyl, ethyl, and propyl), C$_{2-3}$ alkenyl (such as vinyl, 1-propenyl, 2-propenyl, preferably vinyl), phenyl, 5- or 6-membered heteroaryl (preferably a 5- or 6-membered heteroaryl containing 1, 2, or 3 ring nitrogen atoms, such as pyrazinyl), 4-, 5- or 6-membered cycloalkyl, 4-, 5-, or 6-membered heterocyclyl (preferably a 4-, 5-, or 6-membered heterocyclyl containing 1, 2, 3 ring heteroatoms selected from N and O (wherein the maximum number of O ring atoms is 1), e.g., a 4-membered heterocyclyl containing 1 ring nitrogen atom, a 5- or 6-membered heterocyclyl containing 1 or 2 ring nitrogen atoms, or a 5- or 6-membered heterocyclyl containing 1 ring nitrogen atom and 1 ring oxygen atom, such as azetidinyl and oxazinanyl, e.g., 1,4-oxazinyl (morpholinyl)), —C(=O)OH, —C(=O)O(C$_{1-3}$ alkyl), and —C(=O)NH$_{2-z}$(C$_{1-3}$ alkyl)$_z$, wherein z is 0, 1, or 2, wherein each of the C$_{1-6}$ alkyl (such as methyl, ethyl, propyl, isopropyl, 3,3-dimethylbutyl, preferably methyl, ethyl, and propyl), C$_{2-3}$ alkenyl (such as vinyl, 1-propenyl, 2-propenyl, preferably vinyl), phenyl, 5- or 6-membered heteroaryl (preferably a 5- or 6-membered heteroaryl containing 1, 2, or 3 ring nitrogen atoms, such as pyrazinyl), 4-, 5- or 6-membered cycloalkyl, and 4-, 5-, or 6-membered heterocyclyl (preferably a 4-, 5-, or 6-membered heterocyclyl containing 1, 2, 3 ring heteroatoms selected from N and O (wherein the maximum number of O ring atoms is 1), e.g., a 4-membered heterocyclyl containing 1 ring nitrogen atom, a 5- or 6-membered heterocyclyl containing 1 or 2 ring nitrogen atoms, or a 5- or 6-membered heterocyclyl containing 1 ring nitrogen atom and 1 ring oxygen atom, such as azetidinyl and oxazinanyl, e.g., 1,4-oxazinyl (morpholinyl)) groups is optionally substituted with one, two, or three independently selected R$^{30}$ or the methyl, ethyl, propyl, isopropyl group is substituted with one R$^{31}$, and C$_{1-3}$ alkyl is methyl, ethyl, propyl or isopropyl. In one embodiment of the pyrazolopyridine derivative of the general formula (IVa) or (IVb), R$_1$ is selected from the group consisting of —H, methyl, ethyl, propyl, isopropyl, phenyl, 5- or 6-membered heteroaryl, 4-, 5- or 6-membered cycloalkyl, 4-, 5-, or 6-membered heterocyclyl, —C(=O)OH, —C(=O)O(C$_{1-3}$ alkyl), and —C(=O)NH$_{2-z}$(C$_{1-3}$ alkyl)$_z$, wherein z is 0, 1, or 2, wherein each of the methyl, ethyl, propyl, isopropyl, phenyl, 5- or 6-membered heteroaryl, 4-, 5- or 6-membered cycloalkyl, and 4-, 5-, or 6-membered heterocyclyl groups is optionally substituted with one, two, or three independently selected R$^{30}$ or the methyl, ethyl, propyl, isopropyl group is substituted with one R$^{31}$, and C$_{1-3}$ alkyl is methyl, ethyl, propyl or isopropyl.

In any of the above embodiments of the pyrazolopyridine derivative of the general formula (IVa) or (IVb), R$_1$ may be unsubstituted or, alternatively, may bear one or more (such as one, two, or three) R$^{30}$ groups, each R$^{30}$ being independently selected from the group consisting of the typical 1$^{st}$ level substituents, 2$^{nd}$ level substituents, and 3$^{rd}$ level substituents specified above, such as C$_{1-4}$ alkyl, C$_{2-4}$ alkenyl, C$_{2-4}$ alkynyl, 5- or 6-membered aryl (such as phenyl), 5- or 6-membered heteroaryl (preferably a 5- or 6-membered heteroaryl containing 1, 2, or 3 ring nitrogen atoms, such as imidazolyl, pyrazolyl, or pyridinyl), 3- to 7-membered cycloalkyl, 3- to 7-membered heterocyclyl (preferably a 3-, 4-, 5-, 6-, or 7-membered heterocyclyl containing 1, 2, 3 ring heteroatoms selected from N and O, e.g., a 3- or 4-membered heterocyclyl containing 1 ring nitrogen atom, a 5-, 6-, or 7-membered heterocyclyl containing 1 or 2 ring nitrogen atoms, or a 5- or 6- or 7-membered heterocyclyl containing 1 ring nitrogen atom and 1 ring oxygen atom), halogen, —CF$_3$, —CHF$_2$, —CH$_2$F, —CN, azido, —NO$_2$, —OH, —O(C$_{1-3}$ alkyl), —OCF$_3$, —OCHF$_2$, —OCH$_2$F, —S(C$_{1-3}$ alkyl), —NH$_2$, —NH(C$_{1-4}$ alkyl optionally substituted with one OH or NH$_2$ moiety) (such as —NH(C$_{1-3}$ alkyl)), —N(C$_{1-4}$ alkyl optionally substituted with one OH or NH$_2$ moiety)$_2$ (such as —N(C$_{1-3}$ alkyl)$_2$), —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-4}$ alkyl) (such as —C(=O)O-ethyl or —C(=O)O-tert-butyl), —C(=O)NH$_{2-z}$(C$_{1-4}$ alkyl)$_z$ (such as —C(O)NH$_2$), —NHC(=O)(C$_{1-4}$ alkyl) (such as —NHC(O)CH$_3$), —NHC(=NH)NH$_{z-2}$(C$_{1-4}$ alkyl)$_z$ (such as —NHC(=NH)NH$_2$), and —N(C$_{1-4}$ alkyl)C(=NH)NH$_{2-z}$(C$_{1-4}$ alkyl)$_z$, wherein z is 0, 1, or 2 and C$_{1-4}$ alkyl preferably is methyl, ethyl, propyl, isopropyl, butyl or tert-butyl. In one embodiment, each of the substituents R$^{30}$ is selected from the group consisting of C$_{1-4}$ alkyl, C$_{2-4}$ alkenyl, C$_{2-4}$ alkynyl, 5- or 6-membered aryl, 5- or 6-membered heteroaryl, 3- to 7-membered cycloalkyl, 3- to 7-membered heterocyclyl, halogen, —CF$_3$, —CHF$_2$, —CH$_2$F, —CN, azido, —NO$_2$, —OH, —O(C$_{1-3}$ alkyl), —OCF$_3$, —OCHF$_2$, —OCH$_2$F, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-4}$ alkyl), —C(=O)NH$_{2-z}$(C$_{1-4}$ alkyl)$_z$, —NHC(=O)(C$_{1-4}$ alkyl), —NHC(=NH)NH$_{z-2}$(C$_{1-4}$ alkyl)$_z$, and —N(C$_{1-4}$ alkyl)C(=NH)NH$_{2-z}$(C$_{1-4}$ alkyl)$_z$, wherein z is 0, 1, or 2. In one embodiment, each of the substituents R$^{30}$ is selected from the group consisting of C$_{1-3}$ alkyl, phenyl, 6-membered heteroaryl, 6-membered heterocyclyl, halogen (in particular, —F, —Cl, —Br), —CF$_3$, —CHF$_2$, —CH$_2$F, —CN, —OH, —O(C$_{1-3}$ alkyl), —OCF$_3$, —OCHF$_2$, —OCH$_2$F, —S(C$_{1-3}$ alkyl), —NH$_2$, —NH(C$_{1-3}$ alkyl), —N(C$_{1-3}$ alkyl)$_2$, —C(=O)O(C$_{1-4}$ alkyl), —C(=O)NH$_{2-z}$(C$_{1-3}$ alkyl)$_z$, and —NHC(=O)(C$_{1-3}$ alkyl), wherein z is 0, 1, or 2 and C$_{1-3}$ alkyl is methyl, ethyl, propyl or isopropyl. Thus, in one embodiment of the pyrazolopyridine derivative of the general formula (IVa) or (IVb), R$_1$ is selected from the group consisting of —H; C$_{1-6}$ alkyl, optionally substituted with one substituent selected from the group consisting of OH, —C(=O)O(C$_{1-4}$ alkyl), phenyl, 6-membered heteroaryl (such as pyridyl), and 6-membered heterocyclyl (such as morpholino); —C(=O)O(C$_{1-3}$ alkyl); phenyl; 6-membered heteroaryl (such as pyrazinyl); and 5- or 6-membered cycloalkyl. In an alternative embodiment of the pyrazolopyridine derivative of the general formula (IVa) or (IVb), when R$_1$ is bears one R$^{31}$ group, R$^{31}$ may be —Y$_4$—B, wherein Y$_4$ is preferably selected from the group consisting of —C(=X)X—, —XC(=X)—, and —XC(=X)X— and B is a molecular probe, especially a fluorescent dye. For example, when R$_1$ is C$_{1-6}$ alkyl optionally substituted with one, two, or three independently selected R$^{30}$, it is preferred that R$_1$ is C$_{1-6}$ alkyl (preferably C$_{1-4}$ alkyl) optionally substituted with one or two (preferably one) independently selected R$^{30}$, wherein R$^{30}$ is selected from the group consisting of —OH, —NH$_2$, —NH(C$_{1-4}$ alkyl optionally substituted with one OH or NH$_2$ moiety), —N(C$_{1-4}$ alkyl optionally substituted with one OH or NH$_2$ moiety)$_2$, —NHC(=NH)NH$_2$, —NHC(=O)(C$_{1-4}$ alkyl) (such as —NHC(O)CH$_3$), —C(=O)OH, —C(=O)O(C$_{1-4}$ alkyl) (such as —C(=O)O-ethyl or —C(=O)O-tert-butyl), —C(=O)NH$_{2-z}$(C$_{1-4}$ alkyl)$_z$ (such as —C(O)NH$_2$), phenyl, and 5- or 6-membered heteroaryl (preferably a 5- or 6-membered heteroaryl containing 1, 2, or 3 ring nitrogen atoms, such as imidazolyl, pyrazolyl, or pyridinyl), wherein z is 0, 1, or 2 and C$_{1-4}$ alkyl preferably is methyl, ethyl, propyl, isopropyl, butyl or tert-butyl. If C$_{1-6}$ alkyl is substituted with two R$^{30}$, (i) both substituents R$^{30}$ can be independently selected from the group consisting of —OH, —NH$_2$, —NH(C$_{1-4}$ alkyl optionally substituted with one OH or NH$_2$ moiety), —N(C$_{1-4}$ alkyl optionally substituted with one OH or NH$_2$ moiety)$_2$, —NHC(=NH)NH$_2$, —NHC(=O)(C$_{1-4}$ alkyl) (such as —NHC(O)CH$_3$), —C(=O)OH, —C(=O)O(C$_{1-4}$ alkyl) (such as —C(=O)O-ethyl or —C(=O)O-tert-butyl), —C(=O)NH$_{2-z}$(C$_{1-4}$ alkyl)$_z$ (such as —C(O)NH$_2$), phenyl, and 5- or 6-membered heteroaryl (preferably a 5- or 6-membered heteroaryl containing 1, 2, or 3 ring nitrogen atoms, such as imidazolyl, pyrazolyl, or pyridinyl), wherein z is 0, 1, or 2 and C$_{1-4}$ alkyl preferably is methyl, ethyl, propyl, isopropyl, butyl or tert-butyl; or (ii) one substituent R$^{30}$ is OH, whereas the other substituent R$^{30}$ is selected from the moieties specified under (i).

In one embodiment, the pyrazolopyridine derivative has the general formula (Va) or (Vb)

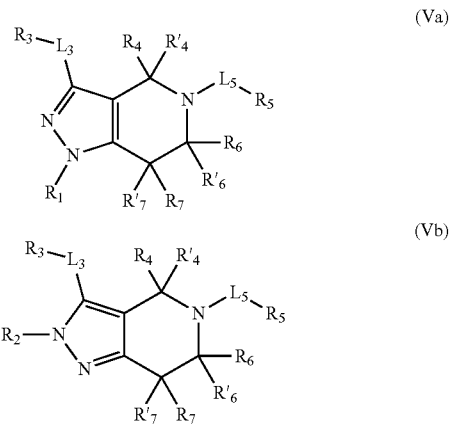

wherein R$_1$, R$_2$, R$_3$, R$_4$, R'$_4$, R$_5$, R$_6$, R'$_6$, R$_7$, R'$_7$, and L$_3$ are as defined above (in particular with respect to formulas (Ia), (Ib), (IIa), (IIb), (IIIa), (IIIb), (IVa), and (IVb)) or below and L$_5$ is selected from the group consisting of C$_{1-3}$ alkylene, —(C$_{1-3}$ alkylene)-Y$_1$—(C$_{1-3}$ alkylene)$_m$-* and —Y$_3$—(C$_{1-3}$ alkylene)$_o$-*, wherein * is the attachment point to R$_5$; m is 0 or 1; Y$_1$ is selected from the group consisting of —C(=X)—, —C(=X)X—, —XC(=X)—, —S(O)$_{1-2}$—, —S(O)$_{1-2}$N(R$^9$)—, and —N(R$^9$)—S(O)$_{1-2}$—, wherein X is O or S; Y$_3$ is selected from the group consisting of —C(=O)— and —S(O)$_{1-2}$—; o is 0 or 1; and each of the C$_{1-3}$ alkylene groups is optionally substituted with one or more (such as 1 to the maximum number of hydrogen atoms bound to the C$_{1-3}$ alkylene group, e.g., 1, 2, 3, 4, 5, or 6, such as between 1 to 5, 1 to 4, or 1 to 3, or 1 or 2) independently selected R$^{30}$. In one embodiment of the pyrazolopyridine derivative of the general formula (Va) or (Vb), L$_5$ is —(C$_{1-3}$ alkylene optionally substituted with one R$^{30}$)—*, —C(O)—(C$_{1-3}$ alkylene)-*, or —C(O)—*. In one embodiment of the pyrazolopyridine derivative of the general formula (Va) or (Vb), L$_5$ is —CH$_2$—*, —CH$_2$CH$_2$—*, —CH$_2$CH(phenyl)-*, —C(O)—CH$_2$— or —C(O)—*.

In any of the above embodiments of the pyrazolopyridine derivative of the general formula (Va) or (Vb), R$_5$ may be selected from the group consisting of C$_{6-14}$ aryl, 5- to 7-membered heteroaryl, 3- to 10-membered cycloalkyl, or 4- to 10-membered heterocyclyl, such as phenyl, naphthyl, phenantryl, furanyl, thienyl, pyrrolyl, imidazolyl, pyrazolyl, thiazolyl, isothiazolyl, oxazaolyl, isoxazolyl, pyranyl, pyridinyl, pyrazinyl, pyrimidinyl, pyridazinyl, pyrrolizinyl, indolizinyl, indolyl, isoindolyl, indazolyl, quinolizinyl, quinolinyl, isochinolinyl, phthalizinyl, naphthyridinyl, quinoxalinyl, quinazolinyl, cinnolinyl, pteridinyl, purinyl, carbazolyl, phenanthridinyl, acridinyl, phenanthrolinyl, benzodioxolyl, imidazothiazolyl, imidazoimidazolyl, pyrrolopyrrolyl, chromenyl, benzofuranyl, isobenzofuranyl, benzodioxinyl, benzoxazolyl, benzoisoxazolyl, partially or completely hydrogenated forms of these heteroaryl or heterocyclyl groups (such as partially or completely hydrogenated forms of naphthyl, e.g., tetrahydronaphthyl such as 5,6,7,8-tetrahydronaphthalen-1-yl), cyclopropyl, cyclobutyl, cyclopentyl, cyclohexyl, cyclohexenyl, cycloheptyl, and cyclononyl, wherein each of these groups is optionally substituted with one, two or three independently selected $R^{30}$. In one embodiment of the pyrazolopyridine derivative of the general formula (Va) or (Vb), $R_5$ is selected from the group consisting of phenyl, naphthyl, tetrahydronaphthyl (such as 5,6,7,8-tetrahydronaphthalen-1-yl), phenantryl, indolyl, pyrazolyl, pyrrolyl, quinolinyl, benzodioxolyl, imidazothiazolyl, tetrahydrochromenyl, benzofuranyl, benzodioxinyl, tetrahydrobenzoxazolyl (e.g., 4,5,6,7-tetrahydro-1,2-benzoxazolyl), cyclopropyl, cyclohexenyl, indazolyl, and tetrahydroisoquinolinyl (e.g., 1,2,3,4-tetrahydroisoquinolinyl), each of which is optionally substituted with one, two or three independently selected $R^{30}$. In one embodiment of the pyrazolopyridine derivative of the general formula (Va) or (Vb), $R_5$ is selected from the group consisting of phenyl, naphthyl, phenantryl, indolyl, pyrazolyl, pyrrolyl, quinolinyl, benzodioxolyl, imidazothiazolyl, tetrahydrochromenyl, benzofuranyl, benzodioxinyl, tetrahydrobenzoxazolyl (e.g., 4,5,6,7-tetrahydro-1,2-benzoxazolyl), cyclopropyl, cyclohexenyl, indazolyl, and tetrahydroisoquinolinyl (e.g., 1,2,3,4-tetrahydroisoquinolinyl), each of which is optionally substituted with one, two or three independently selected $R^{30}$.

In one embodiment of the pyrazolopyridine derivative of the general formula (Va) or (Vb), -$L_5R_5$ is selected from the group consisting of —($C_{1-3}$ alkylene)-$R_5$, —($C_{1-3}$ alkylene)-$Y_1$—($C_{1-3}$ alkylene)$_m$-$R_5$ and —$Y_3$—($C_{1-3}$ alkylene)$_o$-$R_5$, wherein m is 0 or 1; $Y_1$ is selected from the group consisting of —C(=X)—, —C(=X)X—, —XC(=X)—, —S(O)$_{1-2}$—, —S(O)$_{1-2}$N($R^9$)—, and —N($R^9$)—S(O)$_{1-2}$—, wherein X is O or S; $Y_3$ is selected from the group consisting of —C(=O)— and —S(O)$_{1-2}$—; o is 0 or 1; each of the $C_{1-3}$ alkylene groups is optionally substituted with one or more (such as 1 to the maximum number of hydrogen atoms bound to the $C_{1-3}$ alkylene group, e.g., 1, 2, 3, 4, 5, or 6, such as between 1 to 5, 1 to 4, or 1 to 3, or 1 or 2) independently selected $R^{30}$; and $R_5$ is selected from the group consisting of $C_{6-14}$ aryl, 5- to 7-membered heteroaryl, 3- to 10-membered cycloalkyl, or 4- to 10-membered heterocyclyl, such as phenyl, naphthyl, phenantryl, furanyl, thienyl, pyrrolyl, imidazolyl, pyrazolyl, thiazolyl, isothiazolyl, oxazaolyl, isoxazolyl, pyranyl, pyridinyl, pyrazinyl, pyrimidinyl, pyridazinyl, pyrrolizinyl, indolizinyl, indolyl, isoindolyl, indazolyl, quinolizinyl, quinolinyl, isochinolinyl, phthalizinyl, naphthyridinyl, quinoxalinyl, quinazolinyl, cinnolinyl, pteridinyl, purinyl, carbazolyl, phenanthridinyl, acridinyl, phenanthrolinyl, benzodioxolyl, imidazothiazolyl, imidazoimidazolyl, pyrrolopyrrolyl, chromenyl, benzofuranyl, isobenzofuranyl, benzodioxinyl, benzoxazolyl, benzoisoxazolyl, partially or completely hydrogenated forms of these heteroaryl or heterocyclyl groups (such as partially or completely hydrogenated forms of naphthyl, e.g., tetrahydronaphthyl such as 5,6,7,8-tetrahydronaphthalen-1-yl), cyclopropyl, cyclobutyl, cyclopentyl, cyclohexyl, cyclohexenyl, cycloheptyl, and cyclononyl, wherein each of these groups is optionally substituted with one, two or three independently selected $R^{30}$. In one embodiment of the pyrazolopyridine derivative of the general formula (Va) or (Vb), -$L_5R_5$ is selected from the group consisting of —($C_{1-3}$ alkylene)-$R_5$, —$Y_3$—$R_5$, and —$Y_3$—($C_{1-3}$ alkylene)-$R_5$, wherein $Y_3$ is selected from the group consisting of —C(=O)— and —S(O)$_{1-2}$—; and each of the $C_{1-3}$ alkylene groups is optionally substituted with one or two independently selected $R^{30}$ (preferably, -$L_5R_5$ is —($C_{1-3}$ alkylene optionally substituted with one $R^{30}$)—$R_5$, —C(O)—($C_{1-3}$ alkylene)-$R_5$, or —C(O)—$R_5$, such as —$CH_2$—$R_5$, —$CH_2CH_2$—$R_5$, —$CH_2CH$(phenyl)-$R_5$, —C(O)—$CH_2$—$R_5$ or —C(O)—$R_5$); and $R_5$ is selected from the group consisting of (i) phenyl, naphthyl, tetrahydronaphthyl (such as 5,6,7,8-tetrahydronaphthalen-1-yl), phenantryl, indolyl, pyrazolyl, pyrrolyl, quinolinyl, benzodioxolyl, imidazothiazolyl, tetrahydrochromenyl, benzofuranyl, benzodioxinyl, tetrahydrobenzoxazolyl (e.g., 4,5,6,7-tetrahydro-1,2-benzoxazolyl), cyclopropyl, cyclohexenyl, indazolyl, and tetrahydroisoquinolinyl (e.g., 1,2,3,4-tetrahydroisoquinolinyl), each of which is optionally substituted with one, two or three independently selected $R^{30}$; or (ii) phenyl, naphthyl, phenantryl, indolyl, pyrazolyl, pyrrolyl, quinolinyl, benzodioxolyl, imidazothiazolyl, tetrahydrochromenyl, benzofuranyl, benzodioxinyl, tetrahydrobenzoxazolyl (e.g., 4,5,6,7-tetrahydro-1,2-benzoxazolyl), cyclopropyl, cyclohexenyl, indazolyl, and tetrahydroisoquinolinyl (e.g., 1,2,3,4-tetrahydroisoquinolinyl), each of which is optionally substituted with one, two or three independently selected $R^{30}$.

In any of the above embodiments of the pyrazolopyridine derivative of the general formula (Va) or (Vb), $R_5$ may be unsubstituted or, alternatively, may bear one or more (such as 1, 2, or 3) $R^{30}$, each $R^{30}$ being independently selected from the group consisting of the typical 1$^{st}$ level substituents, 2$^{nd}$ level substituents, and 3$^{rd}$ level substituents specified above. In an exemplary embodiment of the pyrazolopyridine derivative of the general formula (Va) or (Vb), when $R_5$ bears one or more (such as 1, 2, or 3) $R^{30}$, each $R^{30}$ is independently selected from the group consisting of $C_{1-6}$ alkyl (such as $C_{1-4}$ alkyl), $C_{2-6}$ alkenyl (such as $C_{2-4}$ alkenyl), $C_{2-6}$ alkynyl (such as $C_{2-4}$ alkynyl), 3- to 14-membered (such as 5-, 6-, 10, or 14-membered) aryl, 3- to 14-membered (such as monocyclic (e.g., 5- or 6-membered), bicyclic (e.g., 9- or 10-membered), or tricyclic (e.g., 13- or 14-membered)) heteroaryl, 3- to 14-membered (such as monocyclic (e.g., 3-, 4-, 5-, 6-, or to 7-membered), bicyclic (e.g., 8-, 9-, or 10-membered), or tricyclic (e.g., 12-, 13-, or 14-membered)) cycloalkyl, 3- to 14-membered (such as monocyclic (e.g., 3-, 4-, 5-, 6-, or to 7-membered), bicyclic (e.g., 8-, 9-, or 10-membered), or tricyclic (e.g., 12-, 13-, or 14-membered)) heterocyclyl, halogen, —CN, azido, —$NO_2$, —$OR^{71}$, —N($R^{72}$)($R^{73}$), —S(O)$_{0-2}R^{71}$, —S(O)$_{0-2}OR^{71}$, —OS(O)$_{0-2}R^{71}$, —OS(O)$_{0-2}OR^{71}$, —S(O)$_{0-2}$N($R^{72}$)($R^{73}$), —OS(O)$_{0-2}$N($R^{72}$)($R^{73}$), —N($R^{71}$)S(O)$_{0-2}R^{71}$, —$NR^{71}$S(O)$_{0-2}OR^{71}$, —C(=$X^1$)$R^{71}$, —C(=$X^1$)$X^1R^{71}$, —$X^1$C(=$X^1$)$R^{71}$, and —$X^1$C(=$X^1$)$X^1R^{71}$, wherein the $C_{1-6}$ alkyl, 3- to 14-membered aryl, 3- to 14-membered heteroaryl, 3- to 14-membered cycloalkyl, and 3- to 14-membered heterocyclyl groups are optionally substituted with 1, 2, or 3 substituents independently selected from the 2$^{nd}$ level substituents as specified above, e.g., halogen, $C_{1-3}$ alkyl, OH, and $OCH_3$; $R^{71}$, $R^{72}$, and $R^{73}$ are independently selected from the group consisting of —H; $C_{1-6}$ alkyl (such as $C_{1-3}$ alkyl); $C_{1-6}$ alkyl (such as $C_{1-3}$ alkyl) substituted with 1, 2, or 3 substituents independently selected from halogen, $C_{1-3}$ alkyl, OH, and $OCH_3$; —($C_{1-6}$ alkylene)phenyl (such as —($C_{1-3}$ alkylene)phenyl); 3- to 7-membered cycloalkyl; 5- or 6-membered aryl (such as phenyl); 5- or 6-membered heteroaryl; and 3- to 7-membered heterocyclyl; and $X^1$ is independently selected from O, S, and $NR^{84}$, wherein $R^{84}$ is —H or $C_{1-3}$ alkyl; and/or any two $R^{30}$ which are bound to the same carbon atom of a cycloalkyl or heterocyclyl group may join together to form =O. For example, if $R^{30}$ is $C_{1-6}$ alkyl (such as $C_{1-4}$ alkyl) it may be substituted with 1, 2, or 3 independently selected halogens; or if $R^{30}$ is 3- to 14-membered (such as 5-, 6-, 10, or 14-membered) aryl, 3- to 14-membered (such as monocyclic (e.g., 5- or 6-membered), bicyclic (e.g., 9- or 10-membered), or tricyclic (e.g., 13- or 14-membered)) heteroaryl, 3- to 14-membered (such as monocyclic (e.g., 3-, 4-, 5-, 6-, or to 7-membered), bicyclic (e.g., 8-, 9-, or 10-membered), or tricyclic (e.g., 12-, 13-, or 14-membered)) cycloalkyl, or 3- to 14-membered (such as monocyclic (e.g., 3-, 4-, 5-, 6-, or to 7-membered), bicyclic (e.g., 8-, 9-, or 10-membered), or tricyclic (e.g., 12-, 13-, or 14-membered)) heterocyclyl it may be substituted with 1, 2, or 3 substituents independently selected from halogen (in particular F, Cl, Br), $C_{1-3}$ alkyl, OH, and $OCH_3$. In any of the above embodiments of the pyrazolopyridine derivative of the general formula (Va) or (Vb), when $R_5$ bears one or more (such as 1, 2, or 3) $R^{30}$, each $R^{30}$ may be independently selected from the group consisting of $C_{1-4}$ alkyl (such as methyl, ethyl, n-propyl, or isobutyl); $C_{1-4}$ alkyl (such as methyl, ethyl, n-propyl, or isobutyl) substituted with 1, 2, or 3 independently selected halogens (such as —$CF_3$, —$CHF_2$, —$CH_2F$); $C_{2-4}$ alkenyl (such as $C_{2-3}$ alkenyl); 5- or 6-membered aryl (such as phenyl); 5- or 6-membered aryl (such as phenyl) substituted with 1, 2, or 3 substituents independently selected from halogen, $C_{1-3}$ alkyl, and OH; 5- or 6-membered heteroaryl (such as furyl or pyridyl); 5- to 6-membered cycloalkyl; 5- to 6-membered heterocyclyl; halogen (in particular F, Cl, Br); —OH; —O($C_{1-3}$ alkyl); —$OCF_3$; —$OCHF_2$; —$OCH_2F$; —$OCH_2$(phenyl); —$NH_2$; —NH($C_{1-3}$ alkyl); —N($C_{1-3}$ alkyl)$_2$; —C(=O)($C_{1-3}$ alkyl); —COOH; —C(=O)O($C_{1-3}$ alkyl); —C(=O)$NH_{2-z}$($C_{1-3}$ alkyl)$_z$; and —NHC(=O)($C_{1-3}$ alkyl), wherein z is 0, 1, or 2 and $C_{1-3}$ alkyl is methyl, ethyl, propyl or isopropyl, and/or any two $R^{30}$ which are bound to the same carbon atom of a cycloalkyl or heterocyclyl group may join together to form =O. In any of the above embodiments of the pyrazolopyridine derivative of the general formula (Va) or (Vb), when $R_5$ bears one or more (such as 1, 2, or 3) $R^{30}$, each $R^{30}$ may be independently selected from the group consisting of $C_{1-4}$ alkyl (such as methyl, ethyl, n-propyl, or isobutyl); $C_{1-4}$ alkyl (such as methyl, ethyl, n-propyl, or isobutyl) substituted with 1, 2, or 3 independently selected halogens (such as —$CF_3$, —$CHF_2$, —$CH_2F$); $C_{2-4}$ alkenyl (such as $C_{2-3}$ alkenyl); 5- or 6-membered aryl (such as phenyl); 5- or 6-membered aryl (such as phenyl) substituted with 1, 2, or 3 substituents independently selected from halogen, $C_{1-3}$ alkyl, and OH; 5- or 6-membered heteroaryl (such as furyl or pyridyl); 5- to 6-membered cycloalkyl; 5- to 6-membered heterocyclyl; halogen (in particular F, Cl, Br); —OH; —O($C_{1-3}$ alkyl); —$OCF_3$; —$OCHF_2$; —$OCH_2F$; —$OCH_2$(phenyl); —$NH_2$; —NH($C_{1-3}$ alkyl); —N($C_{1-3}$ alkyl)$_2$; —C(=O)($C_{1-3}$ alkyl); —C(=O)O($C_{1-3}$ alkyl); —C(=O)$NH_{2-z}$($C_{1-3}$ alkyl)$_z$; and —NHC(=O)($C_{1-3}$ alkyl), wherein z is 0, 1, or 2 and $C_{1-3}$ alkyl is methyl, ethyl, propyl or isopropyl, and/or any two $R^{30}$ which are bound to the same carbon atom of a cycloalkyl or heterocyclyl group may join together to form =O.

In one embodiment, the pyrazolopyridine derivative has the general formula (VIa) or (VIb)

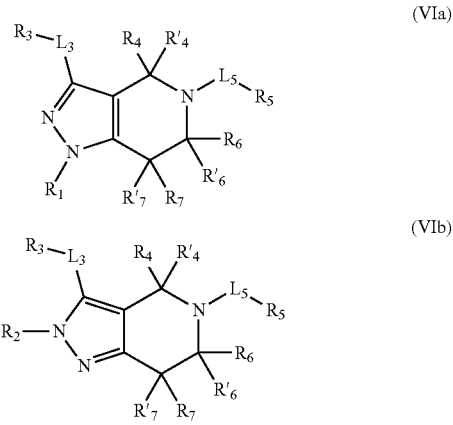

wherein $R_1$, $R_2$, $R_3$, $R_5$, $L_3$, and $L_5$ are as defined above (in particular with respect to formulas (Ia), (Ib), (IIa), (IIb), (IIIa), (IIIb), (IVa), (IVb), (Va), and (Vb)) or below and $R_4$, $R'_4$, $R_6$, $R'_6$, $R_7$, and $R'_7$ are independently selected from the group consisting of H, $C_{1-3}$ alkyl, halogen, —$CF_3$, —OH, —$OCH_3$, —$SCH_3$, —$NH_{2-z}(CH_3)_z$, —C(=O)OH, and —C(=O)$OCH_3$, wherein z is 0, 1, or 2. In one embodiment of the pyrazolopyridine derivative of the general formula (VIa) or (VIb), each of $R_4$, $R'_4$, $R_6$, $R'_6$, $R_7$, and $R'_7$ is H. In one embodiment of the pyrazolopyridine derivative of the general formula (VIa) or (VIb), one of $R_4$, $R'_4$, $R'_6$, $R_7$, and $R'_7$ is selected from the group consisting of $C_{1-3}$ alkyl, halogen, —$CF_3$, —OH, —$OCH_3$, —$SCH_3$, —$NH_{2-z}(CH_3)_z$, —C(=O)OH, and —C(=O)$OCH_3$, wherein z is 0, 1, or 2, and the remainder of $R_4$, $R'_4$, $R_6$, $R'_6$, $R_7$, and $R'_7$ is H.

In one embodiment, the pyrazolopyridine derivative has the general formula (VIIa) or (VIIb)

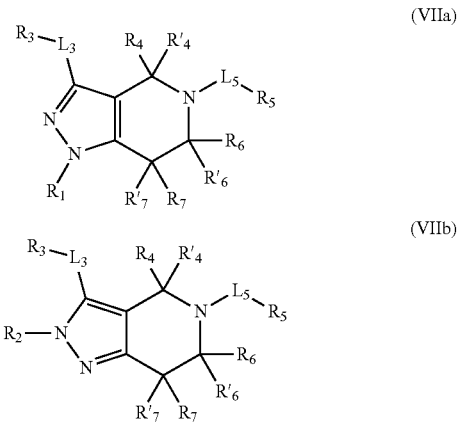

wherein $L_3$ is as defined for formulas (IIa) and (IIb) above; $R_4$, $R'_4$, $R_6$, $R'_6$, $R_7$, and $R'_7$ are as defined for formulas (VIa) and (VIb) above; and $R_1$, $R_2$, $R_3$, $R_5$, and $L_5$ are as defined above (in particular with respect to formulas (Ia), (Ib), (IIIa), (IIIb), (IVa), (IVb), (Va), and (Vb)). In one embodiment of the pyrazolopyridine derivative of formula (VIIa) or (VIIb), -$L_3R_3$ is —C(O)—N($R^8$)—($C_{1-6}$ alkylene)-$R_3$, preferably —C(O)—N($R^8$)—($C_{1-3}$ alkylene)-$R_3$, such as —C(O)—N($R^8$)—$CH_2$—$R_3$ or —C(O)—N($R^8$)—CH($CH_3$)—$R_3$; either each of $R_4$, $R'_4$, $R_6$, $R'_6$, $R_7$, and $R'_7$ is H or one of $R_4$, $R'_4$, $R_6$, $R'_6$, $R_7$, and $R'_7$ is selected from the group consisting of $C_{1-3}$ alkyl, halogen, —$CF_3$, —OH, —$OCH_3$, —$SCH_3$, —$NH_{2-z}(CH_3)_z$, —C(=O)OH, and —C(=O)$OCH_3$, wherein z is 0, 1, or 2, and the remainder of $R_4$, $R'_4$, $R_6$, $R'_6$, $R_7$, and $R'_7$ is H (preferably all of $R_4$, $R'_4$, $R_6$, $R'_6$, $R_7$, and $R'_7$ are H); and $R_1$, $R_2$, $R_3$, $R_5$, and $L_5$ are as defined above (in particular with respect to formulas (Ia), (Ib), (IIIa), (IIIb), (IVa), (IVb), (Va), and (Vb)).

In one embodiment, the pyrazolopyridine derivative has the general formula (VIIIa) or (VIIIb)

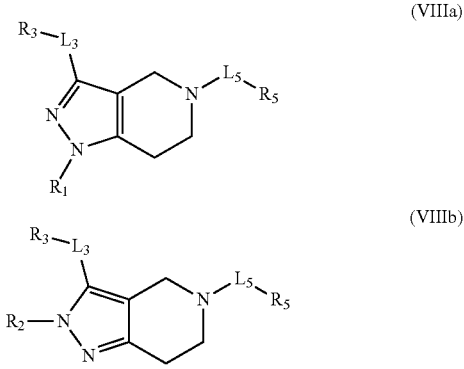

wherein -$L_3R_3$ is —C(O)—N($R^8$)—($C_{1-6}$ alkylene)-$R_3$, preferably —C(O)—N($R^8$)—($C_{1-3}$ alkylene)-$R_3$ (such as —C(O)—N($R^8$)—$CH_2$—$R_3$ or —C(O)—N($R^8$)—CH($CH_3$)—$R_3$); -$L_5R_5$ is selected from the group consisting of —($C_{1-3}$ alkylene)-$R_5$, —$Y_3$—$R_5$, and —$Y_3$—($C_{1-3}$ alkylene)-$R_5$, wherein $Y_3$ is selected from the group consisting of —C(=O)— and —S(O)$_{1-2}$—; and each of the $C_{1-3}$ alkylene groups is optionally substituted with one or two independently selected $R^{30}$ (preferably, -$L_5R_5$ is —($C_{1-3}$ alkylene optionally substituted with one $R^{30}$)—$R_5$, —C(O)—($C_{1-3}$ alkylene)-$R_5$, or —C(O)—$R_5$, such as —$CH_2$—$R_5$, —$CH_2CH_2$—$R_5$, —$CH_2$CH(phenyl)-$R_5$, —C(O)—$CH_2$—$R_5$ or —C(O)—$R_5$); and $R_1$, $R_2$, $R_3$, and $R_5$ are as defined above (in particular with respect to formulas (Ia), (Ib), (IIIa), (IIIb), (IVa), (IVb), (Va), and (Vb)). In a preferred embodiment of the pyrazolopyridine derivative of formula (VIIIa) or (VIIIb), $R_5$ is selected from the group consisting of phenyl, naphthyl, phenantryl, furanyl, thienyl, pyrrolyl, imidazolyl, pyrazolyl, thiazolyl, isothiazolyl, oxazaolyl, isoxazolyl, pyranyl, pyridinyl, pyrazinyl, pyrimidinyl, pyridazinyl, pyrrolizinyl, indolizinyl, indolyl, isoindolyl, indazolyl, quinolizinyl, quinolinyl, isochinolinyl, phthalizinyl, naphthyridinyl, quinoxalinyl, quinazolinyl, cinnolinyl, pteridinyl, purinyl, carbazolyl, phenanthridinyl, acridinyl, phenanthrolinyl, benzodioxolyl, imidazothiazolyl, imidazoimidazolyl, pyrrolopyrrolyl, chromenyl, benzofuranyl, isobenzofuranyl, benzodioxinyl, benzoxazolyl, benzoisoxazolyl, partially or completely hydrogenated forms of these heteroaryl or heterocyclyl groups (such as partially or completely hydrogenated forms of naphthyl, e.g., tetrahydronaphthyl such as 5,6,7,8-tetrahydronaphthalen-1-yl), cyclopropyl, cyclobutyl, cyclopentyl, cyclohexyl, cyclohexenyl, cycloheptyl, and cyclononyl, wherein each of these groups is optionally substituted with one, two or three independently selected $R^{30}$; preferably, $R_5$ is selected from the group consisting of (i) phenyl, naphthyl, tetrahydronaphthyl (such as 5,6,7,8-tetrahydronaphthalen-1-yl)phenantryl, indolyl, pyrazolyl, pyrrolyl, quinolinyl, benzodioxolyl, imidazothiazolyl, tetrahydrochromenyl, benzofuranyl, benzodioxinyl, tetrahydrobenzoxazolyl (e.g., 4,5,6,7-tetrahydro-1,2-benzoxazolyl), cyclopropyl, cyclohexenyl, indazolyl, and tetrahydroisoquinolinyl (e.g., 1,2,3,4-tetrahydroisoquinolinyl), each of which is optionally substituted with one, two or three independently selected $R^{30}$, or (ii) phenyl, naphthyl, phenantryl, indolyl, pyrazolyl, pyrrolyl, quinolinyl, benzodioxolyl, imidazothiazolyl, tetrahydrochromenyl, benzofuranyl, benzodioxinyl, tetrahydrobenzoxazolyl (e.g., 4,5,6, 7-tetrahydro-1,2-benzoxazolyl), cyclopropyl, cyclohexenyl, indazolyl, and tetrahydroisoquinolinyl (e.g., 1,2,3,4-tetrahydroisoquinolinyl), each of which is optionally substituted with one, two or three independently selected $R^{30}$. Each $R^{30}$ bound to $R_5$ may be selected from the particular $R^{30}$ groups bound to $R_5$ as specified above, in particular with respect to any one of formulas (Va) and (Vb).

In any of the above embodiments of the pyrazolopyridine derivative of the general formula (VIIa), (VIIb), (VIIIa) or (VIIIb), $R_1$, $R_2$, and $R_3$ may have the following preferred meanings:

(1) In one embodiment, $R_1$ is selected from the group consisting of —H, $C_{1-6}$ alkyl, $C_{2-6}$ alkenyl, $C_{6-14}$ aryl (such as phenyl), 5- to 10-membered heteroaryl (such as 5- or 6-membered heteroaryl), 4- to 10-membered cycloalkyl (such as 4- to 6-membered cycloalkyl), 4- to 10-membered heterocyclyl (such as 4- to 6-membered heterocyclyl), —C(=X)$R^{11}$, and —C(=X)X$R^{11}$ (such as —C(=O)O($C_{1-3}$ alkyl) and —C(=O)$NH_{2-z}(C_{1-3}$ alkyl)$_z$, wherein z is 0, 1, or 2 and $C_{1-3}$ alkyl is methyl, ethyl, propyl or isopropyl), wherein each of the $C_{1-6}$ alkyl, $C_{2-6}$ alkenyl, $C_{6-14}$ aryl (such as phenyl), 5- to 10-membered heteroaryl (such as 5- or 6-membered heteroaryl), 4- to 10-membered cycloalkyl (such as 4- to 6-membered cycloalkyl), and 4- to 10-membered heterocyclyl (such as 4- to 6-membered heterocyclyl) groups is optionally substituted with one, two or three independently selected $R^{30}$ or the $C_{1-6}$ alkyl group is substituted with one $R^{31}$. In one embodiment, $R_1$ is selected from the group consisting of —H, $C_{1-6}$ alkyl (such as methyl, ethyl, propyl, isopropyl, 3,3-dimethylbutyl, preferably methyl, ethyl, and propyl), $C_{2-3}$ alkenyl (such as vinyl, 1-propenyl, 2-propenyl, preferably vinyl), phenyl, 5- or 6-membered heteroaryl (preferably a 5- or 6-membered heteroaryl containing 1, 2, or 3 ring nitrogen atoms, such as pyrazinyl), 4-, 5- or 6-membered cycloalkyl, 4-, 5-, or 6-membered heterocyclyl (preferably a 4-, 5-, or 6-membered heterocyclyl containing 1, 2, 3 ring heteroatoms selected from N and O (wherein the maximum number of O ring atoms is 1), e.g., a 4-membered heterocyclyl containing 1 ring nitrogen atom, a 5- or 6-membered heterocyclyl containing 1 or 2 ring nitrogen atoms, or a 5- or 6-membered heterocyclyl containing 1 ring nitrogen atom and 1 ring oxygen atom, such as azetidinyl and oxazinanyl, e.g., 1,4-oxazinyl (morpholinyl)), —C(=O)OH, —C(=O)O($C_{1-3}$ alkyl), and —C(=O)$NH_{2-z}(C_{1-3}$ alkyl)$_z$, wherein z is 0, 1, or 2 and $C_{1-3}$ alkyl is methyl, ethyl, propyl or isopropyl, wherein each of the $C_{1-6}$ alkyl (such as methyl, ethyl, propyl, isopropyl, 3,3-dimethylbutyl, preferably methyl, ethyl, and propyl), $C_{2-3}$ alkenyl (such as vinyl, 1-propenyl, 2-propenyl, preferably vinyl), phenyl, 5- or 6-membered heteroaryl (preferably a 5- or 6-membered heteroaryl containing 1, 2, or 3 ring nitrogen atoms, such as pyrazinyl), 4-, 5- or 6-membered cycloalkyl, and 4-, 5-, or 6-membered heterocyclyl (preferably a 4-, 5-, or 6-membered heterocyclyl containing 1, 2, 3 ring heteroatoms selected from N and O, e.g., a 4-membered heterocyclyl containing 1 ring nitrogen atom, a 5- or 6-membered heterocyclyl containing 1 or 2 ring nitrogen atoms, or a 5- or 6-membered heterocyclyl containing 1 ring nitrogen atom and 1 ring oxygen atom, such as azetidinyl and oxazinanyl, e.g., 1,4-oxazinyl (morpholinyl)) groups is optionally substituted with one, two, or three independently selected $R^{30}$ or the methyl, ethyl, propyl, isopropyl group is substituted with one $R^{31}$, and $C_{1-3}$ alkyl is methyl, ethyl, propyl or isopropyl. In one embodiment, $R_1$ is selected from the group consisting of —H, methyl, ethyl, propyl, isopropyl, phenyl, 5- or 6-membered heteroaryl, 4-, 5- or 6-membered cycloalkyl, 4-, 5-, or 6-membered heterocyclyl, —C(=O)OH, —C(=O)O($C_{1-3}$ alkyl), and —C(=O)$NH_{2-z}$($C_{1-3}$ alkyl)$_z$, wherein z is 0, 1, or 2, wherein each of the methyl, ethyl, propyl, isopropyl, phenyl, 5- or 6-membered heteroaryl, 4-, 5- or 6-membered cycloalkyl, and 4-, 5-, or 6-membered heterocyclyl groups is optionally substituted with one, two, or three independently selected $R^{30}$ or the methyl, ethyl, propyl, isopropyl group is substituted with one $R^{31}$, and $C_{1-3}$ alkyl is methyl, ethyl, propyl or isopropyl. In any case, $R^{30}$ may be selected from the group consisting of $C_{1-4}$ alkyl, $C_{2-4}$ alkenyl, $C_{2-4}$ alkynyl, 5- or 6-membered aryl (such as phenyl), 5- or 6-membered heteroaryl (preferably a 5- or 6-membered heteroaryl containing 1, 2, or 3 ring nitrogen atoms, such as imidazolyl, pyrazolyl, or pyridinyl), 3- to 7-membered cycloalkyl, 3- to 7-membered heterocyclyl (preferably a 3-, 4-, 5-, 6-, or 7-membered heterocyclyl containing 1, 2, 3 ring heteroatoms selected from N and O, e.g., a 3- or 4-membered heterocyclyl containing 1 ring nitrogen atom, a 5-, 6-, or 7-membered heterocyclyl containing 1 or 2 ring nitrogen atoms, or a 5-, 6- or 7-membered heterocyclyl containing 1 ring nitrogen atom and 1 ring oxygen atom), halogen, —$CF_3$, —$CHF_2$, —$CH_2F$, —CN, azido, —$NO_2$, —OH, —O($C_{1-3}$ alkyl), —$OCF_3$, —$OCHF_2$, —$OCH_2F$, —S($C_{1-3}$ alkyl), —$NH_2$, —NH($C_{1-4}$ alkyl optionally substituted with one OH or $NH_2$ moiety), —N($C_{1-4}$ alkyl optionally substituted with one OH or $NH_2$ moiety)$_2$, —NHS(O)$_2$($C_{1-3}$ alkyl), —S(O)$_2NH_{2-z}$($C_{1-3}$ alkyl)$_z$, —C(=O)OH, —C(=O)O($C_{1-4}$ alkyl) (such as —C(=O)O-ethyl or —C(=O)O-tert-butyl), —C(=O)$NH_{2-z}$($C_{1-4}$ alkyl)$_z$ (such as —C(O)$NH_2$), —NHC(=O)($C_{1-4}$ alkyl) (such as —NHC(O)$CH_3$), —NHC(=NH)$NH_{2-z}$($C_{1-4}$ alkyl)$_z$ (such as —NHC(=NH)$NH_2$), and —N($C_{1-4}$ alkyl)C(=NH)$NH_{2-z}$($C_{1-4}$ alkyl)$_z$, wherein z is 0, 1, or 2 and $C_{1-4}$ alkyl preferably is methyl, ethyl, propyl, isopropyl, butyl or tert-butyl. In one embodiment, each of the substituents $R^{30}$ is selected from the group consisting of $C_{1-4}$ alkyl, $C_{2-4}$ alkenyl, $C_{2-4}$ alkynyl, 5- or 6-membered aryl (such as phenyl), 5- or 6-membered heteroaryl (such as imidazolyl, pyrazolyl, or pyridinyl), 3- to 7-membered cycloalkyl, 3- to 7-membered heterocyclyl, halogen, —$CF_3$, —$CHF_2$, —$CH_2F$, —CN, azido, —$NO_2$, —OH, —O($C_{1-3}$ alkyl), —$OCF_3$, —$OCHF_2$, —$OCH_2F$, —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2NH_{2-z}$($C_{1-3}$ alkyl)$_z$, —C(=O)OH, —C(=O)O($C_{1-4}$ alkyl), —C(=O)$NH_{2-z}$($C_{1-4}$ alkyl)$_z$, —NHC(=O)($C_{1-4}$ alkyl), —NHC(=NH)$NH_{2-z}$($C_{1-4}$ alkyl)$_z$, and —N($C_{1-4}$ alkyl)C(=NH)$NH_{2-z}$($C_{1-4}$ alkyl)$_z$, wherein z is 0, 1, or 2. For example, $R^{30}$ may be selected from the group consisting of $C_{1-3}$ alkyl, phenyl, 6-membered heteroaryl, 6-membered heterocyclyl, halogen (in particular, —F, —Cl, —Br), —$CF_3$, —$CHF_2$, —$CH_2F$, —CN, —OH, —O($C_{1-3}$ alkyl), —$OCF_3$, —$OCHF_2$, —$OCH_2F$, —S($C_{1-3}$ alkyl), —$NH_2$, —NH($C_{1-3}$ alkyl), —N($C_{1-3}$ alkyl)$_2$, —C(=O)O($C_{1-4}$ alkyl), —C(=O)$NH_{2-z}$($C_{1-3}$ alkyl)$_z$, and —NHC(=O)($C_{1-3}$ alkyl), wherein z is 0, 1, or 2 and $C_{1-3}$ alkyl is methyl, ethyl, propyl or isopropyl; and $R^{31}$ may be —$Y_4$—B, wherein $Y_4$ is preferably selected from the group consisting of —C(=X)X—, —XC(=X)—, and —XC(=X)X— and B is a molecular probe, especially a fluorescent dye. For example, when $R_1$ is $C_{1-6}$ alkyl optionally substituted with one, two, or three independently selected $R^{30}$, it is preferred that $R_1$ is $C_{1-6}$ alkyl (preferably $C_{1-4}$ alkyl) optionally substituted with one or two (preferably one) independently selected $R^{30}$, wherein $R^{30}$ is selected from the group consisting of —OH, —$NH_2$, —NH($C_{1-4}$ alkyl optionally substituted with one OH or $NH_2$ moiety), —N($C_{1-4}$ alkyl optionally substituted with one OH or $NH_2$ moiety)$_2$, —NHC(=NH)$NH_2$, —NHC(=O)($C_{1-4}$ alkyl) (such as —NHC(O)$CH_3$), —C(=O)OH, —C(=O)O($C_{1-4}$ alkyl) (such as —C(=O)O-ethyl or —C(=O)O-tert-butyl), —C(=O)$NH_{2-z}$($C_{1-4}$ alkyl)$_z$ (such as —C(O)$NH_2$), phenyl, and 5- or 6-membered heteroaryl (preferably a 5- or 6-membered heteroaryl containing 1, 2, or 3 ring nitrogen atoms, such as imidazolyl, pyrazolyl, or pyridinyl), wherein z is 0, 1, or 2 and $C_{1-4}$ alkyl preferably is methyl, ethyl, propyl, isopropyl, butyl or tert-butyl. If $C_{1-6}$ alkyl is substituted with two $R^{30}$, (i) both substituents $R^{30}$ can be independently selected from the group consisting of —OH, —$NH_2$, —NH($C_{1-4}$ alkyl optionally substituted with one OH or $NH_2$ moiety), —N($C_{1-4}$ alkyl optionally substituted with one OH or $NH_2$ moiety)$_2$, —NHC(=NH)$NH_2$, —NHC(=O)($C_{1-4}$ alkyl) (such as —NHC(O)$CH_3$), —C(=O)OH, —C(=O)O($C_{1-4}$ alkyl) (such as —C(=O)O-ethyl or —C(=O)O-tert-butyl), —C(=O)$NH_{2-z}$($C_{1-4}$ alkyl)$_z$ (such as —C(O)$NH_2$), phenyl, and 5- or 6-membered heteroaryl (preferably a 5- or 6-membered heteroaryl containing 1, 2, or 3 ring nitrogen atoms, such as imidazolyl, pyrazolyl, or pyridinyl), wherein z is 0, 1, or 2 and $C_{1-4}$ alkyl preferably is methyl, ethyl, propyl, isopropyl, butyl or tert-butyl; or (ii) one substituent $R^{30}$ is OH, whereas the other substituent $R^{30}$ is selected from the moieties specified under (i).

(2) In one embodiment, $R_2$ does not join together with $R^8$ and is selected from the group consisting of —H, methyl, ethyl, propyl, isopropyl, phenyl, 5- or 6-membered heteroaryl, 4-, 5- or 6-membered cycloalkyl, 4-, 5-, or 6-membered heterocyclyl, —C(=O)O($C_{1-3}$ alkyl), and —C(=O)$NH_{2-z}$($C_{1-3}$ alkyl)$_z$, wherein z is 0, 1, or 2, wherein each of the methyl, ethyl, propyl, isopropyl, phenyl, 5- or 6-membered heteroaryl, 4-, 5- or 6-membered cycloalkyl, and 4-, 5-, or 6-membered heterocyclyl groups is optionally substituted with one, two, or three independently selected $R^{30}$ or the methyl, ethyl, propyl, isopropyl group is substituted with one $R^{31}$, and $C_{1-3}$ alkyl is methyl, ethyl, propyl or isopropyl. $R^{30}$ may be selected from the group consisting of $C_{1-3}$ alkyl, phenyl, 6-membered heteroaryl, 6-membered, heterocyclyl, halogen (in particular, —F, —Cl, —Br), —$CF_3$, —$CHF_2$, —$CH_2F$, —CN, —OH, —O($C_{1-3}$ alkyl), —$OCF_3$, —$OCHF_2$, —$OCH_2F$, —S($C_{1-3}$ alkyl), —$NH_2$, —NH($C_{1-3}$ alkyl), —N($C_{1-3}$ alkyl)$_2$, —C(=O)O($C_{1-4}$ alkyl), —C(=O)$NH_{2-z}$($C_{1-3}$ alkyl)$_z$, and —NHC(=O)($C_{1-3}$ alkyl), wherein z is 0, 1, or 2 and $C_{1-3}$ alkyl is methyl, ethyl, propyl or isopropyl; and $R^{31}$ may be —$Y_4$—B, wherein $Y_4$ is preferably selected from the group consisting of —C(=X)X—, —XC(=X)—, and —XC(=X)X— and B is a molecular probe, especially a fluorescent dye. $R^8$ may be selected from the particular groups specified above with respect to formulas (IIIa) and (IIIb).

(3) In one embodiment, $R_2$ and $R^8$ join together with the atoms to which they are attached to form a ring selected from di- and tetrahydroimidazolyl, piperazinyl, and diazepanyl, wherein the ring is optionally substituted with =O.

(4) In one embodiment, $R_3$ does not join together with $R^8$ and -$L_3R_3$ may be —C(O)—N($R^8$)—$CH_2$—$R_3$, —N($R^8$)—C(O)—$CH_2$—$R_3$, —C(O)—N($R^8$)—CH($CH_3$)—$R_3$, or —N($R^8$)—C(O)—CH($CH_3$)—$R_3$ (preferably —C(O)—N($R^8$)—$CH_2$—$R_3$ or —C(O)—N($R^8$)—CH($CH_3$)—$R_3$), wherein $R_3$ is preferably selected from the group consisting of (i) bicyclic aryl, tricyclic aryl, bicyclic heteroaryl, and tricyclic heteroaryl (such as naphthyl, indolyl, isoindolyl, indazolyl, indolizinyl, quinolizinyl, quinolinyl, isoquinolinyl, phthalazinyl, naphthyridinyl, quinoxalinyl, quinazolinyl, cinnolinyl, and pteridinyl) or (ii) phenyl, pyridyl, pyrazinyl, pyrimidinyl, pyridazinyl, naphthyl, indolyl, isoindolyl, indazolyl, indolizinyl, quinolizinyl, quinolinyl, isoquinolinyl, phthalazinyl, naphthyridinyl, quinoxalinyl, quinazolinyl, cinnolinyl, and pteridinyl (more preferably, selected from the group consisting of phenyl, naphthyl, indolyl, and quinolinyl, such as naphthyl, indolyl, and quinolinyl), each of which is optionally substituted with one, two or three independently selected $R^{30}$. $R^8$ may be selected from the particular groups specified above with respect to formulas (IIIa) and (IIIb). $R^8$ may be H and/or $R^{30}$ may be selected from methyl, halogen (in particular, —F, —Cl, —Br), and —$CF_3$.

(5) In one embodiment, $R_3$ and $R^8$ join together with the atoms to which they are attached to form a polycyclic ring which is selected from quinolinyl, isoquinolinyl, and partially or fully hydrated forms thereof (e.g., 1,2,3,4-tetrahydroisoquinolinyl), wherein the polycyclic ring is optionally substituted with one, two or three independently selected $R^{30}$. Each $R^{30}$ bound to the polycyclic ring may be selected from the particular $R^{30}$ groups bound to the polycyclic ring as specified above, in particular with respect to any one of formulas (IIIa) and (IIIb).

It is intended that the compounds of the present invention (in particular, the compounds of any one of formulas (Ia), (Ib), (IIa), (IIb), (IIIa), (IIIb), (IVa), (IVb), (Va), (Vb), (VIa), (VIb), (VIIa), (VIIb), (VIIIa), and (VIIIb), such as those depicted in Table 1, below) encompass not only the compounds as depicted but also their solvates (e.g., hydrates), salts (in particular, pharmaceutically acceptable salts), complexes, polymorphs, crystalline forms, non-crystalline forms, amorphous forms, racemic mixtures, non-racemic mixtures, diastereomers, enantiomers, tautomers, unlabeled forms, isotopically labeled forms, prodrugs, and any combinations thereof.

A selection of compounds within the scope of, or for use within the methods of, the present invention is listed in the following Table 1.

TABLE 1

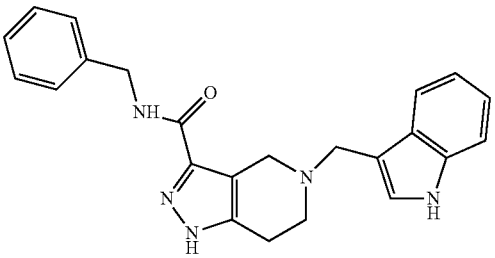 [SMILES: O=C(NCc1ccccc1)c1n[nH]c2c1CN(Cc1c[nH]c3ccccc13)CC2]

1

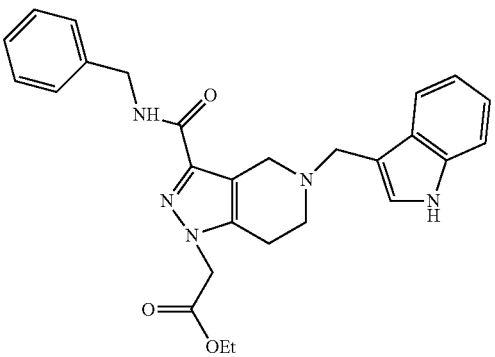 [SMILES: CCOC(=O)Cn1nc(C(=O)NCc2ccccc2)c2c1CCN(Cc1c[nH]c3ccccc13)C2]

2

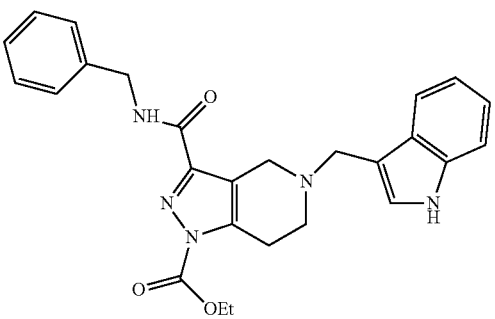 [SMILES: CCOC(=O)n1nc(C(=O)NCc2ccccc2)c2c1CCN(Cc1c[nH]c3ccccc13)C2]

3

TABLE 1-continued
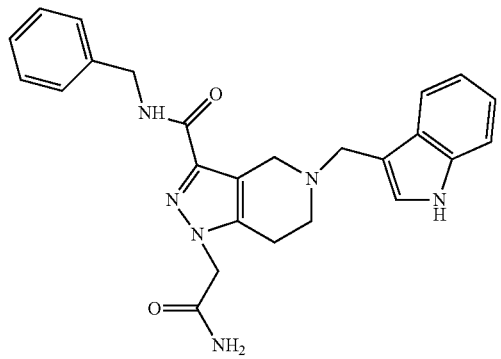 [SMILES: NC(=O)Cn1nc(C(=O)NCc2ccccc2)c2c1CCN(Cc1c[nH]c3ccccc13)C2]
4
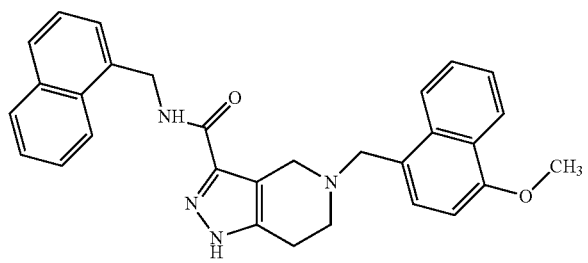 [SMILES: COc1ccc(CN2CCc3[nH]nc(C(=O)NCc4cccc5ccccc45)c3C2)c2ccccc12]
5
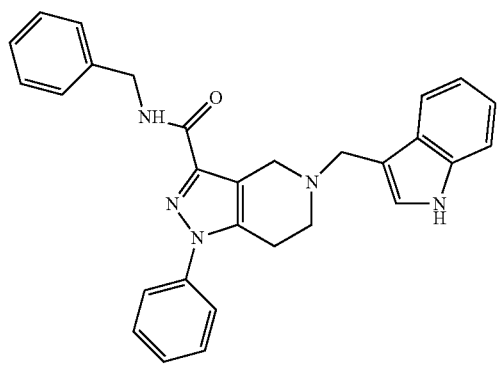 [SMILES: O=C(NCc1ccccc1)c1nn(-c2ccccc2)c2c1CN(Cc1c[nH]c3ccccc13)CC2]
6
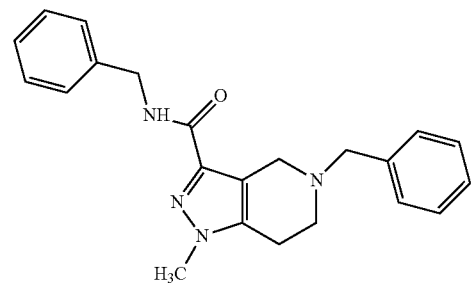 [SMILES: Cn1nc(C(=O)NCc2ccccc2)c2c1CCN(Cc1ccccc1)C2]
7
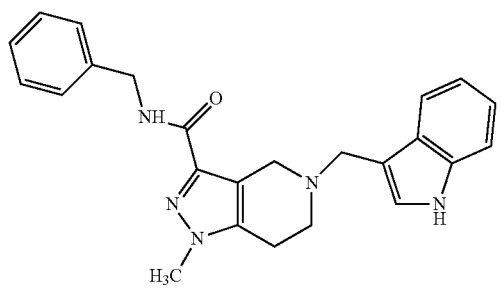 [SMILES: Cn1nc(C(=O)NCc2ccccc2)c2c1CCN(Cc1c[nH]c3ccccc13)C2]
8

TABLE 1-continued
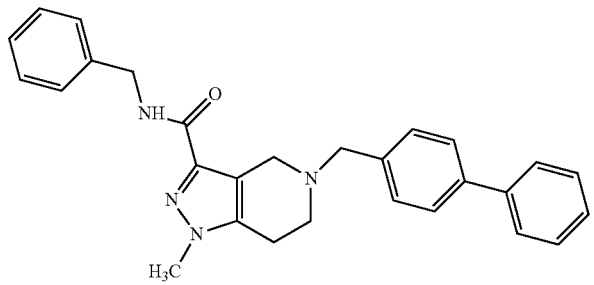 [SMILES: Cn1nc(C(=O)NCc2ccccc2)c2c1CCN(Cc1ccc(-c3ccccc3)cc1)C2]
9
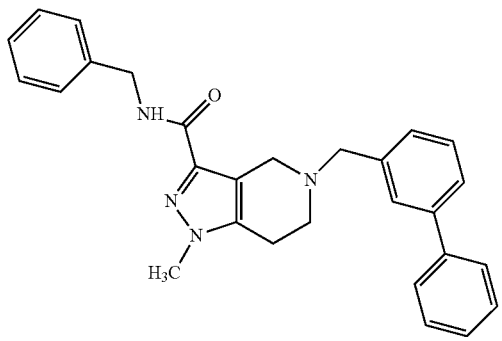 [SMILES: Cn1nc(C(=O)NCc2ccccc2)c2c1CCN(Cc1cccc(-c3ccccc3)c1)C2]
10
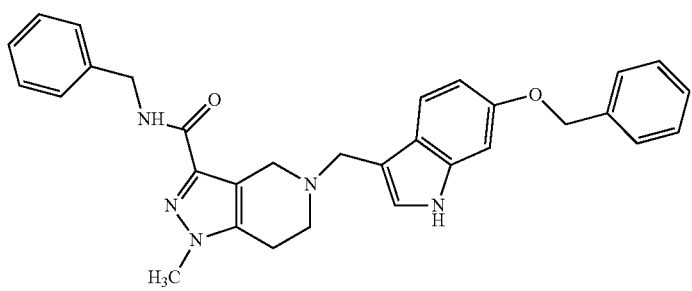 [SMILES: Cn1nc(C(=O)NCc2ccccc2)c2c1CCN(Cc1c[nH]c3cc(OCc4ccccc4)ccc13)C2]
11
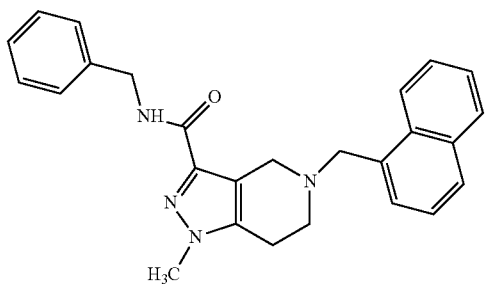 [SMILES: Cn1nc(C(=O)NCc2ccccc2)c2c1CCN(Cc1cccc3ccccc13)C2]
12
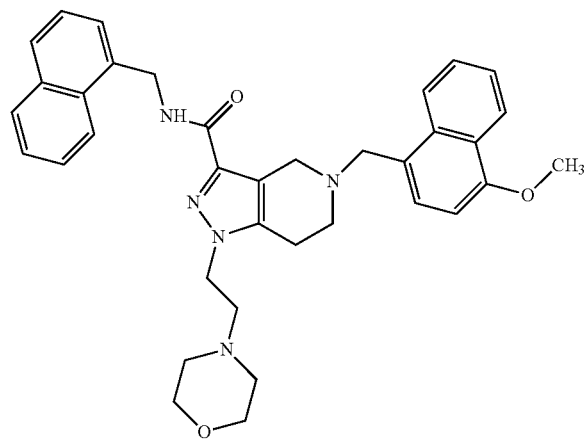 [SMILES: COc1ccc(CN2CCc3c(c(C(=O)NCc4cccc5ccccc45)nn3CCN3CCOCC3)C2)c2ccccc12]
13

TABLE 1-continued
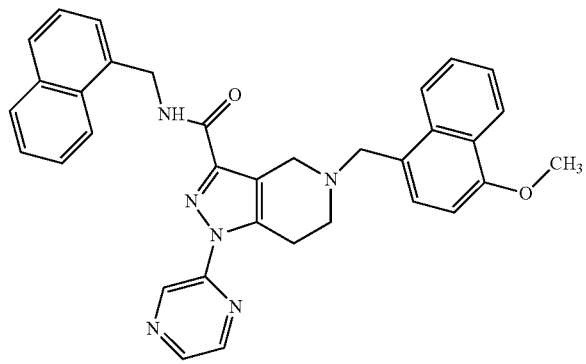 [SMILES: COc1ccc(CN2CCc3c(c(C(=O)NCc4cccc5ccccc45)nn3-c3cnccn3)C2)c2ccccc12]
14
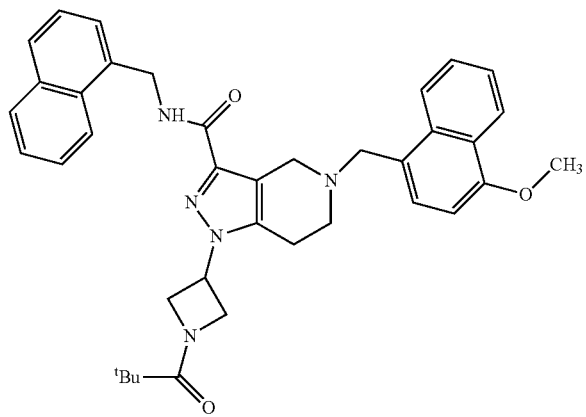 [SMILES: COc1ccc(CN2CCc3c(c(C(=O)NCc4cccc5ccccc45)nn3C3CN(C(=O)C(C)(C)C)C3)C2)c2ccccc12]
15
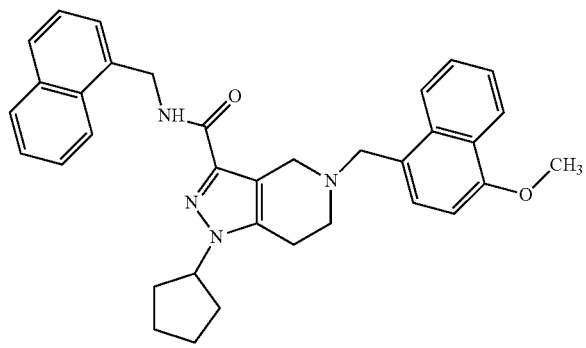 [SMILES: COc1ccc(CN2CCc3c(c(C(=O)NCc4cccc5ccccc45)nn3C3CCCC3)C2)c2ccccc12]
16
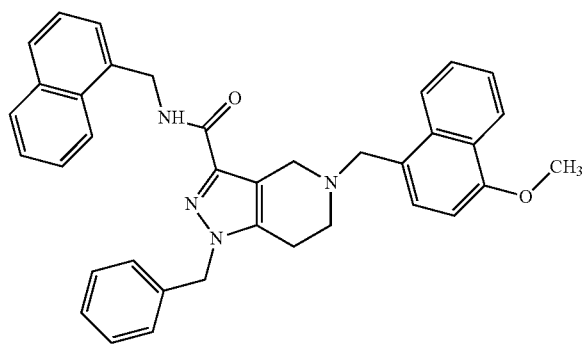 [SMILES: COc1ccc(CN2CCc3c(c(C(=O)NCc4cccc5ccccc45)nn3Cc3ccccc3)C2)c2ccccc12]
17

TABLE 1-continued
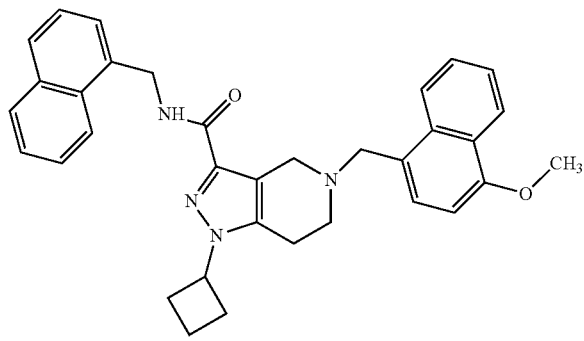 [SMILES: COc1ccc(CN2CCc3c(c(C(=O)NCc4cccc5ccccc45)nn3C3CCC3)C2)c2ccccc12]
18
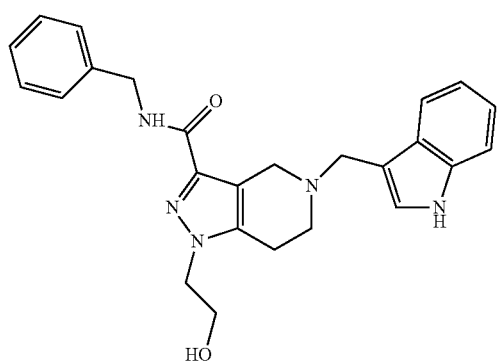 [SMILES: O=C(NCc1ccccc1)c1nn(CCO)c2c1CN(Cc1c[nH]c3ccccc13)CC2]
19
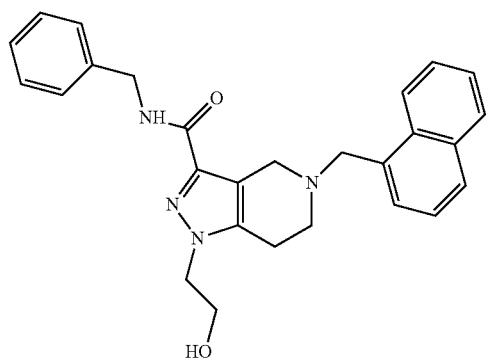 [SMILES: O=C(NCc1ccccc1)c1nn(CCO)c2c1CN(Cc1cccc3ccccc13)CC2]
20
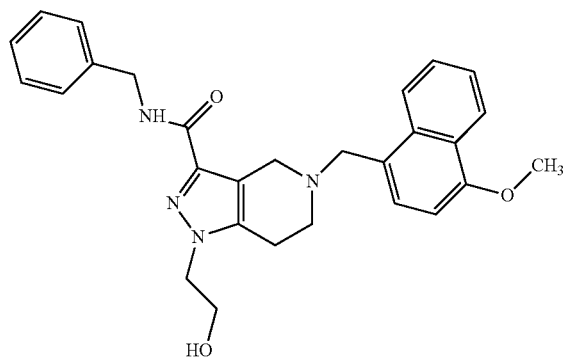 [SMILES: COc1ccc(CN2CCc3c(c(C(=O)NCc4ccccc4)nn3CCO)C2)c2ccccc12]
21

TABLE 1-continued
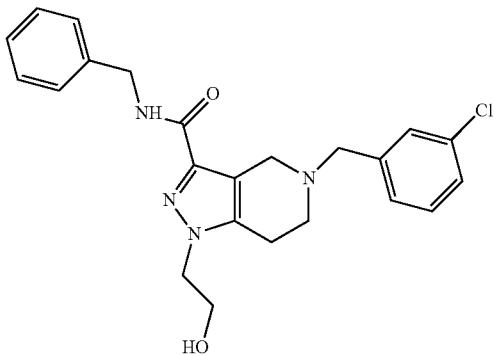 [SMILES: O=C(NCc1ccccc1)c1nn(CCO)c2c1CN(Cc1cccc(Cl)c1)CC2]
22
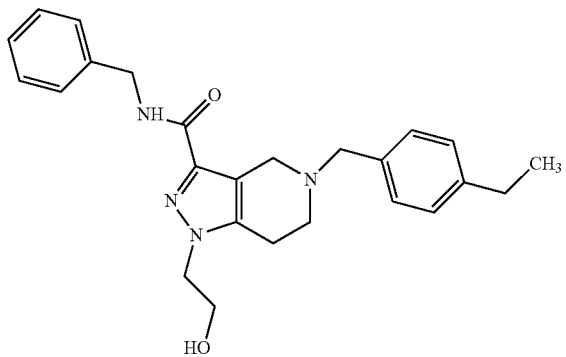 [SMILES: CCc1ccc(CN2CCc3c(c(C(=O)NCc4ccccc4)nn3CCO)C2)cc1]
23
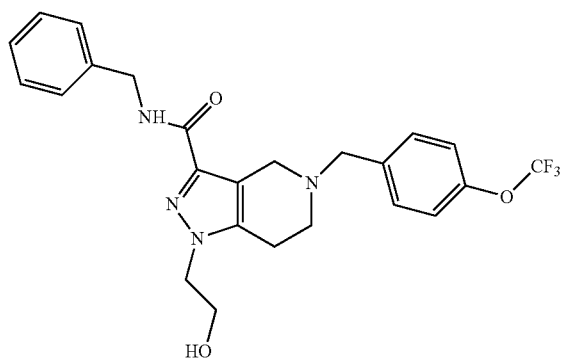 [SMILES: O=C(NCc1ccccc1)c1nn(CCO)c2c1CN(Cc1ccc(OC(F)(F)F)cc1)CC2]
24
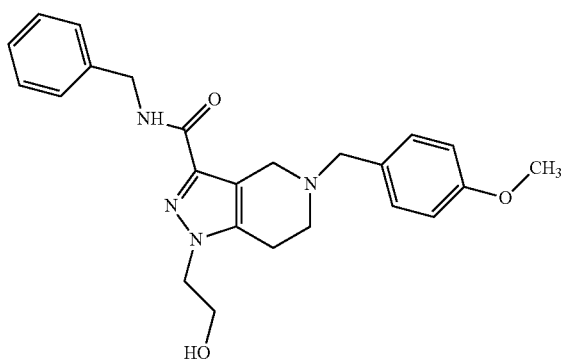 [SMILES: COc1ccc(CN2CCc3c(c(C(=O)NCc4ccccc4)nn3CCO)C2)cc1]
25

TABLE 1-continued
| | |
|---|---|
| 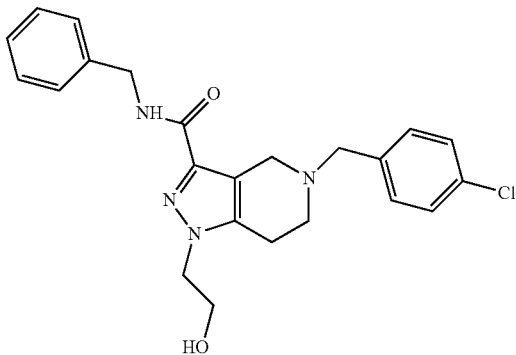 [SMILES: O=C(NCc1ccccc1)c1nn(CCO)c2c1CN(Cc1ccc(Cl)cc1)CC2] | 26 |
| 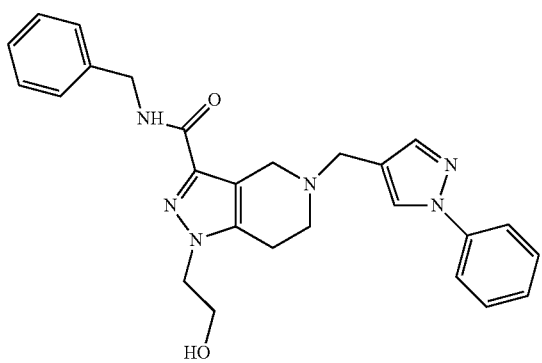 [SMILES: O=C(NCc1ccccc1)c1nn(CCO)c2c1CN(Cc1cnn(-c3ccccc3)c1)CC2] | 27 |
| 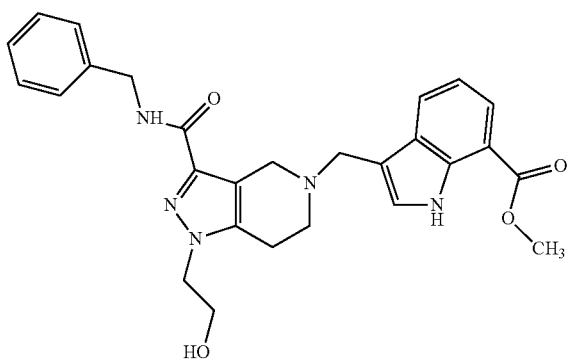 [SMILES: COC(=O)c1cccc2c(CN3CCc4c(c(C(=O)NCc5ccccc5)nn4CCO)C3)c[nH]c12] | 28 |
| 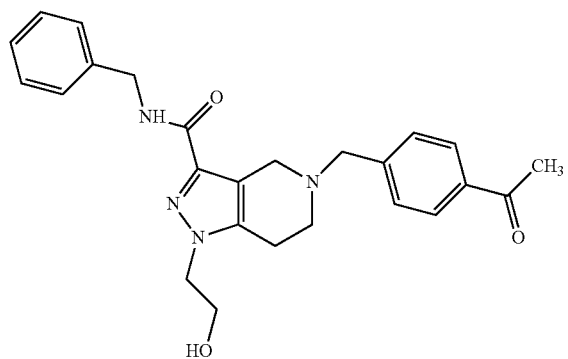 [SMILES: CC(=O)c1ccc(CN2CCc3c(c(C(=O)NCc4ccccc4)nn3CCO)C2)cc1] | 29 |

TABLE 1-continued
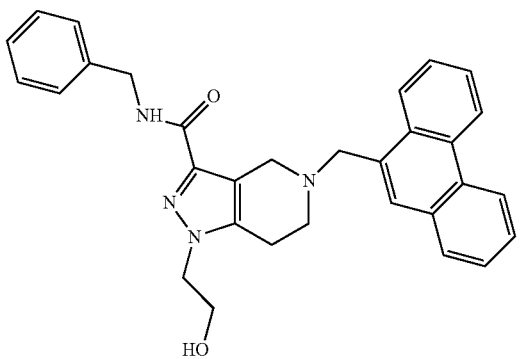 [SMILES: O=C(NCc1ccccc1)c1nn(CCO)c2c1CN(Cc1cc3ccccc3c3ccccc13)CC2]
30
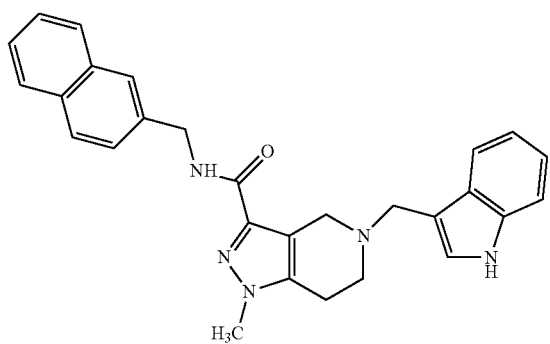 [SMILES: Cn1nc(C(=O)NCc2ccc3ccccc3c2)c2c1CCN(Cc1c[nH]c3ccccc13)C2]
31
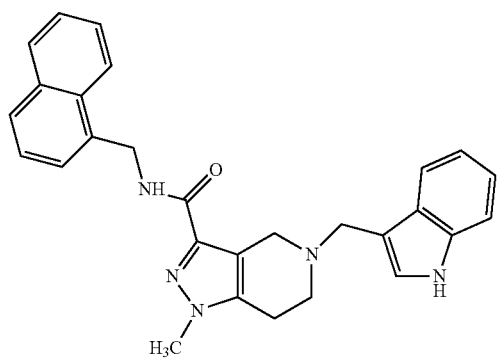 [SMILES: Cn1nc(C(=O)NCc2cccc3ccccc23)c2c1CCN(Cc1c[nH]c3ccccc13)C2]
32
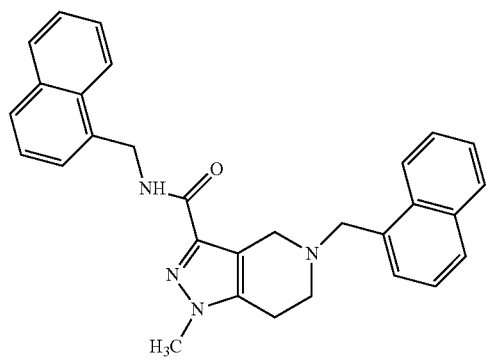 [SMILES: Cn1nc(C(=O)NCc2cccc3ccccc23)c2c1CCN(Cc1cccc3ccccc13)C2]
33

TABLE 1-continued
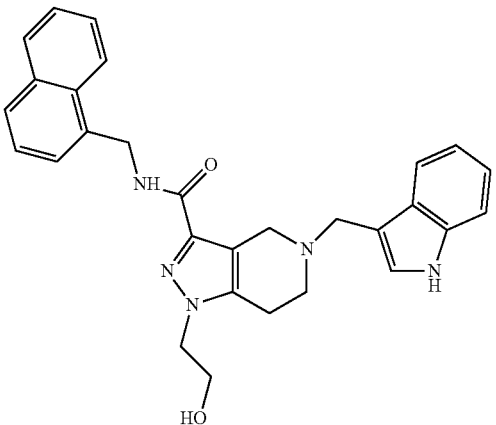 [SMILES: O=C(NCc1cccc2ccccc12)c1nn(CCO)c2c1CN(Cc1c[nH]c3ccccc13)CC2]
34
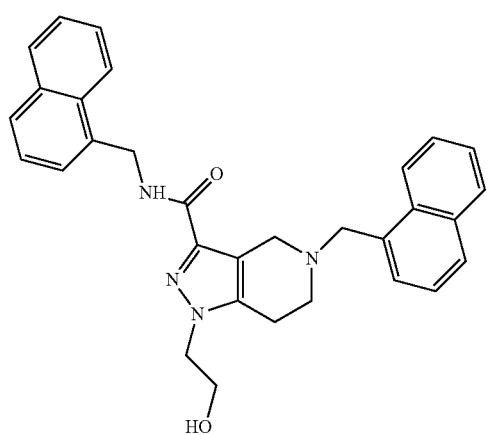 [SMILES: O=C(NCc1cccc2ccccc12)c1nn(CCO)c2c1CN(Cc1cccc3ccccc13)CC2]
35
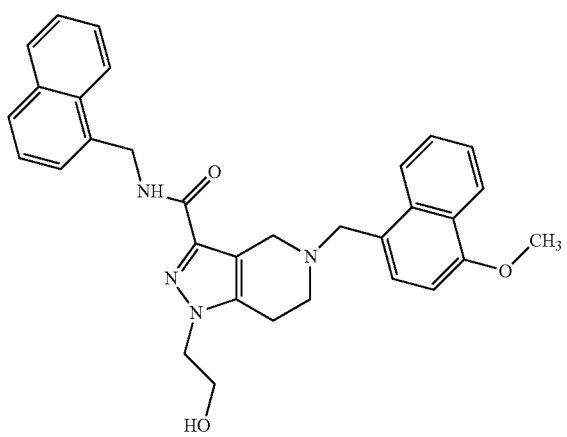 [SMILES: COc1ccc(CN2CCc3c(c(C(=O)NCc4cccc5ccccc45)nn3CCO)C2)c2ccccc12]
36

TABLE 1-continued
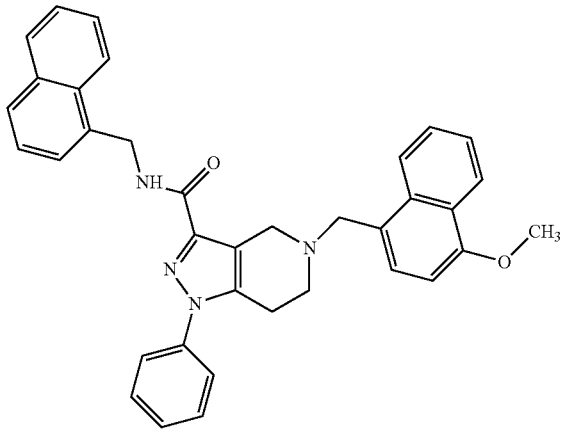 [SMILES: COc1ccc(CN2CCc3c(c(C(=O)NCc4cccc5ccccc45)nn3-c3ccccc3)C2)c2ccccc12]
37
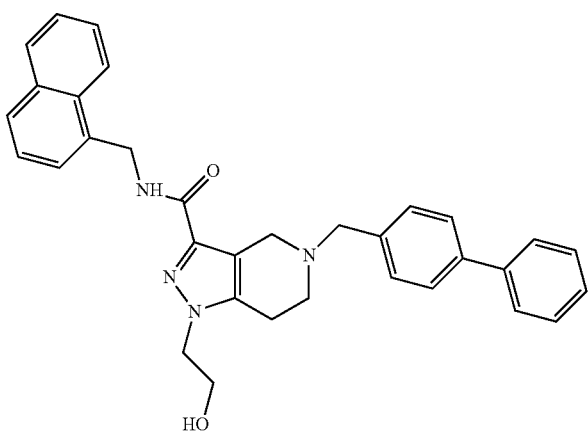 [SMILES: O=C(NCc1cccc2ccccc12)c1nn(CCO)c2c1CN(Cc1ccc(-c3ccccc3)cc1)CC2]
38
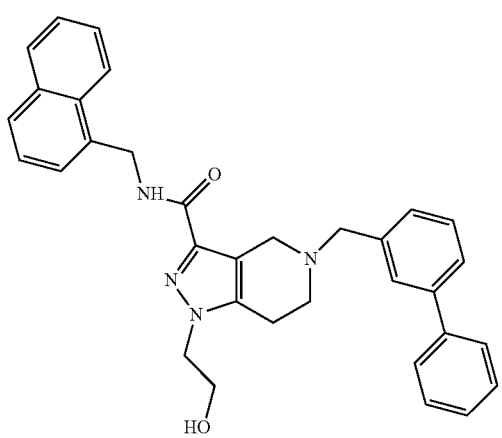 [SMILES: O=C(NCc1cccc2ccccc12)c1nn(CCO)c2c1CN(Cc1cccc(-c3ccccc3)c1)CC2]
39

TABLE 1-continued
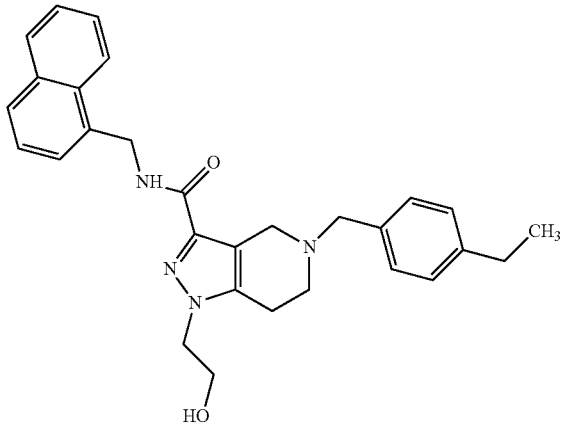 [SMILES: CCc1ccc(CN2CCc3c(c(C(=O)NCc4cccc5ccccc45)nn3CCO)C2)cc1]
40
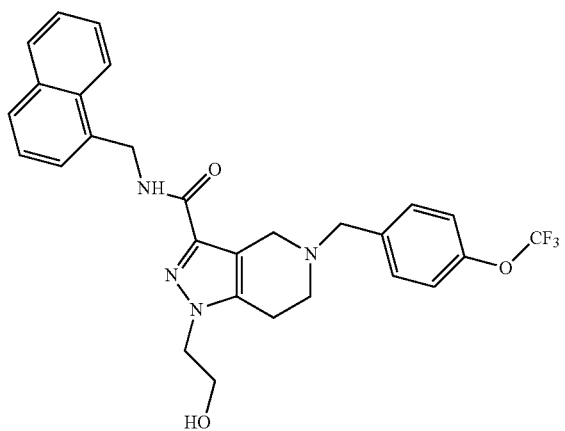 [SMILES: O=C(NCc1cccc2ccccc12)c1nn(CCO)c2c1CN(Cc1ccc(OC(F)(F)F)cc1)CC2]
41
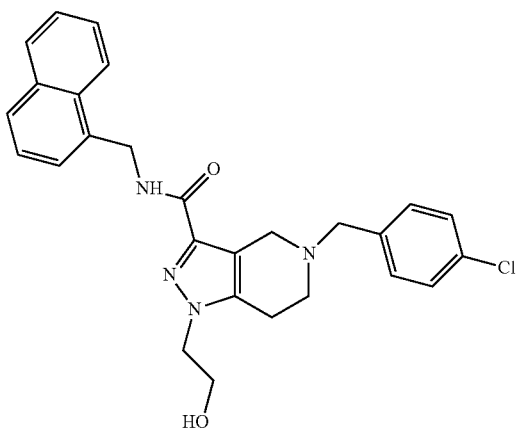 [SMILES: O=C(NCc1cccc2ccccc12)c1nn(CCO)c2c1CN(Cc1ccc(Cl)cc1)CC2]
42

TABLE 1-continued
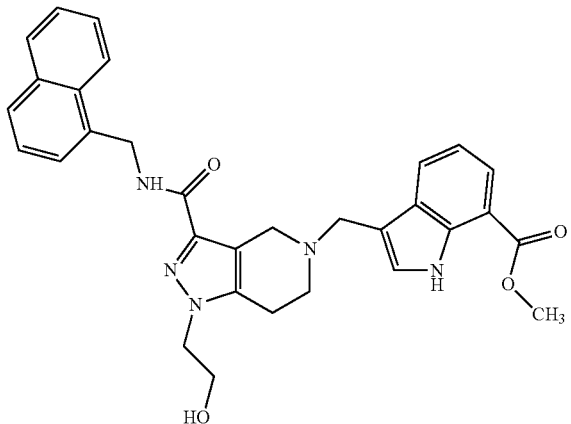 [SMILES: COC(=O)c1cccc2c(CN3CCc4c(c(C(=O)NCc5cccc6ccccc56)nn4CCO)C3)c[nH]c12]
43
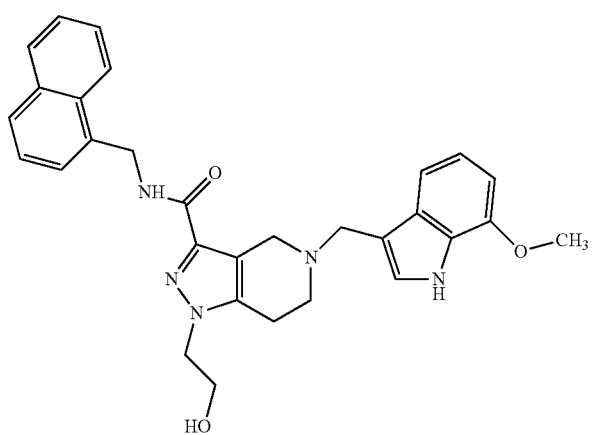 [SMILES: COc1cccc2c(CN3CCc4c(c(C(=O)NCc5cccc6ccccc56)nn4CCO)C3)c[nH]c12]
44
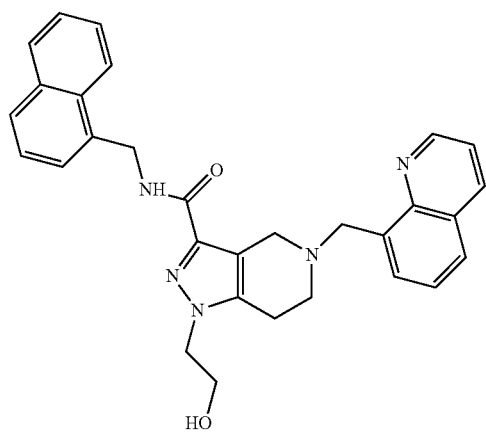 [SMILES: O=C(NCc1cccc2ccccc12)c1nn(CCO)c2c1CN(Cc1cccc3cccnc13)CC2]
45

TABLE 1-continued
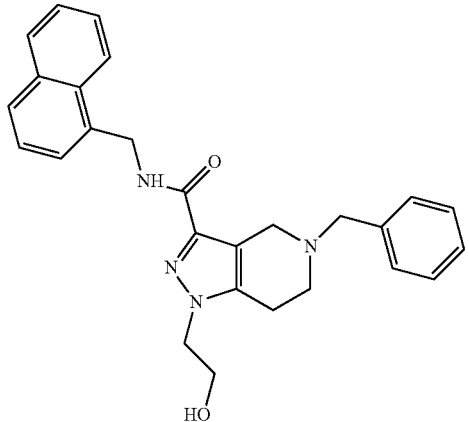 [SMILES: O=C(NCc1cccc2ccccc12)c1nn(CCO)c2c1CN(Cc1ccccc1)CC2]
46
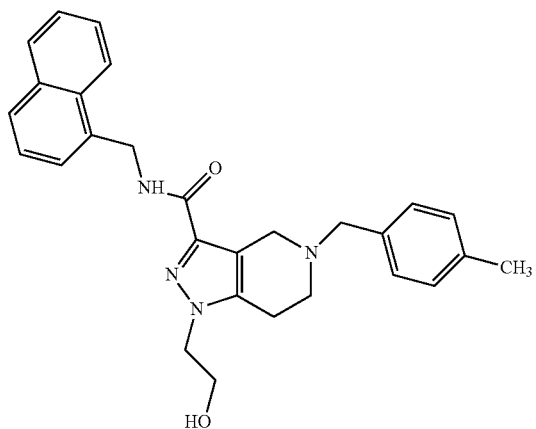 [SMILES: Cc1ccc(CN2CCc3c(c(C(=O)NCc4cccc5ccccc45)nn3CCO)C2)cc1]
47
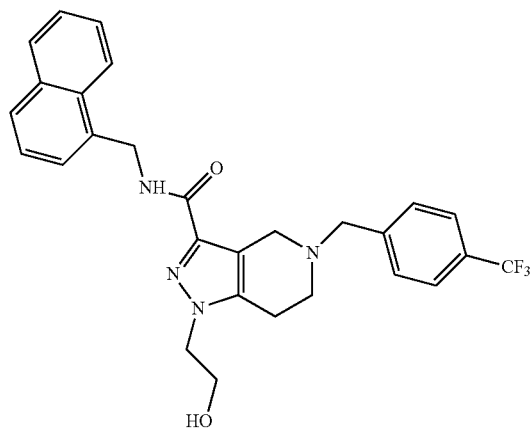 [SMILES: O=C(NCc1cccc2ccccc12)c1nn(CCO)c2c1CN(Cc1ccc(C(F)(F)F)cc1)CC2]
48

TABLE 1-continued
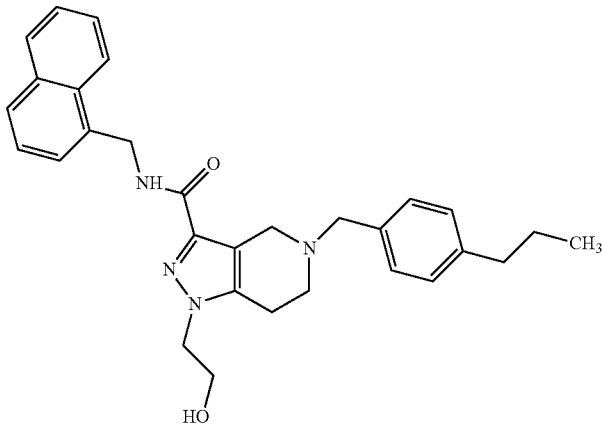 [SMILES: CCCc1ccc(CN2CCc3c(c(C(=O)NCc4cccc5ccccc45)nn3CCO)C2)cc1]
49
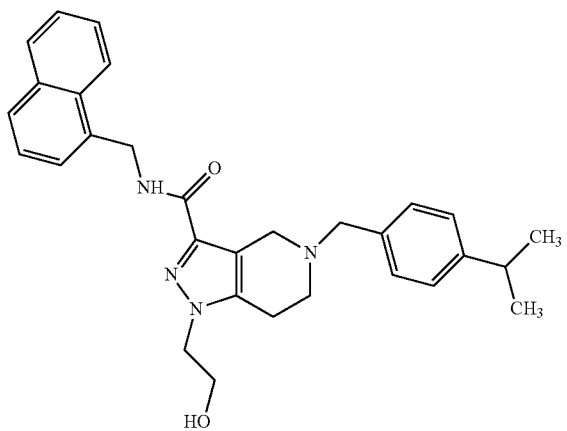 [SMILES: CC(C)c1ccc(CN2CCc3c(c(C(=O)NCc4cccc5ccccc45)nn3CCO)C2)cc1]
50
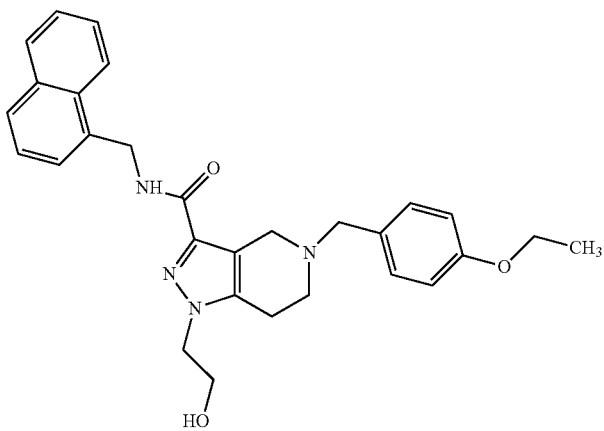 [SMILES: CCOc1ccc(CN2CCc3c(c(C(=O)NCc4cccc5ccccc45)nn3CCO)C2)cc1]
51

TABLE 1-continued
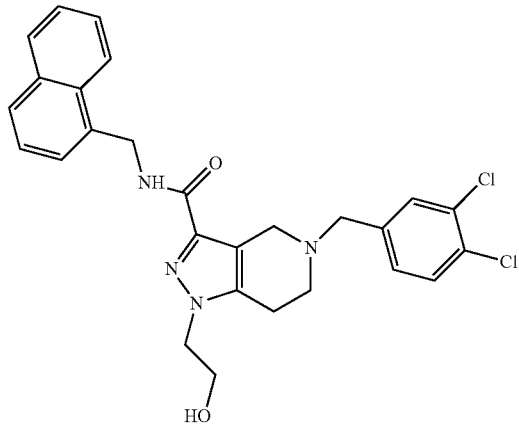 [SMILES: O=C(NCc1cccc2ccccc12)c1nn(CCO)c2c1CN(Cc1ccc(Cl)c(Cl)c1)CC2]
52
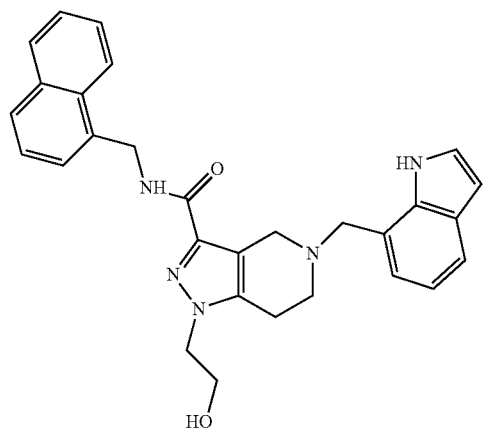 [SMILES: O=C(NCc1cccc2ccccc12)c1nn(CCO)c2c1CN(Cc1cccc3cc[nH]c13)CC2]
53
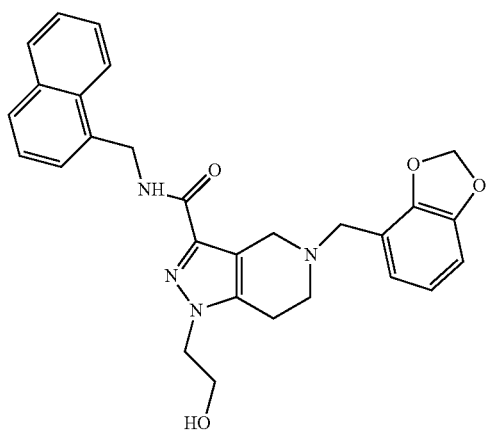 [SMILES: O=C(NCc1cccc2ccccc12)c1nn(CCO)c2c1CN(Cc1cccc3c1OCO3)CC2]
54

TABLE 1-continued
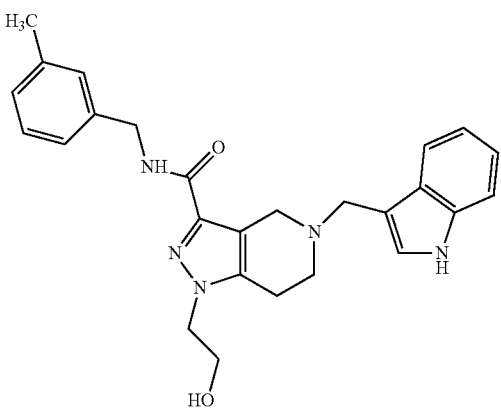 [SMILES: Cc1cccc(CNC(=O)c2nn(CCO)c3c2CN(Cc2c[nH]c4ccccc24)CC3)c1]
55
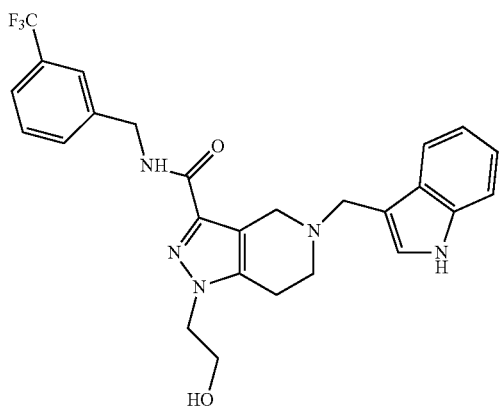
56
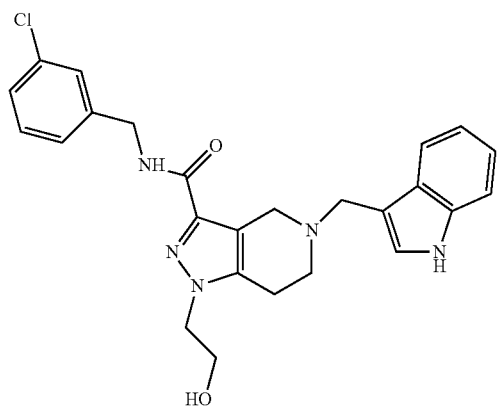 [SMILES: O=C(NCc1cccc(Cl)c1)c1nn(CCO)c2c1CN(Cc1c[nH]c3ccccc13)CC2]
57
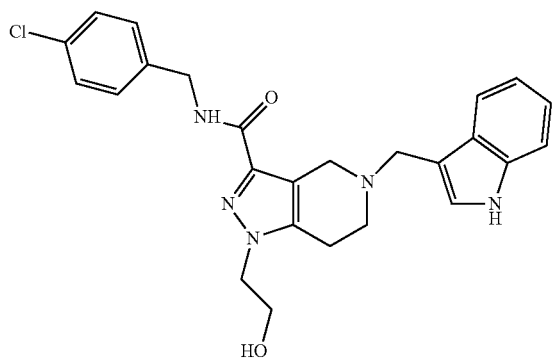 [SMILES: O=C(NCc1ccc(Cl)cc1)c1nn(CCO)c2c1CN(Cc1c[nH]c3ccccc13)CC2]
58

TABLE 1-continued
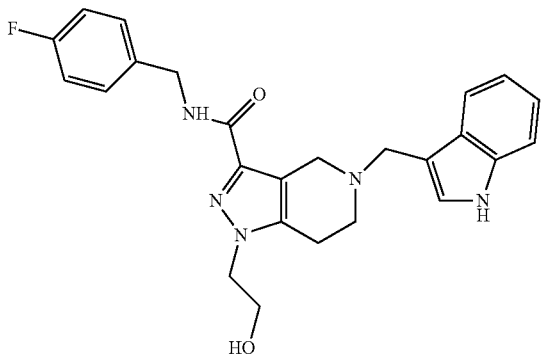 [SMILES: O=C(NCc1ccc(F)cc1)c1nn(CCO)c2c1CN(Cc1c[nH]c3ccccc13)CC2]
59
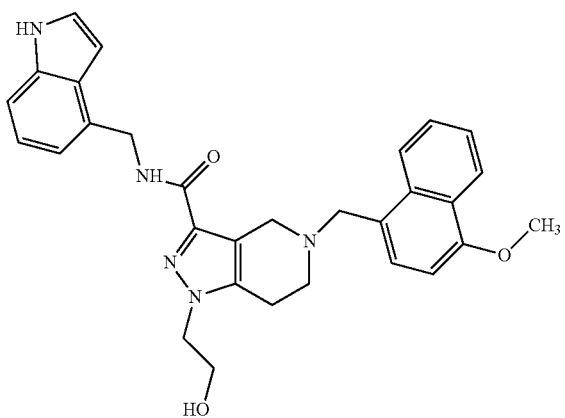 [SMILES: COc1ccc(CN2CCc3c(c(C(=O)NCc4cccc5[nH]ccc45)nn3CCO)C2)c2ccccc12]
60
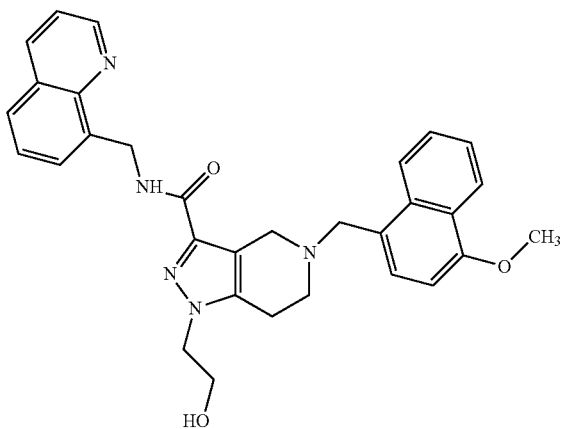 [SMILES: COc1ccc(CN2CCc3c(c(C(=O)NCc4cccc5cccnc45)nn3CCO)C2)c2ccccc12]
61
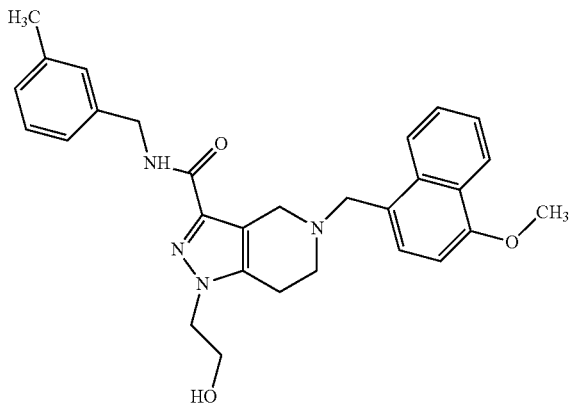 [SMILES: COc1ccc(CN2CCc3c(c(C(=O)NCc4cccc(C)c4)nn3CCO)C2)c2ccccc12]
62

TABLE 1-continued
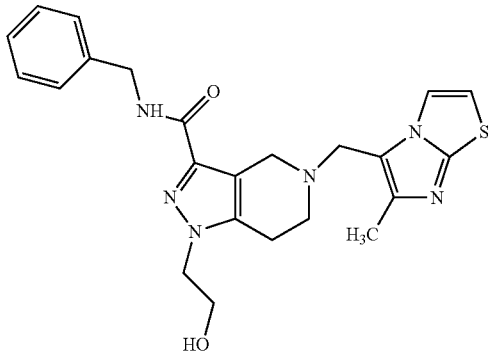 [SMILES: Cc1nc2sccn2c1CN1CCc2c(c(C(=O)NCc3ccccc3)nn2CCO)C1]
63
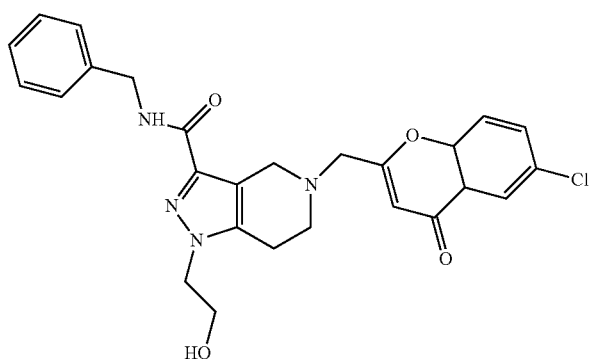 [SMILES: O=C(NCc1ccccc1)c1nn(CCO)c2c1CN(CC1=CC(=O)C3C=C(Cl)C=CC3O1)CC2]
64
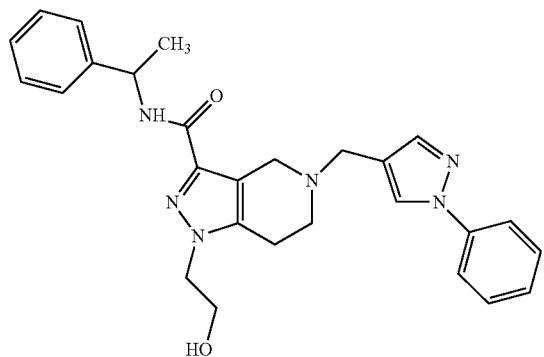 [SMILES: CC(NC(=O)c1nn(CCO)c2c1CN(Cc1cnn(-c3ccccc3)c1)CC2)c1ccccc1]
65
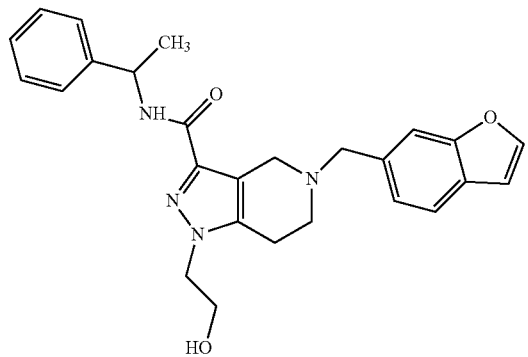 [SMILES: CC(NC(=O)c1nn(CCO)c2c1CN(Cc1ccc3ccoc3c1)CC2)c1ccccc1]
66

TABLE 1-continued
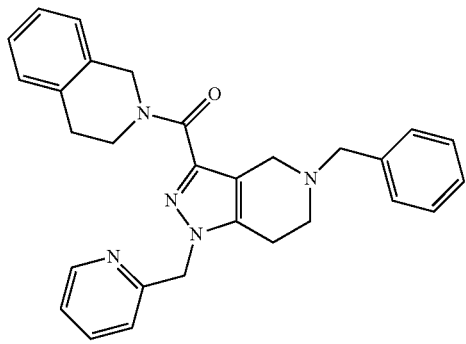 [SMILES: O=C(c1nn(Cc2ccccn2)c2c1CN(Cc1ccccc1)CC2)N1CCc2ccccc2C1]
67
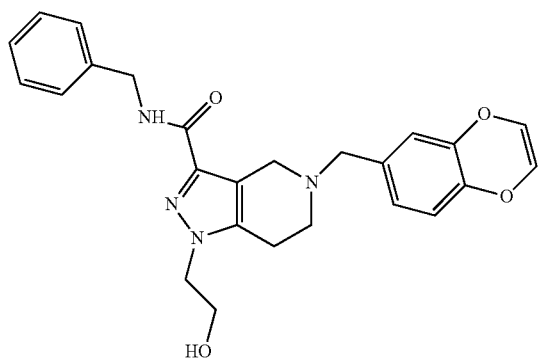 [SMILES: O=C(NCc1ccccc1)c1nn(CCO)c2c1CN(Cc1ccc3c(c1)OC=CO3)CC2]
68
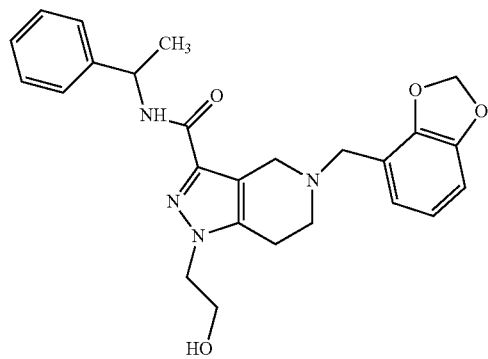 [SMILES: CC(NC(=O)c1nn(CCO)c2c1CN(Cc1cccc3c1OCO3)CC2)c1ccccc1]
69
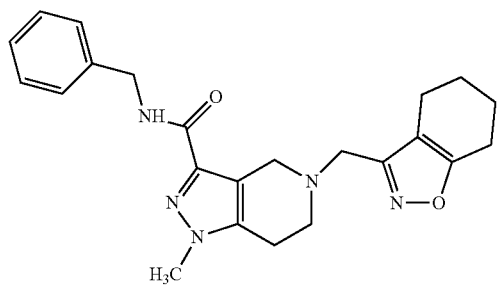 [SMILES: Cn1nc(C(=O)NCc2ccccc2)c2c1CCN(Cc1noc3c1CCCC3)C2]
70

TABLE 1-continued
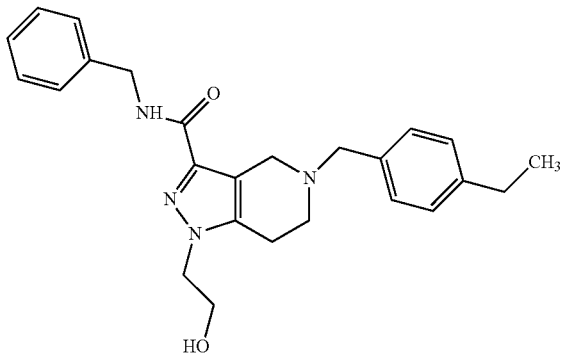
71
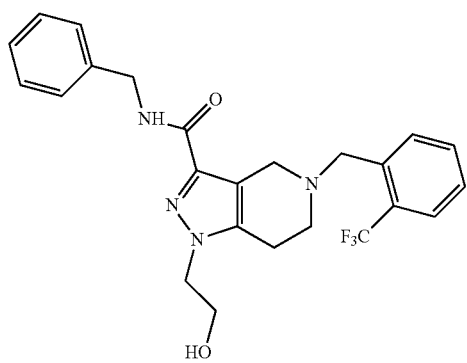 [SMILES: O=C(NCc1ccccc1)c1nn(CCO)c2c1CN(Cc1ccccc1C(F)(F)F)CC2]
72
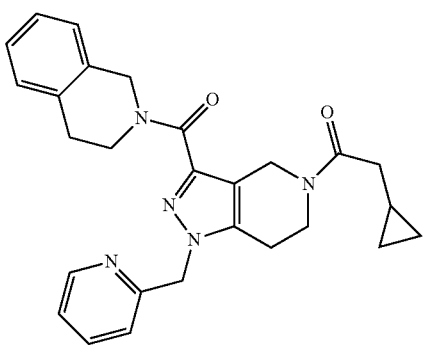 [SMILES: O=C(CC1CC1)N1CCc2c(c(C(=O)N3CCc4ccccc4C3)nn2Cc2ccccn2)C1]
73
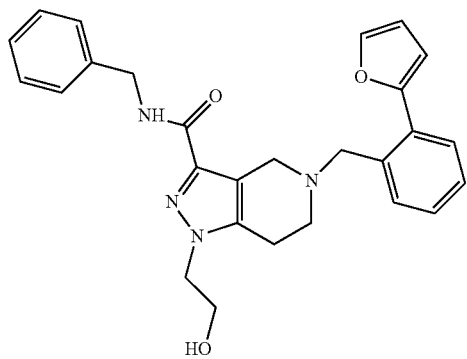 [SMILES: O=C(NCc1ccccc1)c1nn(CCO)c2c1CN(Cc1ccccc1-c1ccco1)CC2]
74

TABLE 1-continued
| | |
|---|---|
| 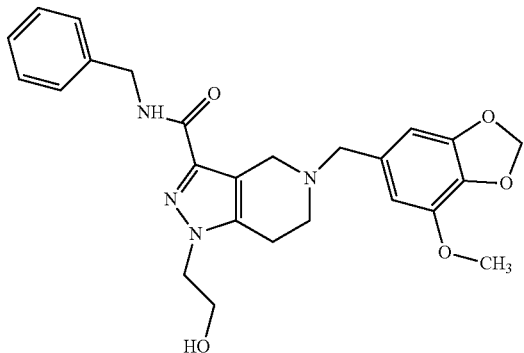 [SMILES: COc1cc(CN2CCc3c(c(C(=O)NCc4ccccc4)nn3CCO)C2)cc2c1OCO2] | 75 |
| 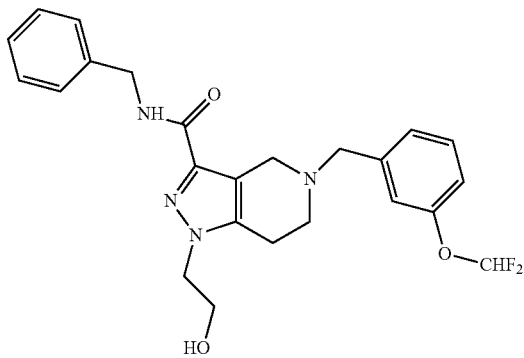 [SMILES: O=C(NCc1ccccc1)c1nn(CCO)c2c1CN(Cc1cccc(OC(F)F)c1)CC2] | 76 |
| 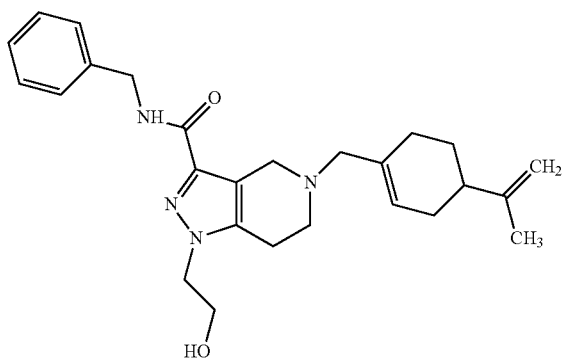 [SMILES: C=C(C)C1CC=C(CN2CCc3c(c(C(=O)NCc4ccccc4)nn3CCO)C2)CC1] | 77 |
| 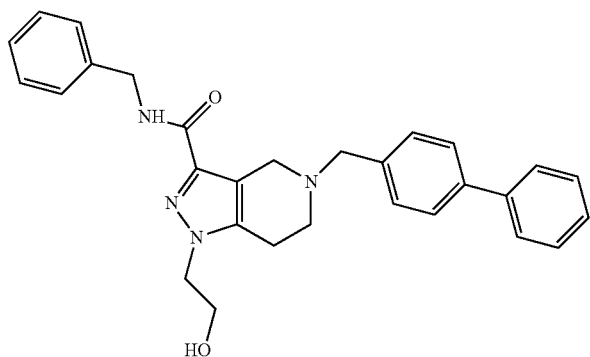 [SMILES: O=C(NCc1ccccc1)c1nn(CCO)c2c1CN(Cc1ccc(-c3ccccc3)cc1)CC2] | 78 |

TABLE 1-continued
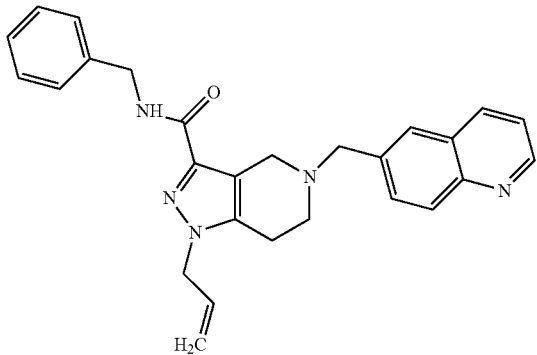 [SMILES: C=CCn1nc(C(=O)NCc2ccccc2)c2c1CCN(Cc1ccc3ncccc3c1)C2]
79
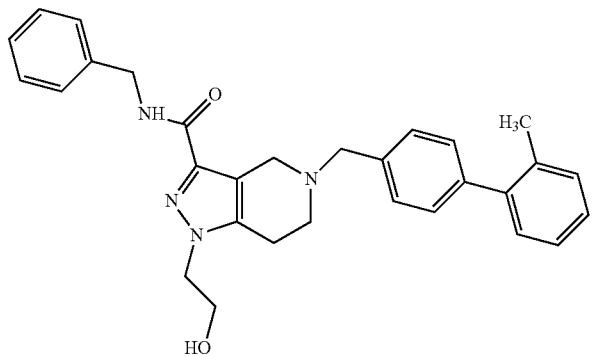 [SMILES: Cc1ccccc1-c1ccc(CN2CCc3c(c(C(=O)NCc4ccccc4)nn3CCO)C2)cc1]
80
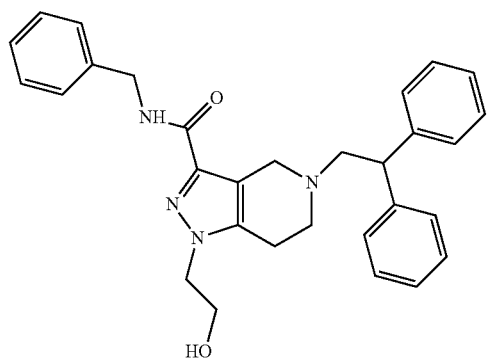 [SMILES: O=C(NCc1ccccc1)c1nn(CCO)c2c1CN(CC(c1ccccc1)c1ccccc1)CC2]
81
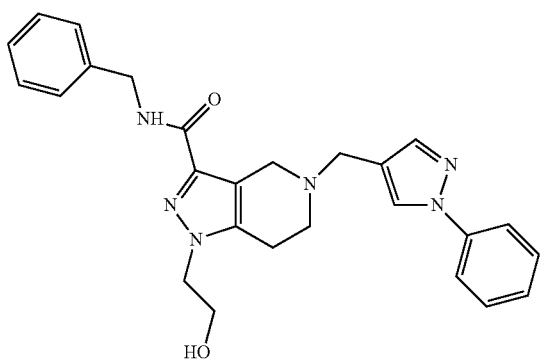 [SMILES: O=C(NCc1ccccc1)c1nn(CCO)c2c1CN(Cc1cnn(-c3ccccc3)c1)CC2]
82

TABLE 1-continued
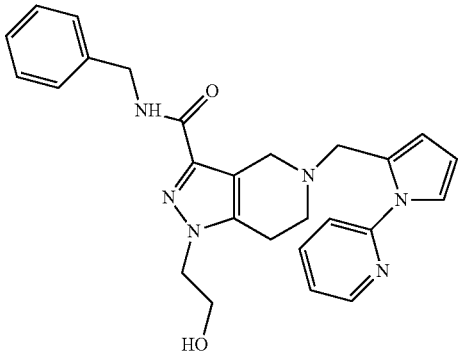 [SMILES: O=C(NCc1ccccc1)c1nn(CCO)c2c1CN(Cc1cccn1-c1ccccn1)CC2]
83
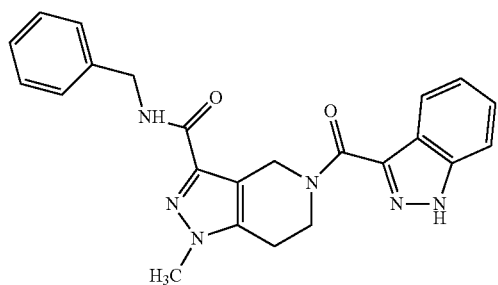 [SMILES: Cn1nc(C(=O)NCc2ccccc2)c2c1CCN(C(=O)c1n[nH]c3ccccc13)C2]
84
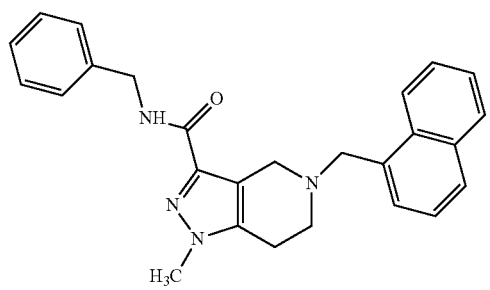 [SMILES: Cn1nc(C(=O)NCc2ccccc2)c2c1CCN(Cc1cccc3ccccc13)C2]
85
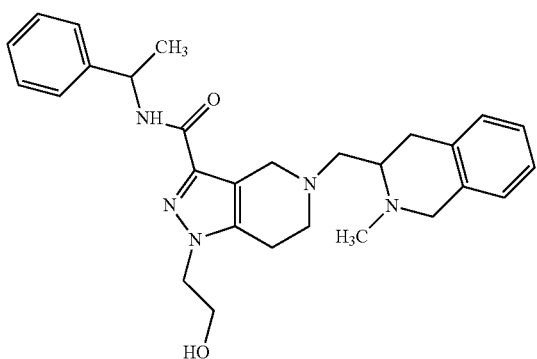 [SMILES: CC(NC(=O)c1nn(CCO)c2c1CN(CC1Cc3ccccc3CN1C)CC2)c1ccccc1]
86

TABLE 1-continued
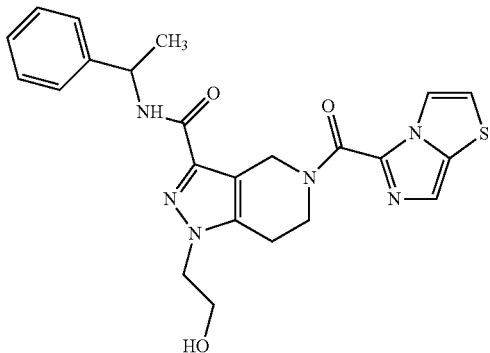 [SMILES: CC(NC(=O)c1nn(CCO)c2c1CN(C(=O)c1ncc3sccn13)CC2)c1ccccc1]
87
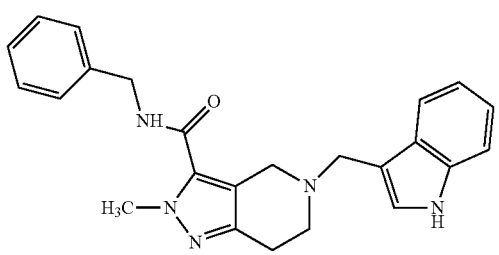 [SMILES: Cn1nc2c(c1C(=O)NCc1ccccc1)CN(Cc1c[nH]c3ccccc13)CC2]
88
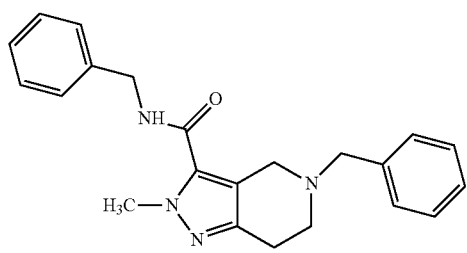 [SMILES: Cn1nc2c(c1C(=O)NCc1ccccc1)CN(Cc1ccccc1)CC2]
89
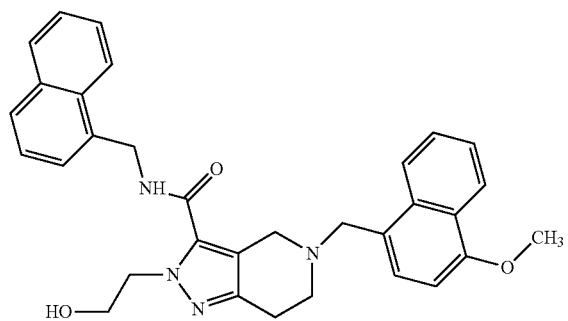 [SMILES: COc1ccc(CN2CCc3nn(CCO)c(C(=O)NCc4cccc5ccccc45)c3C2)c2ccccc12]
90
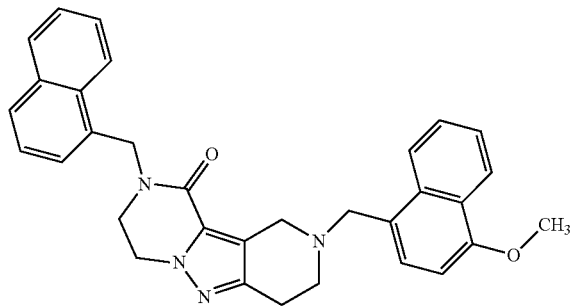 [SMILES: COc1ccc(CN2CCc3nn4c(c3C2)C(=O)N(Cc2cccc3ccccc23)CC4)c2ccccc12]
91

TABLE 1-continued
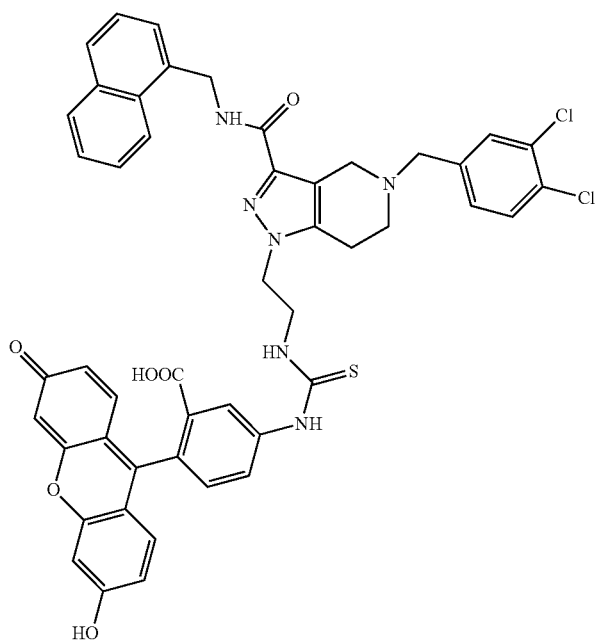 [SMILES: O=C(O)c1cc(NC(=S)NCCn2nc(C(=O)NCc3cccc4ccccc34)c3c2CCN(Cc2ccc(Cl)c(Cl)c2)C3)ccc1-c1c2ccc(=O)cc-2oc2cc(O)ccc12]
92
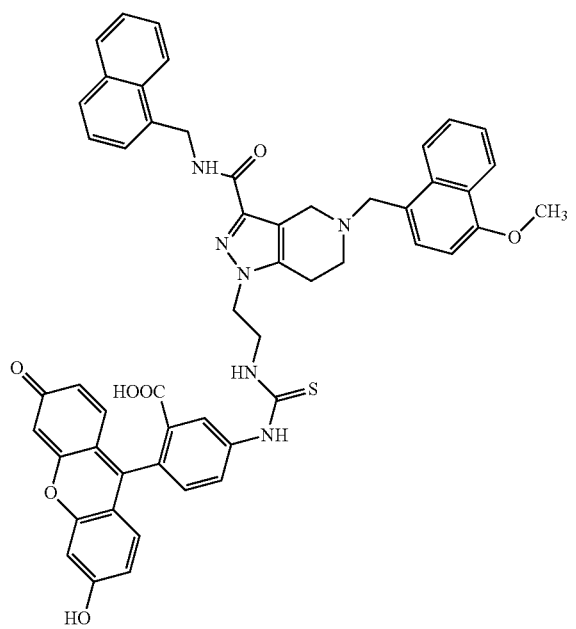 [SMILES: COc1ccc(CN2CCc3c(c(C(=O)NCc4cccc5ccccc45)nn3CCNC(=S)Nc3ccc(-c4c5ccc(=O)cc-5oc5cc(O)ccc45)c(C(=O)O)c3)C2)c2ccccc12]
93

TABLE 1-continued
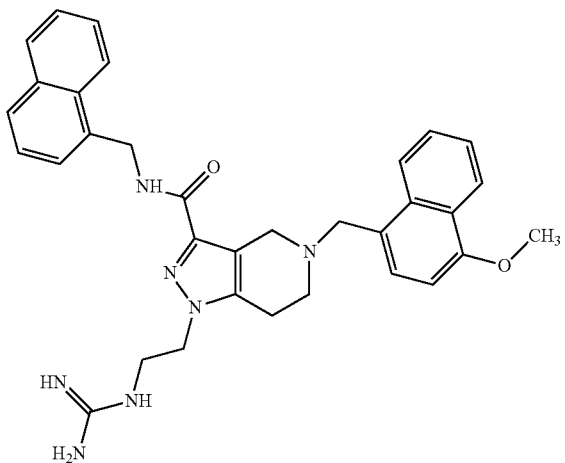 [SMILES: COc1ccc(CN2CCc3c(c(C(=O)NCc4cccc5ccccc45)nn3CCNC(=N)N)C2)c2ccccc12]
94
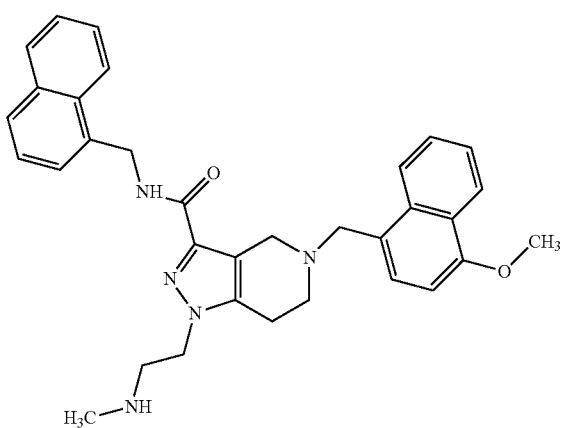 [SMILES: CNCCn1nc(C(=O)NCc2cccc3ccccc23)c2c1CCN(Cc1ccc(OC)c3ccccc13)C2]
95
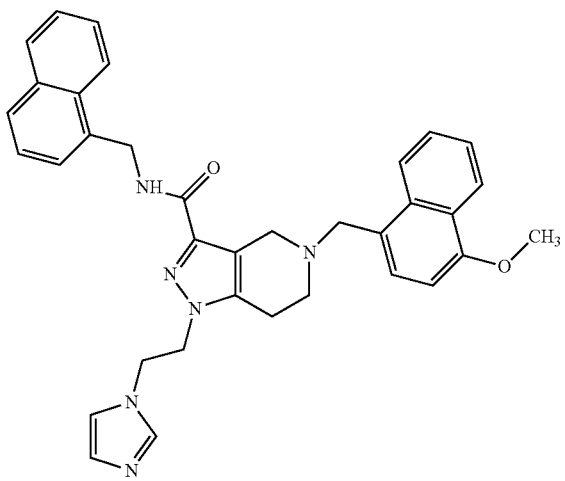 [SMILES: COc1ccc(CN2CCc3c(c(C(=O)NCc4cccc5ccccc45)nn3CCn3ccnc3)C2)c2ccccc12]
96

TABLE 1-continued
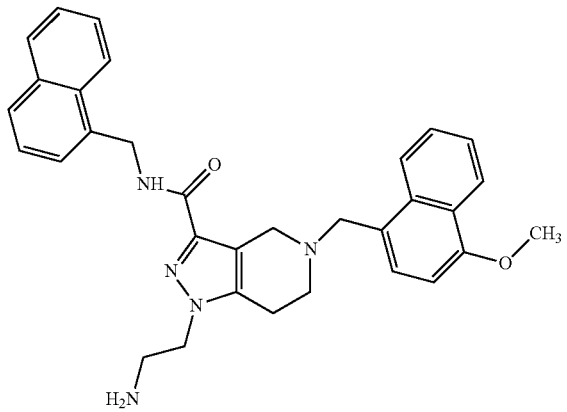 [SMILES: COc1ccc(CN2CCc3c(c(C(=O)NCc4cccc5ccccc45)nn3CCN)C2)c2ccccc12]
97
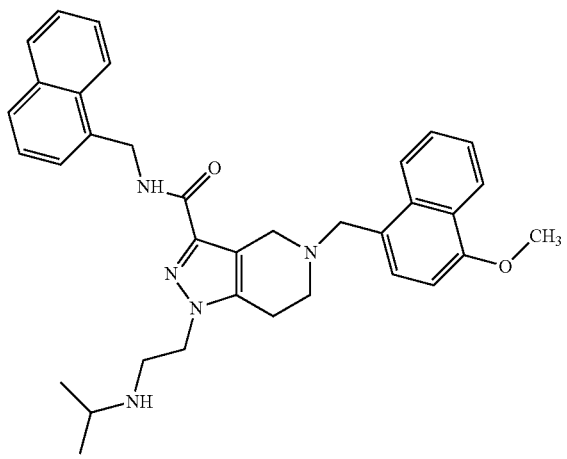 [SMILES: COc1ccc(CN2CCc3c(c(C(=O)NCc4cccc5ccccc45)nn3CCNC(C)C)C2)c2ccccc12]
98
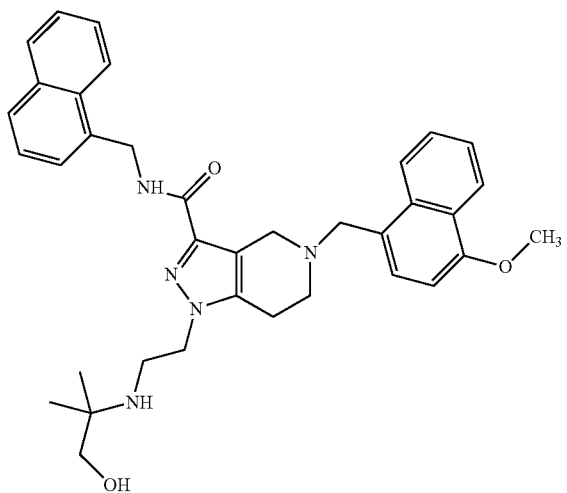 [SMILES: COc1ccc(CN2CCc3c(c(C(=O)NCc4cccc5ccccc45)nn3CCNC(C)(C)CO)C2)c2ccccc12]
99

TABLE 1-continued
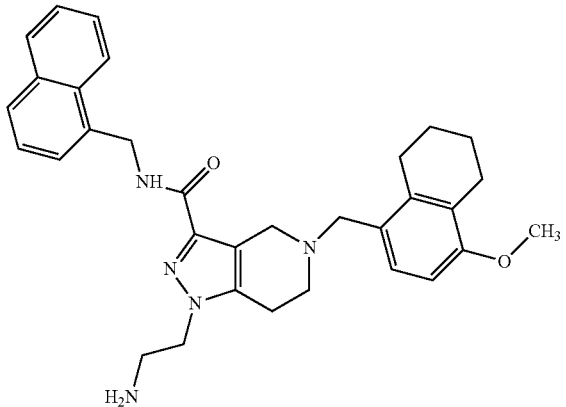 [SMILES: COc1ccc(CN2CCc3c(c(C(=O)NCc4cccc5ccccc45)nn3CCN)C2)c2c1CCCC2]
100
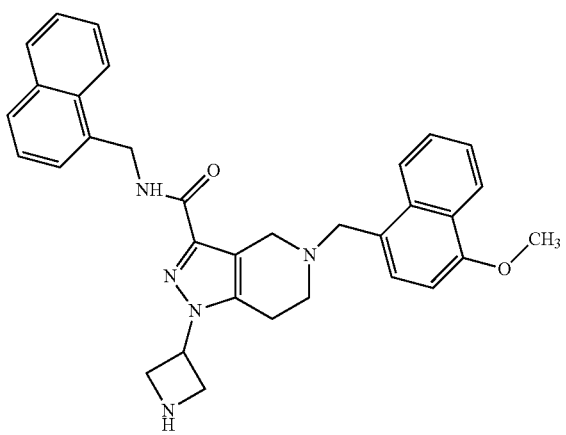 [SMILES: COc1ccc(CN2CCc3c(c(C(=O)NCc4cccc5ccccc45)nn3C3CNC3)C2)c2ccccc12]
101
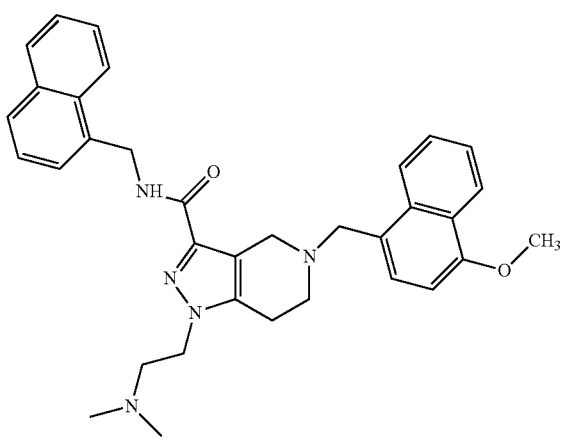 [SMILES: COc1ccc(CN2CCc3c(c(C(=O)NCc4cccc5ccccc45)nn3CCN(C)C)C2)c2ccccc12]
102

TABLE 1-continued
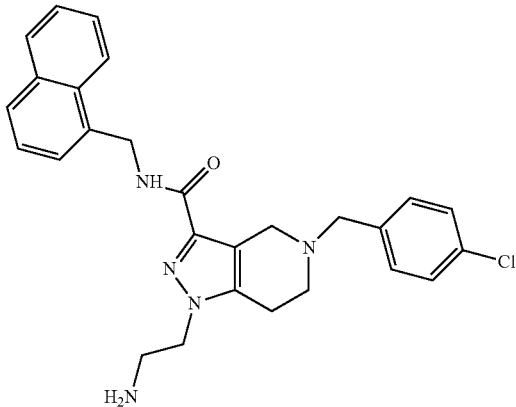 [SMILES: NCCn1nc(C(=O)NCc2cccc3ccccc23)c2c1CCN(Cc1ccc(Cl)cc1)C2]
103
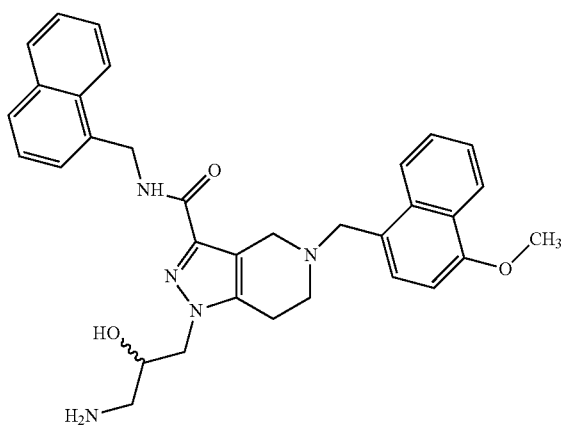 [SMILES: COc1ccc(CN2CCc3c(c(C(=O)NCc4cccc5ccccc45)nn3CC(O)CN)C2)c2ccccc12]
104
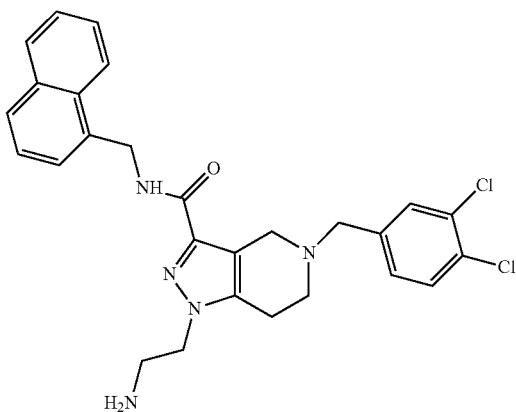 [SMILES: NCCn1nc(C(=O)NCc2cccc3ccccc23)c2c1CCN(Cc1ccc(Cl)c(Cl)c1)C2]
105

TABLE 1-continued
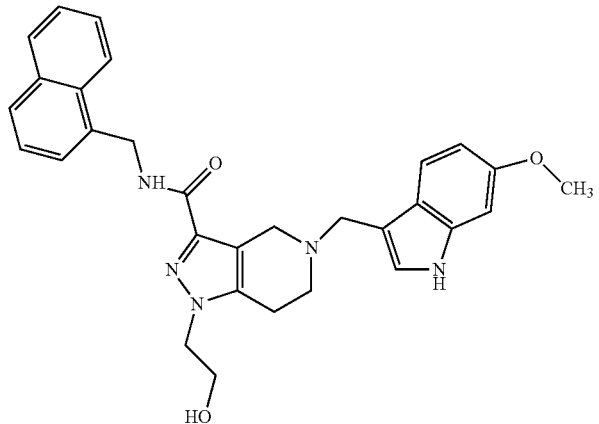 [SMILES: COc1ccc2c(CN3CCc4c(c(C(=O)NCc5cccc6ccccc56)nn4CCO)C3)c[nH]c2c1]
106
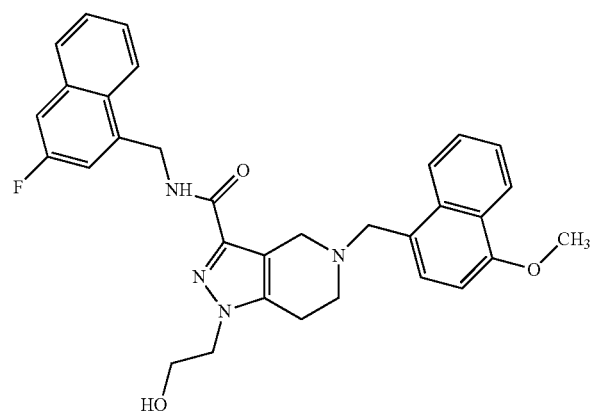 [SMILES: COc1ccc(CN2CCc3c(c(C(=O)NCc4cc(F)cc5ccccc45)nn3CCO)C2)c2ccccc12]
107
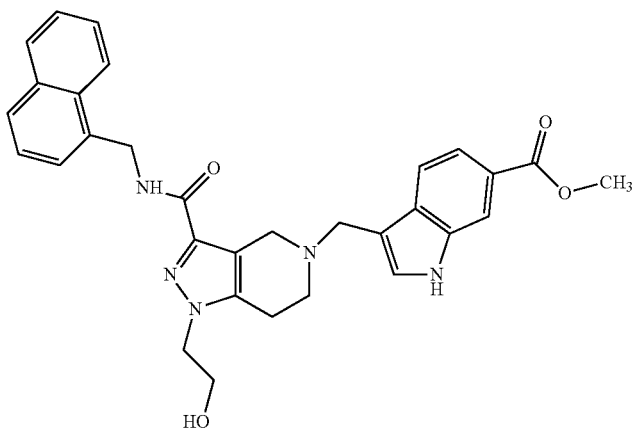 [SMILES: COC(=O)c1ccc2c(CN3CCc4c(c(C(=O)NCc5cccc6ccccc56)nn4CCO)C3)c[nH]c2c1]
108

TABLE 1-continued
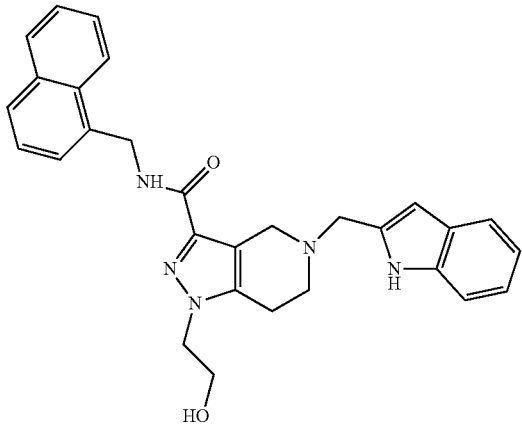 [SMILES: O=C(NCc1cccc2ccccc12)c1nn(CCO)c2c1CN(Cc1cc3ccccc3[nH]1)CC2]
109
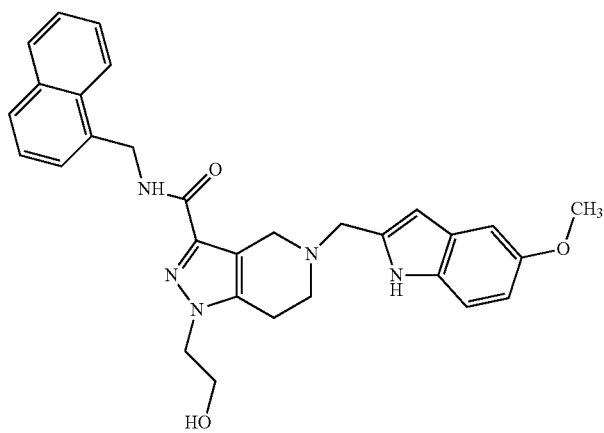 [SMILES: COc1ccc2[nH]c(CN3CCc4c(c(C(=O)NCc5cccc6ccccc56)nn4CCO)C3)cc2c1]
110
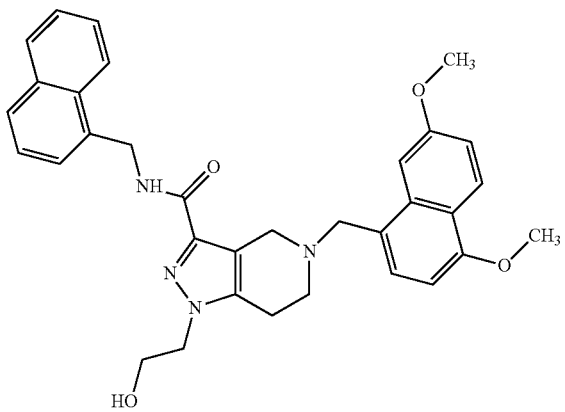 [SMILES: COc1ccc2c(OC)ccc(CN3CCc4c(c(C(=O)NCc5cccc6ccccc56)nn4CCO)C3)c2c1]
111

TABLE 1-continued
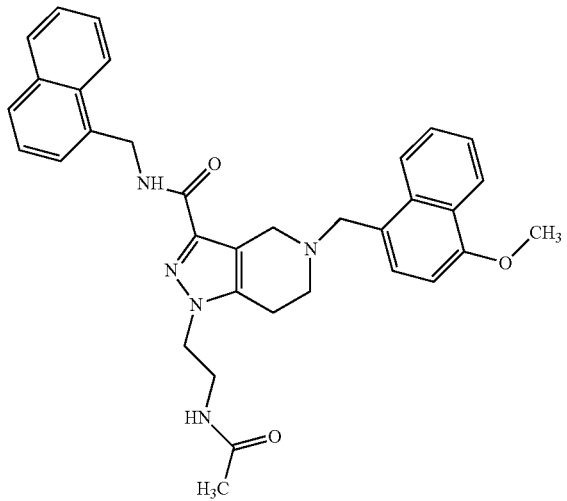 [SMILES: COc1ccc(CN2CCc3c(c(C(=O)NCc4cccc5ccccc45)nn3CCNC(C)=O)C2)c2ccccc12]
112
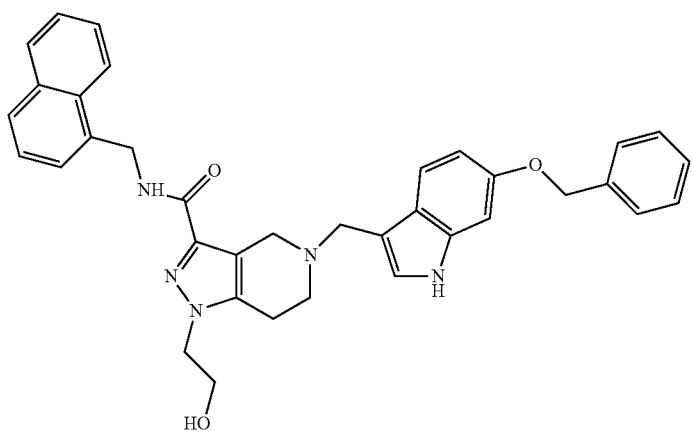 [SMILES: O=C(NCc1cccc2ccccc12)c1nn(CCO)c2c1CN(Cc1c[nH]c3cc(OCc4ccccc4)ccc13)CC2]
113
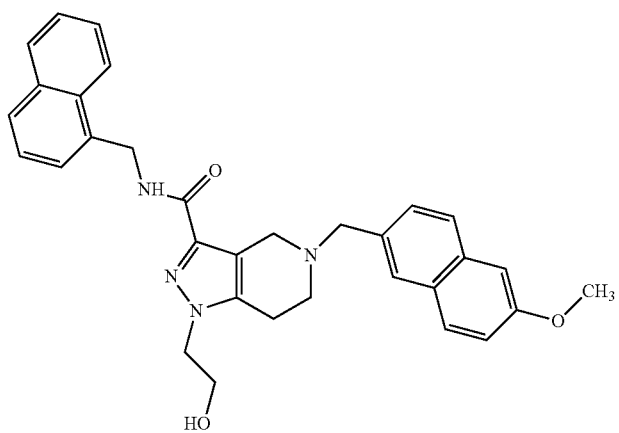 [SMILES: COc1ccc2cc(CN3CCc4c(c(C(=O)NCc5cccc6ccccc56)nn4CCO)C3)ccc2c1]
114

TABLE 1-continued
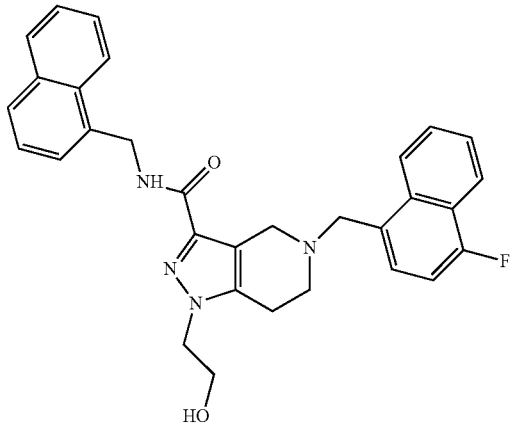 [SMILES: O=C(NCc1cccc2ccccc12)c1nn(CCO)c2c1CN(Cc1ccc(F)c3ccccc13)CC2]
115
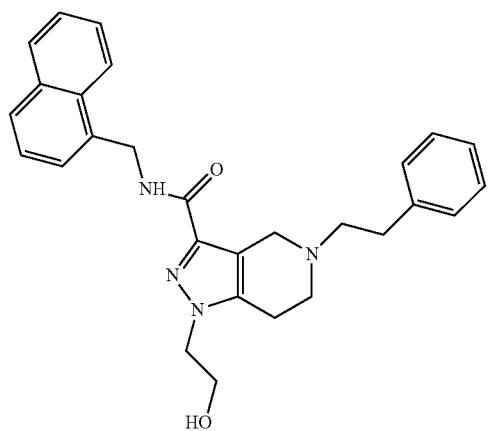 [SMILES: O=C(NCc1cccc2ccccc12)c1nn(CCO)c2c1CN(CCc1ccccc1)CC2]
116
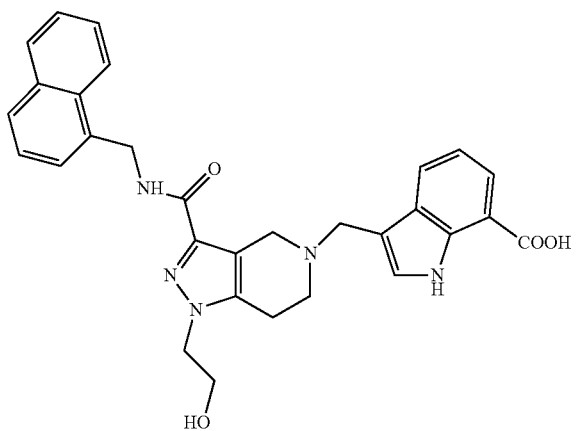 [SMILES: O=C(NCc1cccc2ccccc12)c1nn(CCO)c2c1CN(Cc1c[nH]c3c(C(=O)O)cccc13)CC2]
117

TABLE 1-continued
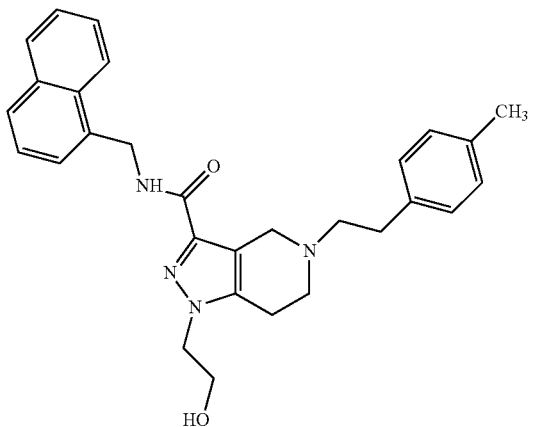 [SMILES: Cc1ccc(CCN2CCc3c(c(C(=O)NCc4cccc5ccccc45)nn3CCO)C2)cc1]
118
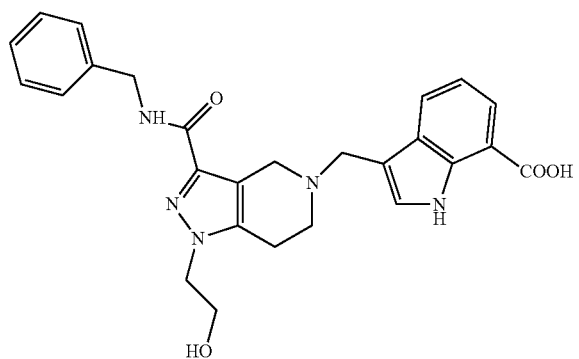 [SMILES: O=C(NCc1ccccc1)c1nn(CCO)c2c1CN(Cc1c[nH]c3c(C(=O)O)cccc13)CC2]
119
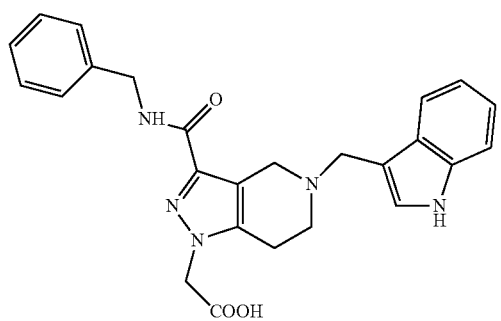 [SMILES: O=C(O)Cn1nc(C(=O)NCc2ccccc2)c2c1CCN(Cc1c[nH]c3ccccc13)C2]
120
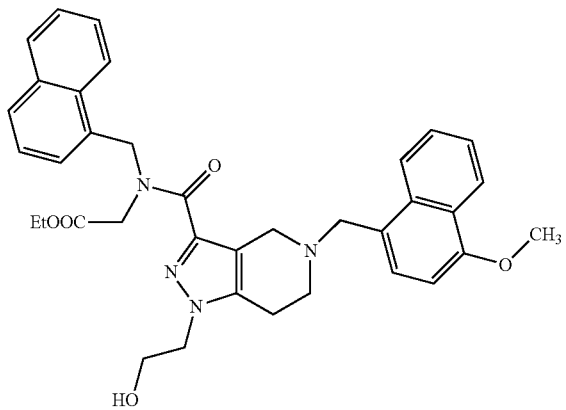
121

TABLE 1-continued
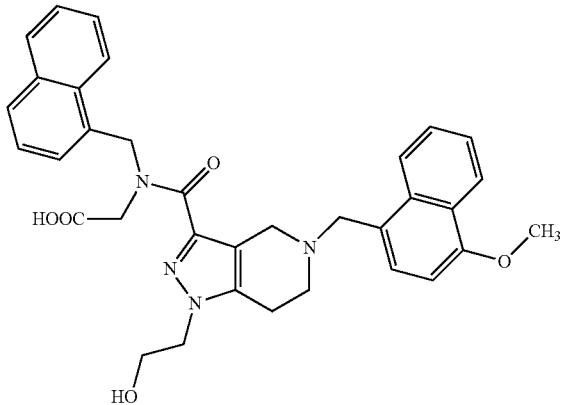 [SMILES: COc1ccc(CN2CCc3c(c(C(=O)N(CC(=O)O)Cc4cccc5ccccc45)nn3CCO)C2)c2ccccc12]
122
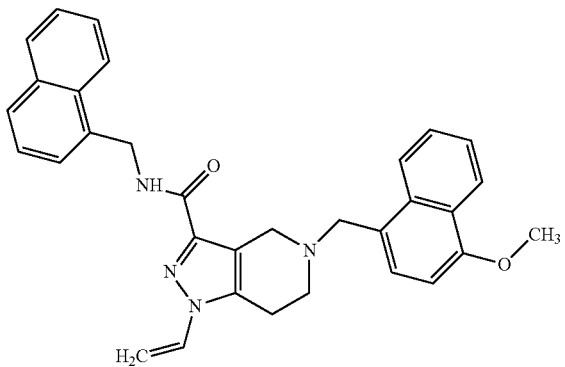 [SMILES: C=Cn1nc(C(=O)NCc2cccc3ccccc23)c2c1CCN(Cc1ccc(OC)c3ccccc13)C2]
123
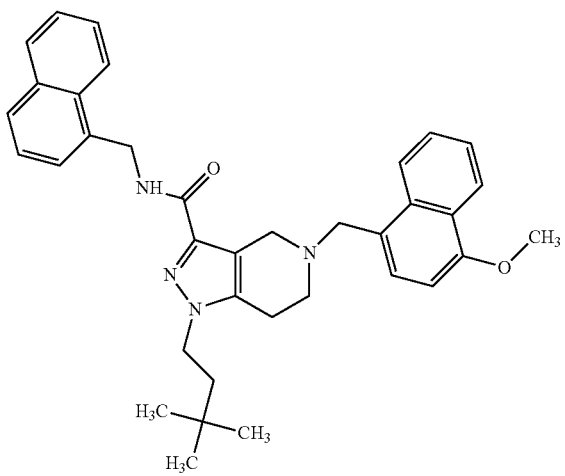 [SMILES: COc1ccc(CN2CCc3c(c(C(=O)NCc4cccc5ccccc45)nn3CCC(C)(C)C)C2)c2ccccc12]
124

TABLE 1-continued

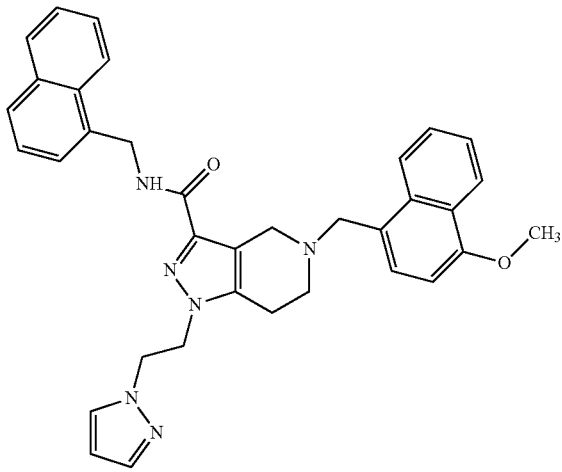 [SMILES: COc1ccc(CN2CCc3c(c(C(=O)NCc4cccc5ccccc45)nn3CCn3cccn3)C2)c2ccccc12]

125

In one embodiment, the compounds of the invention do not encompass compounds of formula (Ia) wherein (i) $R_1$ is alkyl, aryl, $C_{3-12}$ cycloalkyl, —($C_{1-4}$ alkylene)-alkyl, —($C_{1-4}$ alkylene)-aryl or —($C_{1-4}$ alkylene)-($C_{3-12}$ cycloalkyl), wherein the aryl is optionally substituted at one or more positions by halogen; $L_3$ is —C(O)—N($R^8$)—($C_{1-10}$ alkylene)-; $R_3$ and $R^8$ join together with the atoms to which they are attached to form a polycyclic ring; each of $R_4$, $R'_4$, $R_6$, $R'_6$, $R_7$, and $R'_7$ is H; and -$L_5R_5$ is sulfonylaryl, —($C_{1-4}$ alkylene)-carbonylalkoxyaryl, or —($C_{1-4}$ alkylene)-sulfonylaryl, wherein the aryl in sulfonylaryl is optionally substituted at one or more positions by alkyl, wherein, at each occurrence under (i), alkyl has 1 to 10 carbon atoms, alkoxy has 1 to 10 carbon atoms, and aryl has 6, 9, 10, or 14 carbon atoms;

(ii) $R_1$ is alkyl, aryl, $C_{3-12}$ cycloalkyl, ($C_{1-4}$ alkylene)-alkyl, —($C_{1-4}$ alkylene)-aryl or —($C_{1-4}$ alkylene)-($C_{3-12}$ cycloalkyl), wherein the aryl is optionally substituted at one or more positions by halogen; $L_3$ is —C(O)—NH—($C_{1-10}$ alkylene)-; $R_3$ is aryl, $C_{3-12}$ cycloalkyl, heterocyclyl, or heteroaryl, each optionally substituted by one or more hydroxy, alkyl, or alkoxy; each of $R_4$, $R'_4$, $R_6$, $R'_6$, $R_7$, and $R'_7$ is H, and -$L_5R_5$ is sulfonylaryl, —($C_{1-4}$ alkylene)-carbonylalkoxyaryl, or —($C_{1-4}$ alkylene)-sulfonylaryl, wherein the aryl in sulfonylaryl is optionally substituted at one or more positions by alkyl, wherein, at each occurrence under (ii), alkyl has 1 to 10 carbon atoms, alkoxy has 1 to 10 carbon atoms, and aryl has 6, 9, 10, or 14 carbon atoms; and/or (iii) each of $R_4$, $R'_4$, $R_6$, $R'_6$, $R_7$, and $R'_7$ is H;

(1) $R_1$ is 2-hydroxyethyl; -$L_3R_3$ is —C(O)NHCH$_2$-phenyl; and -$L_5R_5$ is (6-methylimidazo[2,1-b][1,3]thiazol-5-yl)methyl, (6-chloro-4-oxo-4a,8a-dihydro-4H-chromen-2-yl)methyl, 1,4-benzo dioxin-6-ylmethyl, (4-methoxynaphthalen-1-yl)methyl, 4-ethylbenzyl, 2-(trifluoromethyl)benzyl, 2-(furan-2-yl)benzyl, (7-methoxy-1,3-benzodioxol-5-yl)methyl, 3-(difluoromethoxy)benzyl, [4-(prop-1-en-2-yl)cyclohex-1-en-1-yl]methyl, biphenyl-4-ylmethyl, (2'-methylbiphenyl-4-yl)methyl, 2,2-diphenylethyl, (1-phenyl-1H-pyrazol-4-yl)methyl, or [1-(pyridin-2-yl)-1H-pyrrol-2-yl]methyl;

(2) $R_1$ is 2-hydroxyethyl; -$L_3R_3$ is —C(O)NHCH(CH$_3$)-phenyl; and -$L_5R_5$ is (1-phenyl-1H-pyrazol-4-yl)methyl, 1-benzofuran-6-ylmethyl, 1,3-benzodioxol-4-ylmethyl, (2-methyl-1,2,3,4-tetrahydroisoquinolin-3-yl)methyl, or (imidazo[5,1-b][1,3]thiazol-5-yl)carbonyl;

(3) $R_1$ is methyl; -$L_3R_3$ is —C(O)NHCH$_2$-phenyl; and -$L_5R_5$ is 4,5,6,7-tetrahydro-1,2-benzoxazol-3-ylmethyl, (1H-indazol-3-yl)carbonyl, or naphthalen-1-ylmethyl;

(4) $R_1$ is prop-2-en-1-yl; -$L_3R_3$ is —C(O)NHCH$_2$-phenyl; and -$L_5R_5$ is quinolin-6-ylmethyl; or (5) $R_1$ is pyridin-2-ylmethyl; $L_3$ is —C(O)—N($R^8$)-(alkylene)-; $R^8$ and $R_3$ join together with the atoms to which they are attached to form unsubstituted 3,4-dihydroisoquinolin-2(1H)-ylmethyl; and -$L_5R_5$ is benzyl or cyclopropylacetyl.

The compounds of the invention which contain a basic functionality may form salts with a variety of inorganic or organic acids. Exemplary inorganic and organic acids/bases as well as exemplary acid/base addition salts of the compounds of the present invention are given in the definition of "pharmaceutically acceptable salt" in the section "Pharmaceutical composition", below. The compounds of the invention which contain an acidic functionality may form salts with a variety of inorganic or organic bases. The compounds of the invention which contain both basic and acidic functionalities may be converted into either base or acid addition salt. The neutral forms of the compounds of the invention may be regenerated by contacting the salt with a base or acid and isolating the parent compound in the conventional manner.

The compounds of the invention may be in a prodrug form. Prodrugs of the compounds of the invention are those compounds that upon administration to an individual undergo chemical conversion under physiological conditions to provide the compounds of the invention. Additionally, prodrugs can be converted to the compounds of the invention by chemical or biochemical methods in an ex vivo environment. For example, prodrugs can be slowly converted to the compounds of the invention when, for example, placed in a transdermal patch reservoir with a suitable enzyme or chemical reagent. Exemplary prodrugs are esters or amides which are hydrolyzable in vivo.

In a further aspect, the present invention provides a compound of the invention (in particular those specified above with respect to any of formulas (Ia), (Ib), (IIa), (IIb), (IIIa), (IIIb), (IVa), (IVb), (Va), (Vb), (VIa), (VIb), (VIIa), (VIIb), (VIIIa), and (VIIIb), such as those depicted in Table 1) for use as medicament.

As it is evident from the examples, the inventors have found that the compounds of the invention target glycosome biogenesis by selectively binding to PEX14, wherein presence of said compounds causes mislocalization of the glycosome component and, thus, the release of the enzymes hexokinase (HK) and phosphofructokinase (PFK) into the cytosol of Trypanosomatidae. The presence of HK and PFK in the cytosol leads to runaway phosphorylation of hexoses (using cytosolic pool of ATP), ATP depletion, and cell death. In contrast, the analogous peroxisomal systems in mammalian cells are not critical to the cell survival. Thus, in one embodiment, the compounds of the invention selectively target PEX14 protein and, consequently, selectively kill parasites of the family Trypanosomatidae.

In one embodiment, the compounds of the invention exhibit pharmacological properties (bioavailability, toxicity, side effects, dosing, patient compliance, compatibility, stability, half-life, effectiveness against parasite strains which are resistant to one or more (e.g., 1, 2, or 3) known trypanolytic drugs; effectiveness against persistent diseases etc.), which are in at least one aspect superior to the pharmacological properties exhibited by known trypanolytic drugs. In one embodiment, the compounds of the invention are more effective against parasite strains of the family Trypanosomatidae which are resistant to one or more known trypanolytic drugs. In one embodiment, the compounds of the invention are more effective against a persistent disease caused by the parasite of the family Trypanosomatidae compared to one or more known trypanolytic drugs. In one embodiment, the compounds of the invention can be administered in lower doses compared to one or more known trypanolytic drugs (preferably, without altering the therapeutic outcome). Preferably, the known trypanolytic drugs are selected from the group consisting of Pentamidine, Suramin, Melarsoprol, Eflornithine, isometamidium chloride, diminazene aceturate and homidium (bromide and chloride).

Pharmaceutical Compositions

In a further aspect, the present invention provides a pharmaceutical composition comprising a compound as specified above under the heading "Compounds" and one or more pharmaceutically acceptable excipients.

The pharmaceutical composition may be administered to an individual by any route, such as enterally or parenterally.

The expressions "enteral administration" and "administered enterally" as used herein mean that the drug administered is taken up by the stomach and/or the intestine. Examples of enteral administration include oral and rectal administration. The expressions "parenteral administration" and "administered parenterally" as used herein mean modes of administration other than enteral administration, usually by injection or topical application, and include, without limitation, intravenous, intramuscular, intraarterial, intrathecal, intracapsular, intraosseous, intraorbital, intracardiac, intradermal, intraperitoneal, transtracheal, subcutaneous, subcuticular, intraarticular, subcapsular, intracerebral, intracerebroventricular, subarachnoid, intraspinal, epidural and intrasternal administration (such as by injection and/or infusion) as well as topical administration (e.g., epicutaneous, inhalational, or through mucous membranes (such as buccal, sublingual or vaginal)).

The compounds and compositions according to the present invention are generally applied in "pharmaceutically acceptable amounts" and in "pharmaceutically acceptable preparations". Such compositions may contain salts, buffers, preserving agents, carriers and optionally other therapeutic agents. "Pharmaceutically acceptable salts" comprise, for example, acid addition salts which may, for example, be formed by mixing a solution of compounds with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, arginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, galactate, galacturonate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isobutyrate, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, phthalate, picrate, pivalate, polygalacturonate, propionate, salicylate, stearate, sulfate, suberate, succinate, tannate, tartrate, teoclate, tosylate, triethiodide, undecanoate, valerate, and the like (see, for example, S. M. Berge et al., "Pharmaceutical Salts", J. Pharm. Sci., 66, pp. 1-19 (1977)).

The term "excipient" when used herein is intended to indicate all substances in a pharmaceutical composition which are not active ingredients (e.g., which are therapeutically inactive ingredients that do not exhibit any therapeutic effect in the amount/concentration used), such as, e.g., carriers, binders, lubricants, thickeners, surface active agents, preservatives, emulsifiers, buffers, flavoring agents, colorants, or antioxidants.

The compositions according to the present invention may comprise a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The "pharmaceutically acceptable carrier" may be in the form of a solid, semisolid, liquid, or combinations thereof. Preferably, the carrier is suitable for enteral (such as oral) or parenteral administration (such as intravenous, intramuscular, subcutaneous, spinal or epidermal administration (e.g., by injection or infusion)). Depending on the route of administration, the active compound, i.e., the compound of the invention, may be coated in a material to protect the compound from the action of acids and other natural conditions that may inactivate the compound.

Examples of suitable aqueous and non-aqueous carriers which may be employed in the pharmaceutical compositions used according to the present invention include water (e.g., water for injection), ethanol, polyols (such as glycerol, propylene glycol, polyethylene glycol, and the like), aqueous solutions of a salt, carbohydrate, sugar alcohol, or an amino acid (such as saline or an aqueous amino acid solution), and suitable mixtures and/or buffered forms thereof, vegetable oils (such as olive oil), and injectable organic esters (such as ethyl oleate). Proper fluidity can be maintained, for example, by the use of coating materials, such as lecithin, by the maintenance of the required particle size in the case of dispersions, and by the use of surfactants.

Pharmaceutically acceptable carriers include sterile aqueous solutions or dispersions and sterile powders for the extemporaneous preparation of sterile injectable solutions or dispersions. The use of such media and agents for pharmaceutically active substances is known in the art. Except insofar as any conventional media or agent is incompatible with the active compound, use thereof in the pharmaceutical compositions of the invention is contemplated.

Additional active compounds can be administered together with, before or after the compound used in the invention (in particular that specified above under the heading "Compounds") or incorporated into the compositions. In one embodiment, the pharmaceutical composition described herein comprises a pyrazolopyridine derivative as described above (e.g. having the general formula (Ia), (Ib), (IIa), (IIb), (IIIa), (IIIb), (IVa), (IVb), (Va), (Vb), (VIa), (VIb), (VIIa), (VIIb), (VIIIa), or (VIIIb) or a hydrate, solvate, salt, complex, racemic mixture, diastereomer, enantiomer, or tautomer thereof or an isotopically enriched form of any of the foregoing), at least one additional active compound, and one or more pharmaceutically acceptable excipients The "additional active compound" may be selected from any compound which can be used in the treatment or prevention of a disease, condition, or disorder caused by or mediated by a parasite of the family Trypanosomatidae, such as trypanolytic drugs, antibodies (which are directed against an antigen of a parasite of the family Trypanosomatidae or an antigen of the parasite progeny), and immunostimulatory agents. Examples of trypanolytic drugs include Pentamidine, Suramin, Melarsoprol, Eflornithine (for humans), isometamidium chloride, diminazene aceturate and homidium (bromide and chloride) (for animals). Examples of immunostimulatory agents include interferons (e.g., interferon alpha or interferon gamma), interferon derivatives (such pegylated interferons (i.e., interferons bearing a polyethylene glycol group), such as peginterferon alfa, peginterferon alfa-2a, peginterferon alfa-2b, peginterferon Lambda-1a,), other cytokines (such as interleukins (e.g., interleukin 7 (IL-7), IL-1. IL-2, IL-12), tumor necrosis factor and colony-stimulating factor), or agents inducing the production of interferons by the host (e.g., agonists of Toll Like Receptor 3 (TLR3)). The additional active compound may induce an additive or synergistic therapeutic effect.

The pharmaceutical composition described herein may comprise, in addition to the pyrazolopyridine derivative as described above, at least one, e.g., 1, 2, 3, 4, 5, 6, 7 or 8, additional active compounds. According to the present teaching, the at least additional active compound, for the immunostimulatory agent, may be formulated together with the pyrazolopyridine derivative as described above in a single pharmaceutical composition. Alternatively, the pharmaceutical composition may be structured as kit of parts, wherein the pyrazolopyridine derivative is provided in a first formulation and the at least one additional active compound, for example the immunostimulatory agent, is provided in a second formulation, i.e., a second pharmaceutical composition. The first and the second pharmaceutical compositions may be combined prior to use. In other words, before administering the pharmaceutical composition, a formulation comprising the additional active compound may be added to the first pharmaceutical composition comprising the pyrazolopyridine derivative. Alternatively, the present teaching envisages administering the pyrazolopyridine derivative formulated in a first pharmaceutical composition and administering the at least one additional active compound formulated in a second pharmaceutical composition. The pharmaceutical compositions may be administered concomitantly or in succession. For example, the first pharmaceutical composition may be administered at a first point in time and the second pharmaceutical composition may be administered at a second point in time, wherein the points in time may be separated by, for example, 0, or up to 1, 2, 3, 4, 5 or 10 min, hours, days or years.

The compositions may also contain adjuvants such as preservatives, wetting agents, emulsifying agents, pH buffering agents, and dispersing agents. Prevention of the presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art (cf., e.g., Remington, "The Science and Practice of Pharmacy" edited by Allen, Loyd V., Jr., $22^{nd}$ edition, Pharmaceutical Sciences, September 2012; Ansel et al., "Pharmaceutical Dosage Forms and Drug Delivery Systems", $7^{th}$ edition, Lippincott Williams & Wilkins Publishers, 1999.).

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., Sustained and Controlled Release Drug Delivery Systems, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to an individual in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., J. Neuroimmunol 7· 27 (1984)).

Pharmaceutical compositions typically are sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

An injectable composition should be sterile and fluid to the extent that the composition is deliverable by syringe. In addition to water, the carrier can be an isotonic buffered saline solution, ethanol, polyol (for example, glycerol, propylene glycol, and liquid polyethylene glycol, and the like), and suitable mixtures thereof. Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the individuals to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the pharmaceutical formulations, compositions of the present invention include those suitable for enteral administration (such as oral or rectal) or parenteral administration (such as nasal, topical (including vaginal, buccal and sublingual)). The compositions may conveniently be presented in unit dosage form and may be prepared by any methods known in the art of pharmacy. The amount of active ingredient (in particular, the amount of a compound of the present invention) which can be combined with a carrier material to produce a pharmaceutical composition (such as a single dosage form) will vary depending upon the individual being treated, and the particular mode of administration. The amount of active ingredient which can be combined with a carrier material to produce a single dosage form will generally be that amount of the composition which produces a therapeutic effect.

Generally, out of 100% (for the pharmaceutical formulations/compositions), the amount of active ingredient (in particular, the amount of the compound of the present invention, optionally together with other therapeutically active agents, if present in the pharmaceutical formulations/compositions) will range from about 0.01% to about 99%, preferably from about 0.1% to about 70%, most preferably from about 1% to about 30%, wherein the reminder is preferably composed of the one or more pharmaceutically acceptable excipients.

The amount of active ingredient, e.g., a compound of the invention, in a unit dosage form and/or when administered to an individual or used in therapy, may range from about 0.1 mg to about 1000 mg (for example, from about 1 mg to about 500 mg, such as from about 10 mg to about 200 mg) per unit, administration or therapy. In certain embodiments, a suitable amount of such active ingredient may be calculated using the mass or body surface area of the individual, including amounts of between about 1 mg/kg and 10 mg/kg (such as between about 2 mg/kg and 5 mg/kg), or between about 1 mg/m$^2$ and about 400 mg/m$^2$ (such as between about 3 mg/m$^2$ and about 350 mg/m$^2$ or between about 10 mg/m$^2$ and about 200 mg/m$^2$).

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start with doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be oral, intravenous, intramuscular, intraperitoneal, or subcutaneous, preferably administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation/composition.

For oral administration, the pharmaceutical composition of the invention can take the form of, for example, tablets or capsules prepared by conventional means with pharmaceutical acceptable excipients such as binding agents (e.g., pregelatinised maize starch, polyvinylpyrrolidone, hydroxypropyl methylcellulose), fillers (e.g., lactose, microcrystalline cellulose, calcium hydrogen phosphate), lubricants (e.g., magnesium stearate, talc, silica), disintegrants (e.g., potato starch, sodium starch glycolate), or wetting agents (e.g., sodium lauryl sulphate). Liquid preparations for oral administration can be in the form of, for example, solutions, syrups, or suspensions, or can be presented as a dry product for constitution with water or other suitable vehicle before use. Such liquid preparation can be prepared by conventional means with pharmaceutically acceptable additives such as suspending agents (e.g., sorbitol, syrup, cellulose derivatives, hydrogenated edible fats), emulsifying agents (e.g., lecithin, acacia), non-aqueous vehicles (e.g., almond oil, oily esters, ethyl alcohol, fractionated vegetable oils), preservatives (e.g., methyl or propyl-p-hydroxycarbonates, sorbic acids). The preparations can also contain buffer salts, flavouring, coloring and sweetening agents as deemed appropriate. Preparations for oral administration can be suitably formulated to give controlled release of the pharmaceutical composition of the invention.

The pharmaceutical composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

For administration by inhalation, the pharmaceutical composition of the invention is conveniently delivered in the form of an aerosol spray presentation from a pressurized pack or a nebulizer, with the use of a suitable propellant (e.g., dichlorodifluoromethane, trichlorofluoromethane, dichlorotetrafluoroethane, carbon dioxide, nitrogen, or other suitable gas). In the case of a pressurized aerosol, the dosage unit can be determined by providing a valve to deliver a metered amount. Capsules and cartridges of, for example, gelatin, for use in an inhaler or insufflator can be formulated containing a powder mix of the pharmaceutical composition of the invention and a suitable powder base such as lactose or starch.

In one embodiment, the compounds or compositions of the invention may be administered by infusion, preferably slow continuous infusion over a long period, such as more than 24 hours, in order to reduce toxic side effects. The administration may also be performed by continuous infusion over a period of from 2 to 24 hours, such as of from 2 to 12 hours. Such regimen may be repeated one or more times as necessary, for example, after 6 months or 12 months.

In yet another embodiment, the compounds or compositions of the invention are administered by maintenance therapy, such as, e.g., once a week for a period of 6 months or more.

Formulations for injection can be presented in units dosage form (e.g., in phial, in multi-dose container), and with an added preservative. The pharmaceutical composition of the invention can take such forms as suspensions, solutions or emulsions in oily or aqueous vehicles, and can contain formulatory agents such as suspending, stabilizing, or dispersing agents. Alternatively, the agent can be in powder form for constitution with a suitable vehicle (e.g., sterile pyrogen-free water) before use. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

Compositions of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

Pharmaceutical compositions can be administered with medical devices known in the art. For example, in a preferred embodiment, a therapeutic/pharmaceutical composition of the invention can be administered with a needleless hypodermic injection device, such as the devices disclosed in U.S. Pat. No. 5,399,163; U.S. Pat. No. 5,383,851; U.S. Pat. No. 5,312,335; U.S. Pat. No. 5,064,413; U.S. Pat. No. 4,941,880; U.S. Pat. No. 4,790,824; or U.S. Pat. No. 4,596,556. Examples of well-known implants and modules useful in the present invention include those described in: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system.

Many other such implants, delivery systems, and modules are known to those skilled in the art. In certain embodiments, the compounds of the invention can be formulated to ensure proper distribution in vivo. For example, the blood-brain barrier (BBB) excludes many highly hydrophilic compounds. To ensure that the compounds of the invention cross the BBB (if desired), they can be formulated, for example, in liposomes. For methods of manufacturing liposomes, see, e.g., U.S. Pat. No. 4,522,811; U.S. Pat. No. 5,374,548; and U.S. Pat. No. 5,399,331. The liposomes may comprise one or more moieties which are selectively transported into specific cells or organs, and thus enhance targeted drug delivery (see, e.g., V. V. Ranade (1989) J. Clin. Pharmacol. 29: 685). Exemplary targeting moieties include folate or biotin (see, e.g., U.S. Pat. No. 5,416,016 to Low et al.);

mannosides (Umezawa et al., (1988) Biochem. Biophys. Res. Commun. 153: 1038); antibodies (P. G. Bloeman et al. (1995) FEBS Lett. 357: 140; M. Owais et al. (1995) Antimicrob. Agents Chemother. 39: 180); and surfactant protein A receptor (Briscoe et al. (1995) Am. J. Physiol. 1233: 134).

In one embodiment of the invention, the compounds of the invention are formulated in liposomes. In a more preferred embodiment, the liposomes include a targeting moiety. In a most preferred embodiment, the compounds in the liposomes are delivered by bolus injection to a site proximal to the desired area. Such liposome-based composition should be fluid to the extent that easy syringability exists, should be stable under the conditions of manufacture and storage and should be preserved against the contaminating action of microorganisms such as bacteria and fungi.

A "therapeutically effective dosage" for therapy/treatment can be measured by objective responses which can either be complete or partial. A complete response (CR) is defined as no clinical, radiological or other evidence of a condition, disorder or disease. A partial response (PR) results from a reduction in disease of greater than 50%. Median time to progression is a measure that characterizes the durability of the objective response.

A "therapeutically effective dosage" for therapy/treatment can also be measured by its ability to stabilize the progression of a condition, disorder or disease. The ability of a compound to inhibit, reduce or ameliorate non-apoptotic regulated cell-death and/or to reduce oxidative stress can be evaluated in appropriate animal model systems as such as one or more of those set forth below. Alternatively, these properties of a compound of the present invention can be evaluated by examining the ability of the compound using in vitro assays known to the skilled practitioner such as one or more of those set forth below. A therapeutically effective amount of a compound of the present invention can cure, heal, alleviate, relieve, alter, remedy, ameliorate, improve or affect the condition, disorder or disease or the symptoms of the condition, disorder or disease or the predisposition toward the condition, disorder or disease in an individual. One of ordinary skill in the art would be able to determine such amounts based on such factors as the individual's size, the severity of the individual's symptoms, and the particular composition or route of administration selected.

The pharmaceutical composition of the invention can also, if desired, be presented in a pack, or dispenser device which can contain one or more unit dosage forms containing the said agent. The pack can for example comprise metal or plastic foil, such as blister pack. The pack or dispenser device can be accompanied with instruction for administration.

The pharmaceutical composition of the invention can be used to administer the compound of the invention as sole active agent or it can be administered in combination with other therapeutically and/or cosmetically active agents. In one embodiment, the pharmaceutical composition according to the invention contains, or is administered with, one or more other therapeutically active agents selected from the group consisting of trypanolytic drugs (e.g., Pentamidine, Suramin, Melarsoprol, Eflornithine (for humans) isometamidium chloride, diminazene aceturate and homidium (bromide and chloride) (for animals)); antibodies (which are directed against an antigen of a parasite of the family Trypanosomatidae, its progeny or another microorganism (e.g., a pathogenic bacterium or fungi)); and agents stimulating the immune system of the subject (e.g., interferons, such as interferon alpha or interferon beta, imiquimod, and resiquimod).

Therapeutic and Other Applications

Generally, the present invention demonstrates that the pyrazolopyridine derivatives described herein are capable of selectively binding to PEX14 and, thus, selectively killing parasites of the family Trypanosomatidae.

Thus, the present invention provides a compound of the invention (in particular those specified above with respect to any of formulas (Ia), (Ib), (IIa), (IIb), (IIIa), (IIIb), (IVa), (IVb), (Va), (Vb), (VIa), (VIb), (VIIa), (VIIb), (VIIIa), (VIIIb)) for use in a method of treating and/or preventing a condition, disorder or disease that is caused or mediated by a parasite of the family Trypanosomatidae.

In a further aspect, the present invention provides a pharmaceutical composition for use in a method of treating and/or preventing a condition, disorder or disease that is caused or mediated by a parasite of the family Trypanosomatidae, said composition comprising a compound of the invention (in particular those specified above with respect to any of formulas (Ia), (Ib), (IIa), (IIb), (IIIa), (IIIb), (IVa), (IVb), (Va), (Vb), (VIa), (VIb), (VIIa), (VIIb), (VIIIa), (VIIIb)) and one or more excipients, and optionally at least one additional active compound.

In a further aspect, the present invention provides a method of treating an individual with a need thereof, comprising administering a pharmaceutically effective amount of a compound of the invention (in particular those specified above with respect to any of formulas (Ia), (Ib), (IIa), (IIb), (IIIa), (IIIb), (IVa), (IVb), (Va), (Vb), (VIa), (VIb), (VIIa), (VIIb), (VIIIa), (VIIIb)) to the individual, optionally together with a therapeutically effective amount of at least one additional active compound. In one embodiment, the individual is suffering from, or is susceptible to or at risk of, one or more of the conditions, disorders or diseases disclosed herein. The condition, disorder or disease may be caused or mediated by a parasite of the family Trypanosomatidae.

In any of the above therapeutic aspects, the at least one additional active compound may be selected from the additional active compounds described above. Preferably, the at least one additional active compound (such as 1, 2, 3, 4, 5, 6, 7, 8, 9, or 10 additional compounds) are independently selected from the group consisting of interferons (e.g., interferon alpha or interferon gamma), interferon derivatives (such pegylated interferons, such as peginterferon alfa, peginterferon alfa-2a, peginterferon alfa-2b, peginterferon Lambda-1a,), other cytokines (such as interleukins (e.g., interleukin 7 (IL-7), IL-1. IL-2, IL-12)), or agents inducing the production of interferons by the host (e.g., agonists of Toll Like Receptor 3 (TLR3)).

In one embodiment, the parasite of the family Trypanosomatidae is selected from the genera *Leishmania, Crithidia*, and *Trypanosoma* disclosed herein, preferably from the genera *Leishmania* and *Trypanosoma*. In one embodiment, the parasite of the family Trypanosomatidae is selected from the group consisting of *T. brucei* (in particular *T. brucei gambiense* (T.b.g) and *T. brucei rhodesiense* (T.b.r)), *T. cruzi, T. vivax, T. equiperdum, T evansi, T. congolense, T. equinum, L. donovani, L. chagasi* (syn. *L. infanturn*), *L. braziliensis, L. major, L. tropica, L. mexicana*, and *L. amazonensis*.

In one embodiment, the condition, disorder or disease is mediated or caused by a parasite strain of the family Trypanosomatidae which is resistant against one or more trypanolytic drugs. Preferably, the trypanolytic drugs are selected from the group consisting Pentamidine, Suramin, Melarsoprol, Eflornithine, isometamidium chloride, diminazene aceturate and homidium (bromide and chloride).

In one embodiment, the compounds of the invention (as well as any pharmaceutical composition described herein which contains at least on such compound) may be used to treat and/or prevent a persistent infection, such as a chronic or latent infection.

Particular examples of a disease, disorder or condition which are caused or mediated by a parasite of the family Trypanosomatidae include:

Sleeping Sickness (caused by *Trypanosoma brucei* and transmitted by Tsetse flies);

South American trypanosomiasis (also called Chagas Disease; caused by *Trypanosoma cruzi* and transmitted by triatomine bugs);

leishmaniasis (a set of trypanosomal diseases caused by various species of *Leishmania* transmitted by sandflies) e.g., visceral leishmaniasis (caused by *L. Donovani* or *L. chagasi* (syn. *L. infantum*)), mucocutaneous leishmaniasis (caused by *L. braziliensis*), or cutaneous leishmaniasis (caused by *L. major, L. tropica, L. mexicana*, or *L. amazonensis*);

Nagana, also known as nagana pest or animal African trypanosomiasis (caused by *Trypanosoma brucei* or *Trypanosoma vivax*);

dourine or covering sickness (caused by *Trypanosoma equiperdum*);

animal trypanosomiasis (caused by, e.g., *T. congolense*); and surra (caused by *Trypanosoma evansi*).

In further aspects, the present application provides a compound as specified above under the heading "Compounds" or a pharmaceutical composition as specified above under the heading "Pharmaceutical compositions" for use in therapy, such as in human and/or veterinary medicine.

It is contemplated that the compound as specified above under the heading "Compounds" may be used for the inhibition, reduction or amelioration of an infection with a parasite of the family Trypanosomatidae and/or the reduction of the growth of a parasite (or its progeny) of the family Trypanosomatidae in vivo and/or in vitro, such as in an isolated cell culture, or a sample, tissue or organ isolated from an individual. In certain embodiments, such culture, sample, tissue or organ is used in research; while in other embodiments it is exposed to the compound ex-vivo prior to reintroduction to the same (or a different) individual, such as in tissue or organ transplant, and the inhibition, reduction or amelioration of regulated necrosis of such cell, cell culture, sample, tissue or organ takes place when ex vivo.

Treatment including the compounds of the invention may be provided at home, the doctor's office, a clinic, a hospital's outpatient department, or a hospital. Treatment generally begins under medical supervision so that medical personnel can observe the treatment's effects closely and make any adjustments that are needed. The duration of the treatment depends on the age and condition of the patient, as well as how the patient responds to the treatment.

A person having a greater risk of developing a condition, disorder or disease may receive prophylactic treatment to inhibit or delay symptoms of the condition, disorder or disease.

The term "treatment" is known to the person of ordinary skill, and includes the application or administration of an agent (e.g., a pharmaceutical composition containing said agent) or procedure to a patient or application or administration of an agent (e.g., a pharmaceutical composition containing said agent) or procedure to a cell, cell culture, cell line, sample, tissue or organ isolated from a patient, who has a condition, disorder or disease, a symptom of the condition, disorder or disease or a predisposition toward a condition, disorder or disease, with the purpose to cure, heal, alleviate, relieve, alter, remedy, ameliorate, improve, affect or prevent the condition, disorder or disease, the symptoms of the condition, disorder or disease or the predisposition toward the condition, disorder or disease. Hence, the term "treatment" can include prophylactic treatment of a condition, disorder or disease, or the symptom of a condition, disorder or disease. An agent, when used in treatment, includes the compounds described herein and includes, but is not limited to, other therapeutically active agents that may be small molecules, peptides, peptidomimetics, polypeptides/proteins, antibodies, nucleotides such as DNA or RNA, cells, viruses, ribozymes, siRNA, antisense oligonucleotides, and immunostimulatory agents.

In an alternative aspect, the compounds of the present invention may be evaluated for their pharmacological properties in animal models of diseases. The compounds identified to bind to PEX14 may be structurally modified and subsequently used to decrease growth of a parasite of the family Trypanosomatidae or in treatment (including prophylactic treatment) of a condition, disorder or disease as described herein. The methods used to generate structural derivatives of the small molecules that decrease growth of a parasite of the family Trypanosomatidae are readily known to those skilled in the fields of organic and medicinal chemistry.

The compounds of the invention (or the pharmaceutical composition comprising such compound) may be administered to the individual by any route, preferably by any route described above in section "Pharmaceutical compositions" for the administration of the pharmaceutical composition of the invention.

Synthesis and Intermediates

The compounds of the present invention can be prepared as described below or prepared by methods analogous thereto, which are readily known and available to one of ordinary skill in the art of organic synthesis.

Compounds disclosed herein may be prepared according to the general synthetic sequence shown in Schemes 1 to 4, below.

Scheme 1

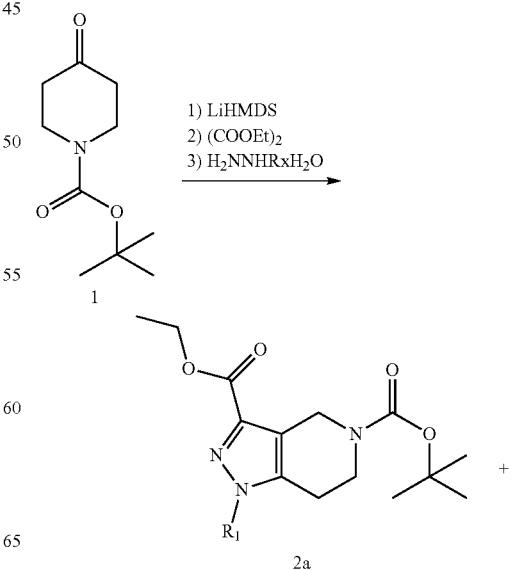

-continued

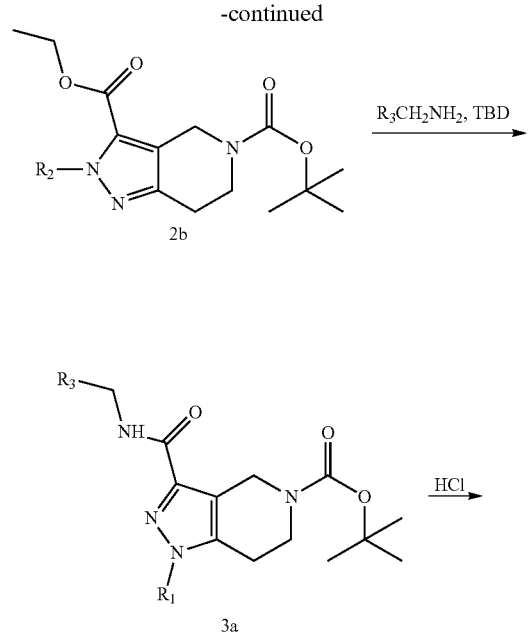

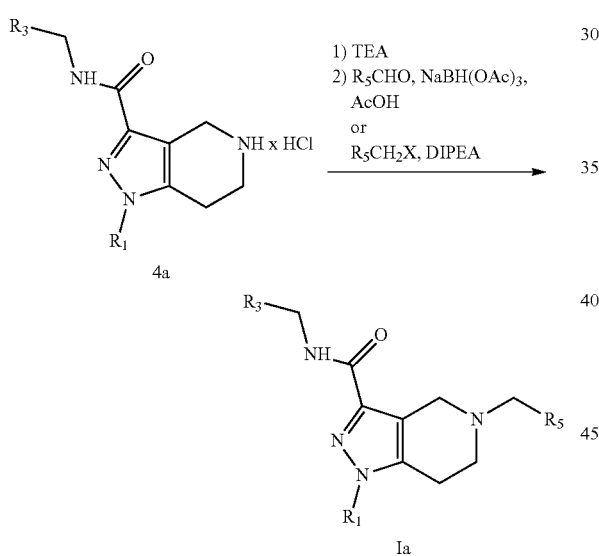

For example, a piperidine derivative (such as the piperidine derivative 1) is converted into its lithium derivative (e.g., using LiHDMS) which is reacted with diethyl oxalate, followed by the in situ condensation with an appropriate hydrazine derivative (e.g., NH$_2$NHR$_x$, wherein Rx is either R$_1$ or R$_2$) to obtain a chromatographically separable mixture of isomers 2a and 2b. The ester derivative 2a (or 2b) is then subjected to aminolysis with an appropriate amine (e.g., R$_3$CH$_2$NH$_2$) in the presence of TBD catalyst. The resulting amide 3a is deprotected with an acid (e.g., hydrogen chloride) to give the corresponding salt 4a (or 4b). The final compounds Ia (or Ib) are obtained by reductive amination using an appropriate aldehyde (e.g., R$_5$CHO) or by N-alkylation using an appropriate alkyl halide (e.g., R$_5$CH$_2$X, wherein X is halogen).

Scheme 2

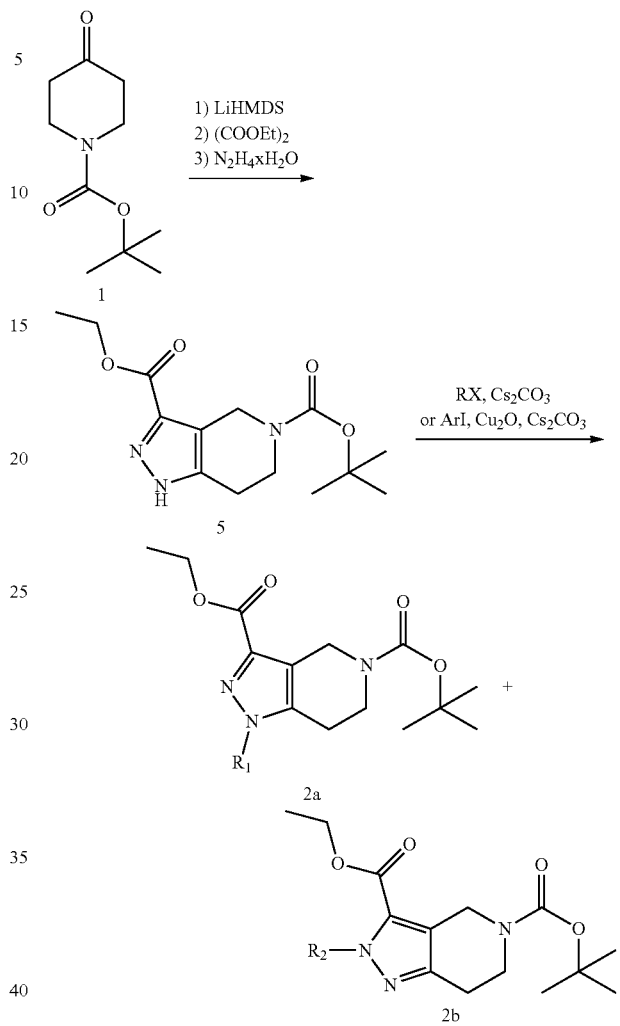

Alternatively, compounds 2a and 2b may be prepared by converting a piperidine derivative (such as the piperidine derivative 1) into its lithium derivative (e.g., using LiHDMS) which is reacted with diethyl oxalate, followed by the in situ condensation with hydrazine to obtain intermediate 5. The intermediate 5 is then N-alkylated with an appropriate alkyl halide (e.g., RX, wherein R is either R$_1$ or R$_2$ and X is halogen) or subjected to N-arylation (using, e.g., copper (I) and ArI, wherein Ar is an aromatic R$_1$ or R$_2$).

Scheme 3

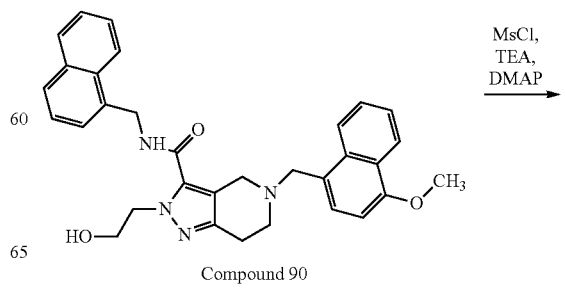

Compound 90

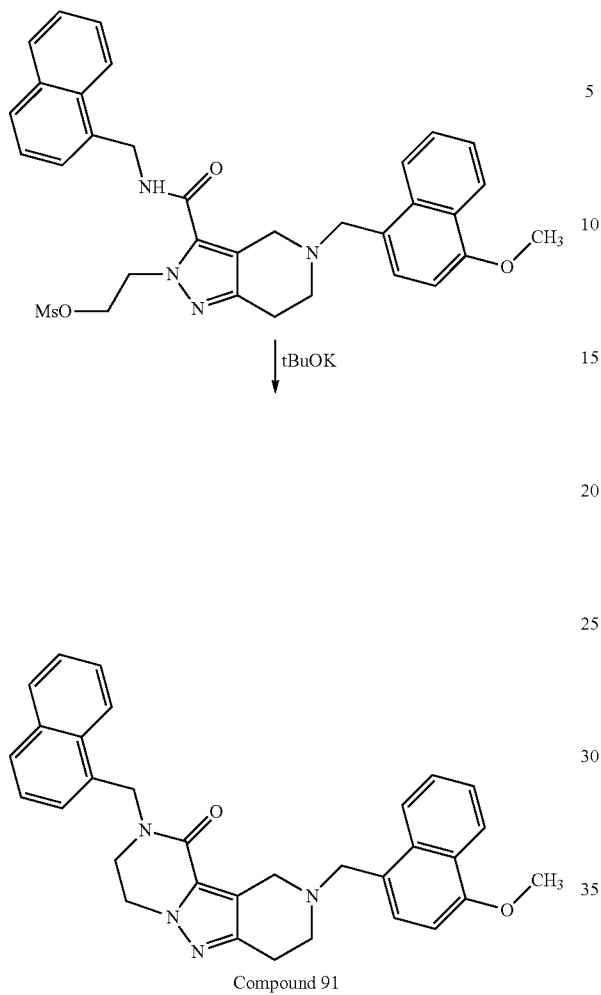

Compound 91

Compounds of formula (Ib), wherein $R_2$ and $R^8$ join together with the atoms to which they are attached to form a ring, may be prepared as shown in Scheme 3, above. For example, the hydroxyl group of compound 90 is converted into a leaving group (e.g., by using methanesulfonyl chloride in presence of triethylamine and DMAP). The resulting compound is then subjected to cyclization conditions (e.g., using potassium tert-butoxide) to give compound 91.

Scheme 4

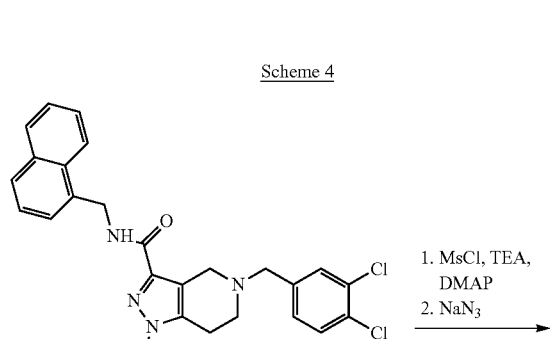

Compound 52

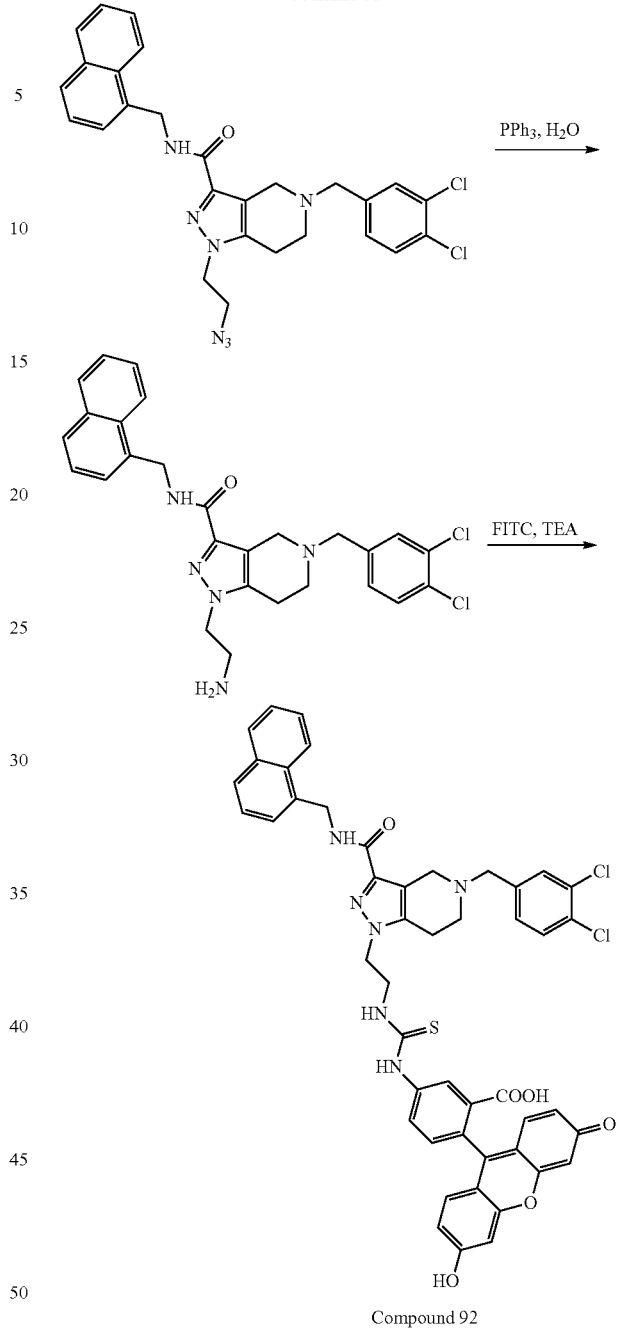

Compound 92

The compounds of the invention may be further modified as exemplified in Scheme 4, above. For example, the hydroxyl group of compound 52 may be converted into a leaving group (e.g., by using methanesulfonyl chloride in presence of triethylamine and DMAP), followed by the nucleophilic substitution of the leaving group with a reagent bearing a desired functional group or a precursor of said functional group (e.g., sodium azide). The thus obtained compound may be reduced (e.g., by using triphenylphosphine and water) and then reacted with another reagent (e.g., fluorescein isothiocyanate) to give compound 92.

A person of ordinary skill will appreciate that other routes of synthesis may be employed as well. In particular, other routes of synthesis may in fact be applied to certain embodiments of the compounds disclosed herein. The person of ordinary skill is referred to general textbooks, such as March's Advanced Organic Chemistry (Michael B. Smith & Jerry March, Wiley-Interscience, 2000), The Practice of Medicinal Chemistry (Camile G. Wermuth, Academia Press, 2003) and Protective Groups in Organic Synthesis (Theosora W. Greene & Peter G. M. Wuts; John Wiley & Sons Inc, 1999).

Other features and advantages of the present invention will be apparent from the following examples which are included to demonstrate preferred embodiments of the present invention but which do not limit the present invention. Rather, in light of the present disclosure, the skilled person will appreciate that many changes can be made in the specific embodiments which are disclosed and still obtain a like or similar result without departing from the scope of the invention.

EXAMPLES

The abbreviations used in the present invention have the following meanings:
AcOEt ethyl acetate
DMAP dimethylaminopyridine
FITC fluorescein isothiocyanate
h hour
kg kilogram
LiHMDS lithium hexamethyl disalazine
M molar (mol/l)
MeOH methanol
min minute
I-LM micromolar (μmol/l)
MsCl methanesulfonyl chloride
nM nanomolar (nmol/l)
PPh$_3$ triphenylphosphine
TBD 1,5,7-triazabicyclo[4.4.0]dec-5-ene
TEA triethanolamine
wt weight
vol or v volume

Example 1—Identification of Candidate Compounds

Figure 1:
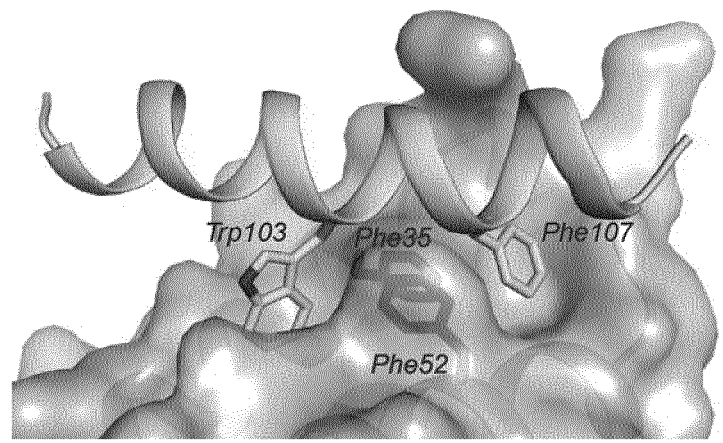
FIG. 1 The model of the interaction between PEX14 and PEX5.

The structure of the *trypanosoma* PEX14 was compared to the published structure of human PEX14 bound to PEX5 protein (Neufeld et al., EMBO J. 28 (2009), 745-54) and a model of *trypanosoma* complex created by molecular modeling (cf. FIG. 1). The structure of unbound *trypanosoma* PEX14 was used for the model generation. The interface model was subsequently used to create a 3D pharmacophore binding model which—together with pharmacophore-based software Pharmer—was utilized for screening and identifying compounds which bind to PEX14. Then, the results were docked to the *trypanosoma* model of PEX14 protein using AutodockVina. The docking poses were inspected and several candidate compounds which were found by this procedure were selected for in vitro testing using the AlphaScreen assay; cf. Example 3. Compounds which were found active in this in vitro assay were selected for further studies and optimization.

Example 2—Synthesis of Compound 52

Step A—5-tert-butyl 3-ethyl 2-(2-hydroxyethyl)-6,7-dihydro-2H-pyrazolo[4,3-c]pyridine-3,5(4H)-dicarboxylate and 5-tert-butyl 3-ethyl 1-(2-hydroxyethyl)-6,7-dihydro-1H-pyrazolo[4,3-c]pyridine

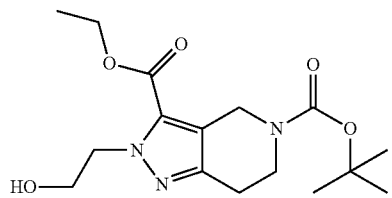

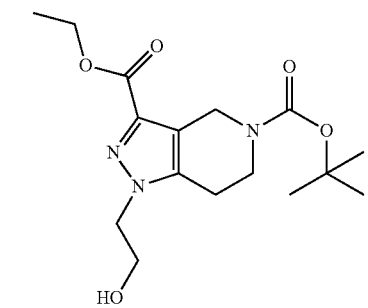

A solution of 7.50 g (37.5 mmol) of tert-butyl 4-oxopiperidine-1-carboxylate in 25 mL of dry THF was added over 30 min to a mixture of 37.5 mL of 1 M LiHMDS (37.5 mmol) and 50 mL of dry THF, at −78° C., under argon. The resulting solution was stirred at this temperature for 1 h and subsequently 5.48 g (37.5 mmol) of diethyl oxalate was added dropwise. The mixture was allowed to warm to room temperature and quenched by the addition of 10 mL of glacial AcOH. Subsequently, 75 mL of absolute EtOH and 2.85 mL (37.5 mmol) of 2-hydroxyethylhydrazine were added. The resulting mixture was refluxed for 2 h and stirred at room temperature overnight. The solvents were evaporated under reduced pressure. The residue was partitioned between 100 mL of AcOEt, and 30 mL of saturated aqueous solution of NaHCO$_3$. The aqueous layer was discarded and the organic fraction was washed with water and brine, dried with anhydrous Na$_2$SO$_4$, filtered and concentrated under reduced pressure. The residue was purified by column chromatography on silica gel using hexane/AcOEt 1:1 (v/v) then AcOEt/MeOH 95:5 (v/v) as eluents to give 2.00 (16%) g of 5-tert-butyl 3-ethyl 2-(2-hydroxyethyl)-6,7-dihydro-2H-pyrazolo[4,3-c]pyridine-3,5(4H)-dicarboxylate, [M+H]+ 340, and 6.15 g (48%) of 5-tert-butyl 3-ethyl 1-(2-hydroxyethyl)-6,7-dihydro-1H-pyrazolo[4,3-c]pyridine-3,5(4H)-dicarboxylate, [M+H]+ 340.

Step B—tert-butyl 1-(2-hydroxyethyl)-3-((naphthalen-1-ylmethyl)carbamoyl)-6,7-dihydro-1H-pyrazolo[4,3-c]pyridine-5(4H)-carboxylate

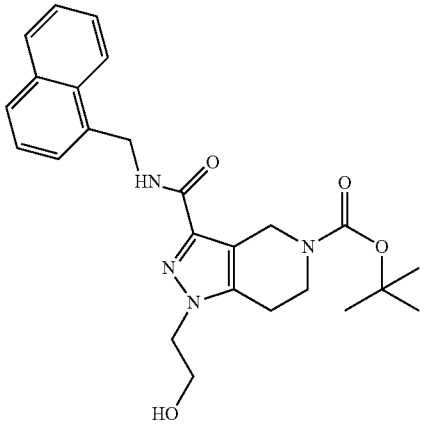 [SMILES: CC(C)(C)OC(=O)N1CCc2c(c(C(=O)NCc3cccc4ccccc34)nn2CCO)C1]

A mixture of 2.30 g (6.78 mmol) of 5-tert-butyl 3-ethyl 1-(2-hydroxyethyl)-6,7-dihydro-1H-pyrazolo[4,3-c]pyridine-3,5(4H)-dicarboxylate, 1.28 g (8.14 mmol) of 1-naphthylmethylamine and 0.28 g (2.03 mmol) of TBD in 5 mL of dry THF was stirred at 70° C. for 12 h, under argon. The mixture was concentrated under reduced pressure and the resulting solid was recrystallized from AcOEt to give 2.05 g (67%) of tert-butyl 1-(2-hydroxyethyl)-3-((naphthalen-1-ylmethyl)carbamoyl)-6,7-dihydro-1H-pyrazolo[4,3-c]pyridine-5(4H)-carboxylate, [M+H]+ 401.

Step C—1-(2-hydroxyethyl)-N-(naphthalen-1-ylmethyl)-4,5,6,7-tetrahydro-1H-pyrazolo[4,3-c]pyridine-3-carboxamide hydrochloride

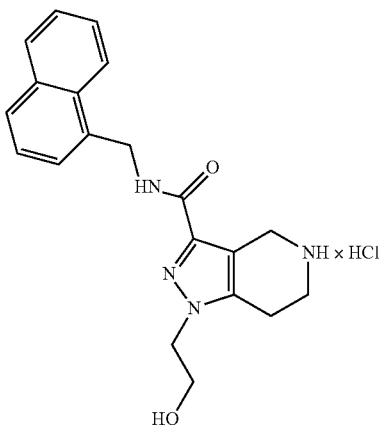

1.05 g (2.33 mmol) of tert-butyl 1-(2-hydroxyethyl)-3-((naphthalen-1-ylmethyl)carbamoyl)-6,7-dihydro-1H-pyrazolo[4,3-c]pyridine-5(4H)-carboxylate was dissolved in 20 mL of DCM. Subsequently, 10 mL of 4 M HCl solution in 1,4-dioxane was added. The resulting mixture was stirred at room temperature for 4 h and concentrated under reduced pressure to give 0.90 g (100%) of 1-(2-hydroxyethyl)-N-(naphthalen-1-ylmethyl)-4,5,6,7-tetrahydro-1H-pyrazolo[4,3-c]pyridine-3-carboxamide hydrochloride, [M+H]+ 301.

Step D—5-(3,4-dichlorobenzyl)-1-(2-hydroxyethyl)-N-(naphthalen-1-ylmethyl)-4,5,6,7-tetrahydro-M-pyrazolo[4,3-c]pyridine-3-carboxamide

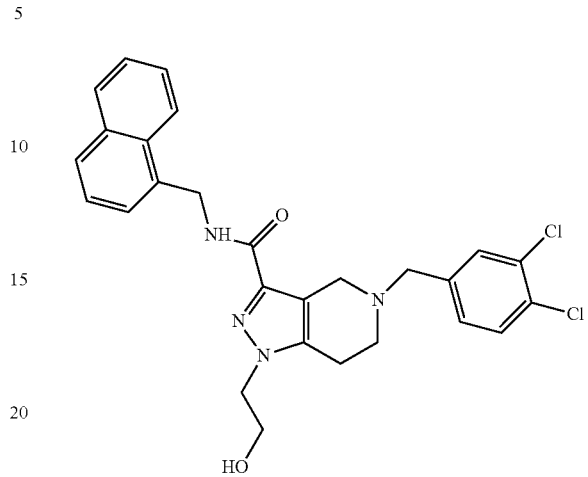

A stirred suspension of 80 mg (0.21 mmol) of 1-(2-hydroxyethyl)-N-(naphthalen-1-ylmethyl)-4,5,6,7-tetrahydro-1H-pyrazolo[4,3-c]pyridine-3-carboxamide hydrochloride in 10 mL of dry THF was treated with 29 μL (0.21 mmol) of triethylamine, under argon. After 30 min 37 mg (0.21 mmol) of 3,4-dichlorobenzaldehyde and 15 μL (0.25 mmol) of glacial acetic acid were added, followed by 66 mg (0.31 mmol) of sodium triacetoxyborohydride. The mixture was stirred for 12 h. 15 mL of AcOEt was added, followed by 5 mL of 1N aqueous solution of NaOH. The aqueous layer was discarded and the organic fraction was washed with water, brine, dried with anhydrous $Na_2SO_4$, filtered and concentrated under reduced pressure. The residue was purified by column chromatography on silica gel using AcOEt/TEA 99:1 (v/v) then AcOEt/MeOH/TEA 97:2:1 (v/v/v) as eluents to give 63 mg (60%) of 5-(3,4-dichlorobenzyl)-1-(2-hydroxyethyl)-N-(naphthalen-1-ylmethyl)-4,5,6,7-tetrahydro-1H-pyrazolo[4,3-c]pyridine-3-carboxamide, [M+H]+ 509.

A selection of compounds within the scope of, or for use within the methods of, the present invention is listed in Table 1. The compounds in Table 1 are synthesized according to Example 2, and the surprising activities (binding to PEX-14 protein and killing parasites of the family Trypanosomatidae) of such compounds are shown in Table 2 and FIG. 2, respectively, as determined according to Examples 3 and 4.

Example 3—AlphaScreen Assay

We have used an AlphaScreen assay to measure in vitro activity of PEX14-PEX5 binding inhibitors. The assay uses two types of beads: donor beads are coupled with streptavidin, and acceptor beads are coupled with an anti His-tag antibody. Upon excitation with light of a wavelength of 680 nm the donor beads produce reactive oxygen species that travel in solution only for a limited distance. If the acceptor beads are within that travel distance, it will absorb the reactive oxygen and emit light in the range of 520-620 nm. In our assay we have used biotin-coupled PEX5 peptide (coupling to donor beads) and His-tagged *T. brucei* PEX14 (coupled to the acceptor beads). Thus, PEX5-PEX14 complex dissociation by a ligand caused decrease in light emission as the donor and acceptor beads were separated.

Typically, we used 30 nM PEX5, 30 nM PEX14 and bead concentrations of 5 µg/mL. The PEX5-PEX14 complex was incubated with varying concentrations of inhibitor for 1 hour. Next, the beads were added and the system allowed to equilibrate for another hour. The raw data were fitted to four parameter sigmoidal curves by Origin software and $EC_{50}$ values calculated. Each measurement was performed in quadruplicate and every experiment was accompanied with blank and reference samples (using non-biotinylated PEX5 peptide as a binding competitor). Results are shown in Table 2, below.

Example 4—Antitrypanosomal Activity Assay

Antitrypanosomal activity was tested on *T. brucei brucei* bloodstream from parasites (strain—Lister 427, VATMITat 1.2). Stock solutions of compounds (50 mM) were prepared in DMSO. Two fold serial dilutions of each compound (10 wells in each row) were prepared in 96 well plates in HMI11 medium (100 µl/well; quadruplicates; cf. also Hirumi et al., J. Parasitol. 75 (1989), 985-989). One well without compound, and one well with media alone were included in each row. Parasites grown in HMI11 were inoculated (100 µl of $4 \times 10^4$/ml) in all wells (except the well with "media alone") giving a final concentration of parasites of $2 \times 10^4$/ml. The plates were incubated for 66 hours at 37° C. in the incubator with 5% $CO_2$. 20 µl resazurin (Sigma, 0.125 mg/ml in Hanks Balanced Salt Solution) was added to all wells and the plate was further incubated for 6 hours. Change in color of resazurin (blue to pink) by living cells was measured with a 96 well plate reader (excitation at 530 nm, emission at 585 nm, filter cut-off: 570 nm). Percent inhibition values were calculated by setting the well without compound to "0% inhibition". Non-linear regression graphs were plotted in Graphpad Prism to yield sigmoidal dose-response curves and $IC_{50}$ values were determined (compound concentration giving 50% inhibition). Results are shown in Table 2, below and FIG. 2.

As can be seen from Table 2 and FIG. 2, the compounds of the invention prevented *trypanosoma* cell growth completely. Generally, the $IC_{50}$ values found in the in vivo assay are much lower than the $EC_{50}$ values found in the in vitro assay. This was expected as even minor malfunction of glycosome biogenesis of a parasite of the family Trypanosomatidae and, thus, minor release of HK and PFK into the cytosol of the parasite should be lethal to the parasite.

TABLE 2

| Cmpd. No. | AlphaScreen $EC_{50}$ [µM] (±SD) | Antitrypanosomal activity $IC_{50}$ [µM] |
|---|---|---|
| 1 | 60.2 (34.26) | |
| 2 | 84.28 (7.17) | 17 |
| 3 | 63.28 (7.05) | 3 |
| 4 | 1375 (2524) | 51 |
| 5 | 16.52 (1.11) | 3.4 |
| 6 | 18.27 (2.27) | 8.0 |
| 7 | 4528 | 45 |
| 8 | 103.21 (7.84) | 21 |
| 9 | 27.77 (4.08) | 6.8 |
| 10 | 33.59 (4.06) | 7.4 |
| 11 | 22.14 (1.7) | 1.1 |
| 12 | 42.02 (6.63) | 12 |
| 13 | 6.72 (0.99) | 3.58 |
| 14 | 11.94 (2.59) | 3.61 |
| 15 | 7.92 (1.09) | 1.47 |
| 16 | 10.58 (1.22) | 2.35 |
| 17 | 10.50 (3.41) | 2.56 |
| 18 | 11.11 (2.00) | 1.85 |
| 19 | 118.21 (15.17) | |
| 20 | 126.81 (50.78) | |
| 21 | 50.3 (2.63) | 9.7 |
| 22 | 105.81 (11.18) | |
| 23 | 132.88 (13.56) | |
| 24 | 80.39 (12.47) | 25 |
| 25 | 148.2 (19.13) | |
| 26 | 139.69 (14.88) | |
| 27 | 195.79 (41.91) | 39 |
| 28 | 154.67 (13.23) | |
| 29 | 221.55 (22.41) | |
| 30 | 29.79 (3.36) | 6.6 |
| 31 | 35.22 (2.62) | |
| 32 | 27.15 (4.79) | 2.5 |
| 33 | 41.82 (4.2) | |
| 34 | 49.78 (3.49) | |
| 35 | 50.06 (2.17) | |
| 36 | 8.71 (1.12) | 3.4 |
| 37 | 7.61 (0.24) | 3.5 |
| 38 | 10.41 (0.88) | 3.7 |
| 39 | 12.67 (1.50) | 5.5 |
| 40 | 51.4 (34.15) | 8.1 |
| 41 | 32.26 (3.75) | 5.6 |
| 42 | 36.16 (4.17) | 4.2 |
| 43 | 21.4 (2.38) | 5.5 |
| 44 | 18.9 (1.27) | 4.6 |
| 45 | 53.76 (6.43) | 10.7 |
| 46 | 61.22 (6.92) | 13.1 |
| 47 | 48.6 (4.95) | 7.6 |
| 48 | 34.01 (2.99) | 5.4 |
| 49 | 32.53 (4.35) | 2.7 |
| 50 | 28.92 (2.89) | 3.3 |
| 51 | 40.05 (4) | 6.2 |
| 52 | 26.47 (2.5) | 4.3 |
| 53 | 39.76 (4.64) | 6.8 |
| 54 | 84.4 (15.89) | 19 |
| 55 | 199.65 (78.57) | 10 |
| 56 | 108.81 (11.75) | 3.3 |
| 57 | 108.7 (12.45) | 2 |
| 58 | 105.4 (13.8) | 4.12 |
| 59 | 130.54 (14.7) | |
| 60 | 20.2 (1.02) | 5.6 |
| 61 | 24.06 (2.96) | 7 |
| 62 | 38.08 (7.69) | 4.5 |
| 63 | 170.93 (27.19) | |
| 64 | 132.41 (35.6) | |
| 65 | 112.35 (14.48) | |
| 66 | 146.8 (16.21) | |
| 67 | 74.27 (9.47) | |
| 68 | 158.77 (23.32) | |
| 69 | 150.58 (17.59) | |
| 70 | 9.69 (44.79) | |
| 71 | 149.72 (14.13) | |
| 72 | 222.88 (57.57) | |
| 73 | 220.4 (55.07) | |
| 74 | 78.26 (6.78) | |
| 75 | 94.95 (11.01) | |
| 76 | 148.21 (19.68) | |
| 77 | 141.83 (16.87) | |
| 78 | 68.8 (5.31) | |
| 79 | 95.36 (9.57) | |
| 80 | 45.92 (2.76) | |
| 81 | 74.86 (5.32) | |
| 82 | 149.17 (12.69) | |
| 83 | 132.41 (10.43) | |
| 84 | 119.89 (4.55) | |
| 85 | 215.01 (58.41) | |
| 86 | 168.7 (13.48) | |
| 87 | 230.45 (50.45) | |
| 88 | 134.42 (30.47) | 22 |
| 90 | 66.14 (23.91) | 3.3 |
| 91 | 19.19 (4.28) | 6.4 |
| 94 | 1.4 (0.22) | 0.74 |
| 95 | 1.75 (0.14) | 0.10 |
| 96 | 1.92 (0.25) | 2.46 |
| 97 | 1.98 (0.16) | 0.10 |
| 98 | 2.27 (0.30) | 0.07 |

TABLE 2-continued

| Cmpd. No. | AlphaScreen EC$_{50}$ [µM] (±SD) | Antitrypanosomal activity IC$_{50}$ [µM] |
|---|---|---|
| 99 | 2.73 (0.30) | 0.25 |
| 100 | 4.62 (0.57) | 0.05 |
| 101 | 3.44 (0.42) | 0.29 |
| 102 | 4.21 (0.85) | 0.24 |
| 103 | 10.0 (0.98) | 0.18 |
| 104 | 10.57 (0.62) | 0.2 |
| 105 | 11.58 (1.27) | 0.34 |
| 106 | 25.0 (2.5) | 4.6 |
| 107 | 28.69 (11.1) | 2.9 |
| 108 | 38.7 (2.7) | |
| 109 | 38.7 (3.3) | 5.4 |
| 110 | 43.8 (7.0) | 2.6 |
| 111 | 52.9 (10.0) | 4.05 |
| 112 | 53.04 (15.6) | 5.7 |
| 113 | 72.05 (9.9) | |
| 114 | 121.0 (18) | 3.9 |
| 115 | 121.5 (34) | 5.9 |
| 116 | 230.5 (27) | |
| 117 | 391 (42.6) | |
| 118 | 632 (114) | |
| 121 | | 5.0 |
| 124 | | 3.5 |
| 125 | | 3.6 |

AlphaScreen: see Example 3 for details;
Antitrypanosomal activity: see Example 4 for details;
SD: standard deviation For several of the compounds of the invention the results of the cellular activity were correlated with the results of the biophysical assay. The resulting correlation graph is shown in FIG. 5 (values are given in log(IM)). According to this graph, the correlation coefficient was determined to be 0.87.

Example 5—Toxicity Assay

For the determination of the toxicity profile of the compounds of the invention, the antitrypanosomal activity assay of Example 4 was repeated with the exception that HEK cells instead of T. brucei were used. It was found that the compounds of the invention exhibited a limited cytotoxic effect against HEK cells, which was significantly weaker than the effect against T. brucei. In most cases, the compounds of the invention exhibited no cytotoxicity against HEK cells up to 50 µM or even up to 100 µM.

Example 6—Crystallographic Analysis

To confirm the binding of the compounds of the invention to PEX14 at the PEX5 binding site and to gain insights into the relationship between the structure of complex and the activity of the compounds, we have undertaken crystallographic studies of the PEX14-ligand complexes. The complexes were crystallized and structures of two compounds of the invention solved at high resolution. As shown in FIG. 3, compounds 21 (A) and 32 (B) fill the same binding sites as PEX5. Thus, the crystallographic data confirmed the assumed binding mode and interaction of the compounds of the invention with the PEX5 binding site of the PEX14.

The PEX14 proteins are well conserved between protozoa. As can be seen from FIG. 4A, the residues responsible for direct formation of PEX5 binding site (highlighted in grey) are nearly identical for several different parasites of the family Trypanosomatidae. Thus, it is plausible that the compounds of the invention for which it has been generally shown that they bind and inhibit PEX14 of T. brucei will also bind and inhibit PEX14 of other parasites of the family Trypanosomatidae, in particular PEX14 of parasites of the genus Leishmania. In fact, a model of Leishmania PEX14 in complex with compound 32 of the invention was generated by PHYRE server; cf. FIG. 4B. As it is evident from this model, the structure of the complex with Leishmania PEX14 is nearly identical to the structure of the complex with trypanosoma PEX14 (RMSD=0.83 Å). This also demonstrates that the structure is conserved and that specific residues which differ with human PEX14 are located in the binding site and can be used to specifically target parasite PEX14.

Example 7—Compounds of the Invention Cause Glycosomal Transport Failure

The function of the glycosomal transport system was tested experimentally. The trypanosoma cells were grown in standard medium. Two hours prior to the experiments a solution of FITC-PTS peptide was added to the cells together with a sublethal amount of compound 97 (in DMSO) or an equivalent amount of DMSO to the control cells. After two hours the parasites were analyzed by fluorescence microscopy. The FITC-PTS peptide is able to bind to Pex5 protein that subsequently interacts with Pex14 membrane protein allowing transport of its cargo (in this case peptide) to the glycosomes. The result of the experiments are shown in FIG. 6. In the upper part of FIG. 6 it is shown that the FITC-PTS peptide is compartmentalized to the glycosomes. The lower part of FIG. 6 demonstrates that in the presence of a compound of the invention the compartmentalization is disrupted and fluorescent cargo spread over cell volume. The same phenotype was observed previously by RNAi knock down of Pex14. The compounds of the invention do not interact directly with Pex5 and therefore cannot influence FITC-PTS peptide binding to Pex5.

The invention claimed is:

1. A compound selected from the group consisting of a pyrazolopyridine derivative having the general formula (Ia) or (Ib)

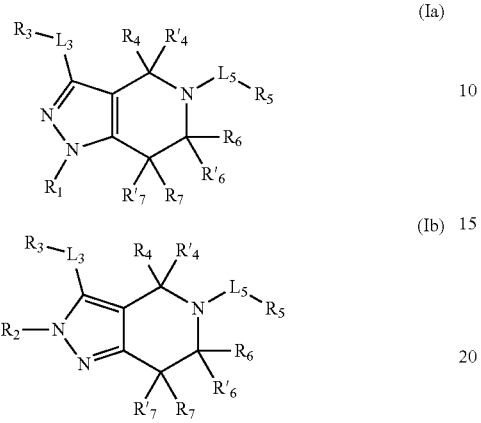

and solvates, salts, complexes, polymorphs, crystalline forms, racemic mixtures, diastereomers, enantiomers, tautomers, isotopically labeled forms, prodrugs, and combinations thereof, wherein $R_1$ is selected from the group consisting of —H, alkyl, alkenyl, alkynyl, aryl, heteroaryl, cycloalkyl, heterocyclyl, —S(O)$_{1-2}$R$^{11}$, —S(O)$_{1-2}$OR$^{11}$, —S(O)$_{1-2}$N(R$^{12}$)(R$^{13}$), —C(=X)R$^{11}$, and —C(=X)XR$^{11}$, wherein each of the alkyl, alkenyl, alkynyl, aryl, heteroaryl, cycloalkyl, and heterocyclyl groups is optionally substituted with one or more independently selected R$^{30}$ or the alkyl group is substituted with one R$^{31}$;

$R_2$ is selected from the group consisting of —H, alkyl, alkenyl, alkynyl, aryl, heteroaryl, cycloalkyl, heterocyclyl, —S(O)$_{1-2}$R$^{11}$, —S(O)$_{1-2}$OR$^{11}$, —S(O)$_{1-2}$N(R$^{12}$)(R$^{13}$), —C(=X)R$^{11}$, and —C(=X)XR$^{11}$, wherein each of the alkyl, alkenyl, alkynyl, aryl, heteroaryl, cycloalkyl, and heterocyclyl groups is optionally substituted with one or more independently selected R$^{30}$ or the alkyl group is substituted with one R$^{31}$;

$R_3$ is selected from the group consisting of aryl, heteroaryl, cycloalkyl, and heterocyclyl, wherein each of the aryl, heteroaryl, cycloalkyl, and heterocyclyl groups is optionally substituted with one or more independently selected R$^{30}$;

$R_4$, R'$_4$, R$_6$, R'$_6$, R$_7$, and R'$_7$ are independently selected from the group consisting of H, alkyl, alkenyl, alkynyl, aryl, heteroaryl, cycloalkyl, heterocyclyl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —C(=X)R$^{11}$, —C(=X)XR$^{11}$, —XC(=X)R$^{11}$, and —XC(=X)XR$^{11}$, wherein each of the alkyl, alkenyl, alkynyl, aryl, heteroaryl, cycloalkyl, and heterocyclyl groups is optionally substituted with one or more independently selected R$^{30}$;

$R_5$ is selected from the group consisting of aryl, heteroaryl, cycloalkyl, and heterocyclyl, wherein each of the aryl, heteroaryl, cycloalkyl, and heterocyclyl groups is optionally substituted with one or more independently selected R$^{30}$;

$L_3$ is —C(O)—N(R$^8$)-(alkylene)-, wherein the alkylene group is optionally substituted with one or more independently selected R$^{30}$;

$L_5$ is selected from the group consisting of alkylene; n is 1, 2, or 3; Y$_3$ is selected from the group consisting of —C(=X)—, S(O)$_{1-2}$, and S(O)$_{1-2}$N(R$^9$) and each of the alkylene groups is optionally substituted with one or more independently selected R$^{30}$;

$R^8$ is selected from the group consisting of —H, alkyl, alkenyl, alkynyl, cycloalkyl, aryl, heteroaryl, heterocyclyl, —OR$^{11}$, and —NHR$^{20}$, wherein each of the alkyl, alkenyl, alkynyl, cycloalkyl, aryl, heteroaryl, and heterocyclyl groups is optionally substituted with one or more independently selected R$^{30}$, or R$^8$ and R$_2$ may join together with the atoms to which they are attached to form a ring which is optionally substituted with one or more independently selected R$^{30}$ or R$^8$ and R$_3$ may join together with the atoms to which they are attached to form a polycyclic ring which is optionally substituted with one or more independently selected R$^{30}$;

$R^9$ is selected from the group consisting of —H, alkyl, alkenyl, alkynyl, cycloalkyl, aryl, heteroaryl, heterocyclyl, —OR$^{11}$, and —NHR$^{20}$, wherein each of the alkyl, alkenyl, alkynyl, cycloalkyl, aryl, heteroaryl, and heterocyclyl groups is optionally substituted with one or more independently selected R$^{30}$;

$R^{10}$ is selected from the group consisting of —H, alkyl, alkenyl, alkynyl, cycloalkyl, aryl, heteroaryl, heterocyclyl, —OR$^{11}$, and —NHR$^{20}$, wherein each of the alkyl, alkenyl, alkynyl, cycloalkyl, aryl, heteroaryl, and heterocyclyl groups is optionally substituted with one or more independently selected R$^{30}$;

X is independently selected from O, S, and N(R$^{14}$);

$R^{11}$ is, in each case, selected from the group consisting of —H, alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more independently selected R$^{30}$;

$R^{12}$ and R$^{13}$ are, in each case, independently selected from the group consisting of —H, alkyl, alkenyl, alkynyl, cycloalkyl, aryl, heteroaryl, and heterocyclyl, or R$^{12}$ and R$^{13}$ may join together with the nitrogen atom to which they are attached to form the group —N=CR$^{15}$R$^{16}$, wherein each of the alkyl, alkenyl, alkynyl, cycloalkyl, aryl, heteroaryl, and heterocyclyl groups is optionally substituted with one or more independently selected R$^{30}$;

$R^{14}$ is independently selected from the group consisting of —H, alkyl, alkenyl, alkynyl, cycloalkyl, aryl, heteroaryl, heterocyclyl, and —OR$^{11}$, wherein each of the alkyl, alkenyl, alkynyl, cycloalkyl, aryl, heteroaryl, and heterocyclyl groups is optionally substituted with one or more independently selected R$^{30}$;

$R^{15}$ and R$^{16}$ are independently selected from the group consisting of —H, alkyl, alkenyl, alkynyl, cycloalkyl, aryl, heteroaryl, heterocyclyl, and —NH$_y$R$^{20}_{2-y}$, or R$^{15}$ and R$^{16}$ may join together with the atom to which they are attached to form a ring which is optionally substituted with one or more independently selected R$^{30}$, wherein each of the alkyl, alkenyl, alkynyl, cycloalkyl, aryl, heteroaryl, and heterocyclyl groups is optionally substituted with one or more independently selected R$^{30}$;

y is an integer from 0 to 2;

$R^{20}$ is selected from the group consisting of alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more independently selected $R^{30}$;

$R^{30}$ is a 1$^{st}$ level substituent and is, in each case, independently selected from the group consisting of alkyl, alkenyl, alkynyl, aryl, heteroaryl, cycloalkyl, heterocyclyl, halogen, —CN, azido, —NO$_2$, —OR$^{71}$, —N(R$^{72}$)(R$^{73}$), —S(O)$_{0-2}$R$^{71}$, —S(O)$_{1-2}$OR$^{71}$, —OS(O)$_{1-2}$R$^{71}$, —OS(O)$_{1-2}$OR$^{71}$, —S(O)$_{1-2}$N(R$^{72}$)(R$^{73}$), —OS(O)$_{1-2}$N(R$^{72}$)(R$^{73}$), —N(R$^{71}$)S(O)$_{1-2}$ R$^{71}$, —NR$^{71}$ S(O)$_{1-2}$OR$^{71}$, —NR$^{71}$S(O)$_{1-2}$N(R$^{72}$)(R$^{73}$), —C(=X$^1$)R$^{71}$, —C(=X$^1$)X$^1$R$^{71}$, —X$^1$C(=X$^1$)R$^{71}$, and —X$^1$C(=X$^1$)X$^1$R$^{71}$, and/or any two R$^{30}$ which are bound to the same carbon atom of a cycloalkyl or heterocyclyl group may join together to form =X$^1$, wherein each of the alkyl, alkenyl, alkynyl, aryl, heteroaryl, cycloalkyl, and heterocyclyl groups being a 1$^{st}$ level substituent is optionally substituted by one or more 2$^{nd}$ level substituents, wherein said 2$^{nd}$ level substituent is, in each case, independently selected from the group consisting of C$_{1-6}$ alkyl, C$_{2-6}$ alkenyl, C$_{2-6}$ alkynyl, 3- to 14-membered aryl, 3- to 14-membered heteroaryl, 3- to 14-membered cycloalkyl, 3- to 14-membered heterocyclyl, halogen, —CF$_3$, —CN, azido, —NO$_2$, —OR$^{81}$, —N(R$^{82}$)(R$^{83}$,) S(O)$_{0-2}$R$^{81}$, —S(O)$_{1-2}$OR$^{81}$, —OS(O)$_{1-2}$R$^{81}$, —OS(O)$_{1-2}$OR$^{81}$, —S(O)$_{1-2}$N(R$^{82}$)(R$^{83}$), —OS(O)$_{1-2}$N(R$^{82}$)(R$^{83}$), —N(R$^{81}$)S(O)$_{1-2}$R$^{81}$, —NR$^{81}$S(O)$_{1-2}$OR$^{81}$, —NR$^{81}$S(O)$_{1-2}$N(R$^{82}$)(R$^{83}$), —C(=X$^2$)R$^{81}$, —C(=X$^2$)X$^2$R$^{81}$, —X$^2$C(=X$^2$)R$^{81}$, and —X$^2$C(=X$^2$)X$^2$R$^{81}$, and/or any two 2$^{nd}$ level substituents which are bound to the same carbon atom of a cycloalkyl or heterocyclyl group being a 1$^{st}$ level substituent may join together to form =X$^2$, wherein each of the C$_{1-6}$ alkyl, C$_{2-6}$ alkenyl, C$_{2-6}$ alkynyl, 3- to 14-membered aryl, 3- to 14-membered heteroaryl, 3- to 14-membered cycloalkyl, 3- to 14-membered heterocyclyl groups being a 2$^{nd}$ level substituent is optionally substituted with one or more 3$^{rd}$ level substituents, wherein said 3$^{rd}$ level substituent is, in each case, independently selected from the group consisting of C$_{1-3}$ alkyl, halogen, —CF$_3$, —CN, azido, —NO$_2$, —OH, —O(C$_{1-3}$ alkyl), —OCF$_3$, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{z-2}$(C$_{1-3}$ alkyl)$_z$, and —N(C$_{1-3}$ alkyl)C(=NH)NH$_{2-z}$ (C$_{1-3}$ alkyl)$_z$, wherein z is 0, 1, or 2 and C$_{1-3}$ alkyl is methyl, ethyl, propyl or isopropyl, and/or any two 3$^{rd}$ level substituents which are bound to the same carbon atom of a 3- to 14-membered cycloalkyl or heterocyclyl group being a 2$^{nd}$ level substituent may join together to form =O, =S, =NH, or =N(C$_{1-3}$ alkyl);

wherein $R^{71}$, $R^{72}$, and $R^{73}$ are independently selected from the group consisting of —H, C$_{1-6}$ alkyl, C$_{2-6}$ alkenyl, C$_{2-6}$ alkynyl, 3- to 7-membered cycloalkyl, 5- or 6-membered aryl, 5- or 6-membered heteroaryl, and 3- to 7-membered heterocyclyl, wherein each of the C$_{1-6}$ alkyl, C$_{2-6}$ alkenyl, C$_{2-6}$ alkynyl, 3- to 7-membered cycloalkyl, 5- or 6-membered aryl, 5- or 6-membered heteroaryl, and 3- to 7-membered heterocyclyl groups is optionally substituted with one, two or three substituents selected from the group consisting of C$_{1-3}$ alkyl, 3- to 7-membered cycloalkyl, 5- or 6-membered aryl, 5- or 6-membered heteroaryl, and 3- to 7-membered heterocyclyl, halogen, —CF$_3$, —CN, azido, —NO$_2$, —OH, —O(C$_{1-3}$ alkyl), —OCF$_3$, =O, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)(C$_{1-3}$ alkyl), —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{z-2}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl;

$R^{81}$, $R^{82}$, and $R^{83}$ are independently selected from the group consisting of —H, C$_{1-4}$ alkyl, C$_{2-4}$ alkenyl, C$_{2-4}$ alkynyl, 3- to 6-membered cycloalkyl, 5- or 6-membered aryl, 5- or 6-membered heteroaryl, and 3- to 6-membered heterocyclyl, wherein each of the C$_{1-4}$ alkyl, C$_{2-4}$ alkenyl, C$_{2-4}$ alkynyl, 3- to 6-membered cycloalkyl, 5- or 6-membered aryl, 5- or 6-membered heteroaryl, and 3- to 6-membered heterocyclyl groups is optionally substituted with one, two or three substituents selected from the group consisting of C$_{1-3}$ alkyl, halogen, —CF$_3$, —CN, azido, —NO$_2$, —OH, —O(C$_{1-3}$ alkyl), —OCF$_3$, =O, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)(C$_{1-3}$ alkyl), —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{z-2}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl;

$X^1$ and $X^2$ are independently selected from O, S, and N(R$^{81}$); and $R^{31}$ is —Y$_4$—B or —B, wherein Y$_4$ is selected from the group consisting of —X—, —C(=X)-(alkylene)$_p$-, —C(=X)X-(alkylene)$_p$-, —XC(=X)-(alkylene)$_p$-, —XC(=X)X-(alkylene)$_p$-, [O—(C$_{1-3}$ alkylene)]$_n$, —[S—(C$_{1-3}$ alkylene)]$_n$, —[N(R$^{10}$)—(C$_{1-3}$ alkylene)]$_n$, —S(O)$_{1-2}$-(alkylene)$_p$-, —OS(O)$_{1-2}$-(alkylene)$_p$-, —OS(O)$_{1-2}$O-(alkylene)$_p$-, —S(O)$_{1-2}$N(R$^9$)-(alkylene)$_p$-, —OS(O)$_{1-2}$N(R$^9$)-(alkylene)$_p$-, —N(R$^9$)S(O)$_{1-2}$-(alkylene)$_p$-, —N(R$^9$)S(O)$_{1-2}$O-(alkylene)$_p$-, and —N(R$^9$)S(O)$_{1-2}$N(R$^9$)-(alkylene)$_p$-, wherein p is 0 or 1; and B is a molecular probe.

2. The compound of claim 1 which has the structure of formula (Ia) with the proviso that (i) when R$_1$ is alkyl, aryl, C$_{3-12}$ cycloalkyl, —(C$_{1-4}$ alkylene)-alkyl, —(C$_{1-4}$ alkylene)-aryl or —(C$_{1-4}$ alkylene)-(C$_{3-12}$ cycloalkyl), wherein the aryl is optionally substituted at one or more positions by halogen; L$_3$ is —C(O)—N(R$^8$)—(C$_{1-10}$ alkylene)-; R$_3$ and R$^8$ join together with the atoms to which they are attached to form a polycyclic ring; and each of R$_4$, R'$_4$, R$_6$, R'$_6$, R$_7$, and R'$_7$ is H, then -L$_5$R$_5$ is not sulfonylaryl, —(C$_{1-4}$ alkylene)-carbonylalkoxyaryl, or —(C$_{1-4}$ alkylene)-sulfonylaryl, wherein the aryl in sulfonylaryl is optionally substituted at one or more positions by alkyl, wherein, at each occurrence under (i), alkyl has 1 to 10 carbon atoms, alkoxy has 1 to 10 carbon atoms, and aryl has 6, 9, 10, or 14 carbon atoms; and/or (ii) when R$_1$ is alkyl, aryl, C$_{3-12}$ cycloalkyl, (C$_{1-4}$ alkylene)-alkyl, —(C$_{1-4}$ alkylene)-aryl or —(C$_{1-4}$ alkylene)-(C$_{3-12}$ cycloalkyl), wherein the aryl is optionally substituted at one or more positions by halogen; L$_3$ is —C(O)—NH—(C$_{1-10}$ alkylene)-; R$_3$ is aryl, C$_{3-12}$ cycloalkyl, heterocyclyl, or heteroaryl, each optionally substituted by one or more hydroxy, alkyl, or alkoxy; and each of R$_4$, R'$_4$, R$_6$, R'$_6$, R$_7$, and R'$_7$ is H, then -L$_5$R$_5$ is not sulfonylaryl, —(C$_{1-4}$ alkylene)-carbonylalkoxyaryl, or —(C$_{1-4}$ alkylene)-sulfonylaryl, wherein the aryl in sulfonylaryl is optionally substituted at one or more positions by alkyl, wherein, at each occurrence under (ii), alkyl has 1 to 10 carbon atoms, alkoxy has 1 to 10 carbon atoms, and aryl has 6, 9, 10, or 14 carbon atoms.

3. The compound of claim 1, wherein L$_3$ is —C(O)—N(R$^8$)—(C$_{1-3}$ alkylene)-, wherein the alkylene group is optionally substituted with one or more independently selected R$^{30}$.

4. The compound of claim 1, wherein R$_3$ is aryl or heteroaryl, each of which is optionally substituted with one or more independently selected R$^{30}$, or R$_3$ and R$^8$ join together with the atoms to which they are attached to form a bi- or tricyclic ring which is optionally substituted with one or more independently selected R$^{30}$.

5. The compound of claim 1, wherein L$_3$ is —C(O)—N(R$^8$)—CH$_2$— or and R$_3$ is aryl or heteroaryl selected from the group consisting of phenyl, pyridinyl, pyrazinyl, pyrimidinyl, pyridazinyl, naphthyl, indolyl, isoindolyl, indazolyl, indolizinyl, quinolizinyl, quinolinyl, isoquinolinyl, phthalazinyl, naphthyridinyl, quinoxalinyl, quinazolinyl, cinnolinyl, and pteridinyl, wherein each of the aryl and heteroaryl groups is optionally substituted with one, two or three independently selected R$^{30}$.

6. The compound of claim 1, wherein L$_5$ is selected from the group consisting of C$_{1-3}$ alkylene; and each of the C$_{1-3}$ alkylene groups is optionally substituted with one or more independently selected R$^{30}$.

7. The compound of claim 1, wherein R$_5$ is aryl, heteroaryl, cycloalkyl, or heterocyclyl selected from the group consisting of phenyl, naphthyl, phenantryl, furanyl, thienyl, pyrrolyl, imidazolyl, pyrazolyl, thiazolyl, isothiazolyl, oxazaolyl, isoxazolyl, pyranyl, pyridinyl, pyrazinyl, pyrimidinyl, pyridazinyl, pyrrolizinyl, indolizinyl, indolyl, isoindolyl, indazinyl, quinolizinyl, quinolinyl, isochinolinyl, phthalizinyl, naphthyridinyl, quinoxalinyl, quinazolinyl, cinnolinyl, pteridinyl, purinyl, carbazolyl, phenanthridinyl, acridinyl, phenanthrolinyl, benzodioxolyl, imidazothiazolyl, imidazoimidazolyl, pyrrolopyrrolyl, chromenyl, benzofuranyl, isobenzofuranyl, benzodioxinyl, benzoxazolyl, benzoisoxazolyl, partially or completely hydrogenated forms of these heteroaryl or heterocyclyl groups, cyclopropyl, cyclobutyl, cyclopentyl, cyclohexyl, cyclohexenyl, cycloheptyl, and cyclononyl, wherein each of these groups is optionally substituted with one, two or three independently selected R$^{30}$.

8. The compound of claim 1, wherein L$_5$ is —(C$_{1-3}$ alkylene optionally substituted with one R$^{30}$); and R$_5$ is selected from the group consisting of phenyl, naphthyl, phenantryl, indolyl, pyrazolyl, pyrrolyl, quinolinyl, benzodioxolyl, imidazothiazolyl, tetrahydrochromenyl, benzofuranyl, benzodioxinyl, tetrahydrobenzoxazolyl, cyclopropyl, cyclohexenyl, indazolyl, and tetrahydroisoquinolinyl, each of which is optionally substituted with one, two or three independently selected R$^{30}$.

9. The compound of claim 1, wherein R$_4$, R'$_4$, R$_6$, R'$_6$, R$_7$, and R'$_7$ are independently selected from the group consisting of H, C$_{1-3}$ alkyl, halogen, —CF$_3$, —OH, —OCH$_3$, —SCH$_3$, —NH$_{2-z}$(CH$_3$)$_z$, —C(=O)OH, and —C(=O)OCH$_3$, wherein z is 0, 1, or 2.

10. The compound of claim 1, wherein R$_1$/R$_2$ is selected from the group consisting of —H, C$_{1-10}$ alkyl, C$_{2-10}$ alkenyl, 5- or 6-membered aryl, 5- to 7-membered heteroaryl, 3- to 10-membered cycloalkyl, 4- to 10-membered heterocyclyl, —C(=X)R$^{11}$, and —C(=X)XR$^{11}$, wherein each of the C$_{1-10}$ alkyl, C$_{2-10}$ alkenyl, 5- or 6-membered aryl, 5- to 7-membered heteroaryl, 3- to 10-membered cycloalkyl, and 4- to 10-membered heterocyclyl groups is optionally substituted with one or more independently selected R$^{30}$ or the C$_{1-10}$ alkyl group is substituted with one R$^{31}$.

11. The compound of claim 1, wherein R$_1$/R$_2$ is selected from the group consisting of —H, C$_{1-6}$ alkyl, C$_{2-6}$ alkenyl, phenyl, 5- or 6-membered heteroaryl, 4- to 6-membered cycloalkyl, 4- to 6-membered heterocyclyl, —C(=O)O(C$_{1-3}$ alkyl), and —C(=O)NH$_{2-z}$(C$_{1-3}$ alkyl)$_z$, wherein z is 0, 1, or 2 and C$_{1-3}$ alkyl is methyl, ethyl, propyl or isopropyl, wherein each of the C$_{1-6}$ alkyl, C$_{2-6}$ alkenyl, phenyl, 5- or 6-membered heteroaryl, 4- to 6-membered cycloalkyl, and 4- to 6-membered heterocyclyl groups is optionally substituted with one, two or three independently selected R$^{30}$ or the C$_{1-6}$ alkyl group is substituted with one R$^{31}$.

12. The compound of claim 1, which has the structure (Ib) and wherein R$_2$ and R$^8$ join together with the atoms to which they are attached to form a 5- to 7-membered ring which is optionally substituted with one, two or three independently selected R$^{30}$.

13. A compound which is selected from the group consisting of:

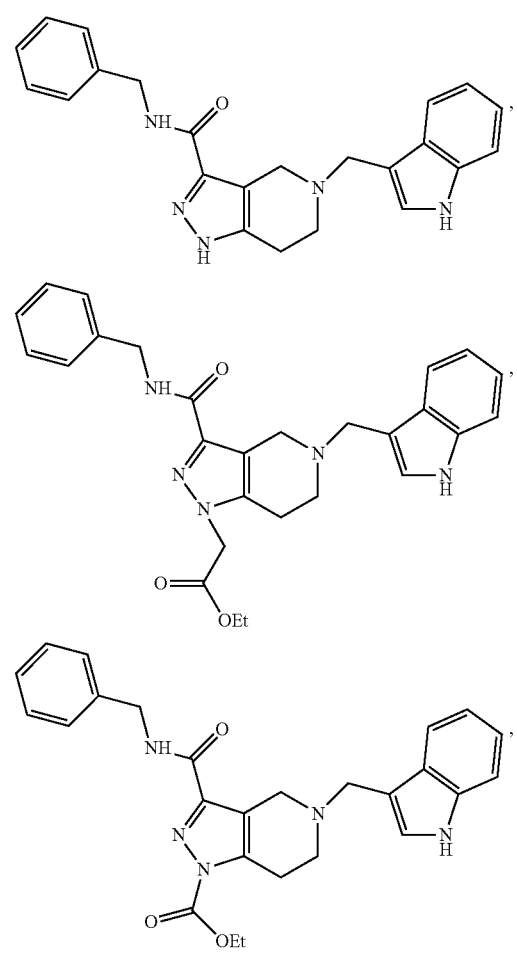

151
-continued
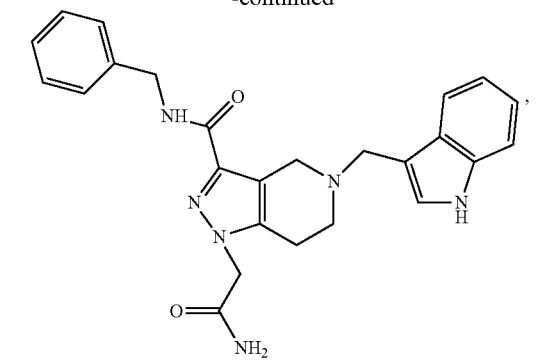
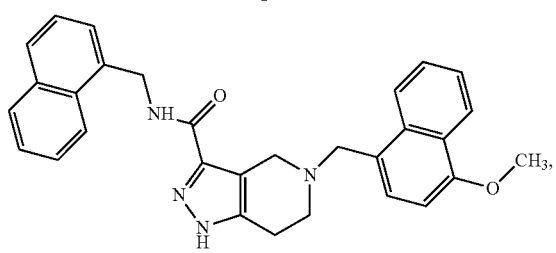
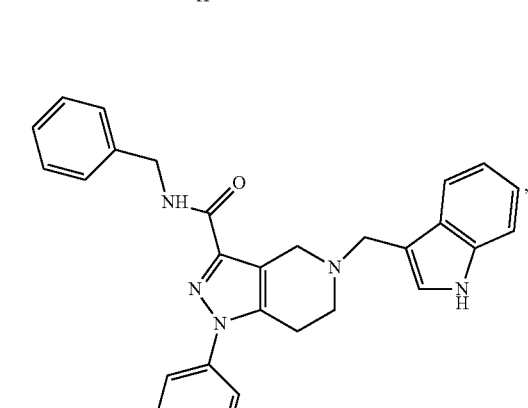
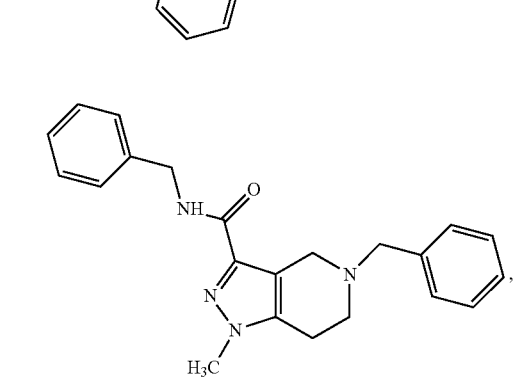
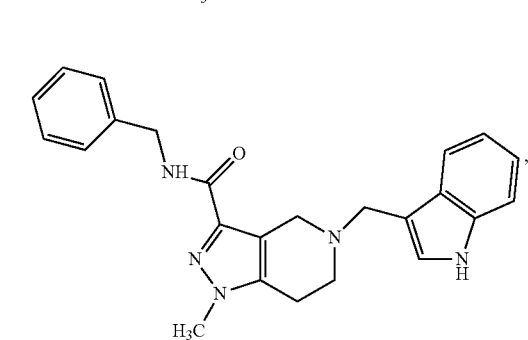
152
-continued
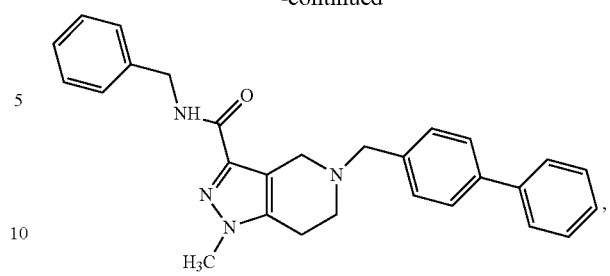
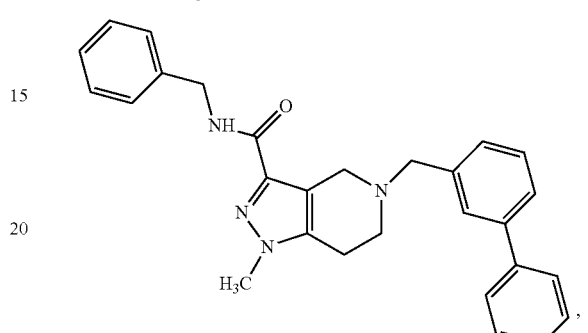
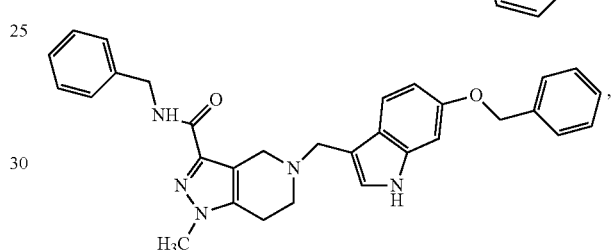
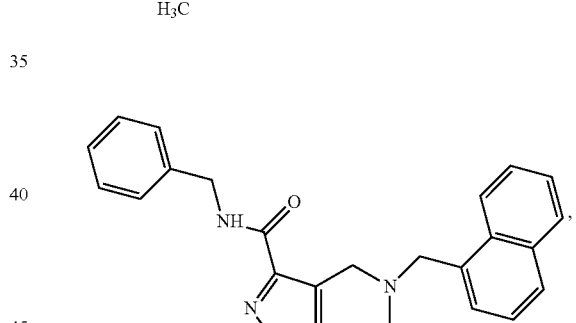
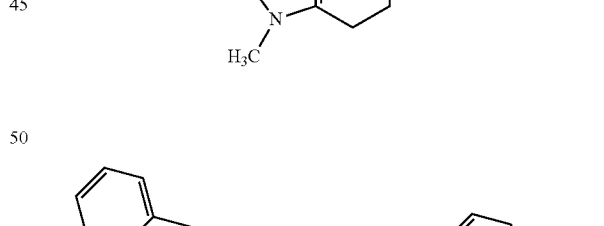
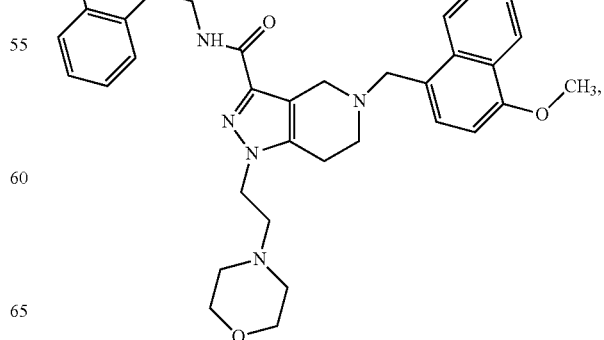

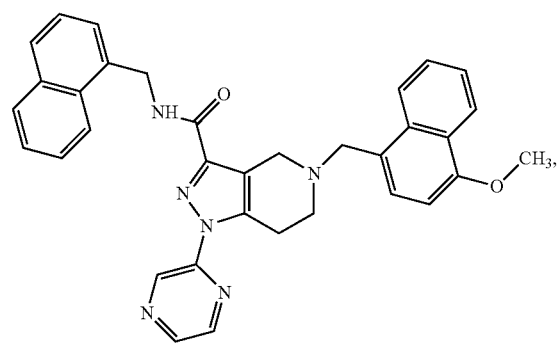
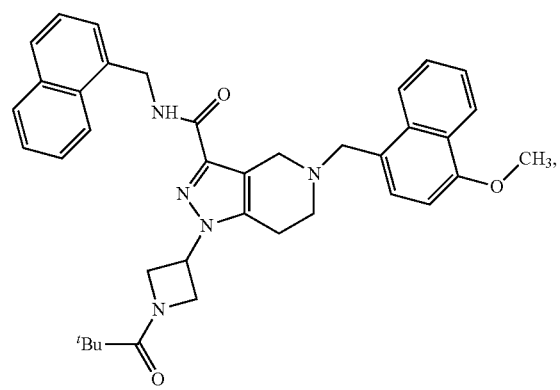
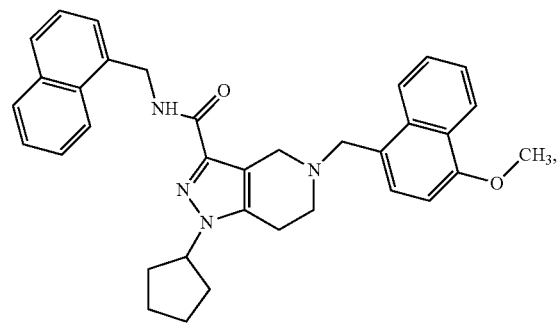
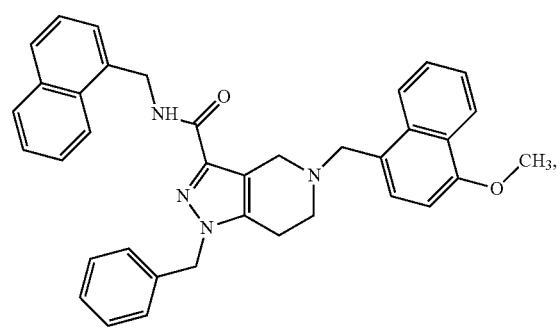
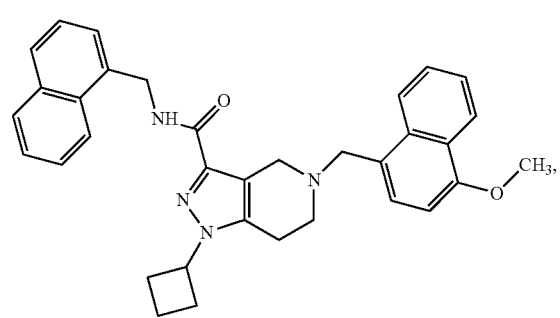
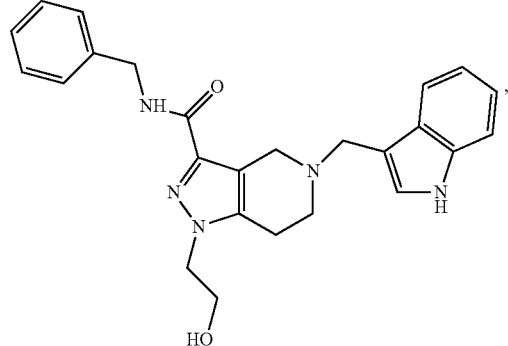
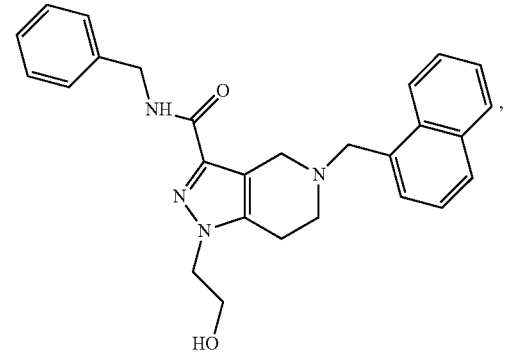
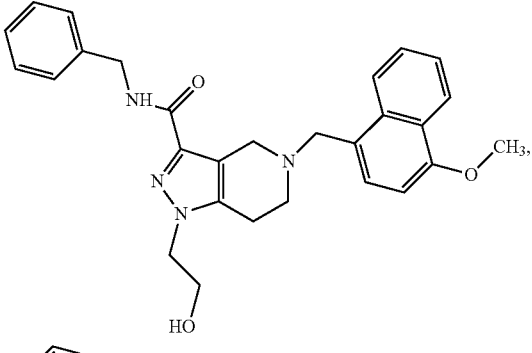
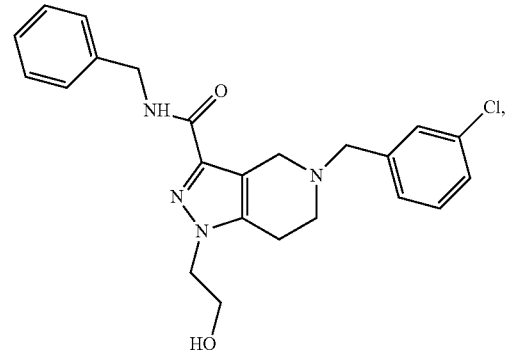
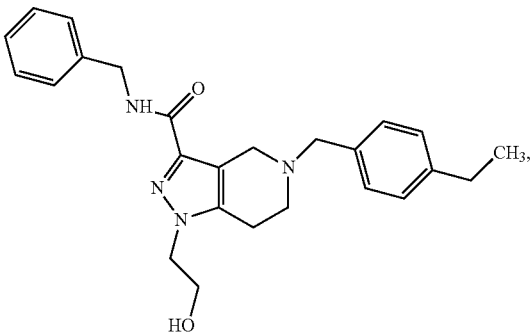

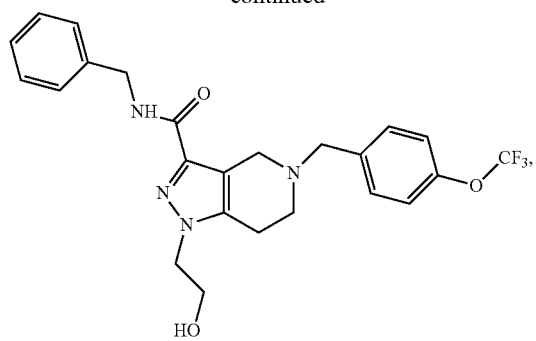
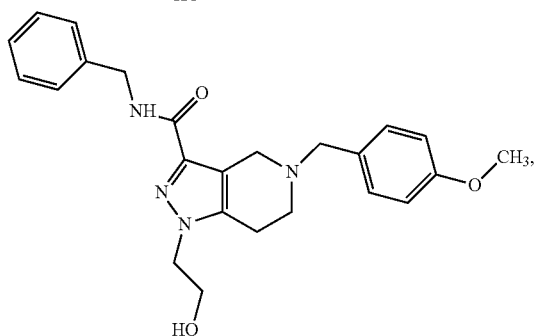
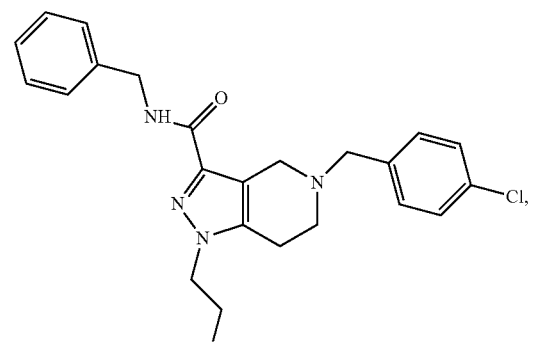
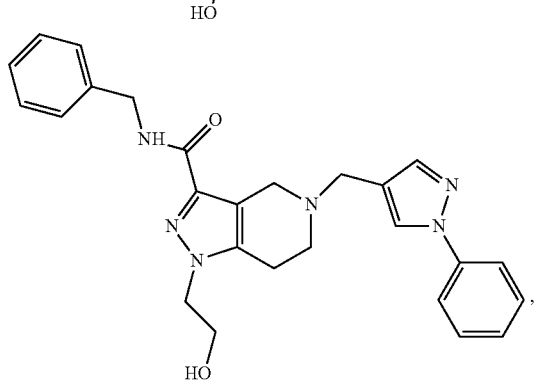
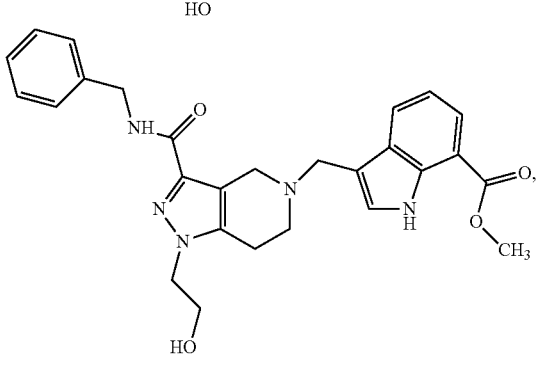
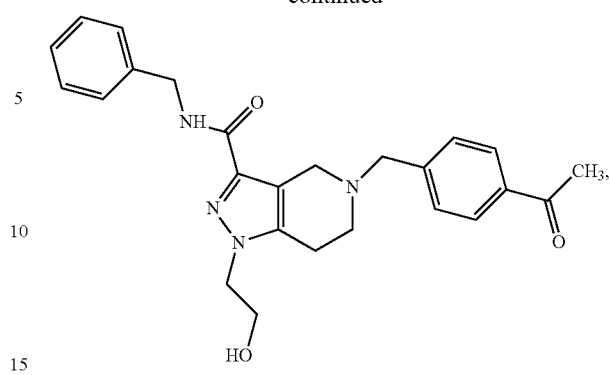
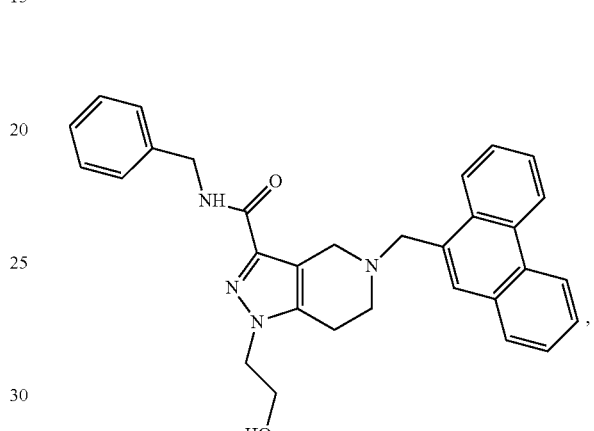
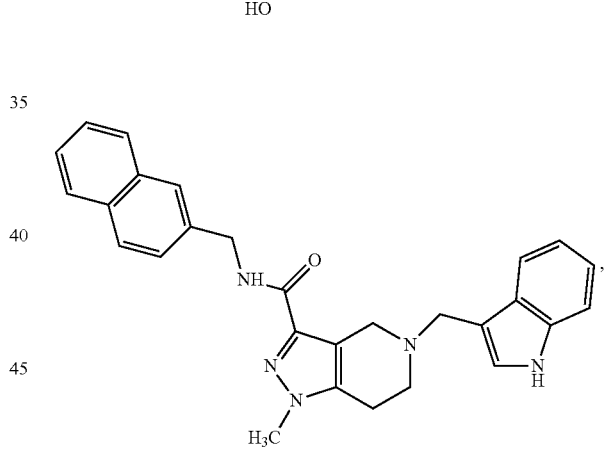
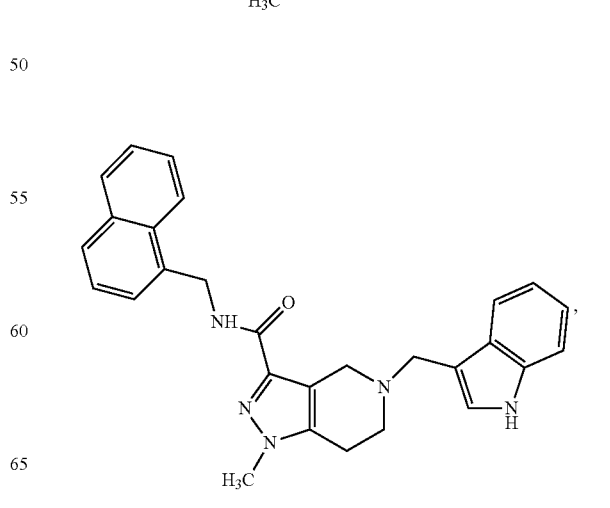

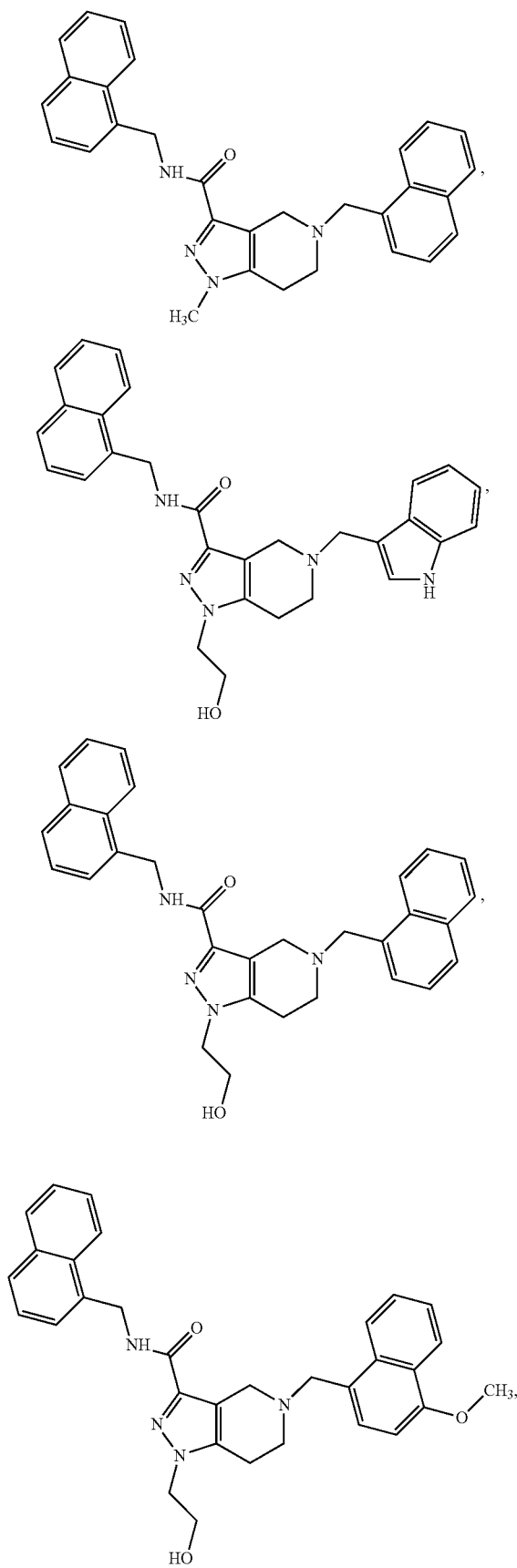
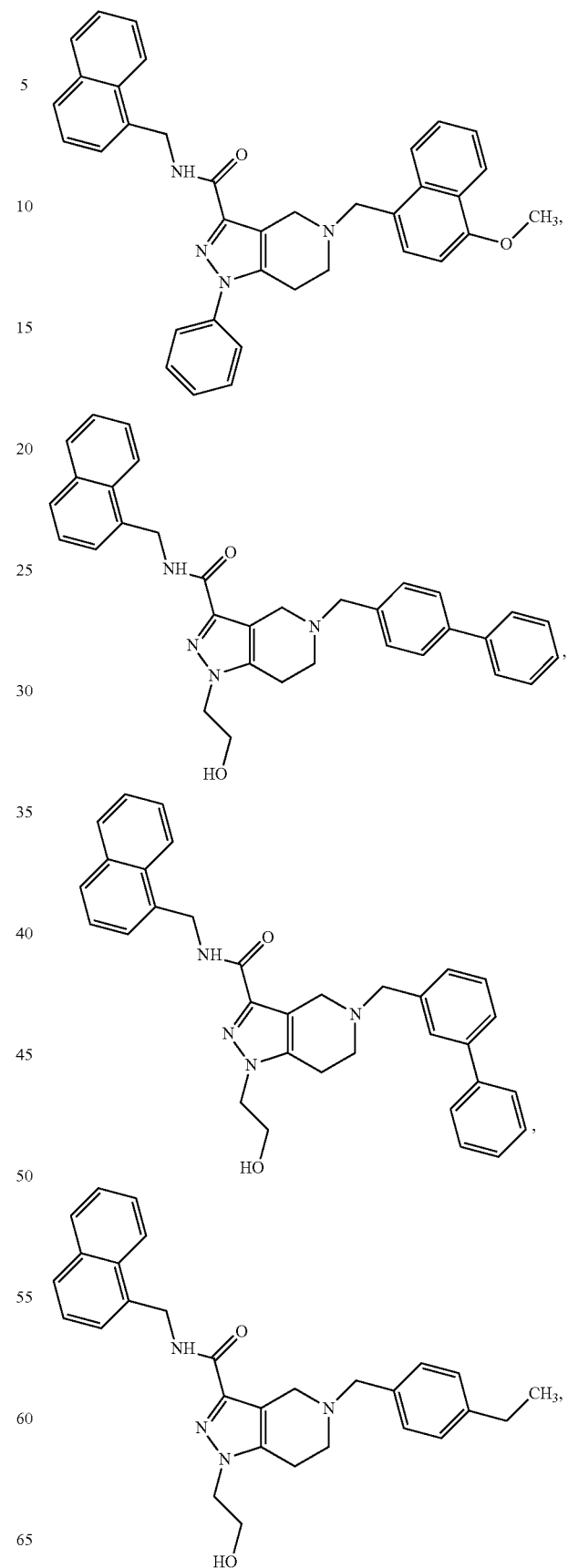

159
-continued
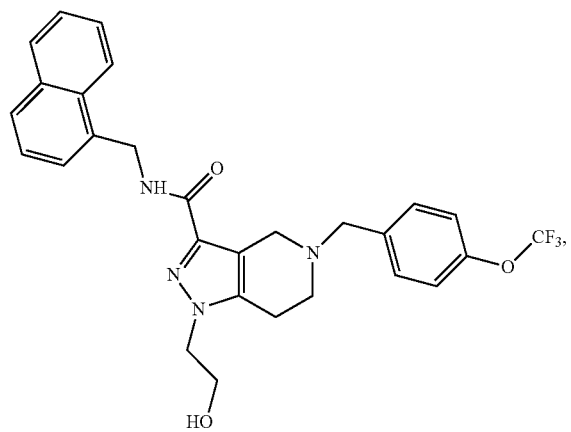
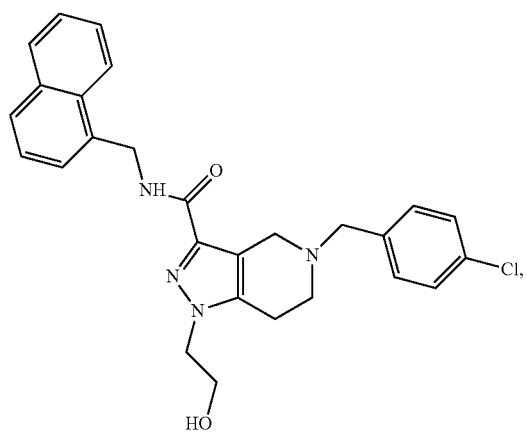
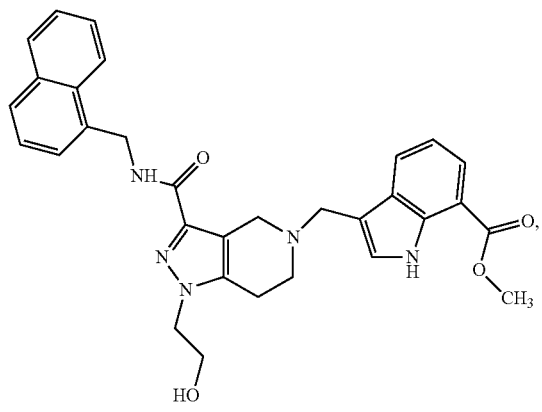
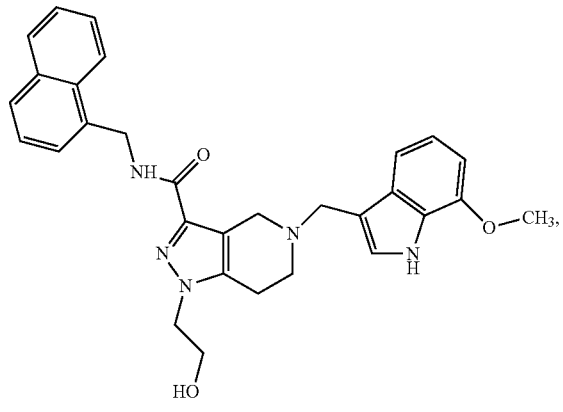
160
-continued
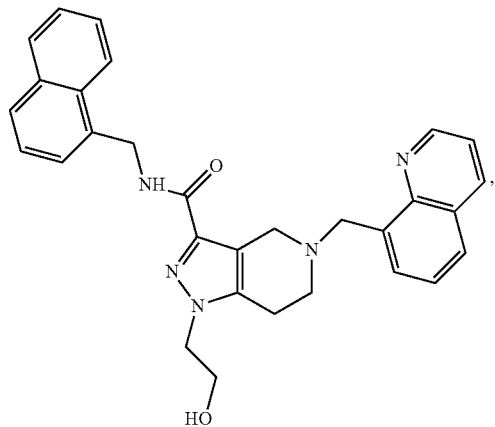
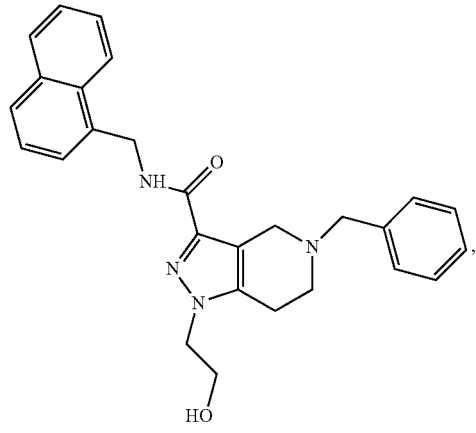
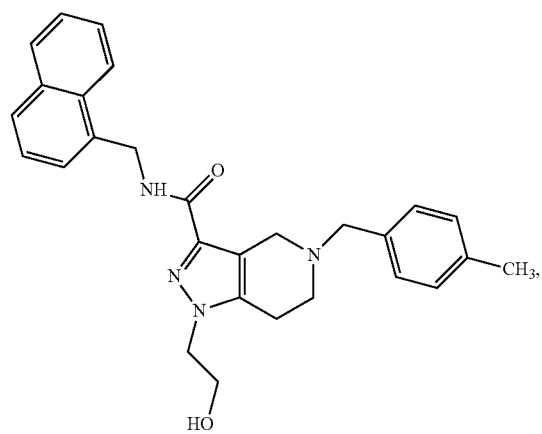
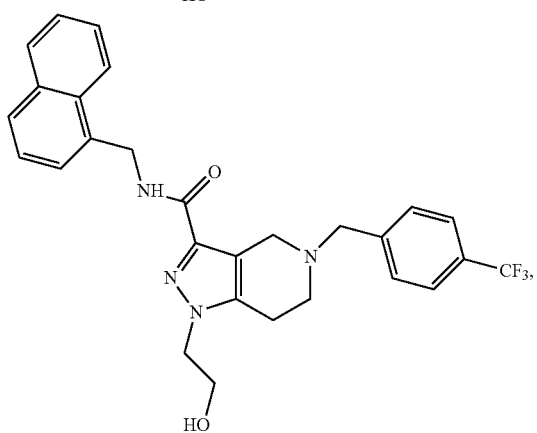

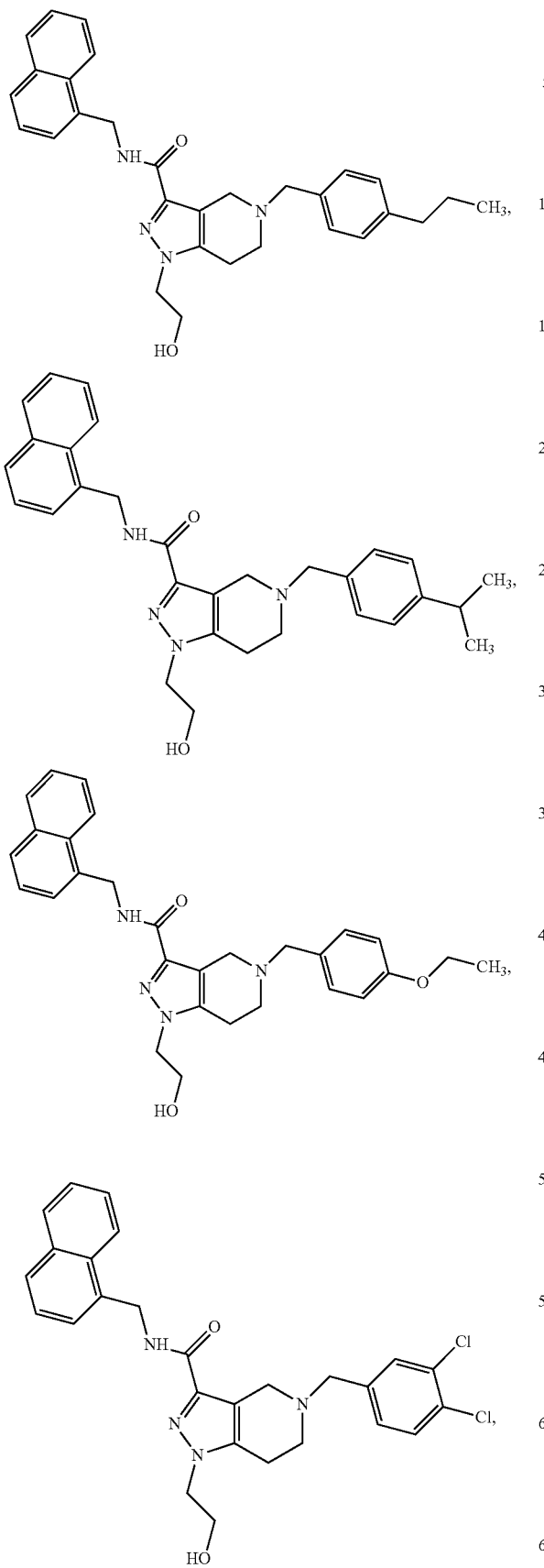
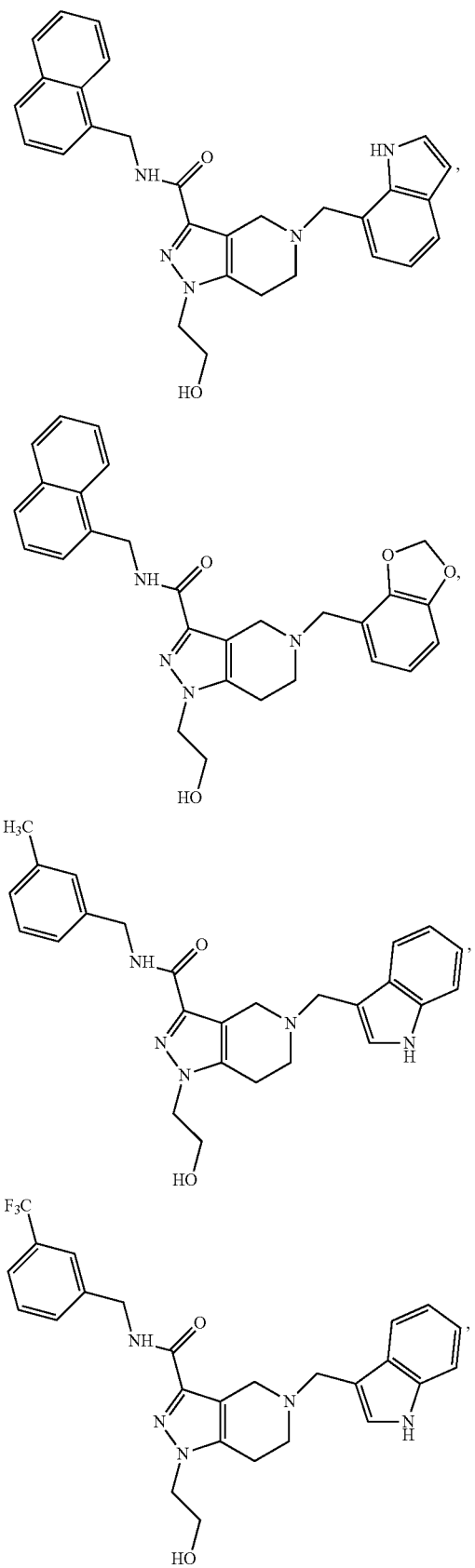

163
-continued
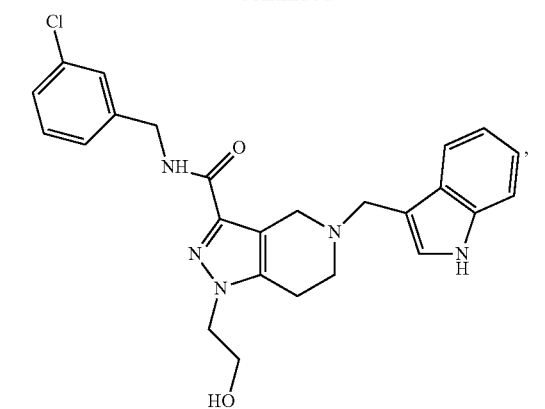
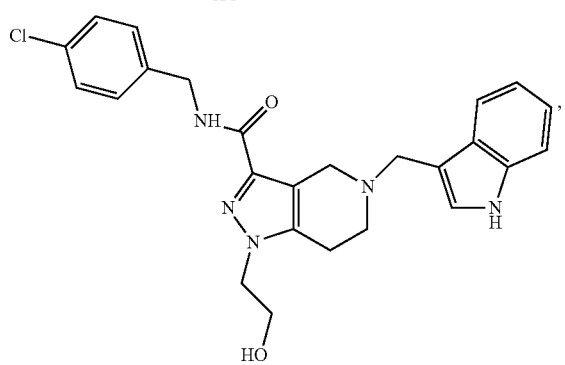
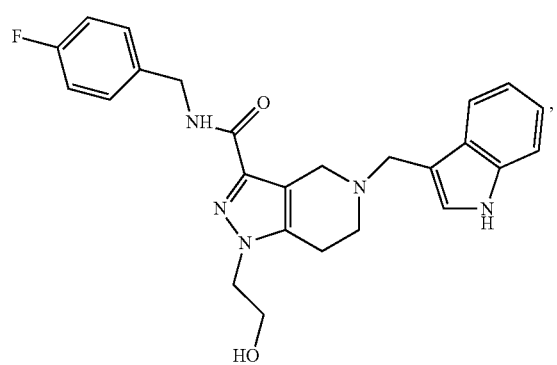
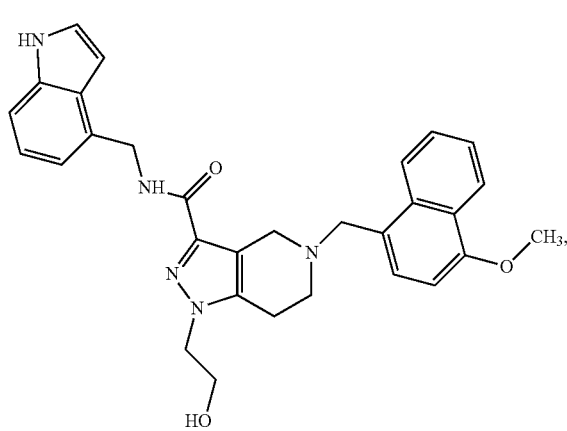
164
-continued
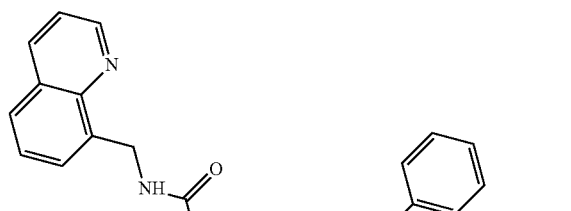
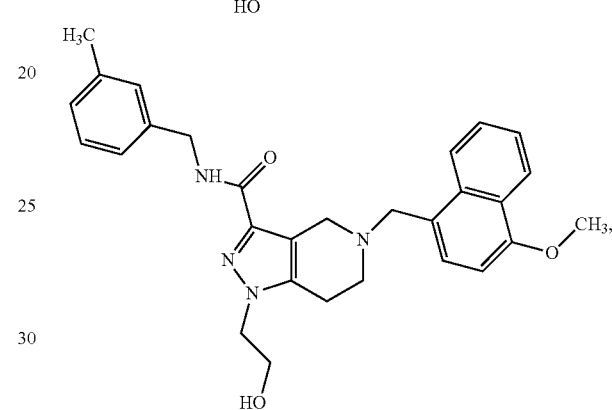
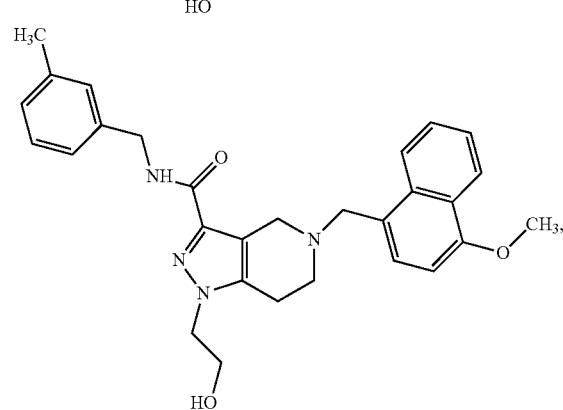
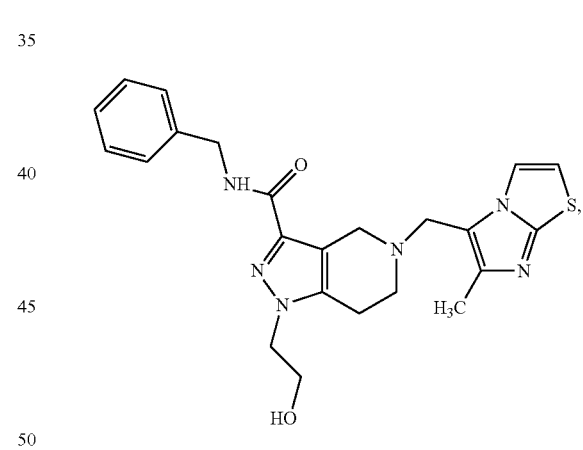
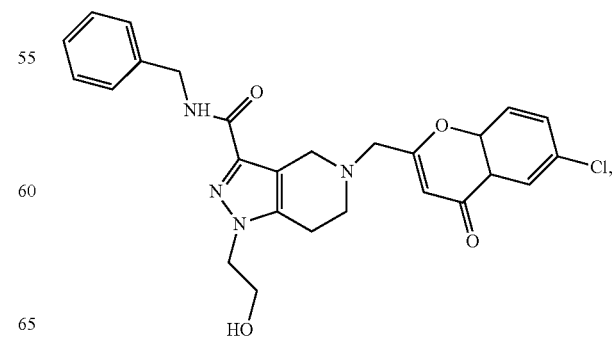

165
-continued
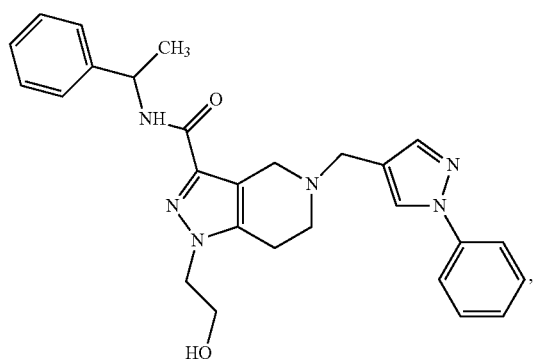
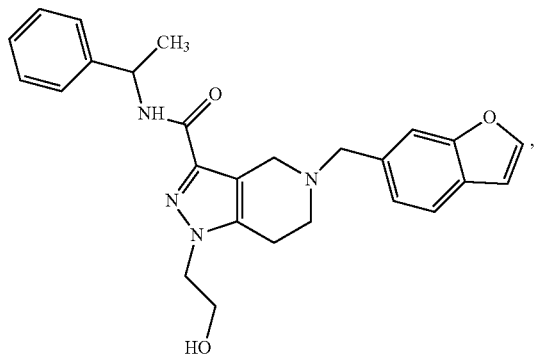
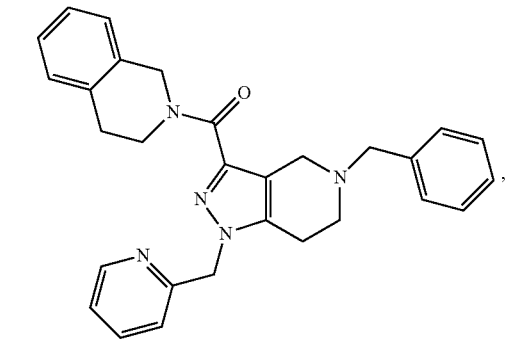
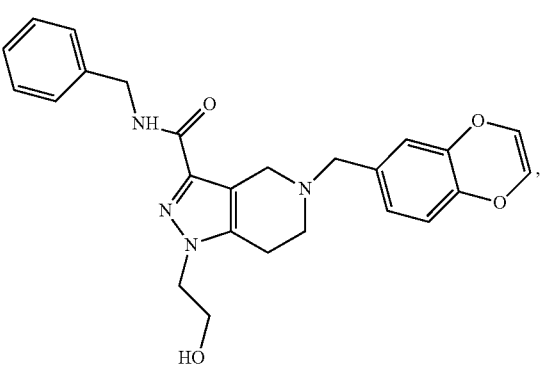
166
-continued
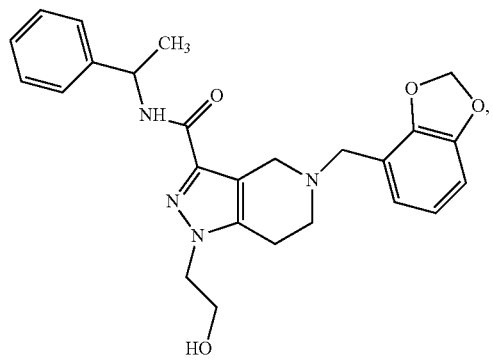
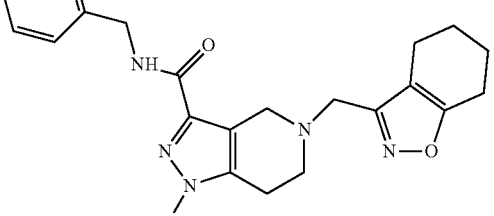
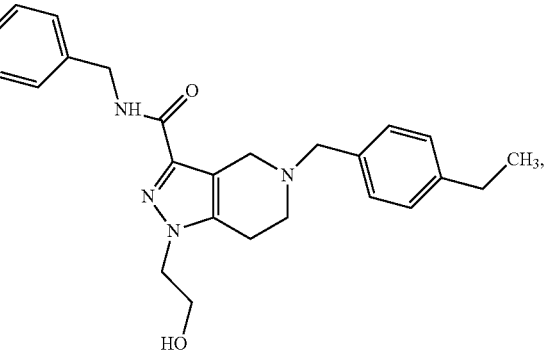
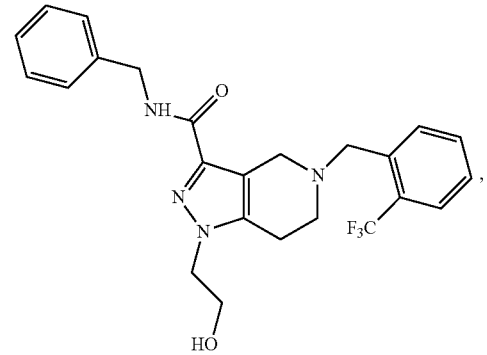
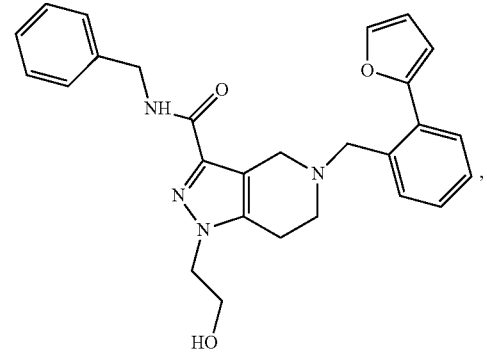

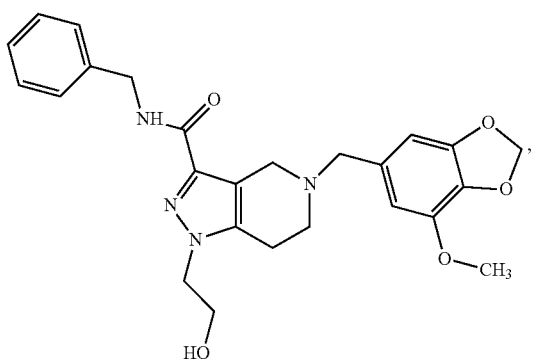
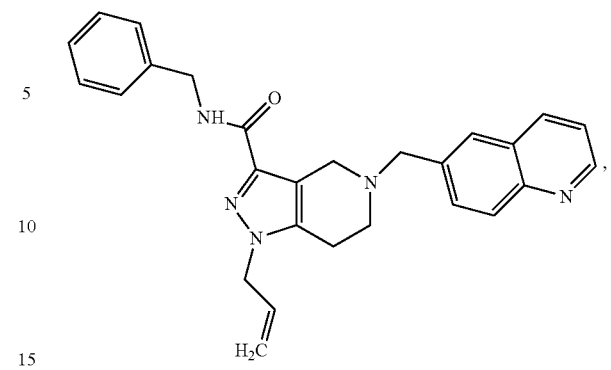
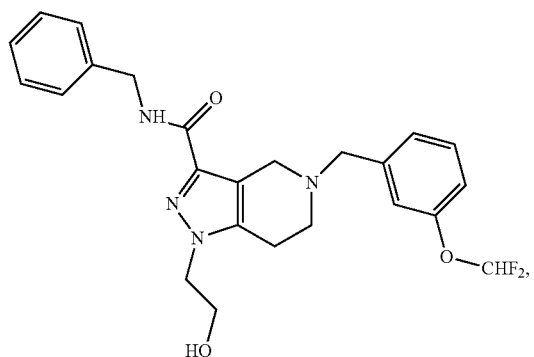
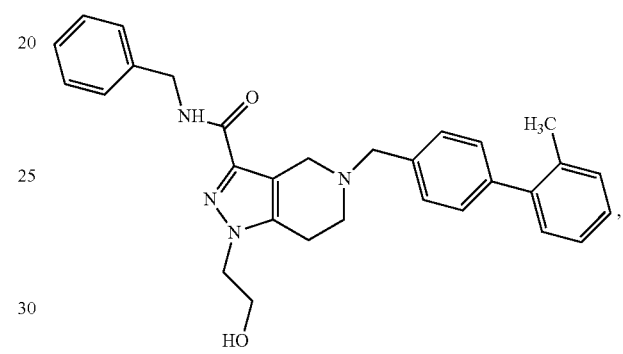
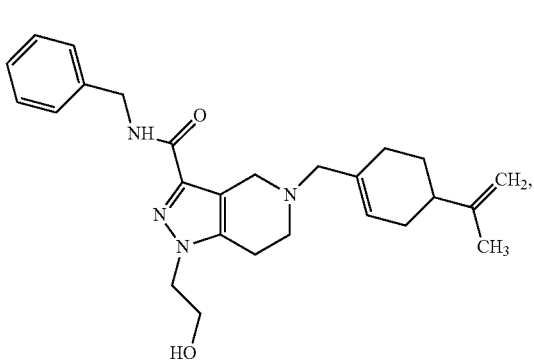
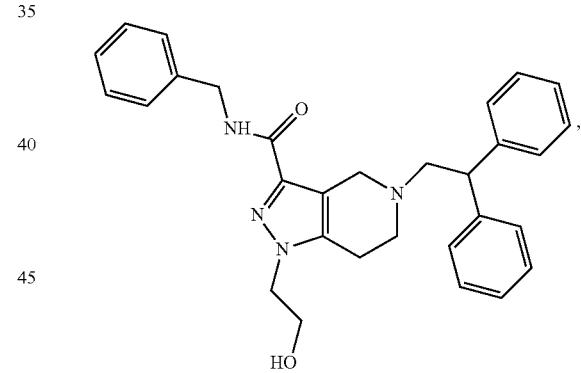
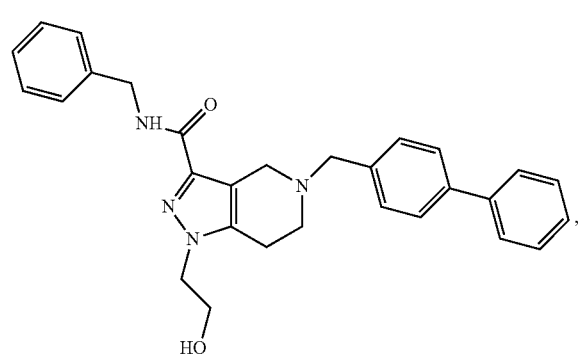
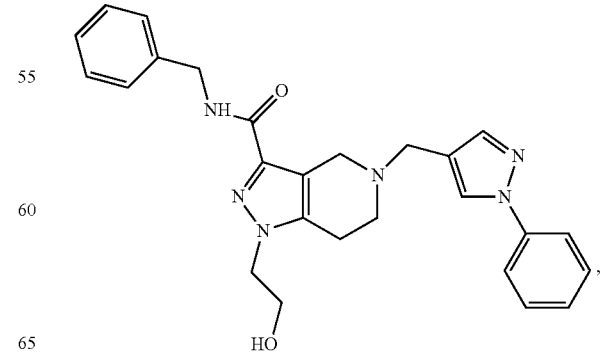

169
-continued
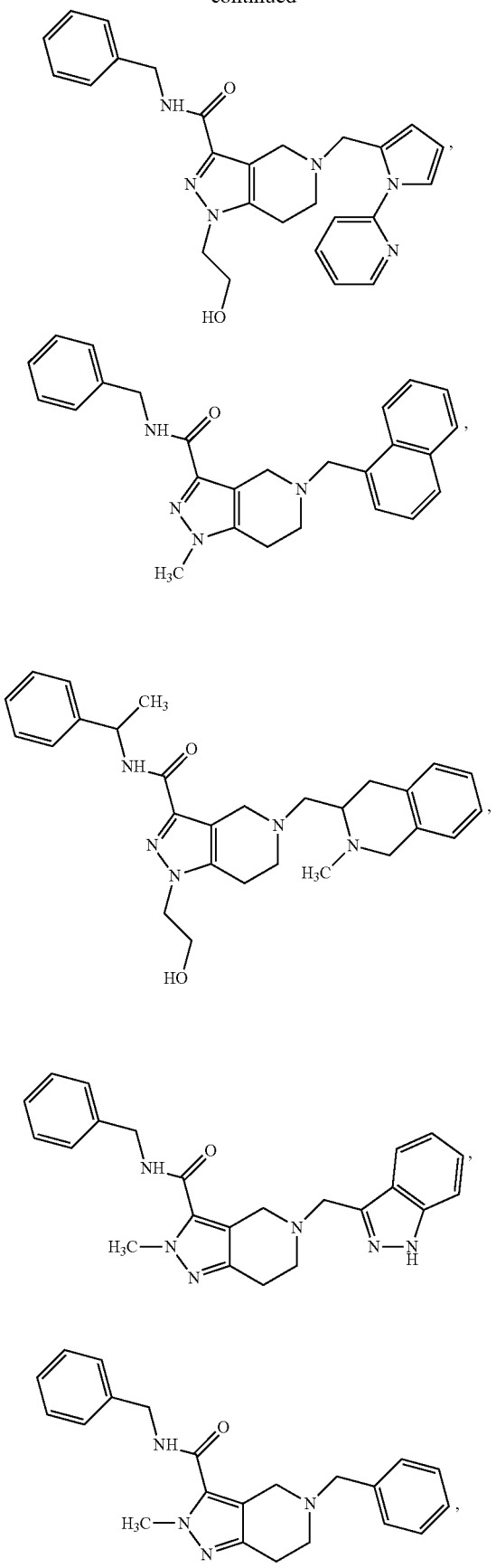
170
-continued
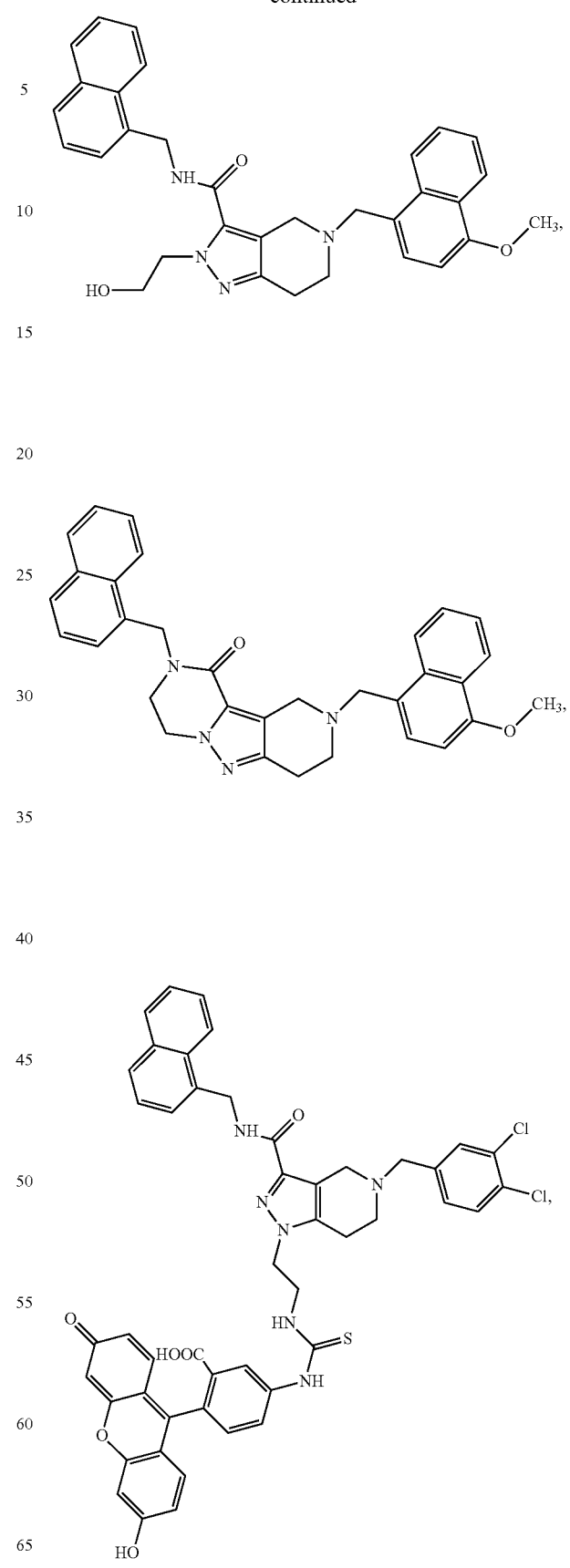

171
-continued
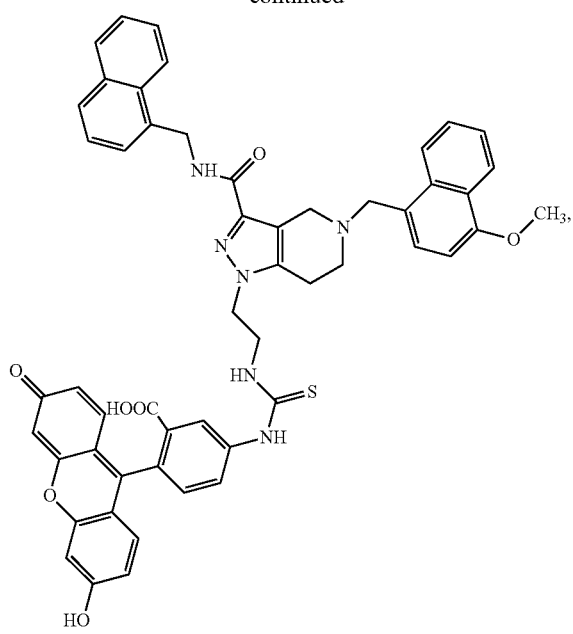
172
-continued
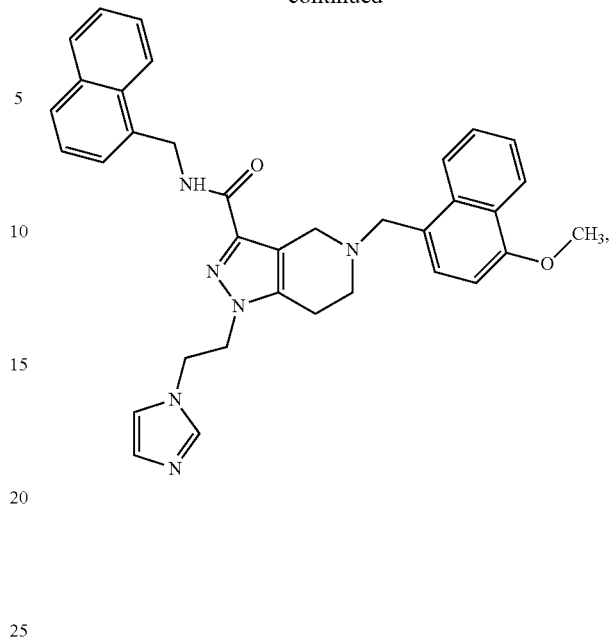
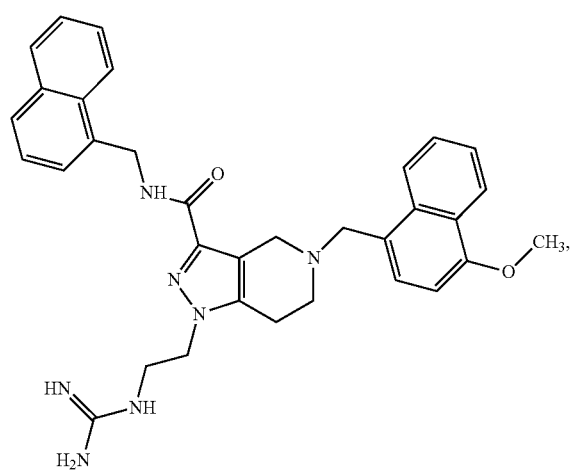
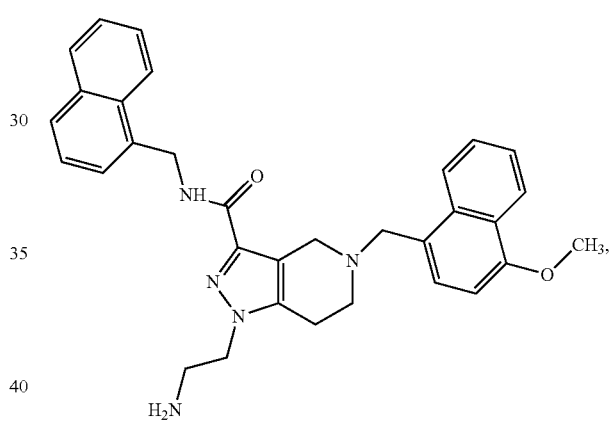
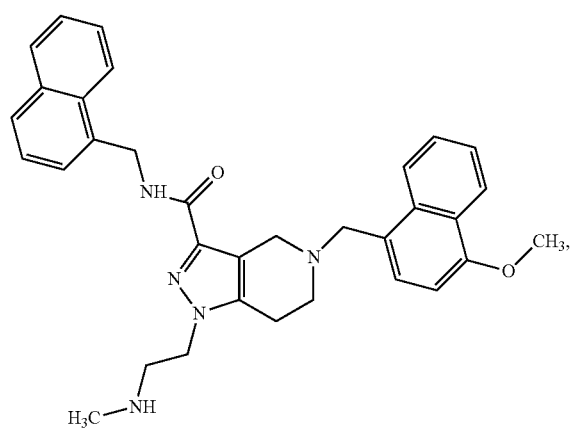
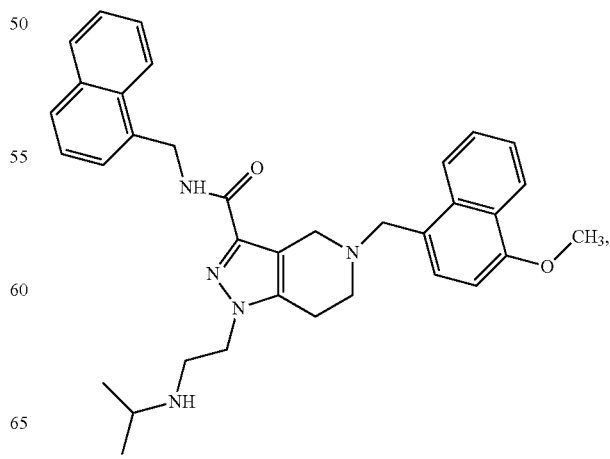

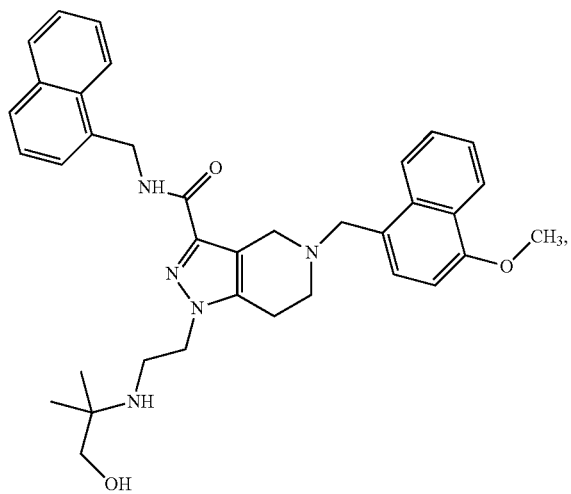
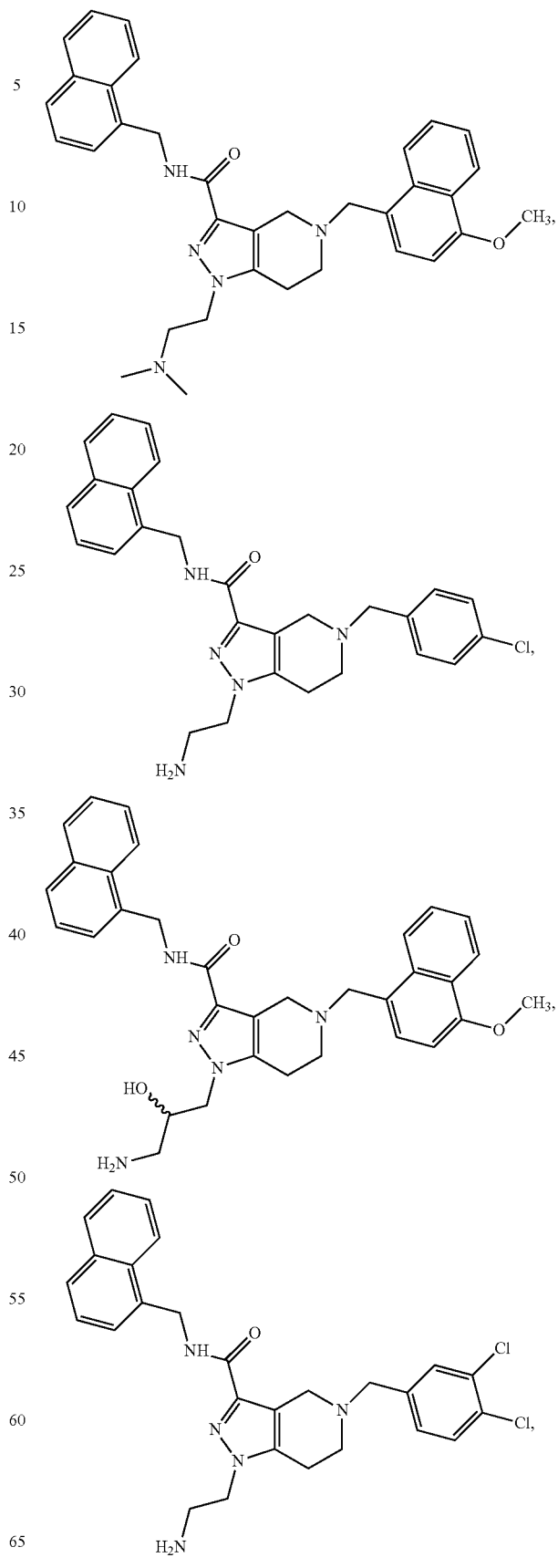

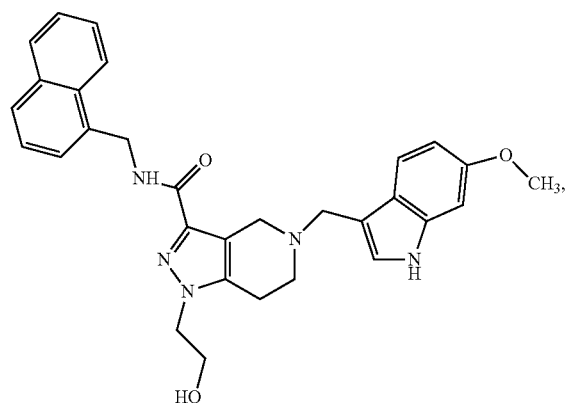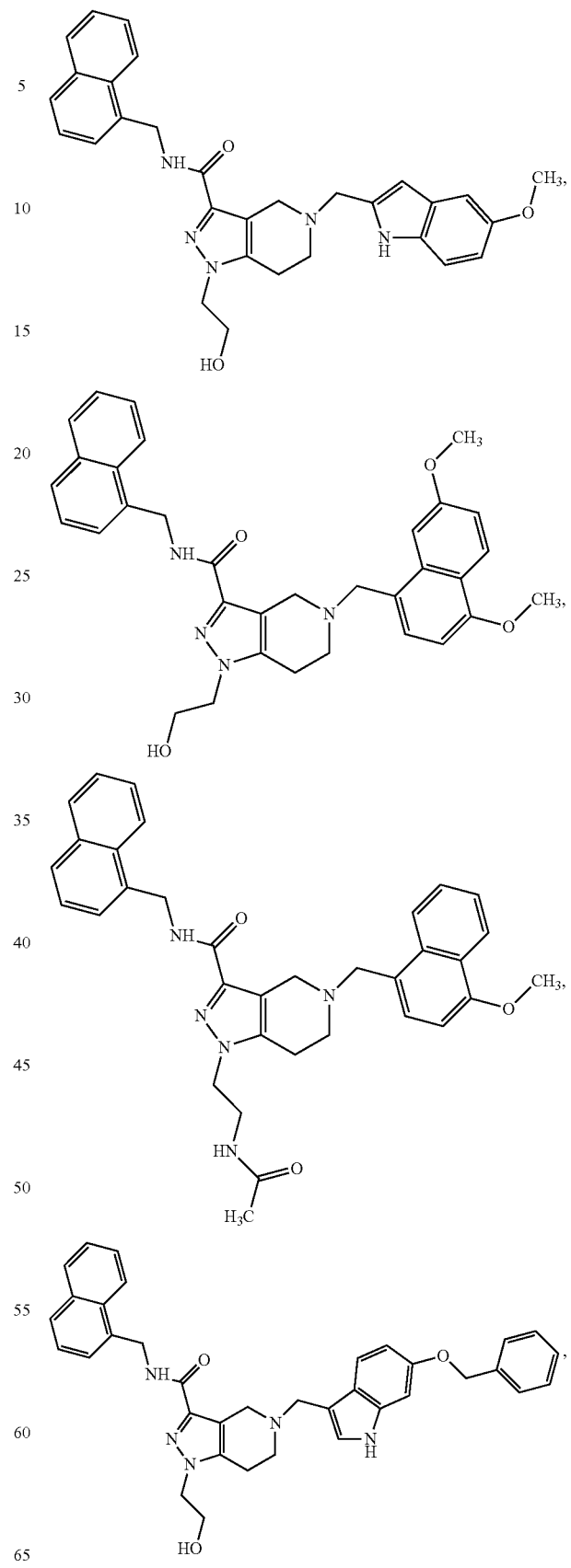

177
-continued
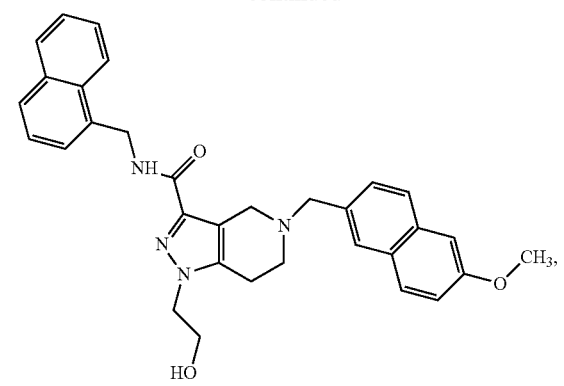
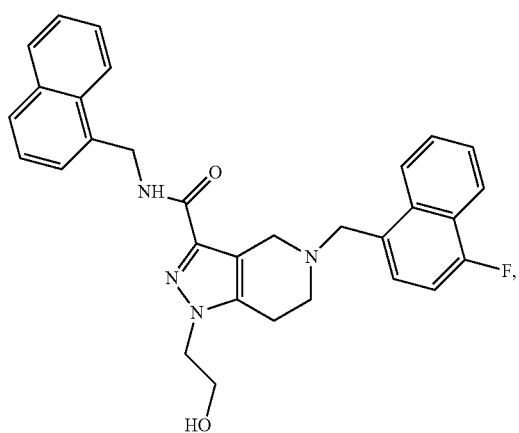
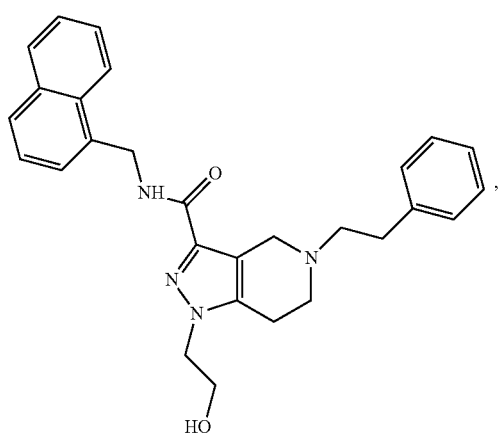
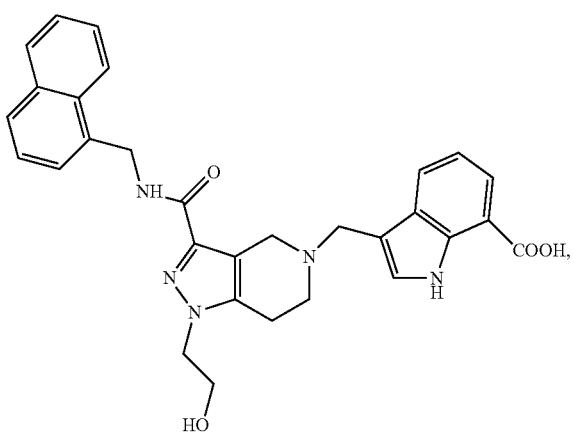
178
-continued
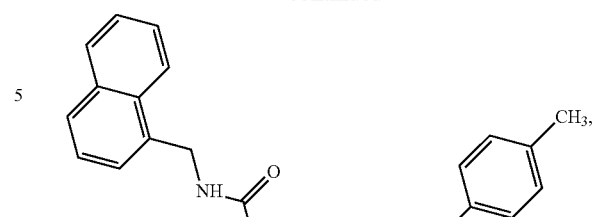
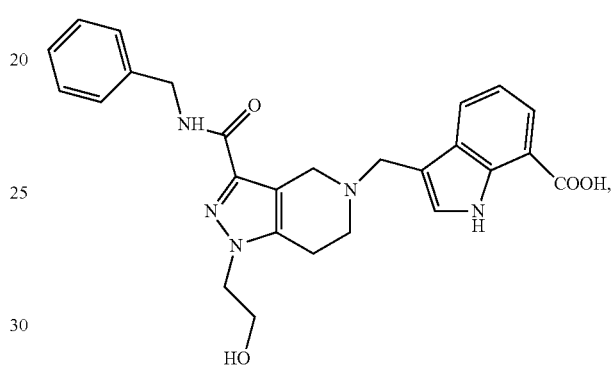
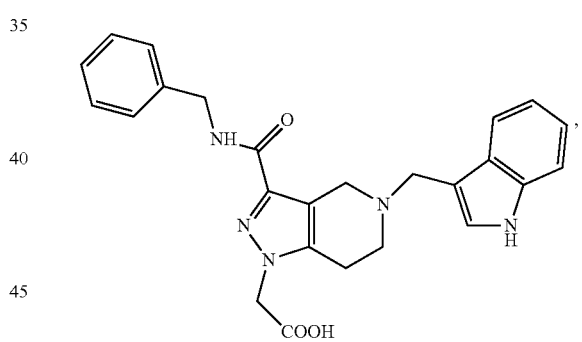
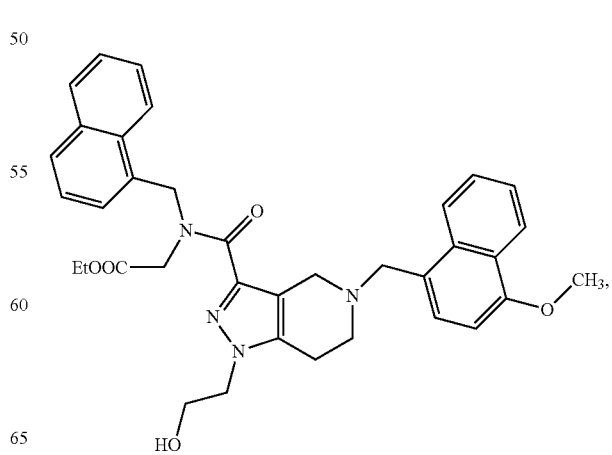

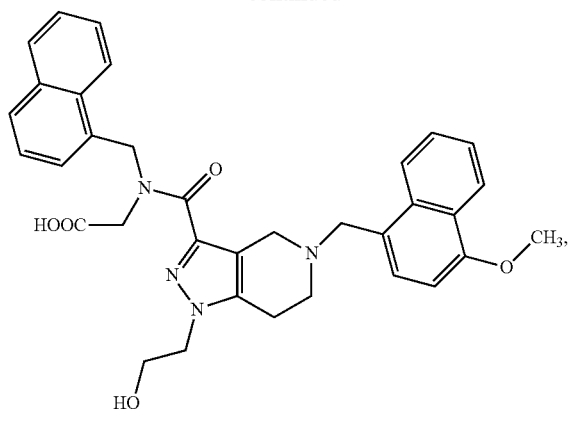

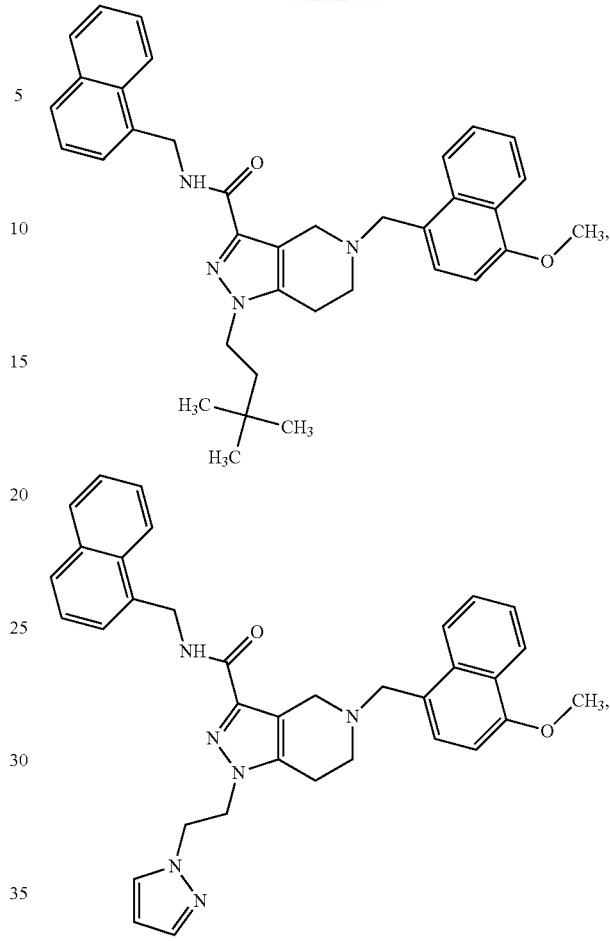

and solvates, salts, complexes, polymorphs, crystalline forms, racemic mixtures, diastereomers, enantiomers, tautomers, isotopically labeled forms, prodrugs, and combinations thereof.

14. The compound of claim 1 for use in medicine.

15. A pharmaceutical composition comprising a pharmaceutically acceptable excipient and a compound of claim 1.

16. A pharmaceutical composition comprising a pharmaceutically acceptable excipient and a compound of claim 13.

* * * * *